US008999982B2

(12) United States Patent
Schultz-Fademrecht et al.

(10) Patent No.: US 8,999,982 B2
(45) Date of Patent: Apr. 7, 2015

(54) PHARMACEUTICALLY ACTIVE COMPOUNDS AS AXL INHIBITORS

(75) Inventors: Carsten Schultz-Fademrecht, Dortmund (DE); Bert Klebl, Dortmund (DE); Axel Choidas, Herdecke (DE); Uwe Koch, Dortmund (DE); Jan Eickhoff, Herdecke (DE); Alexander Wolf, Dortmund (DE); Axel Ullrich, Munich (DE)

(73) Assignees: Lead Discovery Center GmbH, Dortmund (DE); Max-Planck-Gesellschaft zur Förderung der Wissenschaften E.V., München (DE)

( * ) Notice: Subject to any disclaimer, the term of this patent is extended or adjusted under 35 U.S.C. 154(b) by 0 days.

(21) Appl. No.: 13/819,560

(22) PCT Filed: Aug. 26, 2011

(86) PCT No.: PCT/EP2011/004451
§ 371 (c)(1),
(2), (4) Date: Feb. 27, 2013

(87) PCT Pub. No.: WO2012/028332
PCT Pub. Date: Mar. 8, 2012

(65) Prior Publication Data
US 2014/0018365 A1   Jan. 16, 2014

Related U.S. Application Data

(60) Provisional application No. 61/344,959, filed on Nov. 29, 2010.

(30) Foreign Application Priority Data

Aug. 28, 2010   (EP) ..................................... 10075374

(51) Int. Cl.
| | | |
|---|---|---|
| *A61K 31/495* | (2006.01) | |
| *A61K 31/47* | (2006.01) | |
| *C07D 401/12* | (2006.01) | |
| *C07D 401/14* | (2006.01) | |
| *C07D 417/12* | (2006.01) | |
| *C07D 417/14* | (2006.01) | |
| *C07D 413/12* | (2006.01) | |
| *C07D 413/14* | (2006.01) | |
| *C07D 215/233* | (2006.01) | |

(52) U.S. Cl.
CPC ............ *C07D 401/12* (2013.01); *A61K 31/495* (2013.01); *A61K 31/47* (2013.01); *C07D 401/14* (2013.01); *C07D 413/12* (2013.01); *C07D 413/14* (2013.01); *C07D 417/12* (2013.01); *C07D 417/14* (2013.01); *C07D 215/233* (2013.01)

(58) Field of Classification Search
CPC ... A61K 31/496; A61K 31/47; C07D 401/12; C07D 401/14; C07D 417/12; C07D 417/14
USPC ........... 514/235.2, 253.07, 312; 544/128, 363
See application file for complete search history.

(56) References Cited

U.S. PATENT DOCUMENTS

| | | | |
|---|---|---|---|
| 6,143,764 | A | 11/2000 | Kubo et al. |
| 2004/0053908 | A1 | 3/2004 | Funahashi et al. |
| 2008/0004273 | A1 | 1/2008 | Raeppel et al. |
| 2011/0053931 | A1 | 3/2011 | Gaudino et al. |

FOREIGN PATENT DOCUMENTS

| | | |
|---|---|---|
| JP | 2011-063516 | 3/2011 |
| WO | 9717329 | 5/1997 |
| WO | 0121596 | 3/2001 |
| WO | 03033472 | 4/2003 |
| WO | 2005030140 | 4/2005 |
| WO | 2005070891 | 8/2005 |
| WO | 2006004636 | 1/2006 |
| WO | 2006116713 | 11/2006 |
| WO | 2007033196 | 3/2007 |
| WO | 2007099326 | 9/2007 |
| WO | 2007146824 | 12/2007 |
| WO | 2008022013 | 2/2008 |
| WO | 2008035209 | 3/2008 |
| WO | 2008150015 | 12/2008 |
| WO | 2009108670 | 9/2009 |
| WO | 2009127417 | 10/2009 |

OTHER PUBLICATIONS

International Search Report for PCT/EP2011/004451 mailed on Oct. 5, 2011.
Written Opinion for PCT/EP2011/004451 mailed on Oct. 5, 2011.

*Primary Examiner* — Raymond Henley, III
(74) *Attorney, Agent, or Firm* — Amin, Turocy & Watson, LLP

(57) ABSTRACT

The present invention relates to 1-nitrogen-heterocyclic-2-carboxamides and/or pharmaceutically acceptable salts thereof, the use of these derivatives as pharmaceutically active agents, especially for the treatment and/or prevention of Axl receptor tyrosine kinase subfamily induced disorders, including cancer and primary tumor metastases, and pharmaceutical compositions containing at least one of said 1-nitrogen-heterocyclic-2-carboxamide derivatives and/or pharmaceutically acceptable salts thereof.

15 Claims, No Drawings

```
SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: FITC-labeled substrate peptide for Axl kinase
<220> FEATURE:
<221> NAME/KEY: MISC_FEATURE
<222> LOCATION: (1)..(1)
<223> OTHER INFORMATION: FITC konjugated

<400> SEQUENCE: 1

Lys Lys Lys Lys Glu Glu Ile Tyr Phe Phe Phe Gly
1               5                   10
```

PHARMACEUTICALLY ACTIVE COMPOUNDS AS AXL INHIBITORS

The present invention relates to novel compounds which are inhibitors of Axl receptor tyrosine kinase subfamily which comprises Axl, Mer and Tyro3. These compounds are suitable for the treatment or prevention of disorders associated with, accompanied by or caused by hyperfunction of a receptor of the Axl family. The compounds are suitable for the treatment of hyperproliferative disorders, such as cancer, particularly cancer metastases.

Receptor tyrosine kinases (RTKs) are cell surface receptors that transmit signals from the extracellular environment to control growth, differentiation and survival of cells. Deregulated expression of protein kinases by gene deletion, -mutation or amplification has been found to be important for tumor initiation and progression, involving cancer cell proliferation, -survival, -motility and -invasivity as well tumor angiogenesis and chemotherapy resistance. Because of the advanced understanding of their critical role, protein kinases are important targets for novel therapies, especially for cancer (Hananhan et al., 2000; Blume-Jensen et al., 2001).

Axl is a member of the TAM (Tyro-Axl-Mer) receptor tyrosine kinases. This family is characterised by an extracellular domain, consisting of two immunoglobulin-like domains followed by two fibronectin type 3-like domains. The activation of the Axl RTK subfamily occurs by its cognate protein ligand, growth arrest specific 6 (Gas6). The affinity of Gas6 is highest for Axl, followed by Tyro3, and finally Mer, and thereby activates the three proteins to varying degrees. Gas6 is a member of the vitamin K-dependent family and shows a 43% sequence identity to and the same domain organisation as the protein S, a serum protein (Hafizi et al., 2006).

Axl is ubiquitously expressed at low levels and is detectable in a variety of organs. Expression patterns of the other two family members differ from that of Axl. Expression of Tyro3 is predominantly in the brain and CNS (central nervous system), while expression of Mer is almost exclusively in the monocyte cell lineage (Rescigno et al. 1991, Mark et al., 1994, Graham et al., 1994).

TAM family RTKs regulate a diverse range of cellular responses, including cell survival, proliferation, migration and adhesion (Hafizi et al., 2006). TAM receptor signalling has been shown to regulate vascular smooth muscle homeostasis (Korshunov et al., 2007), platelet function, thrombus stabilization (Angelillo-Scherrer et al., 2001; Gould et al., 2005), and erythropoiesis (Angelillo-Scherrer et al., 2008). Furthermore TAM receptors are implicated in the control of oligodendrocyte cell survival (Shankar et al., 2006) and the regulation of osteoclast function (Katagiri et al., 2001). The TAM receptors play pivotal roles in innate immunity (Lemke et al., 2008) and in inflammation (Sharif et al., 2006; Rothlin et al., 2007). The TAM family promotes the phagocytosis of apoptotic cells (Prasas et al., 2006) and stimulates the differentiation of natural killer cells (Park et al., 2009; Caraux et al., 2006). Axl activation is linked to several signal transduction pathways, including Akt, MAP kinases, NF-κB, STAT signal transduction pathways and others (Hafizi et al., 2006).

High Axl expression is observed in many human tumors (Berclaz et al., 2001; Craven et al., 1995; Shieh et al., 2005; Sun et al., 2004; Green et al., 2006; Ito et al., 1999) and it is associated with tumor stage and -progression in cancer patients (Gjerdrum et al., 2010; Sawabu et al., 2007; Green et al., 2006; Shieh et al., 2005; Sun et al., 2003).

It is object of the present invention to provide compounds and/or pharmaceutically acceptable salts thereof which can be used as pharmaceutically active agents, especially for treatment of cell proliferative diseases like cancer, as well as compositions comprising at least one of those compounds and/or pharmaceutically acceptable salts thereof as pharmaceutically active ingredients.

The compounds of the present invention are efficient inhibitors of TAM family RTKs and thus, are suitable for the treatment of disorders associated with, accompanied by and/or caused by TAM family RTKs hyperfunction, and thereby having an effect on cell survival, proliferation, autophagy, vascular smooth muscle homeostasis, migration, adhesion, angiogenesis, platelet aggregation, thrombus stabilization, erythropoiesis, oligodendrocyte cell survival, osteoclast function, innate immunity, inflammation, phagocytosis of apoptotic cells and/or natural killer cell differentiation.

The invention provides efficient inhibitors of Axl receptor tyrosine kinase which are suitable for the treatment of hyperproliferative disorders associated with, accompanied by and/or caused by Axl hyperfunction, particularly Axl receptor tyrosine kinase induced hyperproliferative disorders. The compounds of the invention are capable of inhibiting cell proliferation and thus, are suitable for the treatment and/or prevention of Axl receptor tyrosine kinase induced hyperproliferative disorders, particularly selected from the group comprising cancer and primary tumor metastases. In a preferred embodiment of the invention, the Axl receptor tyrosine kinase induced disorders are associated with Axl receptor tyrosine kinase receptor overexpression and/or hyperactivity, e.g. an increased degree of autophosphorylation compared to normal tissue. The disorders may be selected from breast cancer, colon cancer, prostate cancer, lung cancer, gastric cancer, ovarian cancer, endometrial cancer, renal cancer, hepatocellular cancer, thyroid cancer, uterine cancer, esophagus cancer, squamous cell cancer, leukemia, osteosarcoma, melanoma, glioblastoma and neuroblastoma. In an especially preferred embodiment, the disorders are selected from breast cancer, glioblastoma, renal cancer, non-small cell lung cancer (NSCLC), and melanoma. The compounds are also suitable for the prevention and/or treatment of other hyperproliferative disorders, particulary benign hyperproliferative disorders such as benign prostate hyperplasia.

Examples for disorders associated with, accompanied by and/or caused by Axl hyperfunction are acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, bronchial tumors, burkitt lymphoma, carcinoid tumor, gastrointestinal cancer, central nervous system (CNS) lymphoma, cervical cancer, chordoma, chronic lymphocytic leukemia, chronic myelogenous leukemia, chronic myeloproliferative disorders, colon cancer, colorectal cancer, craniopharyngioma, cutaneous t-cell lymphoma, mycosis fungoides, sézary syndrome, endometrial cancer, ependymoblastoma, ependymoma, esophageal cancer, esthesioneuroblastoma, ewing sarcoma family of tumors, extracranial germ cell tumor, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), gastrointestinal stromal cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, renal cell cancer, kidney cancer, langerhans cell histiocytosis, laryngeal cancer, acute lymphoblastic leukemia, acute myeloid leukemia, chronic lymphocytic leukemia, chronic myelogenous leukemia, leukemia, lip and oral cavity cancer, liver cancer, lung cancer, non-small cell lung cancer, small cell lung cancer, aids-related lymphoma, burkitt lymphoma, (cutaneous t-cell lymphoma, hodgkin lymphoma, non-hodgkin lymphoma, primary central nervous system lymphoma, macroglobulinemia, malignant fibrous histiocytoma of bone and osteosarcoma, medulloblastoma, medulloepithelioma, melanoma, melanoma intraocular (eye), merkel cell carcinoma, mesothelioma, metastatic squamous neck cancer with occult primary, mouth cancer, multiple endocrine neoplasia syndromes, multiple myeloma/plasma cell neoplasm, myelodysplastic syndromes, myelodysplastic/myeloproliferative neoplasms, myelogenous leukemia, myeloid leukemia, myeloma (multiple), myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineoblastoma and supratentorial primitive neuroectodermal tumors, pituitary tumor, plasma cell neoplasm/multiple myeloma, pleuropulmonary blastoma, pregnancy and breast cancer, prostate cancer, rectal cancer, renal cell (kidney) cancer, transitional cell cancer, respiratory tract cancer, retinoblastoma, rhabdomyosarcoma, salivary gland cancer, sarcoma, ewing sarcoma, kaposi sarcoma, uterine sarcoma, nonmelanoma skin cancer, melanoma skin cancer, skin carcinoma, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, testicular cancer, throat cancer, thymoma and thymic carcinoma, thyroid cancer, transitional cell cancer of the renal pelvis and ureter, trophoblastic tumor, gestational cancer, ureter and renal pelvis cancer, transitional cell cancer, urethral cancer, uterine cancer, endometrial cancer, uterine sarcoma, vaginal cancer, vulvar cancer, Waldenström macroglobulinemia and Wilms tumor.

The preferred Axl receptor tyrosine kinase induced disorders are selected from adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary origin), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear tumors, nose tumors and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors of the gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

The compounds of the present invention are efficient inhibitors of TAM family RTKs. The inventive compounds are suitable for the use as a pharmaceutically active agent. The inventive compounds are suitable for the treatment of disorders associated with, accompanied by and/or caused by TAM family RTKs hyperfunction. The inventive compounds are suitable for the treatment and/or prevention of Axl receptor tyrosine induced disorders.

The inventive compounds are used in the manufacture of a medicament or of a pharmaceutical composition for the treatment of disorders associated with, accompanied by and/or caused by TAM family RTKs hyperfunction. The inventive compounds are further used in the manufacture of a medicament or of a pharmaceutical composition for the treatment and/or prevention of Axl receptor tyrosine induced disorders.

The Axl receptor tyrosine kinase induced disorders are disorders caused by, associated with and/or accomplied by Axl kinase hyperfunction. The Axl receptor tyrosine kinase induced disorders are selected from a group comprising hyperproliferative disorders. The Axl receptor tyrosine kinase induced disorders are selected from the group comprising cancer and primary tumor metastases.

Further advantageous features, aspects and details of the invention are evident from the dependent claims, the description, the examples and the drawings.

It has now surprisingly been discovered that 1-nitrogen-heterocyclic-2-carboxamides of the present invention exhibit particularly high levels of inhibition of the activity of the Axl kinase. The novel compounds according to the present invention are defined by the general formula (I):

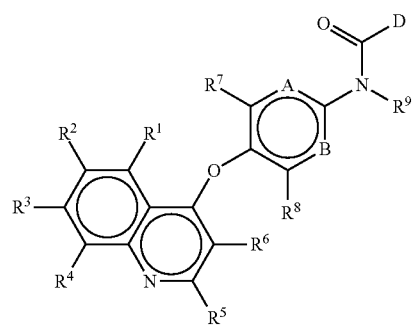

formula (I)

wherein
  A represents C—R$^{10}$, N;
  B represents C—R$^{11}$, N;
  D represents one of the following heterocycles:

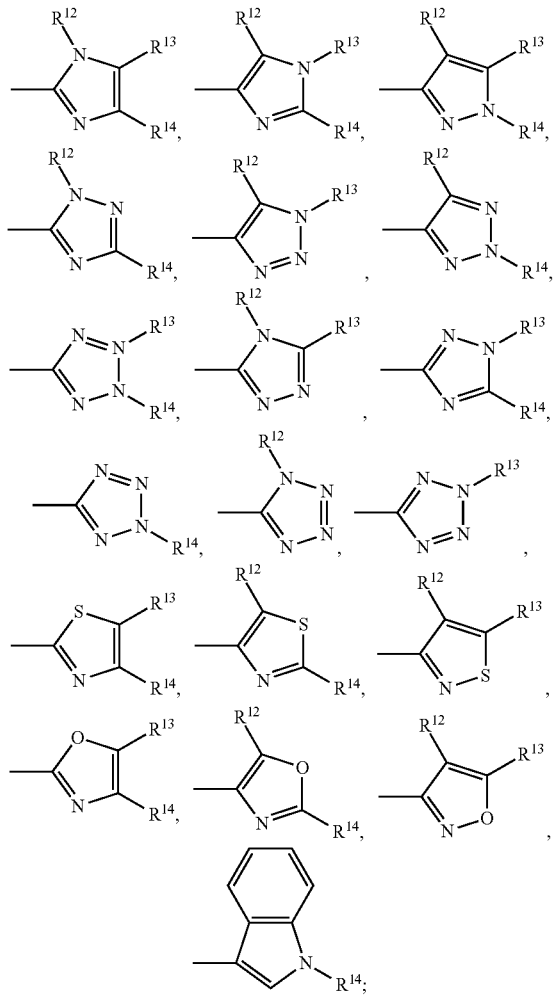

R$^1$, R$^4$, R$^{88}$, R$^{92}$, R$^{100}$ are selected independently of each other from —H, —F, —Cl, —Br, —I, —OH, —NH$_2$, —NHR$^{19}$, —NR$^{19}$R$^{20}$, —OCH$_3$, —OC$_2$H$_5$, —OC$_3$H$_7$, —OCH(CH$_3$)$_2$, —OC(CH$_3$)$_3$, —OC$_4$H$_9$, —NO$_2$, —CHO, —COCH$_3$, —COC$_2$H$_5$, —COC$_3$H$_7$, —O-cyclo-C$_3$H$_5$, —OCH$_2$-cyclo-C$_3$H$_5$, —O—C$_2$H$_4$-cyclo-C$_3$H$_5$, —OPh, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—C$_2$H$_5$, —OOC—C$_3$H$_7$, —OOC—CH(CH$_3$)$_2$, —OOC—C(CH$_3$)$_3$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —OCF$_3$, —OC$_2$F$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, —CH$_2$-cyclo-C$_3$H$_5$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)$_2$—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH$_2$CH=CH—CH=CH—CH$_3$, —CH=CH—CH$_2$—CH=CH—CH$_3$, —CH=CH—CH=CH—C$_2$H$_5$, —CH$_2$—CH=CH—C(CH$_3$)=CH$_2$, —CH$_2$—C(CH$_3$)=CH—CH=CH$_2$, —CH$_2$—C(CH$_3$)=CH—CH=CH$_2$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH$_2$—CH=CH—C=C—CH$_3$, —CH=CH—CH=C(CH$_3$)$_2$, —CH=CH—C(CH$_3$)=CH—CH$_3$, —CH=C(CH$_3$)—CH=CH—CH$_3$, —C(CH$_3$)=CH—CH=CH—CH$_3$, —C(CH$_3$)=CH—

CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, C≡CH, —CH$_2$—C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C$_2$H$_4$—CH(CH$_3$)—C≡CH, —CH$_2$—CH(CH$_3$)—CH$_2$—C≡CH, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —C≡C—C(CH$_3$)$_3$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$, —R$^{21}$, —R$^{35}$, —R$^{38}$;

R$^2$ and R$^3$ are selected independently of each other from —R$^{88}$, —R$^{37}$, —R$^{38}$, —R$^{54}$, —O—R$^{54}$, —R$^{55}$, —O—R$^{55}$, R$^{56}$, —O—R$^{56}$, —R$^{57}$, —O—R$^{57}$, wherein the C$_{1-6}$alkyl, C$_{2-6}$alkenyl, C$_{2-8}$alkynyl or C$_{1-6}$alkoxy groups represented by R$^{88}$ are optionally mono- or polysubstituted by —OH, —F, —Cl, —Br, —I, —O—R$^{71}$, —R$^{72}$, —R$^{138}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$; or R$^2$ and/or R$^3$ are selected independently of each other from —O—R$^{18}$, —O—CR$^{73}$R$^{74}$—R$^{18}$, —O—CR$^{73}$R$^{74}$—CR$^{75}$R$^{76}$—R$^{18}$, —O—CR$^{73}$R$^{74}$—CR$^{75}$R$^{76}$—CR$^{77}$R$^{78}$—R$^{18}$, —O—CR$^{73}$R$^{74}$—CR$^{75}$R$^{76}$—CR$^{77}$R$^{78}$—CR$^{79}$R$^{80}$—R$^{18}$, —O—CR$^{73}$R$^{74}$—CR$^{75}$R$^{76}$—CR$^{77}$R$^{78}$—CR$^{79}$R$^{80}$—CR$^{81}$R$^{82}$—R$^{18}$, —O—CR$^{73}$R$^{74}$—CR$^{75}$R$^{76}$—CR$^{77}$R$^{78}$—CR$^{79}$R$^{80}$—CR$^{81}$R$^{82}$—CR$^{83}$R$^{84}$—R$^{18}$;

R$^{73}$-R$^{84}$ independently of each other represent —H, —OH, —F, —Cl, —Br, —I, —R$^{85}$;

R$^{18}$ represents —H, —OH, —F, —Cl, —Br, —I, —O—R$^{86}$, —R$^{87}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$R$^{16}$R$^{17}$, —NR$^{16}$R$^{17}$; m=0, 1, 2;

R$^5$ and R$^6$, which may be the same or different, represent —H, —OH, —F, —Cl, —Br, —I, —CN, —NO$_2$, —CH$_3$, —C$_2$H$_5$, —C$_3$H$_7$, —CH(CH$_3$)$_2$, cyclo-C$_3$H$_5$, —CH$_2$-cyclo-C$_3$H$_5$, —C$_4$H$_9$, —CH$_2$—CH(CH$_3$)$_2$, —CH(CH$_3$)—C$_2$H$_5$, —C(CH$_3$)$_3$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —C(CH$_3$)=CH—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, CH$_2$—CH=CH—CH=CH—CH$_3$, —CH=CH—CH$_2$—CH=CH—CH$_3$, —CH=CH—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH$_2$—C(CH$_3$)=CH$_2$, —CH=C(CH$_3$)—CH$_2$—CH=CH$_2$, —C(CH$_3$)=CH—CH$_2$—CH=CH$_2$, —CH=CH—CH=C(CH$_3$)$_2$, —CH=CH—C(CH$_3$)=CH—CH$_3$, —CH=C(CH$_3$)—CH=CH—CH$_3$, —C(CH$_3$)=CH—CH=CH—CH$_3$, —C(CH$_3$)=CH$_2$, —CH=CH—C(CH$_3$)=CH$_2$, —C(CH$_3$)=CH—C(CH$_3$)=CH$_2$, —C(CH$_3$)=C(CH$_3$)—CH=CH$_2$, —C(CH$_3$)=CH—CH=CH$_2$, —CH=CH—CH=CH—

CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₆—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, CH₃, —CH(C—CH)₂, —C₂H₄—C≡C—C≡CH, —CH₂—C≡C—CH₂—C≡CH, —C≡C—C₂H₄—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —O—R⁸⁹;

R⁷, R⁸, R¹⁰ and R¹¹, which may be the same or different, represent —H, —F, —Cl, —Br, —I, —CN, —NO₂, —CH₃, —C₂H₅, —C₃H₇, —CH(CH₃)₂, cyclo-C₃H₅, —CH₂-cyclo-C₃H₅, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH₂, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH(CH₃)—CH₂—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH=C(CH₃)₂, —CH(CH₃)—C(CH₃)=CH—CH₃, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH=CH—CH=CH—C₂H₅, CH₂CH=CH—C(CH₃)=CH₂, —CH₂—CH=C(CH₃)—CH=CH₂, —CH₂—C(CH₃)=CH—CH=CH₂, —CH(CH₃)—CH=CH—CH=CH₂, —CH=CH—CH₂—C(CH₃)=CH₂, —CH=CH—CH=C(CH₃)—CH₂, —CH=C(CH₃)—CH₂—CH=CH₂, —C(CH₃)=CH—CH₂—CH=CH₂, —CH=CH—CH=C(CH₃)₂, —CH=CH—C(CH₃)=CH—CH₃, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —O—R⁹⁰, —O—R¹¹⁰, —O—R¹¹¹, wherein the $C_{1-6}$alkyl, $C_{2-6}$alkenyl, $C_{2-6}$alkynyl and $C_{1-6}$alkoxy groups are optionally mono- or polysubstituted by —OH, —F, —Cl, —Br, —I;

$R^9$ represents —H, —$R^{91}$;

$R^{12}$ represent —$R^{92}$, —CN, —$R^{93}$, —$R^{94}$, —$OR^{94}$, phenyl, naphtalinyl, wherein the $C_{1-6}$alkyl, $C_{2-6}$alkenyl, $C_{2-6}$alkynyl or $C_{1-6}$alkoxy groups represented by $R^{92}$ are optionally mono- or polysubstituted by —OH, —F, —Cl, —Br, —I, —O—$R^{95}$, —$R^{96}$, —$R^{137}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$; and wherein the saturated or unsaturated three- to twelve-membered carbocyclic or heterocyclic ring systems represented by $R^{137}$ are optionally mono- or polysubstituted by —OH, —F, —Cl, —Br, —I, —$R^{96}$;

$R^{13}$ is selected from —H, —OH, —F, —Cl, —Br, —I, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH$_3$)—CH(CH$_3$)$_2$, (CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)$_2$—CH=CH$_2$, —C(CH$_3$)=C(CH$_3$)$_2$, —C(CH$_3$)=CH—CH$_2$, —C(CH$_3$)=CH—CH$_2$, —CH=C(CH$_3$)—CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH$_2$—C(CH$_3$)=CH—CH$_3$, —CH(CH$_3$)—CH=C(CH$_3$)$_2$, —C(CH$_3$)$_2$—CH=CH—CH$_3$, —CH(CH$_3$)—
C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, CH$_2$—CH=CH—CH=CH—CH$_3$, —CH=CH—CH$_2$—CH=CH—CH$_3$, —CH=CH—CH=CH—C$_2$H$_5$, CH$_2$CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH=CH—CH=C(CH$_3$)$_2$, —CH=CH—C(CH$_3$)=CH—CH$_3$, —CH=C(CH$_3$)—CH=CH—CH$_3$, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C=CH, —C=C—CH$_3$, —CH$_2$—C=CH, —C$_2$H$_4$—C=CH, —CH$_2$—C=C—CH$_3$, —C=C—C$_2$H$_5$, —C$_3$H$_6$—C=CH, —C$_2$H$_4$—C=C—CH$_3$, —CH$_2$—C=C—C$_2$H$_5$, —C=C—C$_3$H$_7$, —CH(CH$_3$)—C=CH, —CH$_2$—CH(CH$_3$)—C=CH, —CH(CH$_3$)—CH$_2$—C=CH, —CH(CH$_3$)—C=C—CH$_3$, —C$_4$H$_8$—C=CH, —C$_3$H$_6$—C=C—CH$_3$, —C$_2$H$_4$—C=C—C$_2$H$_5$, —CH$_2$—C=C—C$_3$H$_7$, —C=C—C$_4$H$_9$, —C$_2$H$_4$—CH(CH$_3$)—C=CH, —CH$_2$—CH(CH$_3$)—CH$_2$—C=CH, —CH(CH$_3$)—C$_2$H$_4$—C=CH, —CH$_2$—CH(CH$_3$)—C=C—CH$_3$, —CH(CH$_3$)—CH$_2$—C=C—CH$_3$, —CH(CH$_3$)—C=C—C$_2$H$_5$, —CH$_2$—C=C—CH(CH$_3$)$_2$, —C=C—CH(CH$_3$)—C$_2$H$_5$, —C=C—CH$_2$—CH(CH$_3$)$_2$, —C=C—C(CH$_3$)$_3$, —CH(C$_2$H$_5$)—C=C—CH$_3$, —C(CH$_3$)$_2$—C=C—CH$_3$, —CH(C$_2$H$_5$)—CH$_2$—C=CH, —CH$_2$—CH(C$_2$H$_5$)—C=CH, —C(CH$_3$)$_2$—CH$_2$—C=CH, —CH$_2$—C(CH$_3$)$_2$—C=CH, —CH(CH$_3$)—CH(CH$_3$)—C=CH, —CH(C$_3$H$_7$)—C=CH, —C(CH$_3$)(C$_2$H$_5$)—C=CH, —C=C—C=CH, —CH$_2$—C=C—C=CH, —C=C—C=C—CH$_3$, —CH(C=CH)$_2$, —C$_2$H$_4$—C=C—C=CH, —CH$_2$—C=C—CH$_2$—C=CH, —C=C—C=C—C$_2$H$_5$, —CH$_2$—C=C—C=C—CH$_3$, —C=C—C=C—C$_2$H$_5$, —C=C—CH(CH$_3$)—C=CH, —CH(CH$_3$)—C=C—C=CH, —CH(C=CH)—CH$_2$—C=CH, —CH$_2$—CH(C=CH)$_2$, —CH(C=CH)—C=C—CH$_3$, cyclo-C$_3$H$_5$, -Ph, —O—R$^{97}$, —R$^{98}$, —R$^{99}$,

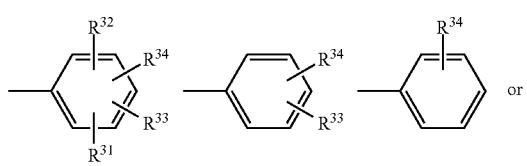 or

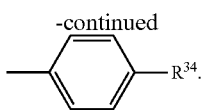

when $R^{12}$ and $R^{13}$ represent alkenylene groups, $R^{12}$ and $R^{13}$ may combine to form a condensed aromatic ring together with the atoms of residue D to which $R^{12}$ and $R^{13}$ are attached in order to form a bicyclic group with residue D;

$R^{14}$ represents (i) —H, —OH, —F, —Cl, —Br, —I, —NO$_2$, —CN, NH$_2$;

(ii) —$R^{100}$, —$R^{101}$, —$R^{102}$, —O—$R^{102}$, —$R^{103}$, —O—$R^{103}$, —$R^{136}$, wherein the C$_{1-6}$alkyl, C$_{2-6}$alkenyl, C$_{2-6}$alkynyl and C$_{1-6}$alkoxy groups represented by $R^{10o}$ and the ether groups represented by —$R^{136}$ are optionally mono- or polysubstituted by —OH, —F, —Cl, —Br, —I, —O—$R^{104}$, —$R^{105}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16\text{-}17}$, —SO$_2$—NR$^{16}$R$^{17}$, —SO$_m$—R$^{16}$R$^{17}$, —CR$^{16}$R$^{17}$H, —NR$^{16}$R$^{17}$;

(iii) —$R^{113}$, wherein the saturated or unsaturated three- to twelve-membered carbocyclic or heterocyclic ring system represented by —$R^{113}$ is optionally mono- or polysubstituted by —F, —Cl, —Br, —I, —OH, —NO$_2$, —NH$_2$, —C$_2$H$_4$—N(CH$_3$)$_2$, —CN, —CF$_3$, =O, —$R^{16}$, —$R^{17}$, —$R^{106}$, —O—$R^{107}$, —$R^{108}$, —$R^{109}$, a saturated or unsaturated three- to eight-membered carbocyclic or heterocyclic group, wherein the C$_{1-6}$alkyl groups represented by $R^{106}$, the C$_{1-6}$alkenyl groups represented by $R^{108}$, the C$_{2-6}$alkynyl groups represented by $R^{109}$, the C$_{1-6}$alkoxy groups represented by —O—$R^{107}$ are optionally mono- or polysubstituted by —OH, —F, —Cl, —Br, —I, —O—$R^{104}$, —$R^{105}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$;

$R^{16}$ and $R^{17}$, which may be the same or different, represent —H, —$R^{112}$, optionally substituted by —OH, —F, —Cl, —Br, —I, —NH$_2$, —CN;

or alternatively $R^{16}$ and $R^{17}$ may combine with the nitrogen atom attached thereto to form a saturated or unsaturated five to eight-membered heterocyclic group selected from —$R^{114}$; which is optionally mono- or poysubstituted by —OH, =O, —$R^{116}$, —$R^{117}$, —$R^{118}$, —O—$R^{119}$, —$R^{120}$, or a saturated or unsaturated three- to twelve-membered carbocyclic or heterocyclic ring system selected from —$R^{115}$; wherein the C$_{1-6}$alkyl group represented by $R^{116}$, C$_{2-6}$alkenyl group represented by $R^{117}$, C$_{2-6}$alkynyl group represented by $R^{118}$ are optionally substituted by —OH, —$R^{122}$, or a saturated or unsaturated three- to twelve-membered carbocylic or heterocyclicring system selected from —$R^{121}$;

amino group in which one or two hydrogen atoms on the amino group are optionally substituted by —$R^{123}$, or a saturated or unsaturated three- to twelve-membered carbocyclic or heterocyclic ring system selected from —$R^{124}$, and the C$_{1-6}$alkyl group represented by $R^{123}$ is optionally substituted by —OH, —$R^{125}$, or a saturated or unsaturated three- to twelve-membered carbocyclic or heterocyclic ring system selected from —$R^{126}$;

or a saturated or unsaturated three- to twelve-membered carbocyclic ring system selected from —$R^{127}$; optionally substituted by —OH, =O, —$R^{128}$, —$R^{129}$, —$R^{130}$, —O—$R^{131}$, —$R^{132}$, or a saturated or unsaturated three- to twelve-membered carbocyclic or heterocyclic ring system selected from —$R^{133}$, wherein the C$_{1-6}$alkyl group represented by $R^{128}$, C$_{2-6}$alkenyl group represented by $R^{129}$ and C$_{2-6}$alkynyl group represented by $R^{130}$ are optionally substituted by —OH, —$R^{134}$, or a saturated or unsaturated three- to twelve-membered carbocyclic or heterocyclic ring system selected from —$R^{135}$;

when the carbocyclic or heterocyclic group is substituted by C$_{1-6}$alkyl groups, two alkyl groups may combine together to form an alkylene chain; and the carbocyclic or heterocyclic group may be condensed with another saturated or unsaturated five to seven-membered carbocyclic or heterocyclic group to form a bicyclic group;

$R^{19}$, $R^{20}$, $R^{71}$, $R^{85}$, $R^{86}$, $R^{89}$, $R^{90}$, $R^{91}$, $R^{95}$, $R^{97}$, $R^{104}$, $R^{106}$, $R^{107}$, $R^{110}$, $R^{111}$, $R^{112}$, $R^{116}$, $R^{119}$, $R^{122}$, $R^{123}$, $R^{125}$, $R^{128}$, $R^{131}$ and $R^{134}$ independently of each other represent —CH$_3$, —H, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CF$_3$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_6$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, -Ph, —CH$_2$-Ph;

$R^{21}$ and $R^{98}$ represent independently of each other —CR$^{22}$R$^{23}$R$^{24}$, —CR$^{23}$R$^{24}$—CR$^{25}$R$^{26}$R$^{22}$, —CR$^{23}$R$^{23}$R$^{24}$—CR$^{25}$R$^{26}$—CR$^{27}$R$^{28}$R$^{22}$, —CR$^{23}$R$^{24}$—CR$^{25}$R$^{26}$—CR$^{27}$R$^{28}$—CR$^{29}$R$^{30}$R$^{22}$, —CR$^{23}$R$^{24}$—CR$^{25}$R$^{26}$—CR$^{27}$R$^{28}$—CR$^{29}$R$^{30}$—CR$^{31}$R$^{32}$R$^{22}$, —CR$^{23}$R$^{24}$—CR$^{25}$R$^{26}$—CR$^{27}$R$^{28}$—CR$^{29}$R$^{30}$—CR$^{31}$R$^{32}$—CR$^{33}$R$^{34}$R$^{22}$;

$R^{22}$-$R^{34}$ independently of each other represent —H, —F, —Cl, —Br, —I, —CH$_3$, —CF$_3$, —OCH$_3$, —OCF$_3$, —C$_3$H$_7$;

$R^{35}$ and $R^{99}$ represent independently of each other —O—CR$^{22}$R$^{23}$R$^{24}$, —O—CR$^{23}$R$^{24}$—CR$^{25}$R$^{26}$R$^{22}$, —O—CR$^{23}$R$^{24}$—CR$^{25}$R$^{26}$—CR$^{27}$R$^{28}$R$^{22}$, —O—R$^{23}$R$^{24}$—CR$^{25}$R$^{26}$—CR$^{27}$R$^{28}$—CR$^{29}$R$^{30}$R$^{22}$, —O—CR$^{23}$R$^{24}$—CR$^{25}$R$^{26}$—CR$^{27}$R$^{28}$—CR$^{29}$R$^{30}$—CR$^{31}$R$^{32}$R$^{22}$, —O—CR$^{23}$R$^{24}$—CR$^{25}$R$^{26}$—CR$^{27}$R$^{28}$—CR$^{29}$R$^{30}$—CR$^{31}$R$^{32}$—CR$^{33}$R$^{34}$R$^{22}$;

$R^{36}$, $R^{72}$, $R^{87}$, $R^{96}$, $R^{105}$, $R^{120}$, $R^{132}$ and $R^{136}$ represent independently of each other —CR$^{23}$R$^{24}$—XH, —X—CR$^{22}$R$^{23}$R$^{24}$—X—CR$^{23}$R$^{24}$—CR$^{25}$R$^{26}$R$^{22}$, —CR$^{23}$R$^{24}$—X—CR$^{25}$R$^{26}$R$^{22}$, —CR$^{23}$R$^{24}$—CR$^{25}$R$^{26}$—XH, —X—CR$^{23}$R$^{24}$—CR$^{25}$R$^{26}$—CR$^{27}$R$^{28}$R$^{22}$, —CR$^{23}$R$^{24}$—X—CR$^{25}$R$^{26}$—R$^{27}$R$^{28}$R$^{22}$, —CR$^{23}$R$^{24}$—CR$^{25}$R$^{26}$—X—CR$^{27}$R$^{28}$R$^{22}$, —CR$^{23}$R$^{24}$—CR$^{25}$R$^{26}$—CR$^{27}$R$^{28}$—XH, —X—CR$^{23}$R$^{24}$—CR$^{25}$R$^{26}$—CR$^{27}$R$^{28}$—CR$^{29}$R$^{30}$R$^{22}$, —CR$^{23}$R$^{24}$—X—CR$^{25}$R$^{26}$—CR$^{27}$R$^{28}$—CR$^{29}$R$^{30}$R$^{22}$, —CR$^{23}$R$^{24}$—CR$^{25}$R$^{26}$—X—CR$^{27}$R$^{28}$—CR$^{29}$R$^{30}$R$^{22}$, —CR$^{23}$R$^{24}$—CR$^{25}$R$^{26}$—CR$^{27}$R$^{28}$—X—CR$^{29}$R$^{30}$R$^{22}$, —CR$^{23}$R$^{24}$—CR$^{25}$R$^{26}$—CR$^{27}$R$^{28}$—CR$^{29}$R$^{30}$—XH, —X—CR$^{23}$R$^{24}$—CR$^{25}$R$^{26}$—CR$^{27}$R$^{28}$—CR$^{29}$R$^{30}$—CR$^{31}$R$^{32}$R$^{22}$, —CR$^{23}$R$^{24}$—X—CR$^{25}$R$^{26}$—CR$^{27}$R$^{28}$—CR$^{29}$R$^{30}$—CR$^{31}$R$^{32}$R$^{22}$, —CR$^{23}$R$^{24}$—CR$^{25}$R$^{26}$—X—CR$^{27}$R$^{28}$—CR$^{29}$R$^{30}$—CR$^{31}$R$^{32}$R$^{22}$, —CR$^{23}$R$^{24}$—CR$^{25}$R$^{26}$—CR$^{27}$R$^{28}$—X—CR$^{29}$R$^{30}$—CR$^{31}$R$^{32}$R$^{22}$, —CR$^{23}$R$^{24}$—CR$^{25}$R$^{26}$—CR$^{27}$R$^{28}$—CR$^{29}$R$^{30}$—X—CR$^{31}$R$^{32}$R$^{22}$, —CR$^{27}$R$^{28}$—COR$^{29}$R$^{30}$—CR$^{31}$R$^{32}$—XH, —X—CR$^{23}$R$^{24}$—CR$^{25}$R$^{26}$—CR$^{27}$R$^{28}$—CR$^{29}$R$^{30}$—CR$^{31}$R$^{32}$—CR$^{33}$R$^{34}$R$^{22}$, —CR$^{23}$R$^{24}$—X—CR$^{25}$R$^{26}$—CR$^{27}$R$^{28}$—CR$^{29}$R$^{30}$—CR$^{31}$R$^{32}$—CR$^{33}$R$^{34}$R$^{22}$, —CR$^{23}$R$^{24}$—CR$^{25}$R$^{26}$—X—CR$^{27}$R$^{28}$—CR$^{29}$R$^{30}$—CR$^{31}$R$^{32}$—CR$^{33}$R$^{34}$R$^{22}$, —CR²³R²⁴—CR²⁵R²⁶—CR²⁷R²⁸—X—CR²⁹R³⁰—CR³¹R³²—CR³³R³⁴R²², —CR²³R²⁴—CR²⁵R²⁶—CR²⁷R²⁸—CR²⁹R³⁰—X—CR³¹R³²—CR³³R³⁴R²², —CR²³R²⁴—CR²⁵R²⁶—CR²⁷R²⁸—CR²⁹R³⁰—CR³¹R³²—X—CR³³R³⁴R²², —CR²³R²⁴—CR²⁵R²⁶—CR²⁷R²⁸—CR²⁹R³⁰—OR³¹R³²—CR³³R³⁴—XH;

X represents —O—, —CO—, —O—CO—

$R^{37}, R^{38}, R^{93}$ and $R^{101}$ represent independently of each other —CR⁴⁰R⁴¹—YH, —Y—CR³⁹R⁴⁰R⁴¹, —Y—CR⁴⁰R⁴¹—CR⁴²R⁴³R³⁹, —CR⁴⁰R⁴¹—Y—CR⁴²R⁴³R³⁹, —CR⁴⁰R⁴¹—CR⁴²R⁴³—YH, —Y—CR⁴⁰R⁴¹—CR⁴²R⁴³—CR⁴⁴R⁴⁵R³⁹, —CR⁴⁰R⁴¹—Y—CR⁴²R⁴³—CR⁴⁴R⁴⁵R³⁹, —CR⁴⁰R⁴¹—CR⁴²R⁴³—Y—CR⁴⁴R⁴⁵R³⁹, —CR⁴⁰R⁴¹—CR⁴²R⁴³—CR⁴⁴R⁴⁵—YH, —Y—CR⁴⁰R⁴¹—CR⁴²R⁴³—CR⁴⁴R⁴⁵—CR⁴⁶R⁴⁷R³⁹, —CR⁴⁰R⁴¹—Y—CR⁴²R⁴³—CR⁴⁴R⁴⁵—CR⁴⁶R⁴⁷R³⁹, —CR⁴⁰R⁴¹—CR⁴²R⁴³—Y—CR⁴⁴R⁴⁵—CR⁴⁶R⁴⁷R³⁹, —CR⁴⁰R⁴¹—CR⁴²R⁴³—CR⁴⁴R⁴⁵—Y—CR⁴⁶R⁴⁶R³⁹, —CR⁴⁰R⁴²—CR⁴²R⁴³—CR⁴⁴R⁴⁵—CR⁴⁶R⁴⁷—YH, —Y—CR⁴⁰R⁴¹CR⁴²R⁴³—CR⁴⁴R⁴⁵—CR⁴⁶R⁴⁷—CR⁴⁸R⁴⁹R³⁹, —CR⁴⁰R⁴¹—Y—CR⁴²R⁴³—CR⁴⁴R⁴⁵—CR⁴⁶R⁴⁷—CR⁴⁸R⁴⁹R³⁹, —CR⁴⁰R⁴¹—CR⁴²R⁴³—Y—CR⁴⁴R⁴⁵—CR⁴⁶R⁴⁷—CR⁴⁸R⁴⁹R³⁹, —CR⁴⁰R⁴¹—CR⁴²R⁴³—CR⁴⁴R⁴⁵—Y—CR⁴⁶R⁴⁷—COR⁴⁸R⁴⁹R³⁹, —CR⁴⁰R⁴¹—CR⁴²R⁴³—CR⁴⁴R⁴⁵—CR⁴⁶R⁴⁷—Y—CR⁴⁸R⁴⁹R³⁹, —CR⁴⁰R⁴¹—CR⁴²R⁴³—CR⁴⁴R⁴⁵—CR⁴⁶R⁴⁷—CR⁴⁸R⁴⁹—YH, —Y—CR⁴⁰R⁴¹—CR⁴²R⁴³—CR⁴⁴R⁴⁵—CR⁴⁶R⁴⁷—CR⁴⁸R⁴⁹—CR⁵⁰R⁵¹R³⁹, —CR⁴⁰R⁴¹—Y—CR⁴²R⁴³—CR⁴⁴R⁴⁵—CR⁴⁶R⁴⁷—CR⁴⁸R⁴⁹—CR⁵⁰R⁵¹R³⁹, —CR⁴⁰R⁴¹—CR⁴²R⁴³—Y—CR⁴⁴R⁴⁵—CR⁴⁶R⁴⁷—CR⁴⁸R⁴⁹—CR⁵⁰R⁵¹R³⁹, —CR⁴⁰R⁴¹—CR⁴²R⁴³—CR⁴⁴R⁴⁵—Y—CR⁴⁶R⁴⁷—CR⁴⁸R⁴⁹—CR⁵⁰R⁵¹R³⁹, —CR⁴⁰R⁴¹—CR⁴²R⁴³—CR⁴⁴R⁴⁵—CR⁴⁶R⁴⁷—Y—CR⁴⁸R⁴⁹—CR⁵⁰R⁵¹R³⁹, —CR⁴⁰R⁴¹—CR⁴²R⁴³—CR⁴⁴R⁴⁵—CR⁴⁶R⁴⁷—CR⁴⁸R⁴⁹—Y—CR⁵⁰R⁵¹R³⁹, —CR⁴⁰R⁴¹—CR⁴²R⁴³—CR⁴⁴R⁴⁵—CR⁴⁶R⁴⁷—CR⁴⁸R⁴⁹—CR⁵⁰R⁵¹—YH;

$R^{39}$—$R^{53}$ represent independently of each other —H, —CH₃, —C₂H₅, —C₃H₇;

Y represents —NR⁵²—CO—, —CO—NR¹³—;

$R^{54}, R^{55}$ and $R^{102}$ represent independently of each other

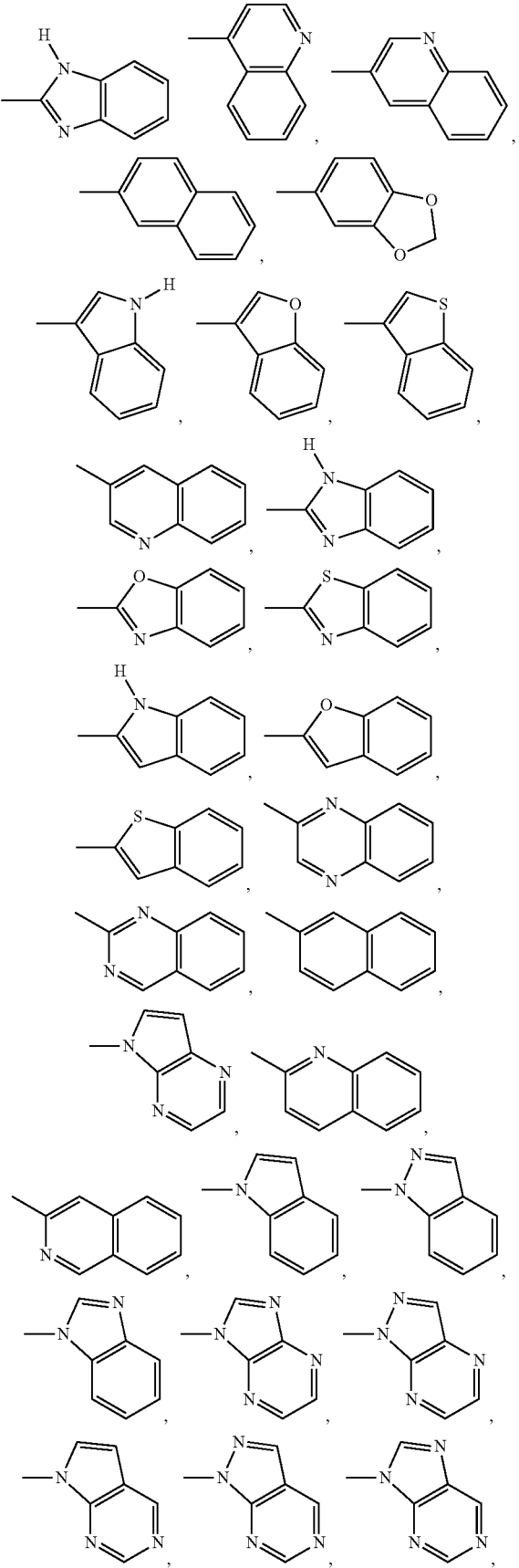

-continued

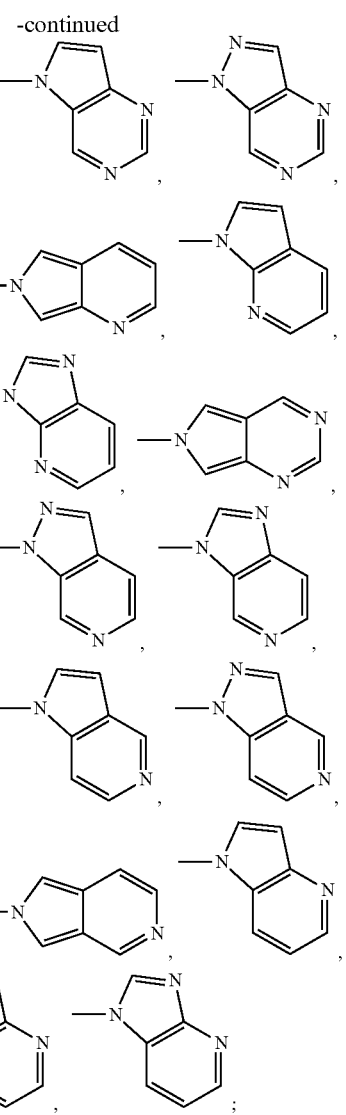

$R^{56}$, $R^{57}$, $R^{94}$ and $R^{103}$ represent independently of each other —$CR^{58}R^{16}R^{17}$, —$CR^{58}R^{59}R^{60}$—$CR^{16}R^{17}$—$CR^{61}R^{62}R^{58}$, —$CR^{59}R^{60}$—$CR^{61}R^{62}R^{58}$, —$CR^{59}R^{60}$—$CR^{16}R^{17}R^{58}$, —$CR^{16}R^{17}$—$CR^{61}R^{62}$—$CR^{63}R^{64}R^{58}$, —$CR^{59}R^{60}$—$CR^{61}R^{62}$—$CR^{63}R^{64}R^{58}$, —$CR^{59}R^{60}$—$CR^{16}R^{17}$—$CR^{63}R^{64}R^{58}$, —$CR^{59}R^{60}$—$CR^{61}R^{62}$—$CR^{16}R^{17}R^{58}$, —$CR^{16}R^{17}$—$CR^{61}R^{62}$—$CR^{63}R^{64}$—$CR^{65}R^{66}R^{58}$, —$CR^{59}R^{60}$—$CR^{61}R^{62}$—$CR^{63}R^{64}$—$CR^{65}R^{66}R^{58}$, —$CR^{59}R^{60}$—$CR^{16}R^{17}$—$CR^{63}R^{64}$—$CR^{66}R^{67}R^{58}$, —$CR^{59}R^{60}$—$CR^{61}R^{62}$—$CR^{16}R^{17}$—$CR^{65}R^{66}R^{58}$, —$CR^{59}R^{60}$—$CR^{61}R^{62}$—$CR^{63}R^{64}$—$CR^{16}R^{17}R^{58}$, —$CR^{16}R^{17}$—$CR^{61}R^{62}$—$CR^{63}R^{64}$—$CR^{65}R^{66}$—$CR^{67}R^{68}R^{58}$, —$CR^{59}R^{60}$—$CR^{61}R^{62}$—$CR^{63}R^{64}$—$CR^{65}R^{66}$—$CR^{67}R^{68}R^{58}$, —$CR^{59}R^{60}$—$CR^{16}R^{17}$—$CR^{63}R^{64}$—$CR^{65}R^{66}$—$CR^{67}R^{68}R^{58}$, —$CR^{59}R^{60}$—$CR^{61}R^{62}$—$CR^{16}R^{17}$—$CR^{65}R^{66}$—$CR^{67}R^{68}R^{69}$, —$CR^{59}R^{60}$—$CR^{61}R^{62}$—$CR^{63}R^{64}$—$CR^{16}R^{17}$—$CR^{67}R^{68}R^{58}$, —$CR^{59}R^{60}$—$CR^{61}R^{62}$—$CR^{63}R^{64}$—$CR^{65}R^{66}$—$CR^{16}R^{17}R^{58}$, —$CR^{16}R^{17}$—$CR^{61}R^{62}$—$CR^{63}R^{64}$—$CR^{65}R^{66}$—$CR^{67}R^{68}$—$CR^{69}R^{70}R^{58}$, —$CR^{59}R^{60}$—$CR^{16}R^{17}$—$CR^{63}R^{64}$—$CR^{65}R^{66}$—$CR^{67}R^{68}$—$CR^{69}R^{70}R^{58}$, —$CR^{59}R^{60}$—$CR^{61}R^{62}$—$CR^{16}R^{17}$—$CR^{65}R^{66}$—$CR^{67}R^{68}$—$CR^{69}R^{70}R^{58}$, —$CR^{59}R^{60}$—$CR^{61}R^{62}$—$CR^{63}R^{64}$—$CR^{16}R^{17}$—$CR^{67}R^{68}$—$CR^{69}R^{70}R^{58}$, —$CR^{59}R^{60}$—$CR^{61}R^{62}$—$CR^{63}R^{64}$—$CR^{65}R^{66}$—$CR^{16}R^{17}$—$CR^{69}R^{70}R^{58}$, —$CR^{59}R^{60}$—$CR^{61}R^{62}$—$CR^{63}R^{64}$—$CR^{65}R^{66}$—$CR^{67}R^{68}$—$CR^{16}R^{17}R^{58}$;

$R^{58}$-$R^{70}$ represent independently of each other —H, —$NH_2$, —OH, —F, —Cl, —Br, —I, —$R^{71}$, —O—$R^{71}$, —$R^{72}$, —O—$R^{95}$, —$R^{96}$, —O—$R^{104}$, —$R^{105}$, —COOH, —$COOCH_3$, —$COOC_2H_5$, —$COOC_3H_7$, —$COOCH(CH_3)_2$, —$COOC(CH_3)_3$, —(C=O)—$NR^{16}R^{17}$, —$SO_2$—$NR^{16}R^{17}$, —$SO_m$—$R^{16}R^{17}$, —$CR^{16}R^{17}H$, —$NR^{16}R^{17}$;

$R^{108}$, $R^{117}$ and $R^{129}$ represent independently of each other —$CH=CH_2$, —$CH_2$—$CH=CH_2$, —H, —$C(CH_3)=CH_2$, —$CH=CH$—$CH_3$, —$C_2H_4$—$CH=CH_2$, —$CH_2$—$CH=CH$—$CH_3$, —$CH=CH$—$C_2H_5$, —$CH_2$—$C(CH_3)=CH_2$, —$CH(CH_3)$—$CH=CH$, —$CH=C(CH_3)_2$, —$C(CH_3)=CH$—$CH_3$, —$CH=CH$—$CH=CH_2$, —$C_3H_6$—$CH=CH_2$, —$C_2H_4$—$CH=CH$—$CH_3$, —$CH_2$—$CH=CH$—$C_2H_5$, —$CH=CH$—$C_3H_7$, —$CH_2$—$CH=CH$—$CH=CH_2$, —$CH=CH$—$CH=CH$—$CH_3$, —$CH=CH$—$CH_2$—$CH=CH_2$, —$C(CH_3)=CH$—$CH=CH_2$, —$CH=C(CH_3)$—$CH=CH_2$, —$CH=CH$—$C(CH_3)=CH_2$, —$C_2H_4$—$C(CH_3)=CH_2$, —$CH_2$—$CH(CH_3)$—$CH=CH_2$, —$CH(CH_3)$—$CH_2$—$CH=CH_2$, —$CH_2$—$CH=C(CH_3)_2$, —$CH_2$—$C(CH_3)=CH$—$CH_3$, —$CH(CH_3)$—$CH=CH$—$CH_3$, —$CH=CH$—$CH(CH_3)_2$, —$CH=C(CH_3)$—$C_2H_5$, —$C(CH_3)=CH$—$C_2H_5$, —$C(CH_3)=C(CH_3)_2$, —$C(CH_3)_2$—$CH=CH_2$, —$CH(CH_3)$—$C(CH_3)=CH_2$, —$C(CH_3)=CH$—$CH=CH_2$, —$CH=C(CH_3)$—$CH=CH_2$, —$CH=CH$—$C(CH_3)=CH_2$, —$C_4H_8$—$CH=CH_2$, —$C_3H_6$—$CH=CH$—$CH_3$, —$C_2H_4$—$CH=CH$—$C_2H_5$, —$CH_2$—$CH=CH$—$C_3H_7$, —$CH=CH$—$C_4H_9$, —$C_3H_6$—$C(CH_3)=CH_2$, —$C_2H_4$—$CH(CH_3)$—$CH=CH_2$, —$CH_2$—$CH(CH_3)$—$CH_2$—$CH=CH_2$, —$CH(CH_3)$—$C_2H_4$—$CH=CH_2$, —$C_2H_4$—$CH=C(CH_3)_2$, —$C_2H_4$—$C(CH_3)=CH$—$CH_3$, —$CH_2$—$CH(CH_3)$—$CH=CH$—$CH_3$, —$CH(CH_3)$—$CH_2$—$CH=CH$—$CH_3$, —$CH_2$—$CH=CH$—$CH(CH_3)_2$, —$CH_2$—$CH=C(CH_3)$—$C_2H_5$, —$CH_2$—$C(CH_3)=CH$—$C_2H_5$, —$CH(CH_3)$—$CH=CH$—$C_2H_5$, —$CH=CH$—$CH_2$—$CH(CH_3)_2$, —$CH=CH$—$CH(CH_3)$—$C_2H_5$, —$CH=C(CH_3)$—$C_3H_7$, —$C(CH_3)=CH$—$C_3H_7$, —$CH_2$—$CH(CH_3)$—$C(CH_3)=CH_2$, —$CH(CH_3)$—$CH_2$—$C(CH_3)=CH_2$, —$CH(CH_3)$—$CH(CH_3)$—$CH=CH_2$, —$CH_2$—$C(CH_3)_2$—$CH=CH_2$, —$C(CH_3)_2$—$CH_2$—$CH=CH_2$, —$CH_2$—$C(CH_3)=C(CH_3)_2$, —$CH(CH_3)$—$CH=C(CH_3)_2$, —$C(CH_3)_2$—$CH=CH$—$CH_3$, —$CH(CH_3)$—$C(CH_3)=CH$—$CH_3$, —$C(CH_3)=CH$—$CH(CH_3)_2$, —$C(CH_3)=CH$—$CH(CH_3)_2$, —$C(CH_3)=C(CH_3)$—$C_2H_5$, —$CH=CH$—$C(CH_3)_3$, —$C(CH_3)_2$—$C(CH_3)=CH_2$, —$CH(C_2H_5)$—$C(CH_3)=CH_2$, —$C(CH_3)(C_2H_5)$—$CH=CH_2$, —$CH(CH_3)$—$C(C_2H_5)=CH_2$, —$CH_2$—$C(C_3H_7)=CH_2$, —$CH_2$—$C(C_2H_5)=CH$—$CH_3$, —$CH(C_2H_5)$—$CH=CH$—$CH_3$, —$C(C_4H_9)=CH_2$, —$C(C_3H_7)=CH$—$CH_3$, —$C(C_2H_5)=CH$—$C_2H_5$, —$C(C_2H_5)=C(CH_3)_2$, —$C[C(CH_3)_3]=CH_2$, —$C[CH(CH_3)(C_2H_5)]=CH_2$, —$C[CH_2$—$CH(CH_3)_2]=CH_2$, —$C_2H_4$—$CH=CH$—$CH=CH_2$, —$CH_2$—$CH=CH$—$CH_2$—$CH=CH_2$, —$CH=CH$—$C_2H_4$—$CH=CH_2$, —$CH_2$—$CH=CH$—$CH=CH$—$CH_3$, —$CH=CH$—$CH_2$—$CH=CH$—$CH_3$, —$CH=CH$—$CH=CH$—$C_2H_5$, —$CH_2$—$CH=CH$—$C(CH_3)=CH_2$, —$CH_2$—$CH=C(CH_3)$—$CH=CH_2$, —$CH_2$—$C(CH_3)=CH$—$CH=CH_2$, —$CH(CH_3)$—$CH=CH$—$CH=CH_2$, —$CH=CH$—$CH$—$C(CH_3)$—$CH_2$—$CH=CH_2$, —$C(CH_3)=CH$—$CH_2$—$CH=CH_2$, —$CH=CH$—$CH=CH$, —$CH=C(CH_3)_2$, —$CH=CH$—$C(CH_3)=CH$—$CH_3$, —$CH=C(CH_3)$—$CH=CH$—$CH_3$, —$C(CH_3)=CH$—$CH=CH$—

CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂;

R¹⁰⁹, R¹¹⁸ and R¹³⁰ represent independently of each other —H, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C—CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃;

R¹¹³, R¹¹⁵, R¹²¹, R¹²⁴, R¹²⁶, R¹²⁷, R¹³³, R¹³⁵, R¹³⁷ and R¹³⁸ independently of each other represent

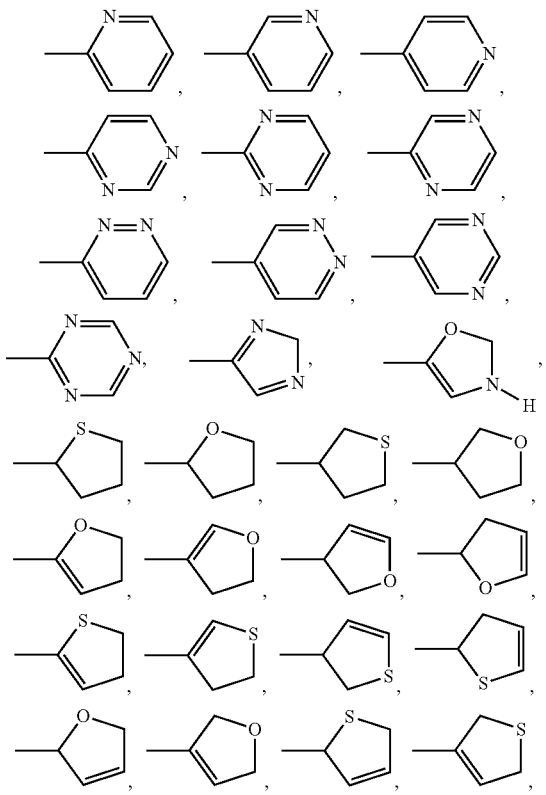

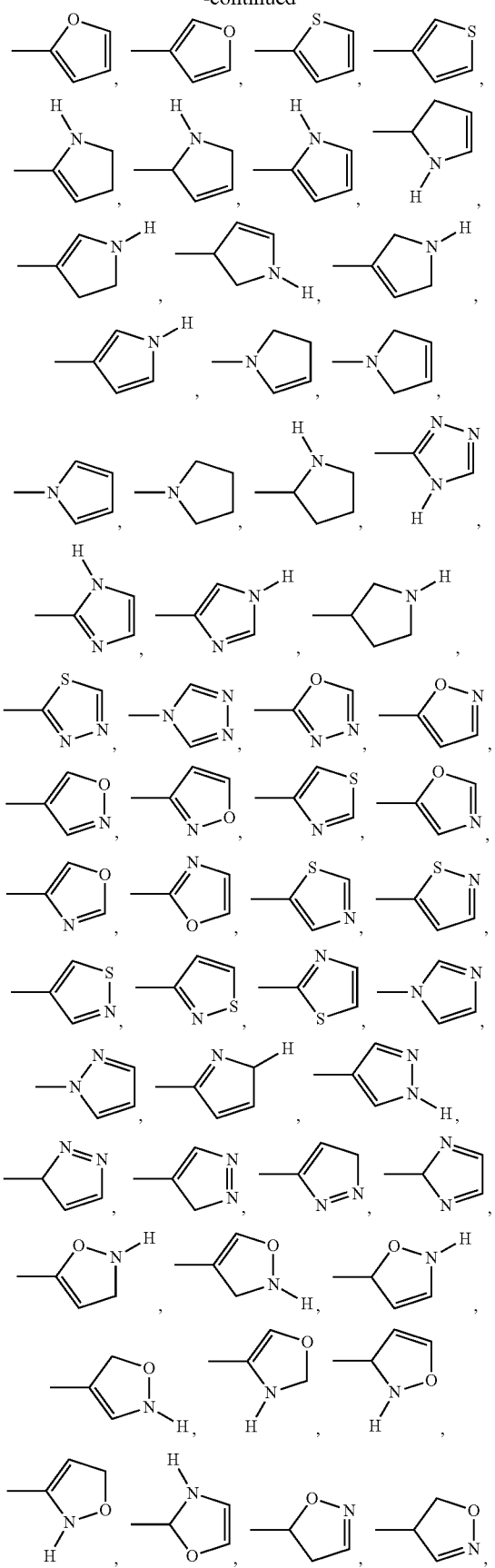

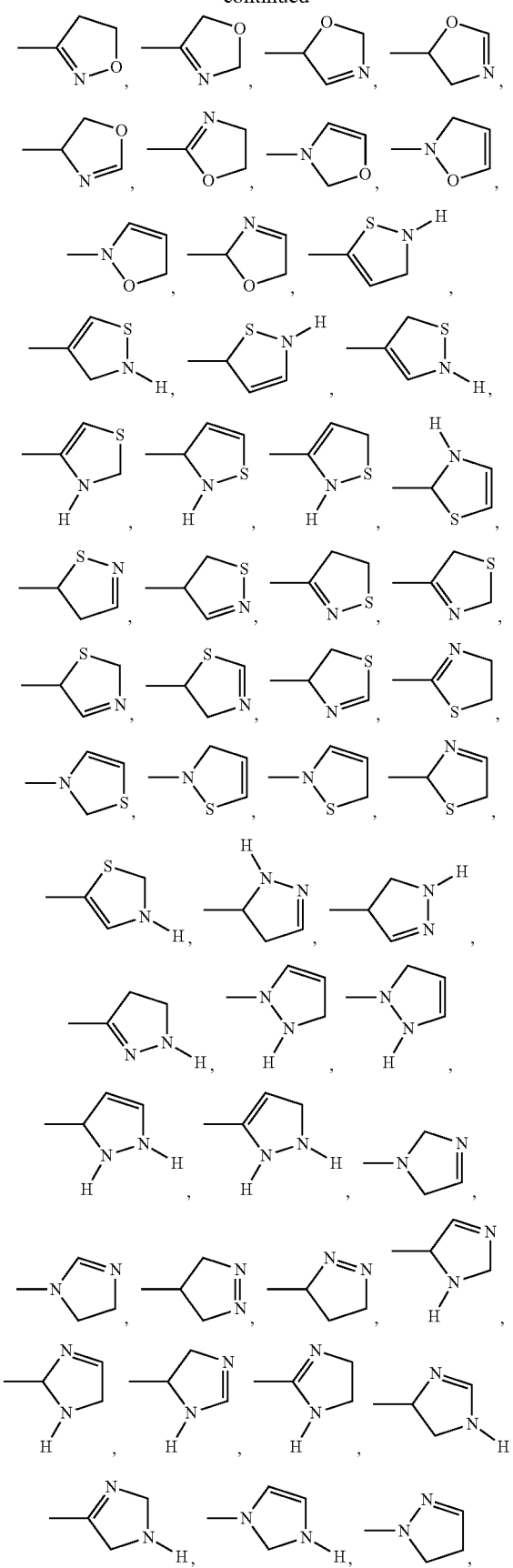
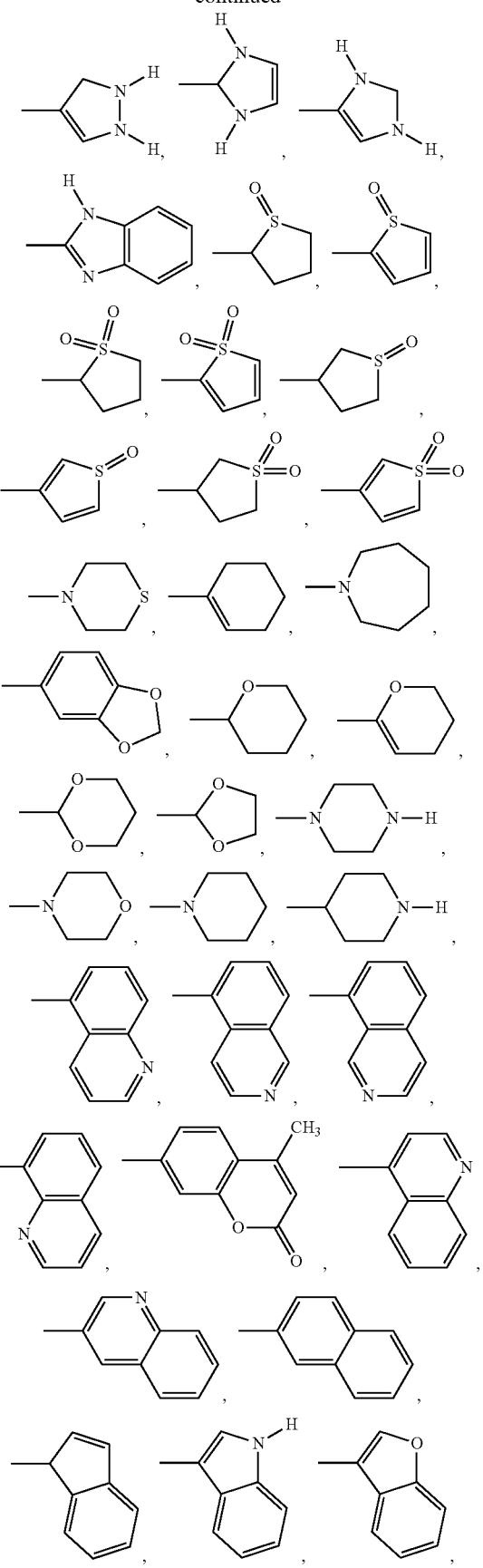

-continued
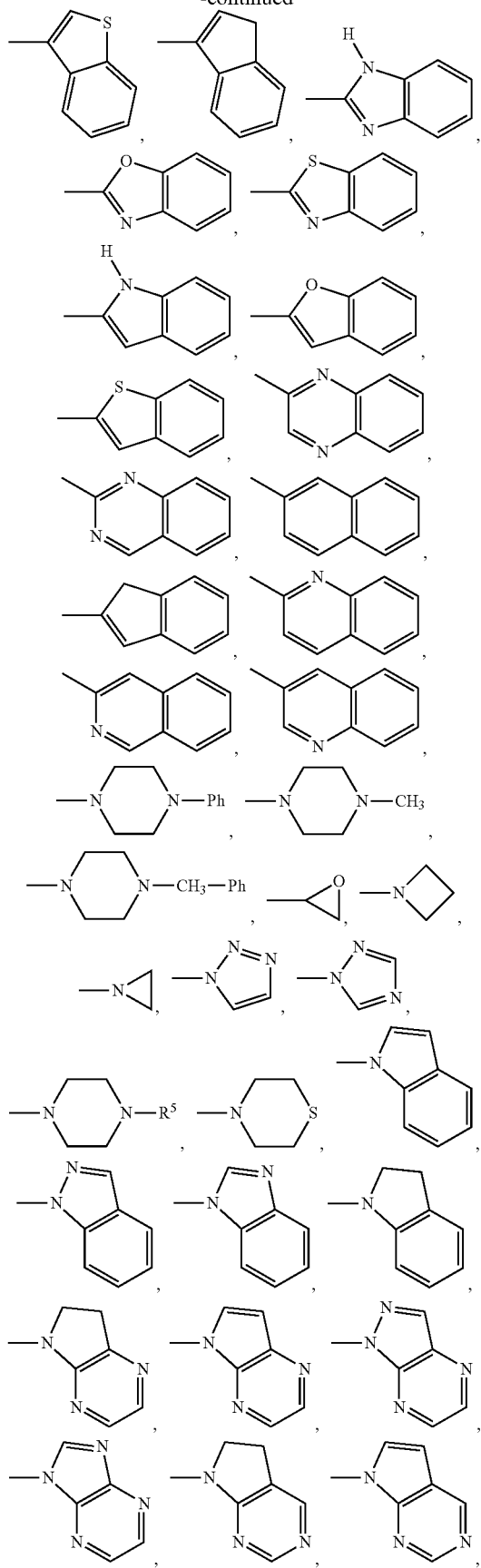
-continued
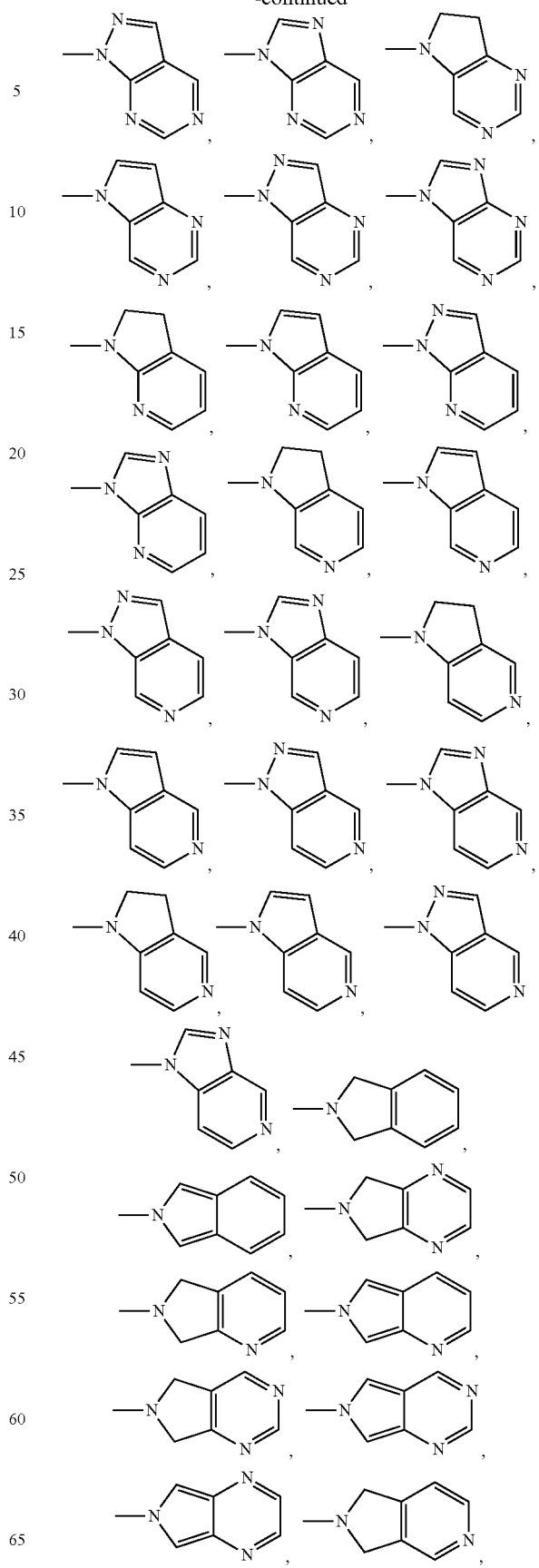

-continued

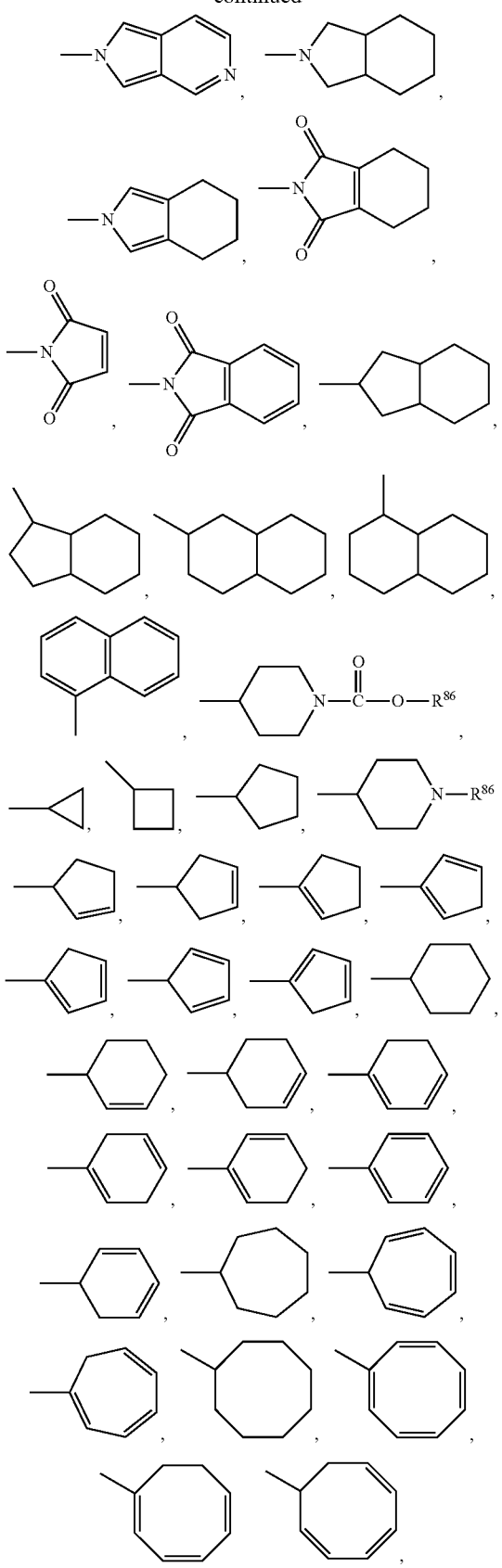

$R^{114}$ represents

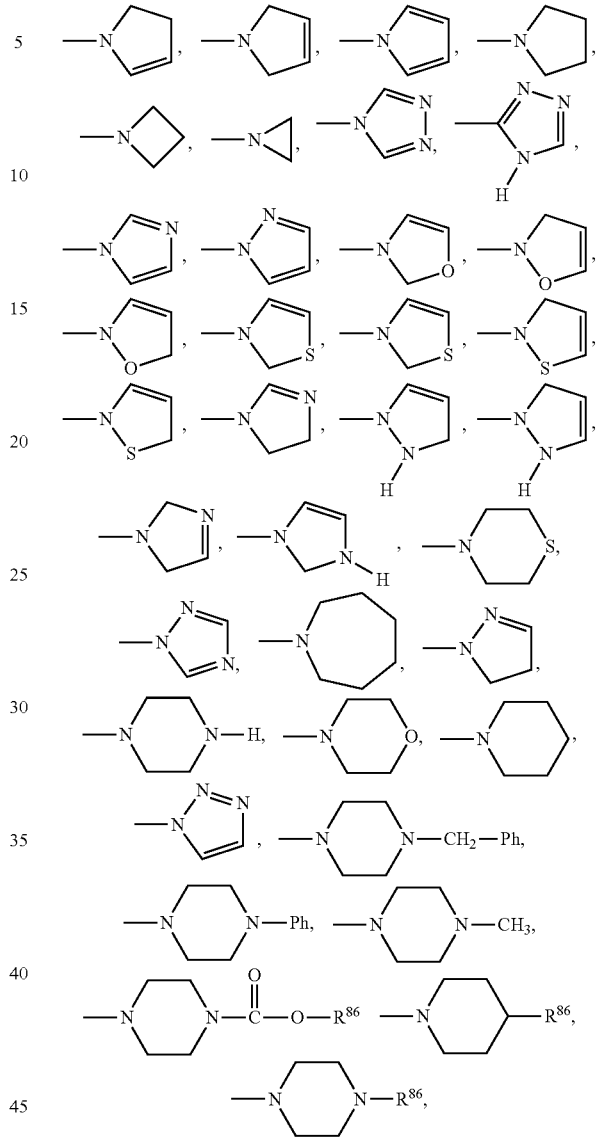

and enantiomers, stereoisomeric forms, mixtures of enantiomers, diastereomers, mixtures of diastereomers, prodrugs, hydrates, solvates, acid salt forms, tautomers, and racemates of the above mentioned compounds and pharmaceutically acceptable salts thereof.

The expression prodrug is defined as a substance, which is applied in an inactive or significantly less active form. Once applied and incorporated, the prodrug is metabolized in the body in vivo into the active compound. Conventional procedures for the selection and preparation of suitable prodrug derivatives are described, for example in "Design of Prodrugs", ed. H. B. Bundgaard, Elsevier, 1985.

The residue D contains at least one nitrogen atom. Said residue may contain one oxygen atom or one sulfur atom in addition to said one nitrogen atom. If no oxygen and no sulfur atom is present, said residue may contain one, two or three additional nitrogen atoms so that said residue contains in total one, two, three or four nitrogen atoms. The position of the nitrogen atom in residue D is essential to the activity of the compound. It is important that this nitrogen atom is in β position to the carbonyl group and that the ring D which is most preferably aromatic forms a conjugated system with the attached carbonyl group or that at least the ring nitrogen in β position together with the alpha carbon atom and the attached carbonyl group form a conjugated system.

Thus, as residues D pyrazoles, imidazoles, oxazoles, isoxazoles, thiazoles, isothiazoles, triazoles, and tetrazoles are preferred. In order to obtain a high anti-cancer activity is seems to be important that the heterocyclic ring D contains a nitrogen atom next to the carbon atom through which the ring D is connected to the amid bond. Moreover pyrazoles, imidazoles, triazoles, and tetrazoles are more preferred than oxazoles, isoxazoles, thiazoles, and isothiazoles and pyrazoles are more preferred than triazoles, and tetrazoles which are again more preferred than imidazoles. Furthermore isoxazoles and isothiazoles are more preferred than oxazoles and thiazoles.

Concerning isoxazole residues as substituent D it is important that the isoxazole residue is linked through the 3-yl-carbon atom to the amide group and not through the 4-yl-carbon atom or the 5-yl-carbon atom. In case of an oxazole group as substituent D it is important that the oxazole group is linked to the amide group through 2-yl-carbon atom or the 4-yl-carbon atom but not through the 5-yl-carbon atom. A pyrazole residue should be linked to the amide group through the 3-yl-carbon atom and not through the 4-yl-carbon atom or the through the 5-yl-carbon atom.

Thiazole residues as substituent D are linked to the amide group through the 2-yl-carbon atom or the 4-yl-carbon atom, but not through the 5-yl-carbon atom. Similiar, isothiazoles are linked through the 3-yl carbon atom, but not through the 4-yl-carbon atom or 5-yl-carbon atom. Imidazoles are linked through the 2-yl-carbon or 4-yl-carbon atom, but not through the 5-yl-carbon position.

Moreover it is important that the residue D is directly connected to the amide group and not through a linker such as a methylene or ethylene linker so that the carbonyl function of the amide group can be in conjugation with the preferably aromatic ring D.

SAR

The structure activity relationship (SAR) of the compounds of the present invention as represented by the Formula (SAR)

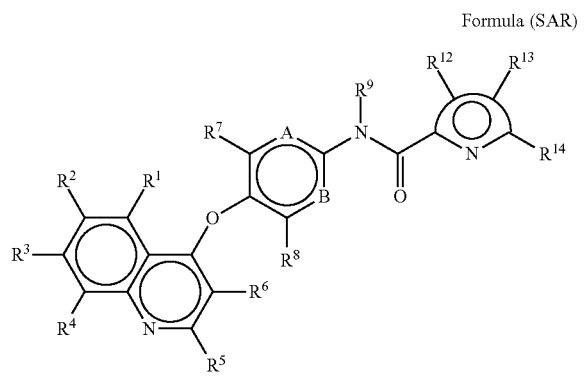

Formula (SAR)

shows that ring D need to be an aromatic 5-membered heterocyclic ring with at least one nitrogen atom attached to the carbon atom of the aromatic ring which is attached to the amide group. Moreover it seems advantageous that the ring D is linked through a carbon atom to the amide group. The nitrogen atom of the amide group may be substituted by alkyl and substituted alkyl residues. Moreover the aromatic 5-membered ring D has to have a specific substitution pattern in order to provide active compounds for the uses disclosed herein. Said specific substitution pattern requires that substituent $R^{13}$ is only a small group such as hydrogen, methyl, trifluoromethyl, fluoro, ethyl, otherwise the activity drops. Furthermore it seems to be advantageous that a larger group such as a substituted phenyl group is attached as $R^{14}$ to the atom next to the ring nitrogen atom as shown in Formula (SAR). In addition a substituent $R^{12}$ in position next to the ring carbon atom of ring D which is attached to the amide group seems to increase the activity. As substituent $R^{12}$ short carbon chains as well as longer carbon chains, short or long alkoxy groups, ether or polyether residues or amines seem to be suitable. Thus compounds with an aromatic nitrogen containing 5-membered ring as substituent D with a small substituent $R^{13}$ and a cyclic substituent $R^{14}$ and a smaller or longer carbon chain as substituent $R^{12}$ containing optionally oxygen (ethers) and/or nitrogen (amines) and/or cyclic structures such as saturated or unsaturated carbocyclic or heterocyclic rings seem to perfectly fit into the active side of the enzyme. In addition it is not important for the activity if A and B are carbon or nitrogen atoms. It seems also not important if substituents $R^7$, $R^8$, $R^5$, $R^6$, $R^2$, and $R^1$ are smaller groups such as nitro, halogen, lower alkyl, lower alkoxy, hydroxy etc. and substituents $R^2$ and $R^3$ can be modified in a broard range. The sort of residue $R^2$ and $R^3$ is not important for the activity so that $R^2$ and $R^3$ can be hydrogen, smaller groups such as methyl or methoxy as well as longer residues with a carbon chain containing optionally oxygen, nitrogen or saturated, unsaturated carbocyclic or heterocyclic rings.

Preferred is the formula (I), wherein the residue D represents one of the following heterocycles:

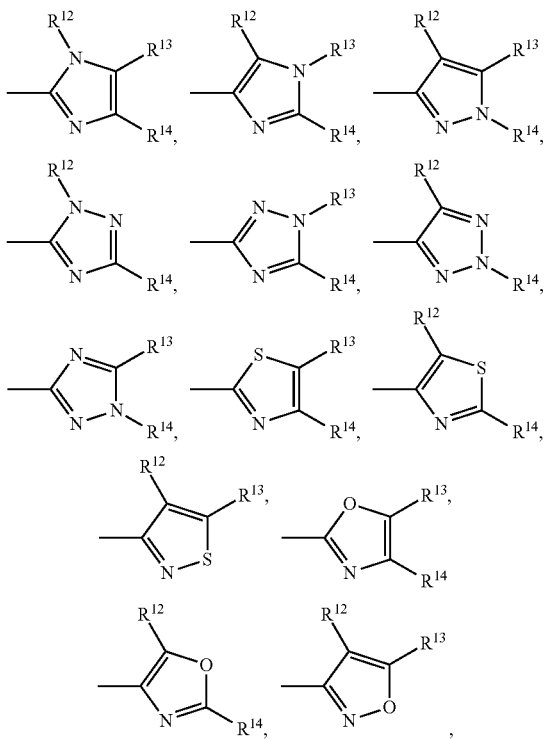

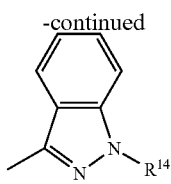

The substituents $R^{12}$-$R^{14}$ have the meanings as defined in formula (I) above.

Still more preferred are the following D residues:

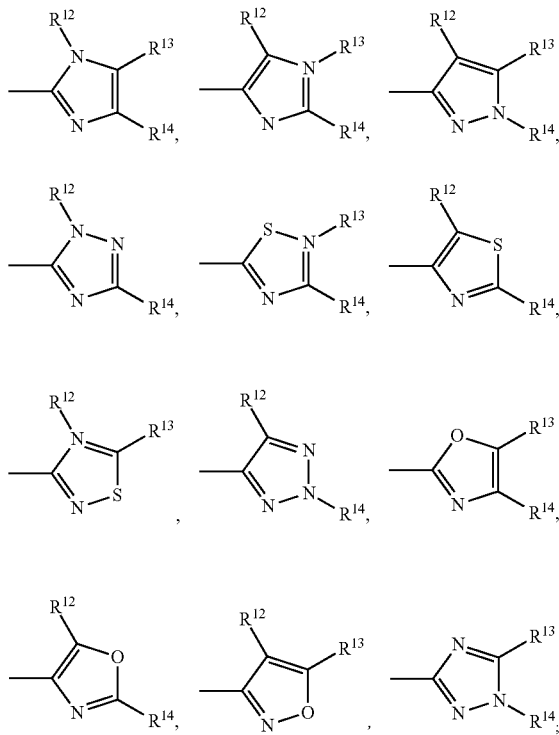

Particularly preferred are compounds of the general formula (Ia),

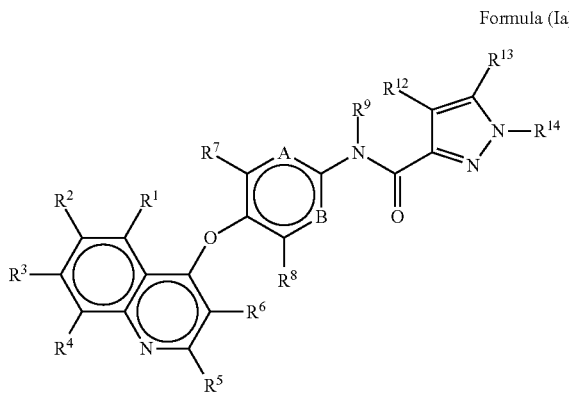

wherein residue D is a substituted or unsubstituted pyrazole ring.

Especially preferred are compounds of the general formula (Ib) or the general formula (Ic),

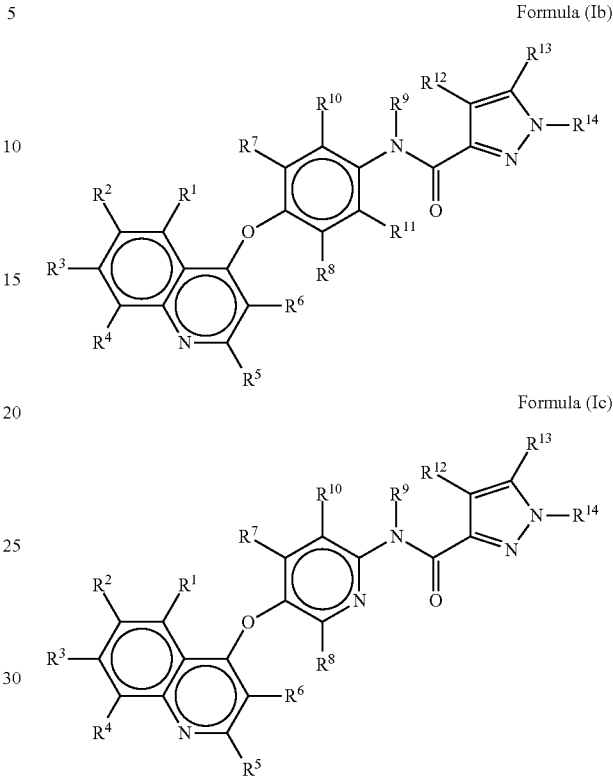

wherein both, group A and group B are carbon atoms or wherein group A is a carbon atom and group B is a nitrogen atom, respectively.

Further preferred are compounds of the general formulas (I), (Ia), (Ib), or (Ic), wherein $R^1$, $R^4$, $R^5$ and $R^6$ are selected from hydrogen or $C_{1-6}$alkyl, particularly from hydrogen.

Furthermore preferred are compounds of the general formulas (I), (Ia), (Ib), or (Ic), wherein $R^9$ is a hydrogen atom.

In regard to A and B it is preferred that non of both or only one of both represents N.

Substituents $R^1$, $R^4$, $R^5$, and $R^6$ are preferably hydrogen.

Substituents $R^2$ and $R^3$ are preferably selected independently of each other from:

—O—$R^{18}$, —O—$CR^{73}R^{74}$—$R^{18}$, —O—$CR^{73}R^{74}$—$CR^{75}R^{76}$—$R^{18}$, —O—$CR^{73}R^{74}$—$CR^{75}R^{76}$—$CR^{77}R^{78}$—$R^{18}$, —C—$CR^{73}R^{74}$—$CR^{75}R^{76}$—$CR^{77}R^{78}$—$CR^{79}R^{80}$—$R^{18}$, —O—$CR^{73}R^{74}$—$CR^{75}R^{76}$—$CR^{77}R^{78}$—$CR^{79}R^{80}$—$CR^{81}R^{82}$—$R^{18}$, —O—$CR^{73}R^{74}$—$CR^{75}R^{76}$—$CR^{77}R^{78}$—$CR^{79}R^{80}$—$CR^{81}R^{82}$—$CR^{83}R^{84}$—$R^{18}$, wherein $R^{73}$— $R^{84}$ independently of each other represent —H, —OH, —F, —Cl, —Br, —I, —$CH_3$, —$CF_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$;

and R$^{18}$ represents —H, —OH, —F, —Cl, —Br, —I, —O—R$^{86}$, —COOH, —COOCH$_3$, —COOC$_2$H$_5$, —COOC$_3$H$_7$, —COOCH(CH$_3$)$_2$, —COOC(CH$_3$)$_3$, —(C═O)—NR$^{16}$R$^{17}$, —CR$^{16}$R$^{17}$H, NR$^{16}$R$^{17}$, —NR$^{16}$R$^{17}$;

R$^{86}$ represents —CH$_3$, —CF$_3$, —H, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—O$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_2$, —CH(CH$_3$)—C(CH$_3$)$_3$;

R$^{16}$ and R$^{17}$ represent independently of each other —CH$_3$, —CF$_3$, —H, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —OH, —F, —Cl, —Br, —I, —NH$_2$, —CN, the residue —NR$^{16}$R$^{17}$ may represent a nitrogen heterocyclic group selected from

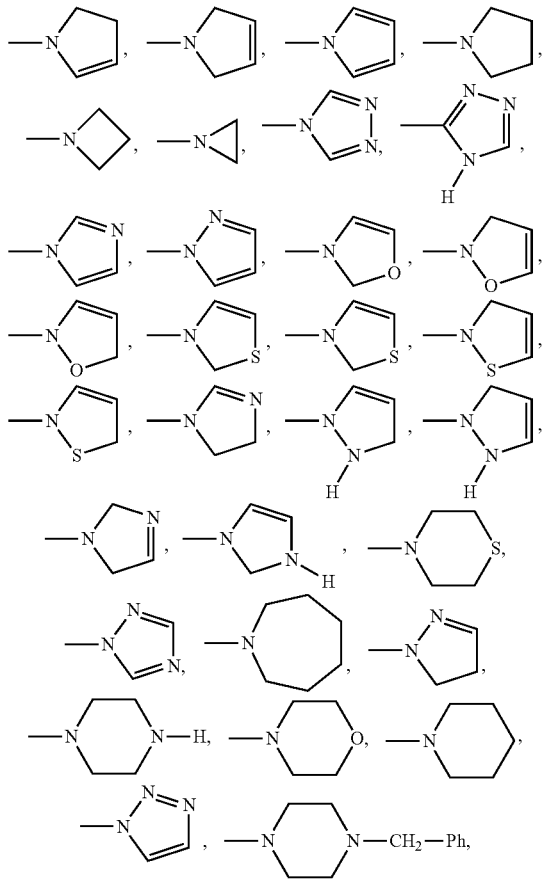

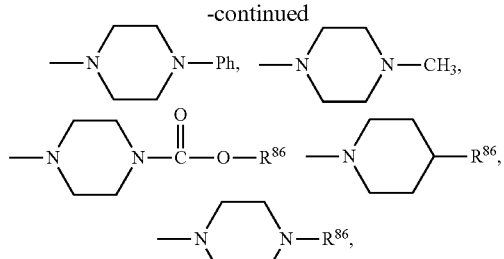

and more preferably selected from

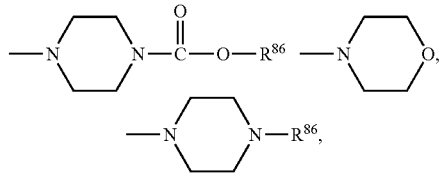

the residue —CR$^{16}$R$^{17}$H may represent a carbocyclic or heterocyclic group selected from

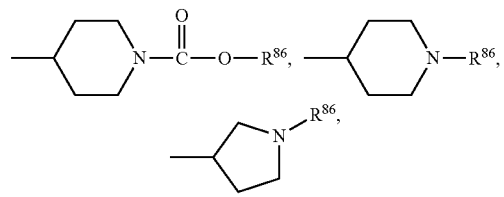

Substituents R$^7$ and R$^8$ are preferably selected independently of each other from:
—H, —F, —Cl, —Br, —I, —CN, —NO$_2$, —CH$_3$, —C$_2$H$_5$, —C$_3$H$_7$, —CH(CH$_3$)$_2$, cyclo-C$_3$H$_5$, —CH$_2$-cyclo-C$_3$H$_5$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —C≡CH, —C≡C—CH$_3$, —CH$_2$—C≡CH, —C$_2$H$_4$—C≡CH, —CH$_2$—C≡C—CH$_3$; and are more preferably selected from —H, —F, —Cl, —Br, —CN, —CH$_3$, —C$_2$H$_5$, —C$_3$H$_7$, —CH(CH$_3$)$_2$, cyclo-C$_3$H$_5$, —CH═CH$_2$, —CH$_2$—CH═CH$_2$, —C(CH$_3$)═CH$_2$, —CH═CH—CH$_3$, —C≡CH, —C≡C—CH$_3$, —CH$_2$—C≡CH; and are still more preferably selected from —H, —F, —Cl, —Br, —CH$_3$, —C$_2$H$_5$, —C$_3$H$_7$, —CH(CH$_3$)$_2$, cyclo-C$_3$H$_5$, —CH═CH$_2$, —CH$_2$—CH═CH$_2$, —C≡CH, —CH$_2$—C≡CH; and R$^7$ and R$^8$ are most preferably selected independently of each other from —H, —F, —Cl, —CH$_3$.

Moreover it is preferred that one of R$^7$ and R$^8$ represents hydrogen.

A and B represent preferably independently of each other C—H, C—F, C—Cl, C—Br, C—CN, C—CH$_3$, C—C$_2$H$_5$, C—C$_3$H$_7$, C—CH(CH$_3$)$_2$, C-cyclo-C$_3$H$_5$, C—CH═CH$_2$, C—CH$_2$—CH═CH$_2$, C—CH═CH—CH$_3$, C—C≡CH, C—C≡C—CH$_3$, C—CH$_2$—C≡CH, C—OCH$_3$, C—OH, C—OC$_2$H$_5$, C—OC$_3$H$_7$, C—OCH(CH$_3$)$_2$, C—OC$_4$H$_9$, C—OCH$_2$—CH(CH$_3$)$_2$, C—OCH(CH$_3$)—C$_2$H$_5$, C—OC(CH$_3$)$_3$, C—OC$_5$H$_{11}$, N. Moreover it is preferred that one of A and B represents C—H. In addition it is preferred that only one of A and B represents N. More preferably A and B represent independently of each other C—H, C—F, C—Cl, C—Br, C—CH$_3$, C—C$_2$H$_5$, C—C$_3$H$_7$, C—CH(CH$_3$)$_2$, C-cyclo-C$_3$H$_5$, C—CH=CH$_2$, C—CH$_2$—CH=CH$_2$, C—C≡CH, C—OCH$_3$, C—OH, C—OC$_2$H$_5$, C—OC$_3$H$_7$, C—OCH(CH$_3$)$_2$, N; still more preferably C—H, C—F, C—Cl, C—CH$_3$, C—C$_2$H$_5$, C—C$_3$H$_7$, C—CH$_2$—CH=CH$_2$, C—OCH$_3$, C—OH, C—OC$_2$H$_5$, C—OC$_3$H$_7$, N; and most preferably A and B represent independently of each other C—H, C—F, C—CH$_3$, C—OCH$_3$, and N.

$R^9$ represents preferably hydrogen.

$R^{14}$ represents preferably —H, —OH, —F, —Cl, —Br, —I, —NO$_2$, —CN, —NH$_2$, —R$^{100}$, —R$^{101}$, —R$^{102}$, —O—R$^{102}$, —R$^{103}$, —O—R$^{103}$, —R$^{136}$, or —R$^{113}$, wherein the saturated or unsaturated three- to twelve-membered carbocyclic or heterocyclic ring system represented by —R$^{113}$ is optionally mono- or polysubstituted by —F, —Cl, —Br, —I, —OH, —NO$_2$, —NH$_2$, —C$_2$H$_4$—N(CH$_3$)$_2$, —CN, —CF$_3$, =O, —R$^{16}$, —R$^{17}$, —R$^{106}$, —O—R$^{107}$, —R$^{108}$, —R$^{109}$, wherein the substituents R$^{16}$, R$^{17}$, R$^{100}$, R$^{101}$, R$^{102}$, R$^{103}$, R$^{106}$, R$^{107}$, R$^{108}$, R$^{109}$, R$^{113}$, and R$^{136}$ have the meanings as disclosed herein.

More preferably $R^{14}$ represents —Cl, —Br, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —R$^{103}$, —R$^{136}$, and —R$^{113}$, wherein the saturated or unsaturated three- to twelve-membered carbocyclic or heterocyclic ring system represented by —R$^{113}$ is optionally mono- or polysubstituted by —F, —Cl, —Br, —OH, —NO$_2$, —NH$_2$, —C$_2$H$_4$—N(CH$_3$)$_2$, —R$^{16}$, —R$^{106}$, —O—R$^{107}$, —R$^{108}$, —R$^{109}$;

Preferably $R^{103}$ represents preferably —CR$^{58}$R$^{16}$R$^{17}$, —CR$^{59}$R$^{60}$—CR$^{16}$R$^{17}$R$^{58}$, —CR$^{59}$R$^{60}$—CR$^{61}$R$^{62}$—CR$^{16}$R$^{17}$R$^{58}$, —CR$^{59}$R$^{60}$—CR$^{61}$R$^{62}$—CR$^{63}$R$^{64}$—CR$^{16}$R$^{17}$R$^{58}$, —CR$^{59}$R$^{60}$—CR$^{61}$R$^{62}$—CR$^{63}$R$^{64}$—CR$^{65}$R$^{66}$—CR$^{16}$R$^{17}$R$^{58}$, —CR$^{59}$R$^{60}$—CR$^{61}$R$^{62}$—CR$^{63}$R$^{64}$—CR$^{65}$R$^{66}$—CR$^{67}$R$^{68}$—CR$^{16}$R$^{17}$R$^{58}$, —CR$^{58}$R$^{59}$R$^{60}$, CR$^{59}$R$^{60}$—CR$^{61}$R$^{62}$R$^{58}$, CR$^{59}$R$^{60}$—CR$^{61}$R$^{62}$—CR$^{63}$R$^{64}$R$^{58}$, —CR$^{59}$R$^{60}$—CR$^{61}$R$^{62}$—CR$^{63}$R$^{64}$—CR$^{65}$R$^{66}$R$^{58}$, —CR$^{59}$R$^{60}$—CR$^{61}$R$^{62}$—CR$^{63}$R$^{64}$—CR$^{65}$R$^{66}$—CR$^{67}$R$^{68}$R$^{58}$, and $R^{58}$-$R^{68}$ represent independently of each other —H, —NH$_2$, —OH, —F, —Cl, —Br, —I, —OCH$_3$, —OCF$_3$, —OC$_2$H$_5$, —CH$_3$, —C$_2$H$_5$, —C$_3$H$_7$, —CH(CH$_3$)$_2$, —C$_4$H$_9$, —CF$_3$, —C(CH$_3$)$_3$, —CR$^{16}$R$^{17}$H, —NR$^{16}$R$^{17}$; wherein R$^{16}$ and R$^{17}$ have the meanings as disclosed herein.

More preferably $R^{103}$ represents —CR$^{68}$R$^{69}$R$^{60}$, —CR$^{59}$R$^{60}$—CR$^{61}$R$^{62}$R$^{58}$, —CR$^{59}$R$^{60}$—CR$^{61}$R$^{62}$—CR$^{63}$R$^{64}$R$^{58}$, —CR$^{59}$R$^{60}$—CR$^{61}$R$^{62}$—CR$^{63}$R$^{64}$—CR$^{65}$R$^{66}$R$^{58}$, —CR$^{59}$R$^{60}$—CR$^{61}$R$^{62}$—CR$^{63}$R$^{64}$—CR$^{65}$R$^{66}$—CR$^{67}$R$^{68}$R$^{58}$, and R$^{58}$ represents —CR$^{16}$R$^{17}$H or —NR$^{18}$R$^{17}$; and $R^{59}$-$R^{68}$ represent independently of each other —H, —NH$_2$, —OH, —F, —Cl, —Br, —I, —OCH$_3$, —OC$_2$H$_5$, —CH$_3$, —C$_2$H$_5$, —C$_3$H$_7$, —CH(CH$_3$)$_2$, —C$_4$H$_9$, —CF$_3$, —C(CH$_3$)$_3$; and R$^{16}$ and R$^{17}$ represent independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C$_5$H$_{11}$, —CF$_3$, -Ph, —CH$_2$-Ph, or represent together with the atom to which they are attached a saturated or unsaturated three- to twelve-membered carbocyclic or heterocyclic ring system selected from —R$^{133}$, wherein R$^{133}$ has the meanings as disclosed herein.

Still more preferably $R^{103}$ represents —CR$^{58}$R$^{59}$R$^{60}$, —CR$^{59}$R$^{60}$—CR$^{61}$R$^{62}$R$^{58}$, —CR$^{59}$R$^{60}$—CR$^{61}$R$^{62}$—CR$^{63}$R$^{64}$R$^{58}$, —CR$^{59}$R$^{60}$—CR$^{61}$R$^{62}$—CR$^{63}$R$^{64}$—CR$^{65}$R$^{66}$R$^{58}$, —CR$^{59}$R$^{60}$—CR$^{61}$R$^{62}$—CR$^{63}$R$^{64}$—CR$^{65}$R$^{66}$—CR$^{67}$R$^{68}$R$^{58}$, and R$^{58}$ represents

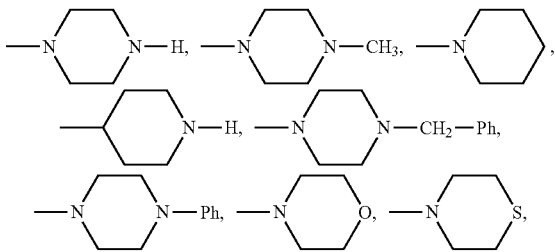

and $R^{59}$-$R^{68}$ represent independently of each other —H, —CH$_3$, —C$_2$H$_5$, —CF$_3$.

Still even more preferably $R^{103}$ represents —CH$_2$R$^{58}$, —CH$_2$—CH$_2$R$^{58}$, —CH$_2$—CH$_2$—CH$_2$R$^{58}$, —CH$_2$—CH$_2$—CH$_2$—CH$_2$R$^{58}$, CH$_2$—CH$_2$—CH$_2$—CH$_2$—CH$_2$R$^{58}$, and R$^{58}$ represents

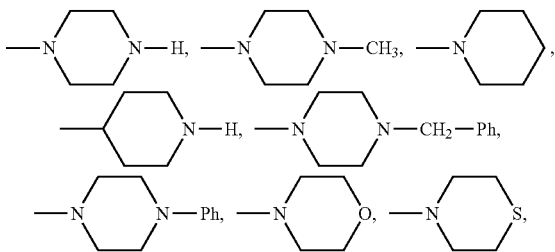

Most preferably $R^{103}$ represents —CH$_2$R$^{58}$, —CH$_2$—CH$_2$R$^{58}$, —CH$_2$—CH$_2$—CH$_2$R$^{58}$, —CH$_2$—CH$_2$—CH$_2$—CH$_2$R$^{58}$, and R$^{58}$ represents

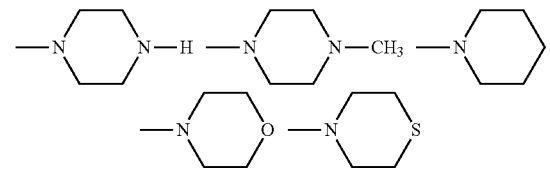

Preferably $R^{136}$ represents —CR$^{23}$R$^{24}$—X—CR$^{25}$R$^{26}$R$^{22}$, —CR$^{23}$R$^{24}$—X—CR$^{25}$R$^{26}$—CR$^{27}$R$^{28}$R$^{22}$, —CR$^{23}$R$^{24}$—CR$^{25}$R$^{26}$—X—CR$^{27}$R$^{28}$R$^{22}$, —CR$^{23}$R$^{24}$—X—CR$^{25}$R$^{26}$—CR$^{27}$R$^{28}$—CR$^{29}$R$^{30}$R$^{22}$, —CR$^{23}$R$^{24}$—CR$^{25}$R$^{26}$—X—CR$^{27}$R$^{28}$—CR$^{29}$R$^{30}$R$^{22}$, —CR$^{23}$R$^{24}$—CR$^{25}$R$^{26}$—CR$^{27}$R$^{28}$—X—CR$^{29}$R$^{30}$R$^{22}$, —CR$^{23}$R$^{24}$—X—CR$^{25}$R$^{26}$—CR$^{27}$R$^{28}$—CR$^{29}$R$^{30}$—CR$^{31}$R$^{32}$R$^{22}$, —CR$^{23}$R$^{24}$—CR$^{25}$R$^{26}$—X—CR$^{27}$R$^{28}$—CR$^{29}$R$^{30}$—CR$^{31}$R$^{32}$R$^{22}$, —CR$^{23}$R$^{24}$—CR$^{25}$R$^{26}$—CR$^{27}$R$^{28}$—X—CR$^{29}$R$^{30}$—CR$^{31}$R$^{32}$R$^{22}$, —CR$^{23}$R$^{24}$—CR$^{25}$R$^{26}$—CR$^{27}$R$^{28}$—CR$^{29}$R$^{30}$—X—CR$^{31}$R$^{32}$R$^{22}$, —CR$^{23}$R$^{24}$—X—CR$^{25}$R$^{26}$—CR$^{27}$R$^{28}$—CR$^{29}$R$^{30}$—CR$^{31}$R$^{32}$—CR$^{33}$R$^{34}$R$^{22}$, —CR$^{23}$R$^{24}$—CR$^{25}$R$^{26}$—X—CR$^{27}$R$^{28}$—CR$^{29}$R$^{30}$—CR$^{31}$R$^{32}$—CR$^{33}$R$^{34}$R$^{22}$, —CR$^{23}$R$^{24}$—CR$^{25}$R$^{26}$—CR$^{27}$R$^{28}$—X—CR$^{29}$R$^{30}$—CR$^{31}$R$^{32}$—CR$^{33}$R$^{34}$R$^{22}$, —CR$^{23}$R$^{24}$—CR$^{25}$R$^{26}$—CR$^{27}$R$^{28}$—CR$^{29}$R$^{30}$—X—CR$^{31}$R$^{32}$—CR$^{33}$R$^{34}$R$^{22}$, —CR$^{23}$R$^{24}$—CR$^{25}$R$^{26}$—CR$^{27}$R$^{28}$—CR$^{29}$R$^{30}$—CR$^{31}$R$^{32}$—X—CR$^{33}$R$^{34}$R$^{22}$; and X represents —O—, —CO—, —O—CO— and R$^{22}$—R$^{34}$ represent independently of each other —H, —F, —Cl, —CH$_3$, —CF$_3$, —C$_2$H$_5$, —C$_3$H$_7$.

More preferably $R^{136}$ represents —CR$^{23}$R$^{24}$—X—CR$^{25}$R$^{26}$R$^{22}$, —CR$^{23}$R$^{24}$—X—CR$^{25}$R$^{26}$—CR$^{27}$R$^{28}$R$^{22}$, —CR²³R²⁴—CR²⁵R²⁶—X—CR²⁷R²⁸R²², —CR²³R²⁴—X—CR²⁵R²⁶—CR²⁷R²⁸—CR²⁹R³⁰R²², —CR²³R²⁴—CR²⁵R²⁶—X—CR²⁷R²⁸—CR²⁹R³⁰R²², —CR²³R²⁴—CR²⁵R²⁶—CR²⁷R²⁸—X—CR²⁹R³⁰R²², —CR²³R²⁴—X—CR²⁵R²⁶—CR²⁷R²⁸—CR²⁹R³⁰—CR³¹R³²R²², —CR²³R²⁴—CR²⁵R²⁶—X—CR²⁷R²⁸—CR²⁹R³⁰—CR³¹R³²R²², —CR²³R²⁴—CR²⁵R²⁶—CR²⁷R²⁸—X—CR²⁹R³⁰—CR³¹R³²R²², —CR²³R²⁴—CR²⁵R²⁶—CR²⁷R²⁸—CR²⁹R³⁰—X—CR³¹R³²R²²; and X represents —O—, and R²²— R³² represent independently of each other —H, —CH₃, —CF₃, —C₂H₅, —C₃H₇.

Still more preferably R¹³⁶ represents —CH₂—O—CH₂R²², —CH₂—O—CH₂—CH₂R²², —CH₂—CH₂—O—CH₂R²², —CH₂—O—CH₂—CH₂—CH₂R²², —CH₂—C₂—CH—O—CH₂—CH₂R²², —CH₂—CH₂—CH₂—O—CH₂R²², —CH₂—O—CH₂—H₂—CH₂—CH₂—CH₂R²², —CH₂—CH₂—O—CH₂—CH₂—CH₂R²², —CH₂—CH₂—CH₂—O—CH₂—CH₂R²², —CH₂—CH₂—CH₂—CH₂—O—CH₂R²²; and R²² represents —H, —CH₃, —CF₃, —C₂H₅, —C₃H₇.

Still even more preferably R¹³⁶ represents —CH₂—O—CH₂R²², —CH₂—O—CH₂—CH₂R²², —CH₂—CH₂—O—CH₂R²², —CH₂—O—CH₂—CH₂—CH₂R²², —CH₂—CH₂—O—CH₂—CH₂R²², —CH₂—CH₂—CH₂—O—CH₂R²²; and R²² represents —H, —CH₃, —CF₃, —C₂H₅.

Most preferably R¹³⁶ represents —CH₂—O—CH₂CF₃, —CH₂—O—CH₂—CH₂CF₃, —CH₂—CH₂—O—CH₂CF₃.

R¹¹³ represents preferably

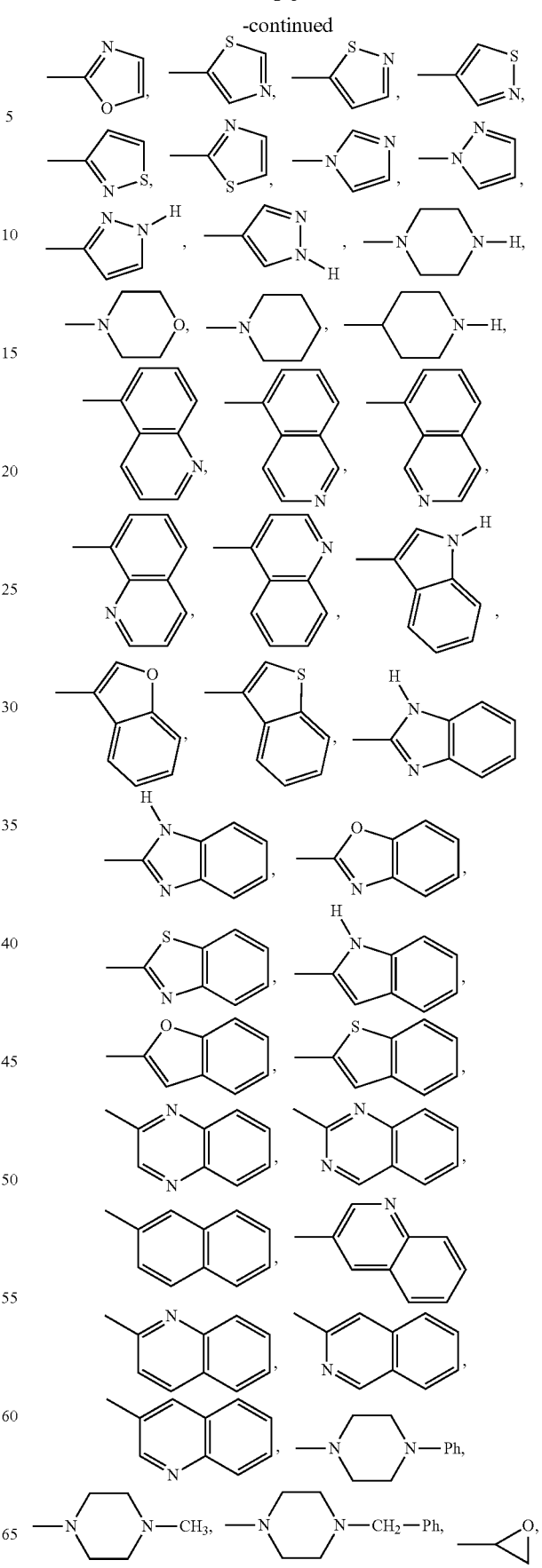

-continued

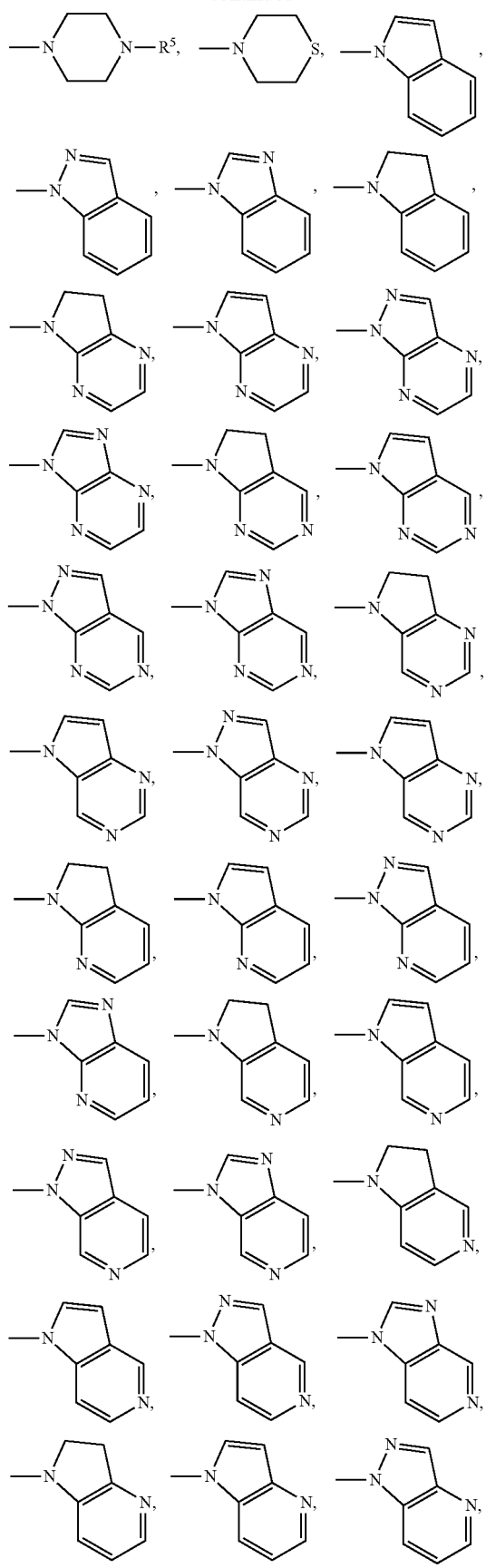
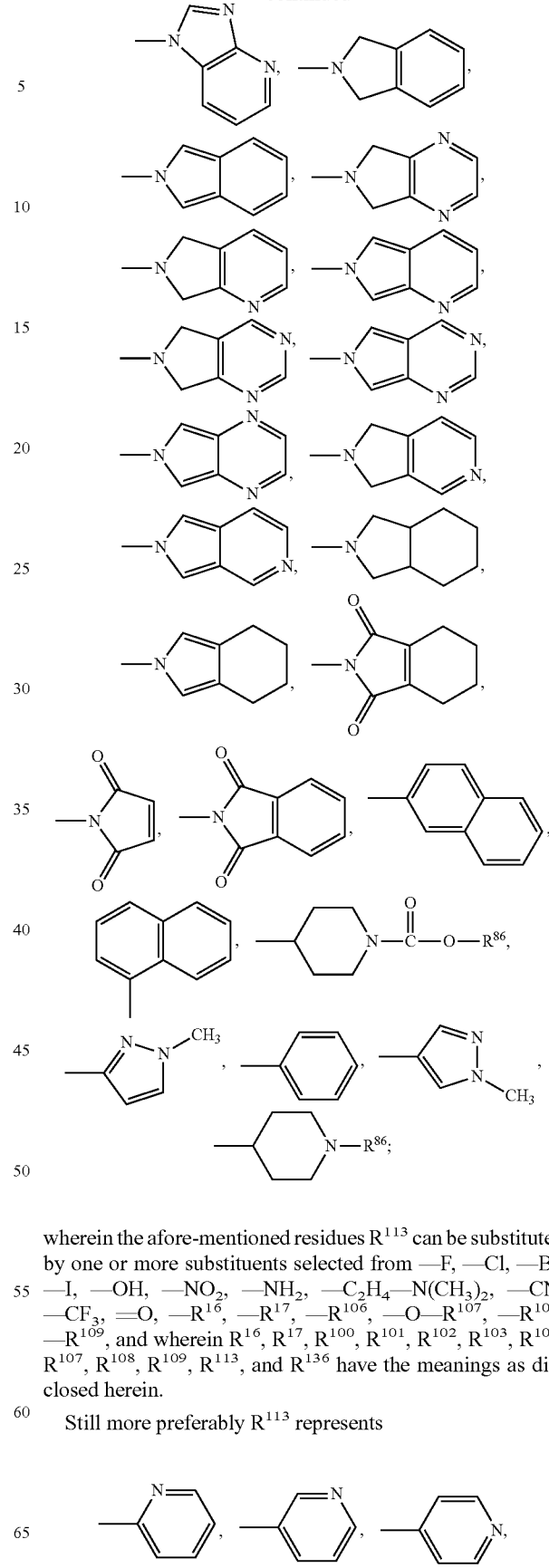
wherein the afore-mentioned residues $R^{113}$ can be substituted by one or more substituents selected from —F, —Cl, —Br, —I, —OH, —NO$_2$, —NH$_2$, —C$_2$H$_4$—N(CH$_3$)$_2$, —CN, —CF$_3$, =O, —R$^{16}$, —R$^{17}$, —R$^{106}$, —O—R$^{107}$, —R$^{108}$, —R$^{109}$, and wherein $R^{16}$, $R^{17}$, $R^{100}$, $R^{101}$, $R^{102}$, $R^{103}$, $R^{106}$, $R^{107}$, $R^{108}$, $R^{109}$, $R^{113}$, and $R^{136}$ have the meanings as disclosed herein.
Still more preferably $R^{113}$ represents
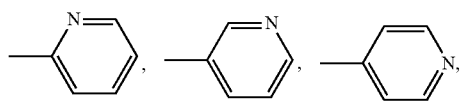

-continued
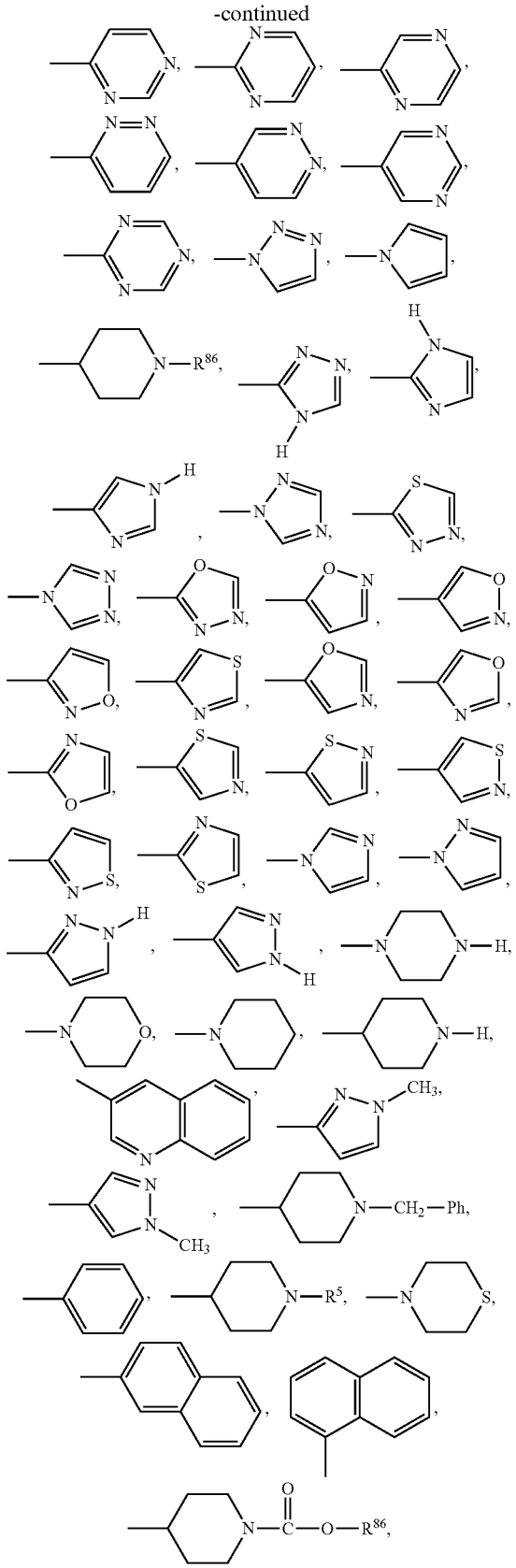
wherein the afore-mentioned residues $R^{113}$ can be substituted by one or more substituents selected from —F, —Cl, —Br, —I, —OH, —NO$_2$, —NH$_2$, —C$_2$H$_4$—N(CH$_3$)$_2$, —CN, —CF$_3$, =O, —R$^{16}$, —R$^{17}$, —R$^{106}$, —O—R$^{107}$, —R$^{108}$, —R$^{109}$, and wherein $R^{16}$, $R^{17}$, $R^{100}$, $R^{101}$, $R^{102}$, $R^{103}$, $R^{106}$, $R^{107}$, $R^{108}$, $R^{109}$, $R^{113}$, and $R^{136}$ have the meanings as disclosed herein.
Still more preferably $R^{113}$ represents
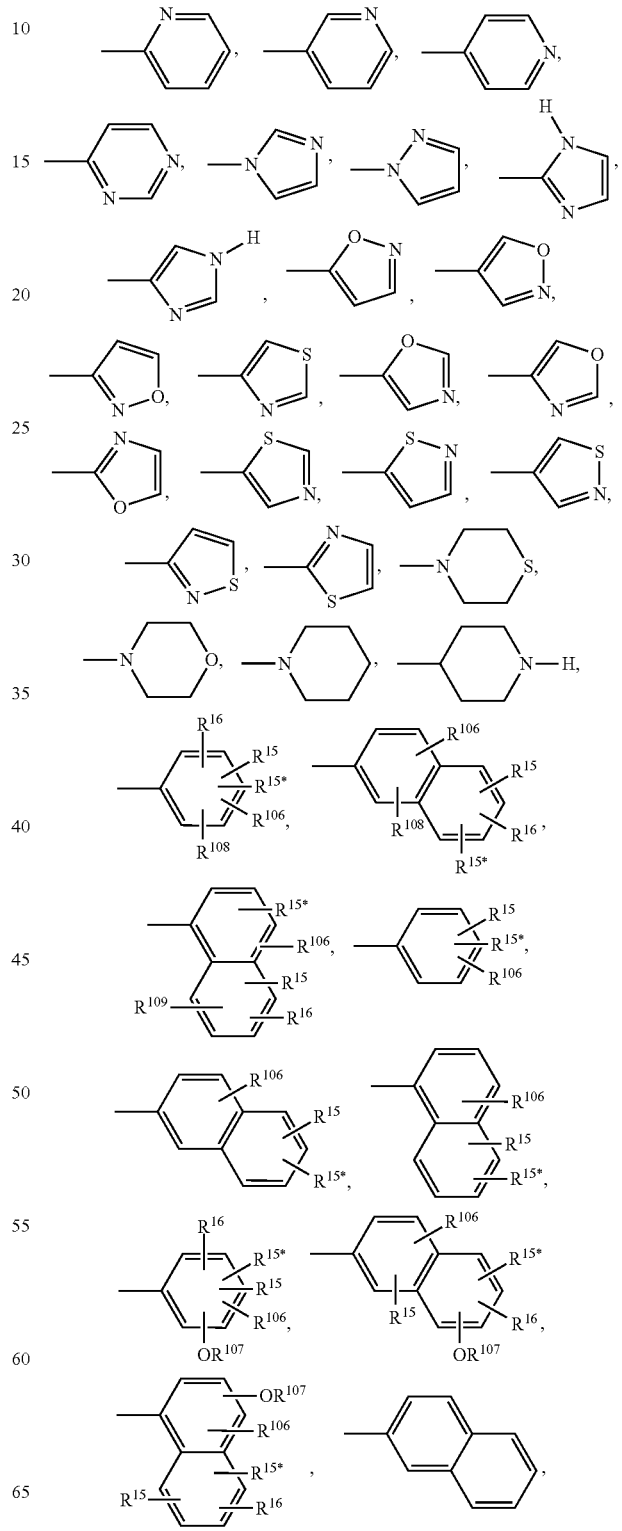

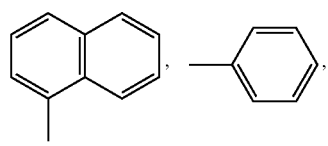

wherein $R^{15}$, $R^{15*}$, $R^{16}$, $R^{106}$, $R^{107}$, $R^{108}$, and $R^{109}$ have the meanings as disclosed herein and more preferably $R^{109}$ represent —H, —C≡CH, or —CH$_2$—C≡CH; and $R^{108}$ represent —H, —CH=CH$_2$, or —CH$_2$—CH=CH$_2$; and $R^{16}$, $R^{106}$ and $R^{107}$ represent independently of each other —H, —CH$_3$, —CF$_3$, -Ph, —CH$_2$-Ph, —O$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$;

and $R^{15}$ and $R^{15*}$ represent independently of each other —H, —F, —Cl, —Br, —I, —OH, —NO$_2$, —NH$_2$, —C$_2$H$_4$—N(CH$_3$)$_2$, —CN, —CF$_3$, =O;

Still more preferably $R^{15}$ and $R^{15*}$ represent independently of each other —H, —F, —Cl, —Br, —OH, —NO$_2$, —NH$_2$, —C$_2$H$_4$—N(CH$_3$)$_2$, and still more preferably $R^{16}$ represents —H, —CH$_3$, —CF$_3$, —C$_2$H$_5$; $R^{106}$ represents more preferably —H, —CH$_3$, —CF$_3$, —C$_2$H$_5$; and $R^{107}$ represents more preferably —H, —CH$_3$, —CF$_3$, -Ph, —CH$_2$-Ph, —C$_2$H$_5$, —C$_3$H$_7$, —CH(CH$_3$)$_2$, —C$_4$H$_9$;

Most preferably $R^{113}$ represents

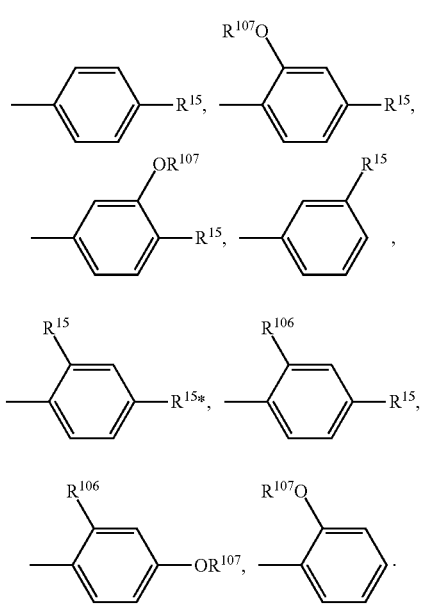

Residues for $R^{14}$ proved by examples and thus preferred residues are: —H, —Br, —CH$_3$, —C$_3$H$_7$, —C(CH$_3$)$_3$, -Ph, —CH$_2$—O—CH$_2$—CF$_3$

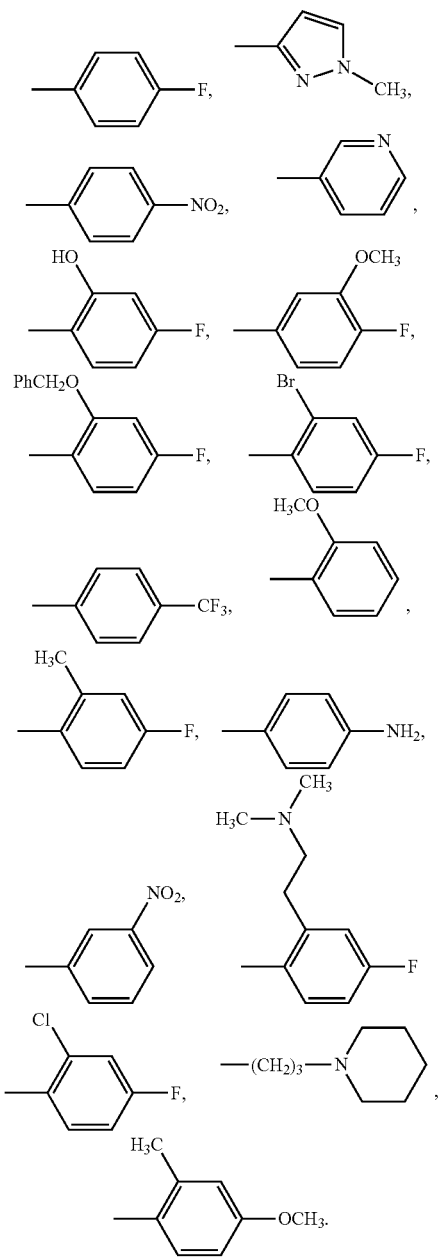

In case $R^{14}$ is attached to a nitrogen atom, $R^{14}$ does not represent —Br.

Preferably $R^{13}$ represents —H, —OH, —F, —Cl, —Br, —NO$_2$, —CH$_3$, —CF$_3$, —C$_2$H$_5$, —C$_3$H$_7$, —CH(CH$_3$)$_2$, —C$_4$H$_9$, —CH=CH$_2$, —CH$_2$—CH=CH$_2$, —CH=CH—CH$_3$, —C≡CH, —C≡C—CH$_3$, —CH$_2$—C≡CH, cyclo-C$_3$H$_5$, —OCH$_3$, —OCF$_3$, —OC$_2$H$_5$, —OC$_3$H$_7$, —OCH(CH$_3$)$_2$, or —OC$_4$H$_9$;

More preferably $R^{13}$ represents —H, —OH, —F, —Cl, —NO$_2$, —CH$_3$, —CF$_3$, —C$_2$H$_5$, —C$_3$H$_7$, —CH=CH$_2$, —CH$_2$—CH=CH$_2$, —C≡CH, —CH$_2$—C≡CH, cyclo-C$_3$H$_5$, —OCH$_3$, —OCF$_3$, —OC$_2$H$_5$, or —OC$_3$H$_7$.

Still more preferably $R^{13}$ represents —H, —OH, —F, —CH$_3$, —CF$_3$, —C$_2$H$_5$, —CH=CH$_2$, —C≡CH, —OCH$_3$, —OCF$_3$, or —OC$_2$H$_5$.

Most preferably $R^{13}$ represents —H, —F, —CH$_3$, —CF$_3$, or —C$_2$H$_5$.

Preferably $R^{12}$ represents —H, —F, —Cl, —Br, —I, —OH, —NH$_2$, —NHR$^{19}$, —NR$^{19}$R$^{20}$, —OCH$_3$, —OCF$_3$, —OC$_2$F$_5$, —OC$_2$H$_5$, —OC$_3$H$_7$, —O-cyclo-C$_3$H$_5$, —OCH$_2$-cyclo-C$_3$H$_5$, —O—C$_2$H$_4$-cyclo-C$_3$H$_5$, —O—C$_3$H$_5$-cyclo-C$_3$H$_5$, —OCH(CH$_3$)$_2$, —OC(CH$_3$)$_3$, —OC$_4$H$_9$, —OPh, —NO$_2$, —R$^{94}$, —OR$^{94}$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, —CH$_2$-cyclo-C$_3$H$_5$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$;

and $R^{94}$ represents preferably —CR$^{58}$R$^{16}$R$^{17}$, —CR$^{59}$R$^{69}$—CR$^{16}$R$^{17}$R$^{58}$, —CR$^{59}$R$^{69}$—CR$^{61}$R$^{62}$—CR$^{16}$R$^{17}$R$^{68}$, —CR$^{59}$R$^{66}$—CR$^{61}$R$^{62}$—CR$^{63}$R$^{64}$—CR$^{16}$R$^{17}$R$^{68}$, —CR$^{59}$R$^{69}$—CR$^{61}$R$^{62}$—CR$^{63}$R$^{64}$—CR$^{66}$R$^{66}$—CR$^{16}$R$^{17}$R$^{68}$, —CR$^{59}$R$^{60}$—CR$^{61}$R$^{62}$—CR$^{63}$R$^{64}$—CR$^{65}$R$^{66}$—CR$^{67}$R$^{68}$—CR$^{16}$R$^{17}$R$^{58}$, —CR$^{58}$R$^{59}$R$^{69}$, —CR$^{59}$R$^{69}$—CR$^{61}$R$^{62}$R$^{58}$, —CR$^{59}$R$^{60}$—CR$^{61}$R$^{62}$—CR$^{63}$R$^{64}$R$^{58}$, —CR$^{59}$R$^{69}$—CR$^{61}$R$^{62}$—CR$^{63}$R$^{64}$—CR$^{65}$R$^{66}$R$^{58}$, —CR$^{59}$R$^{60}$—CR$^{61}$R$^{62}$—CR$^{63}$R$^{64}$—CR$^{66}$R$^{66}$—CR$^{67}$R$^{68}$R$^{58}$, and $R^{58}$—$R^{68}$ preferably represent preferably independently of each other —H, —NH$_2$, —OH, —F, —Cl, —Br, —I, —R$^{71}$, —O—R$^{71}$, —R$^{72}$, —O—R$^{95}$, —R$^{96}$, —O—R$^{104}$, R—R$^{105}$, —CR$^{16}$R$^{17}$H, —NR$^{16}$R$^{17}$;

wherein $R^{16}$, $R^{17}$, $R^{19}$, $R^{20}$, $R^{71}$, $R^{72}$, $R^{95}$, $R^{96}$, $R^{104}$, and $R^{105}$ have the meanings as disclosed herein.

More preferably $R^{12}$ represents —H, —F, —Cl, —Br, —I, —OH, —NH$_2$, —CH$_2$F, —CF$_3$, —CH$_2$—CH$_2$F, —CH$_2$—CF$_3$, cyclo-C$_3$H$_5$, —CH$_2$-cyclo-C$_3$H$_5$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_6$H$_{11}$, —C$_6$H$_{13}$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —OCH$_3$, —OCF$_3$, —OC$_2$F$_5$, —OC$_2$H$_5$, —OC$_3$H$_7$, —O-cyclo-C$_3$H$_5$, —OCH$_2$-cyclo-C$_3$H$_5$, —O—C$_2$H$_4$-cyclo-C$_3$H$_5$, —O—C$_3$H$_8$-cyclo-C$_3$H$_5$, —OCH(CH$_3$)$_2$, —OC(CH$_3$)$_3$, —OC$_4$H$_9$, —OPh, —NO$_2$, —R$^{94}$, —OR$^{94}$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$;

and $R^{94}$ represents preferably —CR$^{58}$R$^{59}$R$^{69}$, —CR$^{59}$R$^{69}$—CR$^{61}$R$^{62}$R$^{58}$—CR$^{59}$R$^{69}$—CR$^{61}$R$^{62}$—CR$^{63}$R$^{64}$R$^{68}$, —CR$^{59}$R$^{69}$—CR$^{61}$R$^{62}$—CR$^{63}$R$^{64}$—CR$^{65}$R$^{66}$R$^{58}$, —CR$^{59}$R$^{69}$—CR$^{61}$R$^{62}$—CR$^{63}$R$^{64}$—CR$^{65}$R$^{66}$—CR$^{67}$R$^{68}$R$^{58}$, and $R^{59}$-$R^{68}$ represent independently of each other —H, —NH$_2$, —OH, —F, —Cl, —Br, —I, —OCH$_3$, —OCF$_3$, —OC$_2$H$_5$, —CH$_3$, —C$_2$H$_5$, —C$_3$H$_7$, —CH(CH$_3$)$_2$, —C$_4$H$_9$, —CF$_3$, —C(CH$_3$)$_3$;

and $R^{58}$ represents preferably —CH$_3$, —CF$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, -Ph, —CH$_2$-Ph, —OCH$_3$, —OCF$_3$, —OC$_2$H$_5$, —OC$_3$H$_7$, —OCH(CH$_3$)$_2$, —OC$_4$H$_9$, —OCH$_2$—CH(CH$_3$)$_2$, —OCH(CH$_3$)—C$_2$H$_5$, —OC(CH$_3$)$_3$, —OCH$_2$—C(CH$_3$)$_3$, —OCH(C$_2$H$_5$)$_2$, —OC$_2$H$_4$—CH(CH$_3$)$_2$, —OC$_6$H$_{13}$, —OPh, —OCH$_2$-Ph, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$,

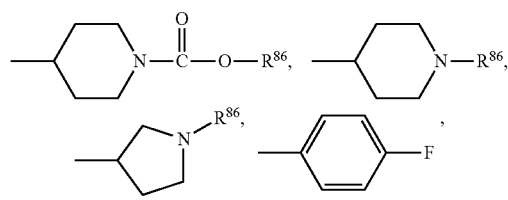

wherein $R^{88}$ has the meanings as disclosed herein.

Still more preferably $R^{12}$ represents —H, —F, —Cl, —Br, —I, —OH, —NH$_2$, —CH$_2$F, —CF$_3$, —CH$_2$—CH$_2$F, —CH$_2$—CF$_3$, cyclo-C$_3$H$_5$, —CH$_2$-cyclo-C$_3$H$_5$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —OCH$_3$, —OCF$_3$, —OC$_2$F$_5$, —OC$_2$H$_5$, —OC$_3$H$_7$, —O-cyclo-C$_3$H$_5$, —OCH$_2$-cyclo-C$_3$H$_5$, —O—C$_2$H$_4$-cyclo-C$_3$H$_5$, —O—C$_3$H$_6$-cyclo-C$_3$H$_5$, —OCH(CH$_3$)$_2$, —OC(CH$_3$)$_3$, —OC$_4$H$_9$, —OPh, —NO$_2$, —R$^{94}$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$;

and $R^{94}$ represents preferably —CH$_2$R$^{58}$, —CH$_2$—CH$_2$R$^{58}$, —CH$_2$—CH$_2$—CH$_2$R$^{58}$, —CH$_2$—CH$_2$—CH$_2$—CH$_2$R$^{58}$, —CH$_2$—CH$_2$—CH$_2$—CH$_2$—CH$_2$R$^{58}$, and $R^{58}$ represents preferably —CH$_3$, —CF$_3$, —C$_2$H$_5$, —C$_3$H$_7$, —CH(CH$_3$)$_2$, —C$_4$H$_9$, -Ph, —CH$_2$-Ph, —OCH$_3$, —OCF$_3$, —OC$_2$H$_5$, —OC$_3$H$_7$, —OCH(CH$_3$)$_2$, —OC$_4$H$_9$, —OCH$_2$—CH(CH$_3$)$_2$, —OCH(CH$_3$)—C$_2$H$_5$, —OC(CH$_3$)$_3$, —OC$_5$H$_{11}$, —OC$_6$H$_{13}$, —OPh, —OCH$_2$-Ph, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$,

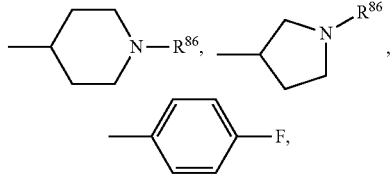

and R$^{86}$ represents preferably —H, —CH$_3$, —CF$_3$, —C$_2$H$_5$, —C$_3$H$_7$, —CH(CH$_3$)$_2$, —C$_4$H$_9$, -Ph, —CH$_2$-Ph.

Even still more preferably R$^{12}$ represents —H, —F, —Cl, —Br, —CF$_3$, cyclo-C$_3$H$_5$, —CH$_3$, —C$_2$H$_5$, —C$_3$H$_7$, —CH(CH$_3$)$_2$, —C$_4$H$_9$, —OH, —NH$_2$, —OCH$_3$, —OCF$_3$, —OC$_2$H$_5$, —OC$_3$H$_7$, —O-cyclo-C$_3$H$_5$, —OCH$_2$-cyclo-C$_3$H$_5$, —OCH(CH$_3$)$_2$, —OC(CH$_3$)$_3$, —OC$_4$H$_9$, —NO$_2$, —N(CH$_3$)$_2$, —N(C$_2$H$_5$)$_2$, —N(C$_3$H$_7$)$_2$, —OCH$_2$R$^{58}$, —OCH$_2$—CH$_2$R$^{58}$, —OCH$_2$—CH$_2$—CH$_2$R$^{58}$, —OCH$_2$—CH$_2$—CH$_2$—CH$_2$R$^{68}$, —CH$_2$R$^{68}$, —CH$_2$—CH$_2$R$^{68}$, —CH$_2$—CH$_2$—CH$_2$R$^{68}$, —CH$_2$—CH$_2$—CH$_2$—CH$_2$R$^{58}$, and R$^{68}$ represents preferably —CH$_3$, —CF$_3$, —C$_2$H$_5$, —C$_3$H$_7$, —CH(CH$_3$)$_2$, -Ph, —OCH$_3$, —OCF$_3$, —OC$_2$H$_5$, —OC$_3$H$_7$, —OCH(CH$_3$)$_2$, —N(CH$_3$)$_2$, —N(C$_2$H$_5$)$_2$, —N(C$_3$H$_7$)$_2$,

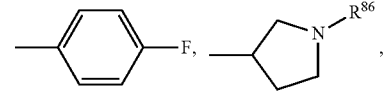

and R$^{86}$ represents preferably —H, —CH$_3$, —CF$_3$, —C$_2$H$_5$, —C$_3$H$_7$, —CH(CH$_3$)$_2$.

Most preferably R$^{12}$ represents —H, —F, —Cl, —Br, —CF$_3$, cyclo-C$_3$H$_5$, —CH$_3$, —C$_2$H$_5$, —C$_3$H$_7$, —CH(CH$_3$)$_2$, —OH, —NH$_2$, —OCH$_3$, —OCF$_3$, —OC$_2$H$_5$, —OC$_3$H$_7$, —O-cyclo-C$_3$H$_5$, —OCH$_2$-cyclo-C$_3$H$_5$, —OCH(CH$_3$)$_2$, —OC(CH$_3$)$_3$, —OC$_4$H$_9$, —NO$_2$, —OCH$_2$R$^{68}$, —OCH$_2$—CH$_2$R$^{68}$, —OCH$_2$—CH$_2$—CH$_2$R$^{68}$, —OCH$_2$—CH$_2$—CH$_2$—CH$_2$R$^{68}$, —CH$_2$R$^{68}$, —CH$_2$—CH$_2$R$^{58}$, —CH$_2$—CH$_2$R$^{58}$, and R$^{58}$ represents preferably -Ph, —OCH$_3$, —OCF$_3$, —OC$_2$H$_5$, —N(CH$_3$)$_2$, —N(C$_2$H$_5$)$_2$,

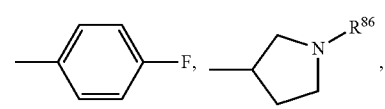

and R$^{86}$ represents preferably —H, —CH$_3$, —CF$_3$, —C$_2$H$_5$.

Residues for R$^{12}$ proved by examples and thus preferred resudes are:

—H, —Br, —CH$_3$, —NH$_2$, —OCH$_3$, —OC$_2$H$_5$, —OCH$_2$-cyclo-C$_3$H$_5$, —OCH(CH$_3$)$_2$, —NO$_2$, —OCH$_2$R$^{68}$, —OCH$_2$—CH$_2$R$^{68}$, —OCH$_2$—CH$_2$—CH$_2$R$^{68}$, —CH$_2$—CH$_2$R$^{68}$, and R$^{58}$ represents preferably -Ph, —OCH$_3$, —N(CH$_3$)$_2$,

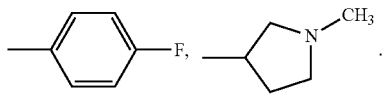

In case R$^{12}$ is attached to a nitrogen atom, R$^{12}$ does preferably not represent an alkoxy group and not a halogen and represents preferably the groups and the preferred groups mentioned herein which are linked through a carbon atom to the ring nitrogen atom.

The present invention also includes within its scope N-oxides of the compounds of formula (I) above. In general, such N-oxides may be formed by conventional means, such as reacting the compound of formula I with oxone in the presence of wet alumina.

The expression tautomer is defined as an organic compound that is interconvertible by a chemical reaction called tautomerization. Tautomerization can be catalyzed preferably by bases or acids or other suitable compounds.

The compounds of the present invention may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, D-o-tolyltartaric acid, tartronic acid, (o, m, p)-toluic acid, naphthylamine sulfonic acid, trifluoroacetic acid, and other mineral or carboxylic acids well known to those skilled in the art. The salts are prepared by contacting the free base form of the compounds of formula (I) with a sufficient amount of the desired acid to produce a salt in the conventional manner well known to those skilled in the art.

The inventive compounds may exist in a number of different polymorphic forms.

In the case the inventive compounds bear acidic groups, salts could also be formed with inorganic or organic bases. Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Syntheses of Compounds

A method to prepare compounds of formula (I) is shown in Scheme 1. The reaction of acid chloride 1 and aniline 2 is carried out in the presence of a base like pyridine and optionally in an inert solvent like DCM (dichloromethane). Many of the acid chlorides 1 are commercially available. The acid chlorides 1 can also be prepared from commercially available carboxylic acids via standard procedures, using thionyl chloride or oxalyl chloride as reagents. Alternatively, carboxylic acids can be directly coupled with anilines 2 under standard procedures, such as using HBTU (N,N,N',N'-Tetramethyl-O-(1H-benzotriazol-1-yl)uronium hexafluorophosphate) or HATU (0-(7-Azabenzotriazol-1-yl)-N,N,N',N'-tetramethyluronium hexafluorophosphate) to give compounds of formula (I).

Scheme 1

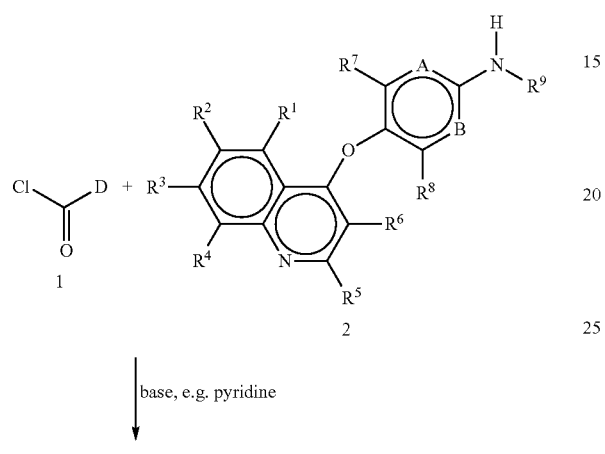

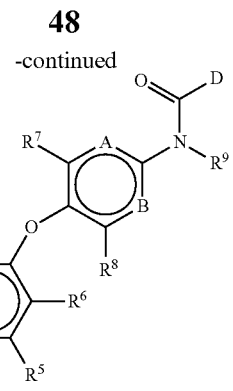

Formula (I)

The synthesis of substituted pyrazoles 8/10 is shown in Scheme 2. Diazonium derivatives 5 are obtained by the reaction of ethyl 4-chloro-3-oxo-butanoate 3 with different anilines 4. Subsequent cyclization of 5 to the corresponding pyrazoles 6 can be achieved using a base such as KOAc (potassium acetate), as described in literature (Chattaway, F. D.; Ashworth, D. R.; Grimwalde, M. *Journal of the Chemical Society* 1935, 117-120). The hydroxyl-group of 6 can be modified by alkylation, for instance using ethyl iodide and $K_2CO_3$ in DMF (dimethylformamide) to give pyrazole 7. Alternatively, the hydroxyl-moiety of 6 can be converted into the corresponding triflate which than can be used for metal-catalyzed cross-couplings to obtain derivatives 9. Finally, hydrolysis of 7/9 and subsequent acid chloride formation yields 8/10.

Scheme 2

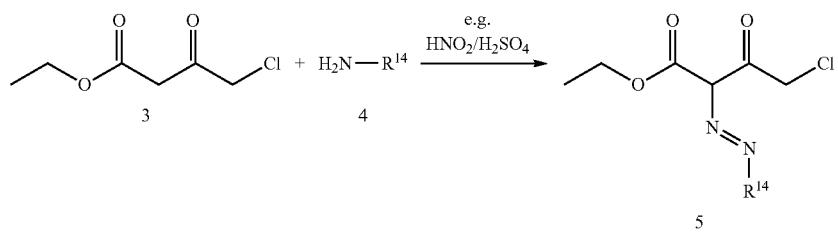

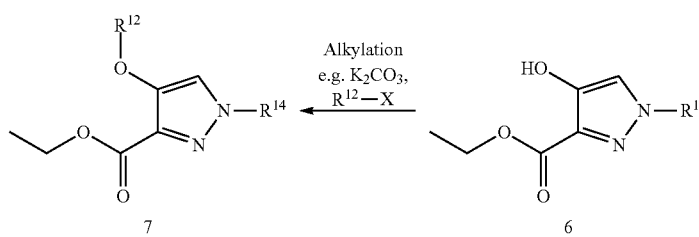

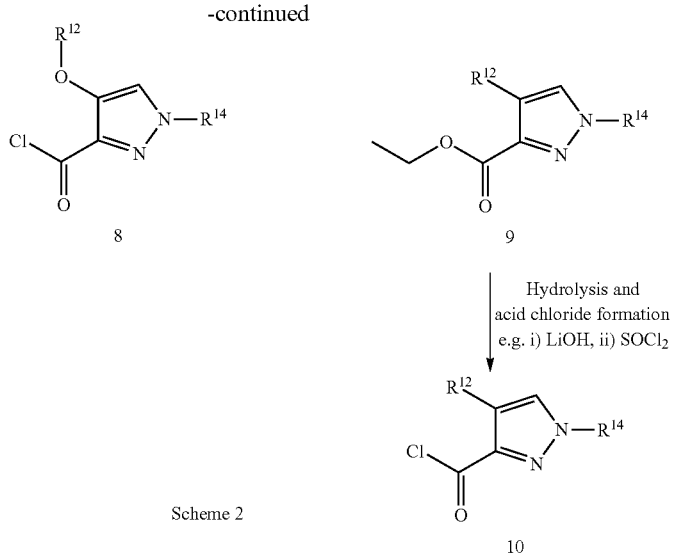

Scheme 2

A modification of the substituents of the pyrazole 11 is shown below in Scheme 3. The bromide derivative 11 can be used in metal-catalyzed cross-couplings, for instance under Sonogashira conditions using an alkyne, copper iodide and dichloro-bis(triphenylphosphine)palladium in the presence of a base like $NEt_3$ (triethylamine). Subsequent modifications yield the pyrazole derivative 12.

Scheme 3

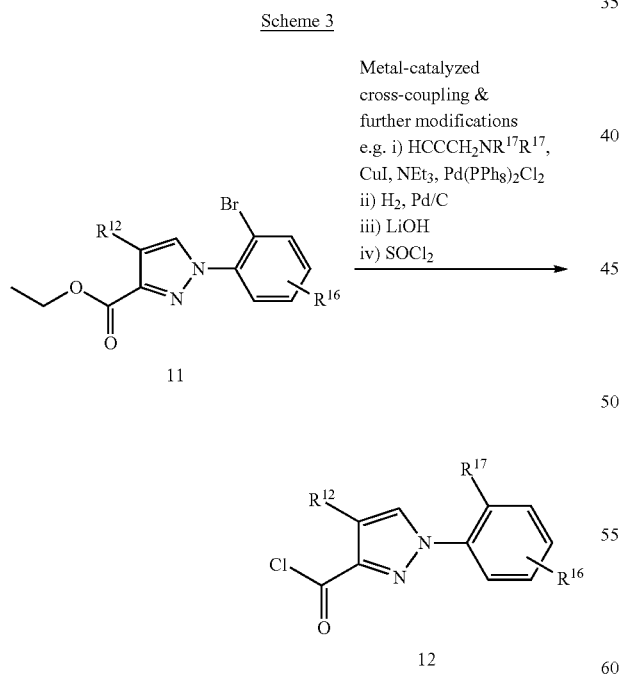

The synthesis of anilines 2 is shown in Scheme 4. Here the quinoline derivative 13 is subjected to nucleophilic aromatic substitution of the appropriate fluoro(hetero) aromatic derivative 14. Subsequent reduction of the nitro derivative 15 yields the anilines 2.

Scheme 4

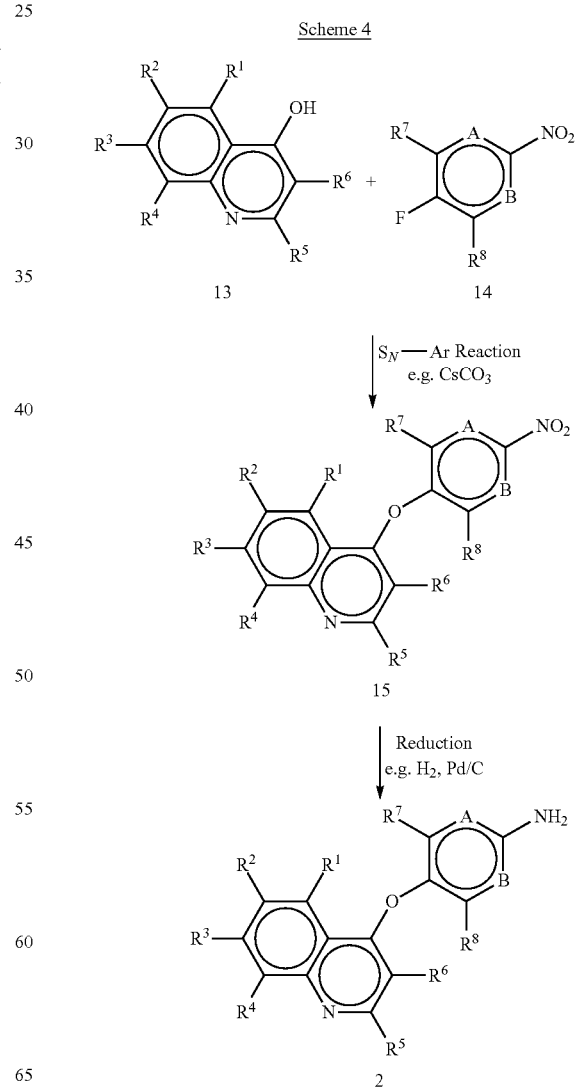

The pharmaceutical compositions according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutaneous, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95-weight % of the derivatives according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. anti-cancer activity or activity against cancer metastases and the like. Suitable dosage forms for sustained release include tablets having layers of varying disintegration rates or controlled release, polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn, rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat, corn, rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The compounds of the present invention are suitable for use in medicine, particulary in human medicine, but also in veterinary medicine. The dosage of the compounds may be determined by a skilled practitioner according to the type and severity of the disorder to be treated.

The compounds of the present invention may be administered as a monotherapy or together with further active agents, particulary chemotherapeutic agents or antitumor antibodies. Furthermore they may be used in combination with surgery and/or irradiation.

Especially preferred compounds according to the present invention include compounds presented by Table 1.

TABLE 1

| Example | Structure | Nomenclature |
|---|---|---|
| 1 | 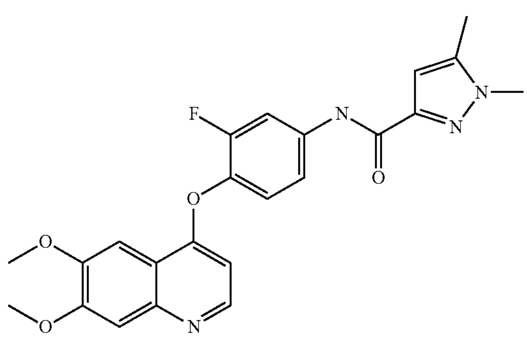 | N-[4-[(6,7-dimethoxy-4-quinolyl)oxy]-3-fluoro-phenyl]-1,5-dimethyl-pyrazole-3-carboxamide |
| 2 | 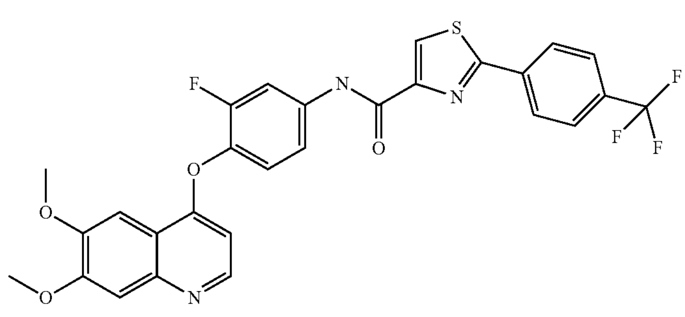 [SMILES: COc1cc2nccc(Oc3ccc(NC(=O)c4csc(-c5ccc(C(F)(F)F)cc5)n4)cc3F)c2cc1OC] | N-[4-[(6,7-dimethoxy-4-quinolyl)oxy]-3-fluoro-phenyl]-2-[4-(trifluoromethyl)phenyl]thiazole-4-carboxamide |

TABLE 1-continued

| Example | Structure | Nomenclature |
|---|---|---|
| 3 | 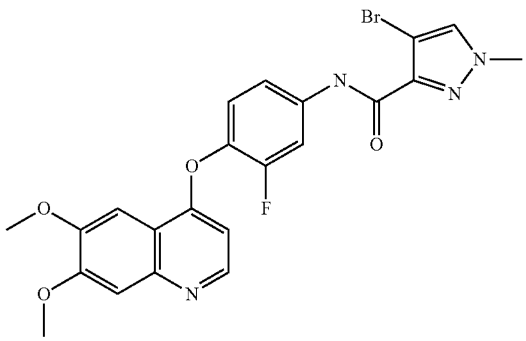 | 4-bromo-N-[4-[(6,7-dimethoxy-4-quinolyl)oxy]-3-fluoro-phenyl]-1-methyl-pyrazole-3-carboxamide |
| 4 | 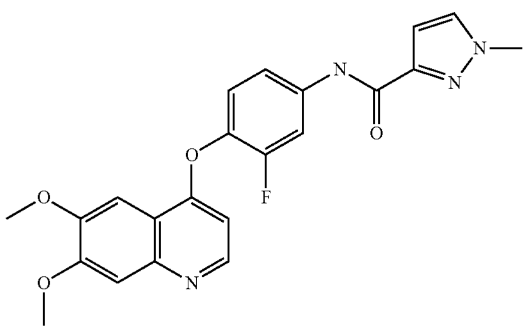 | N-[4-[(6,7-dimethoxy-4-quinolyl)oxy]-3-fluoro-phenyl]-1-methyl-pyrazole-3-carboxamide |
| 5 | 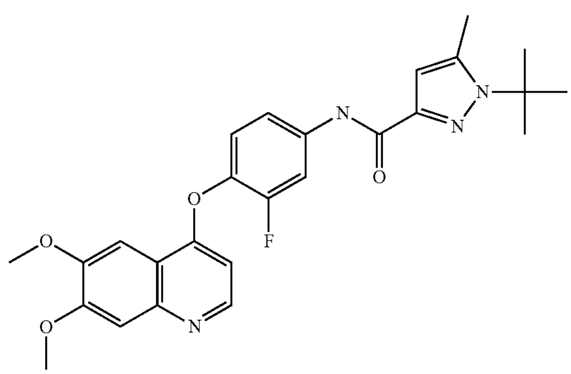 [SMILES: COc1cc2nccc(Oc3ccc(NC(=O)c4cc(C)n(C(C)(C)C)n4)cc3F)c2cc1OC] | 1-tert-butyl-N-[4-[(6,7-dimethoxy-4-quinolyl)oxy]-3-fluoro-phenyl]-5-methyl-pyrazole-3-carboxamide |
| 6 | 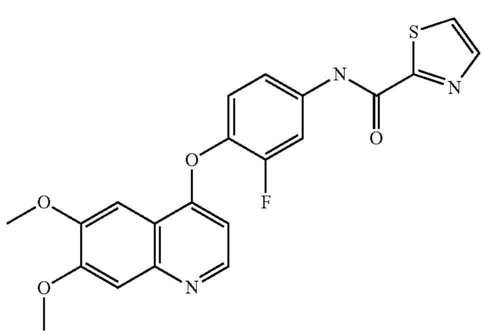 [SMILES: COc1cc2nccc(Oc3ccc(NC(=O)c4nccs4)cc3F)c2cc1OC] | N-[4-[(6,7-dimethoxy-4-quinolyl)oxy]-3-fluoro-phenyl]thiazole-2-carboxamide |

TABLE 1-continued

| Example | Structure | Nomenclature |
|---|---|---|
| 7 | 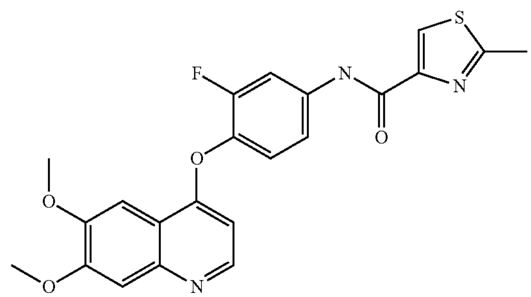 | N-[4-[(6,7-dimethoxy-4-quinolyl)oxy]-3-fluoro-phenyl]-2-methyl-thiazole-4-carboxamide |
| 8 | 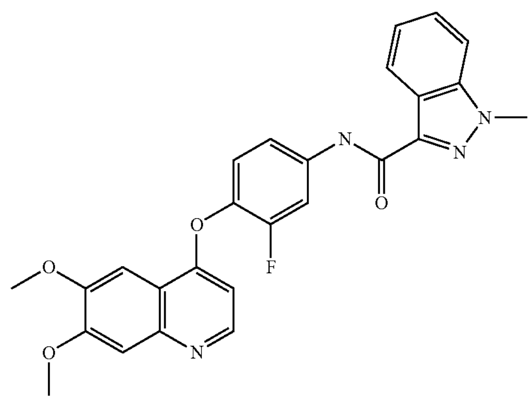 | N-[4-[(6,7-dimethoxy-4-quinolyl)oxy]-3-fluoro-phenyl]-1-methyl-indazole-3-carboxamide |
| 9 | 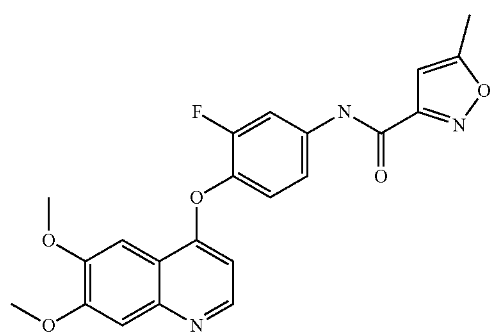 [SMILES: COc1cc2nccc(Oc3ccc(NC(=O)c4cc(C)on4)cc3F)c2cc1OC] | N-[4-[(6,7-dimethoxy-4-quinolyl)oxy]-3-fluoro-phenyl]-5-methyl-isoxazole-3-carboxamide |
| 10 | 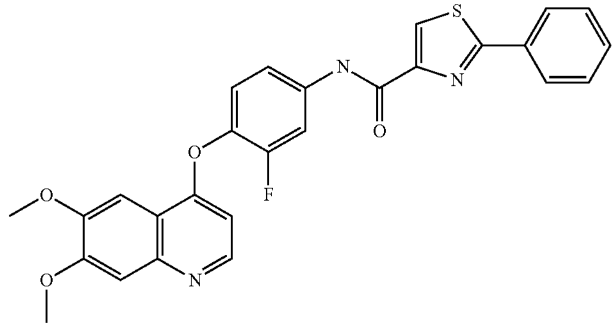 [SMILES: COc1cc2nccc(Oc3ccc(NC(=O)c4csc(-c5ccccc5)n4)cc3F)c2cc1OC] | N-[4-[(6,7-dimethoxy-4-quinolyl)oxy]-3-fluoro-phenyl]-2-phenyl-thiazole-4-carboxamide |

TABLE 1-continued

| Example | Structure | Nomenclature |
|---|---|---|
| 11 | 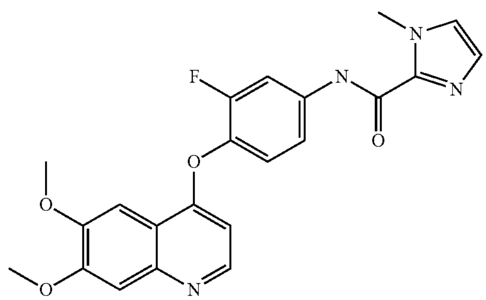 [SMILES: COc1cc2nccc(Oc3ccc(NC(=O)c4nccn4C)cc3F)c2cc1OC] | N-[4-[(6,7-dimethoxy-4-quinolyl)oxy]-3-fluoro-phenyl]-1-methyl-imidazole-2-carboxamide |
| 12 | 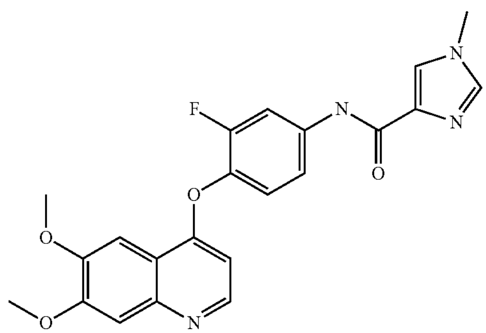 [SMILES: COc1cc2nccc(Oc3ccc(NC(=O)c4cn(C)cn4)cc3F)c2cc1OC] | N-[4-[(6,7-dimethoxy-4-quinolyl)oxy]-3-fluoro-phenyl]-1-methyl-imidazole-4-carboxamide |
| 13 | 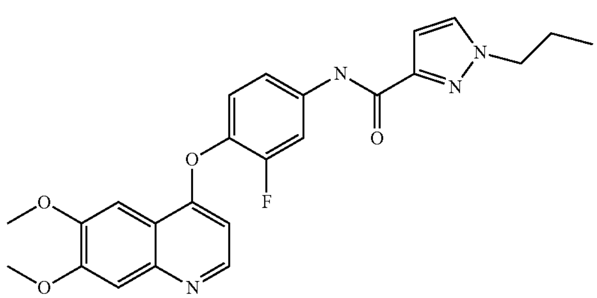 [SMILES: CCCn1ccc(C(=O)Nc2ccc(Oc3ccnc4cc(OC)c(OC)cc34)c(F)c2)n1] | N-[4-[(6,7-dimethoxy-4-quinolyl)oxy]-3-fluoro-phenyl]-1-propyl-pyrazole-3-carboxamide |
| 14 | 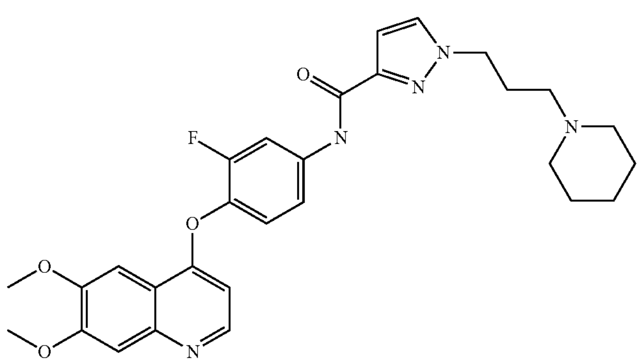 [SMILES: COc1cc2nccc(Oc3ccc(NC(=O)c4ccn(CCCN5CCCCC5)n4)cc3F)c2cc1OC] | N-[4-[(6,7-dimethoxy-4-quinolyl)oxy]-3-fluoro-phenyl]-1-[3-(1-piperidyl)propyl]pyrazole-3-carboxamide |

TABLE 1-continued

| Example | Structure | Nomenclature |
|---|---|---|
| 15 | 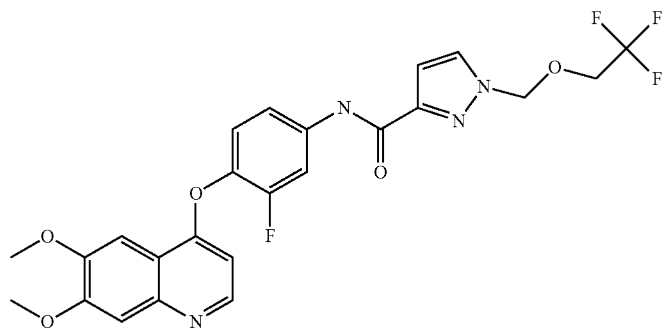 [SMILES: COc1cc2nccc(Oc3ccc(NC(=O)c4ccn(COCC(F)(F)F)n4)cc3F)c2cc1OC] | N-[4-[(6,7-dimethoxy-4-quinolyl)oxy]-3-fluoro-phenyl]-1-(2,2,2-trifluoroethoxymethyl)pyrazole-3-carboxamide |
| 16 | 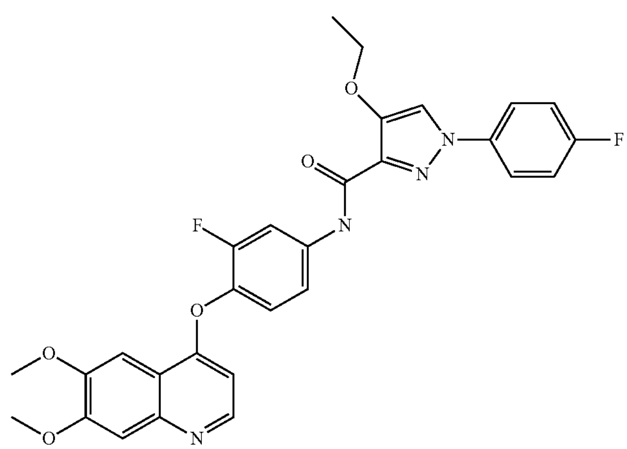 [SMILES: CCOc1cn(-c2ccc(F)cc2)nc1C(=O)Nc1ccc(Oc2ccnc3cc(OC)c(OC)cc23)c(F)c1] | N-[4-[(6,7-dimethoxy-4-quinolyl)oxy]-3-fluoro-phenyl]-4-ethoxy-1-(4-fluorophenyl)pyrazole-3-carboxamide |
| 17 | 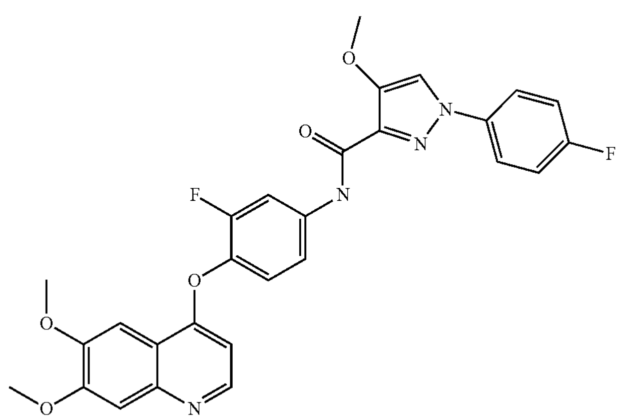 [SMILES: COc1cc2nccc(Oc3ccc(NC(=O)c4nn(-c5ccc(F)cc5)cc4OC)cc3F)c2cc1OC] | N-[4-[(6,7-dimethoxy-4-quinolyl)oxy]-3-fluoro-phenyl]-1-(4-fluorophenyl)-4-methoxy-pyrazole-3-carboxamide |

TABLE 1-continued

| Example | Structure | Nomenclature |
|---|---|---|
| 18 | 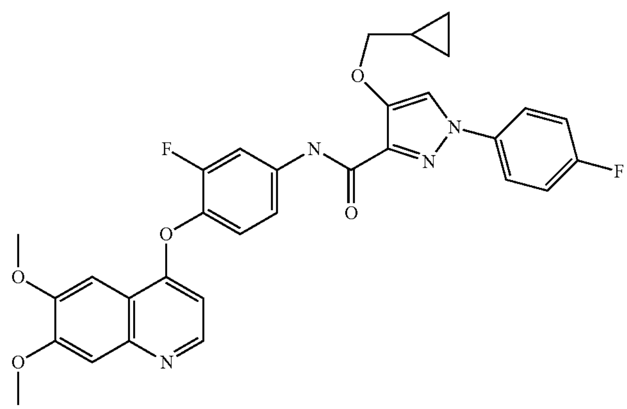 [SMILES: COc1cc2nccc(Oc3ccc(NC(=O)c4nn(-c5ccc(F)cc5)cc4OCC4CC4)cc3F)c2cc1OC] | 4-(cyclopropylmethoxy)-N-[4-[(6,7-dimethoxy-4-quinolyl)oxy]-3-fluoro-phenyl]-1-(4-fluorophenyl)pyrazole-3-carboxamide |
| 19 | 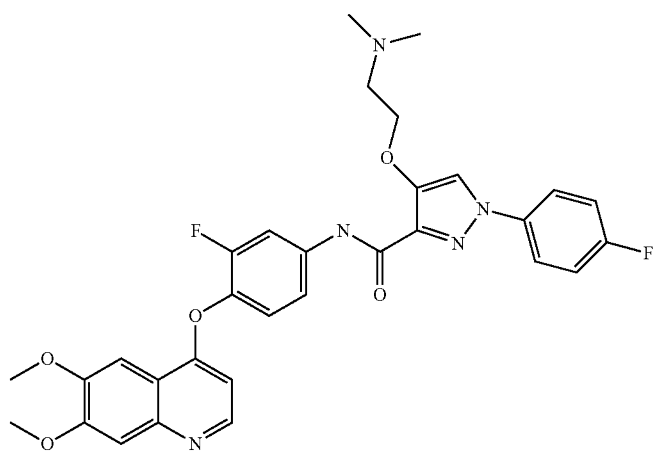 [SMILES: COc1cc2nccc(Oc3ccc(NC(=O)c4nn(-c5ccc(F)cc5)cc4OCCN(C)C)cc3F)c2cc1OC] | N-[4-[(6,7-dimethoxy-4-quinolyl)oxy]-3-fluoro-phenyl]-4-(2-dimethylaminoethoxy)-1-(4-fluorophenyl)pyrazole-3-carboxamide |
| 20 | 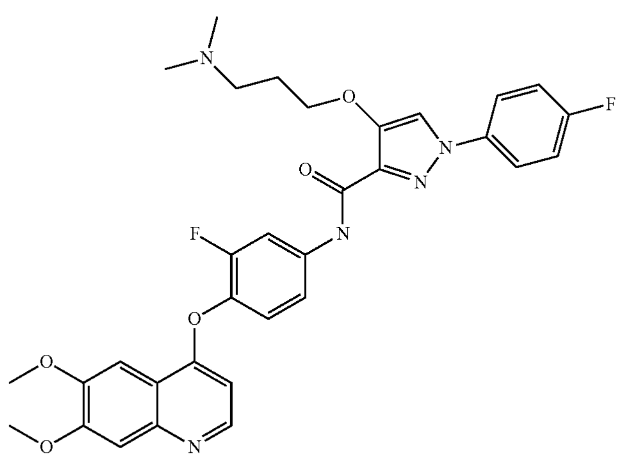 [SMILES: COc1cc2nccc(Oc3ccc(NC(=O)c4nn(-c5ccc(F)cc5)cc4OCCCN(C)C)cc3F)c2cc1OC] | N-[4-[(6,7-dimethoxy-4-quinolyl)oxy]-3-fluoro-phenyl]-4-(2-dimethylaminoethoxy)-1-(4-fluorophenyl)pyrazole-3-carboxamide |

TABLE 1-continued

| Example | Structure | Nomenclature |
|---|---|---|
| 21 | 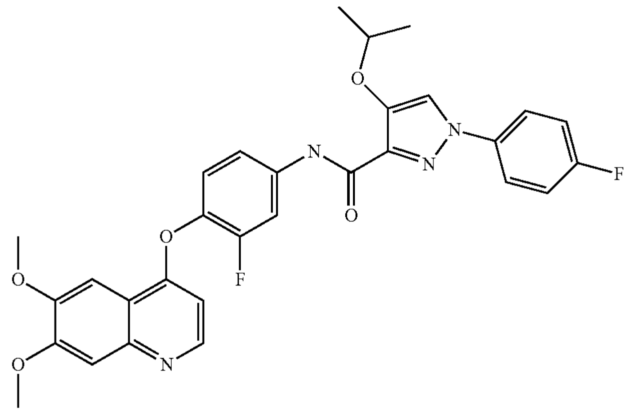 [SMILES: COc1cc2nccc(Oc3ccc(NC(=O)c4nn(-c5ccc(F)cc5)cc4OC(C)C)cc3F)c2cc1OC] | N-[4-[(6,7-dimethoxy-4-quinolyl)oxy]-3-fluoro-phenyl]-1-(4-fluorophenyl)-4-isopropoxy-pyrazole-3-carboxamide |
| 22 | 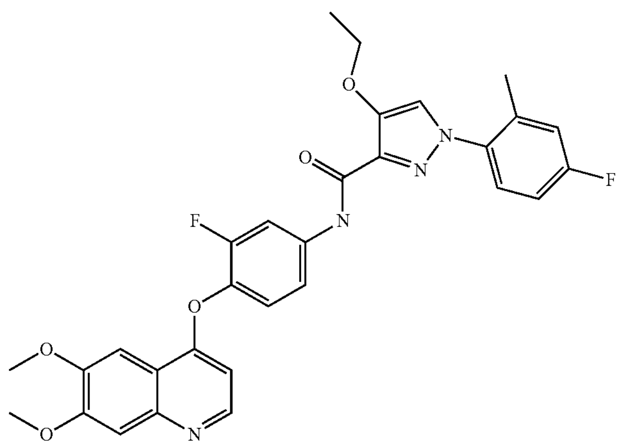 [SMILES: CCOc1cn(-c2ccc(F)cc2C)nc1C(=O)Nc1ccc(Oc2ccnc3cc(OC)c(OC)cc23)c(F)c1] | N-[4-[(6,7-dimethoxy-4-quinolyl)oxy]-3-fluoro-phenyl]-4-ethoxy-1-(4-fluoro-2-methyl-phenyl)pyrazole-3-carboxamide |
| 23 | 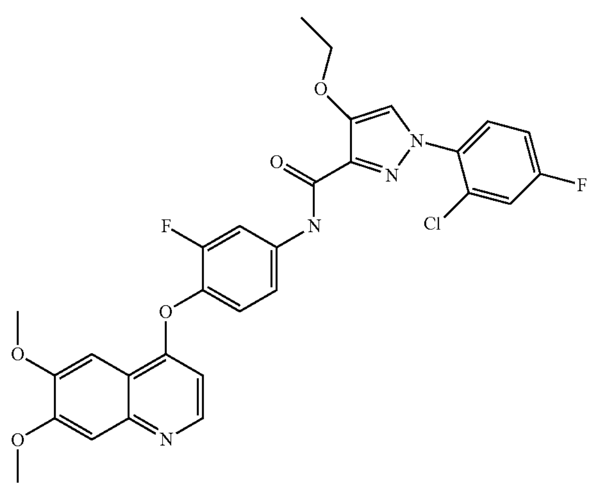 [SMILES: CCOc1cn(-c2ccc(F)cc2Cl)nc1C(=O)Nc1ccc(Oc2ccnc3cc(OC)c(OC)cc23)c(F)c1] | 1-(2-chloro-4-fluoro-phenyl)-N-[4-[(6,7-dimethoxy-4-quinolyl)oxy]-3-fluoro-phenyl]-4-ethoxy-pyrazole-3-carboxamide |

TABLE 1-continued

| Example | Structure | Nomenclature |
|---|---|---|
| 24 | 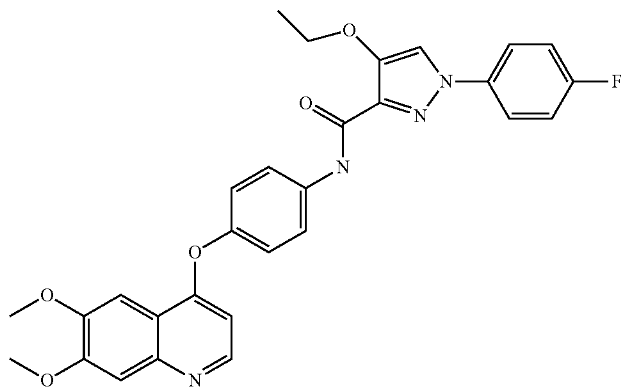 [SMILES: CCOc1cn(-c2ccc(F)cc2)nc1C(=O)Nc1ccc(Oc2ccnc3cc(OC)c(OC)cc23)cc1] | N-[4-[(6,7-dimethoxy-4-quinolyl)oxy]phenyl]-4-ethoxy-1-(4-fluorophenyl)pyrazole-3-carboxamide |
| 25 | 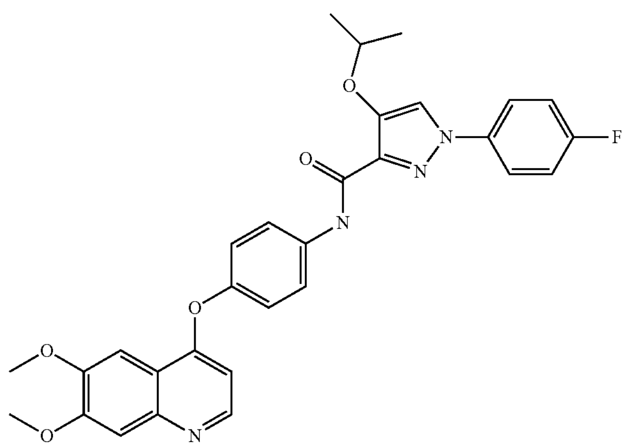 [SMILES: COc1cc2nccc(Oc3ccc(NC(=O)c4nn(-c5ccc(F)cc5)cc4OC(C)C)cc3)c2cc1OC] | N-[4-[(6,7-dimethoxy-4-quinolyl)oxy]phenyl]-1-(4-fluorophenyl)-4-isopropoxy-pyrazole-3-carboxamide |
| 26 | 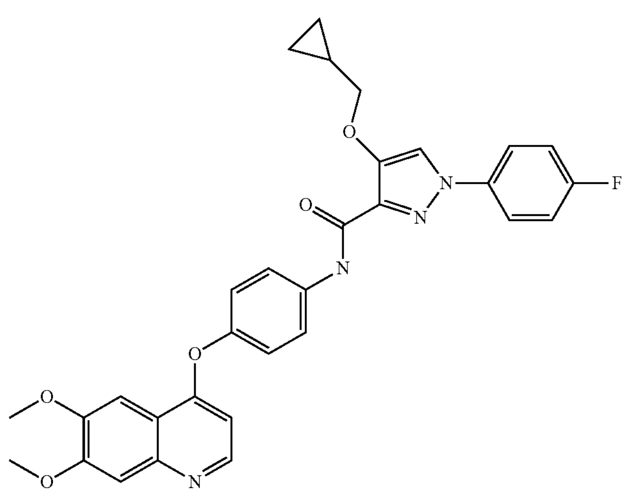 [SMILES: COc1cc2nccc(Oc3ccc(NC(=O)c4nn(-c5ccc(F)cc5)cc4OCC4CC4)cc3)c2cc1OC] | 4-(cyclopropylmethoxy)-N-[4-[(6,7-dimethoxy-4-quinolyl)oxy]phenyl]-1-(4-fluorophenyl)pyrazole-3-carboxamide |

TABLE 1-continued

| Example | Structure | Nomenclature |
|---|---|---|
| 27 | 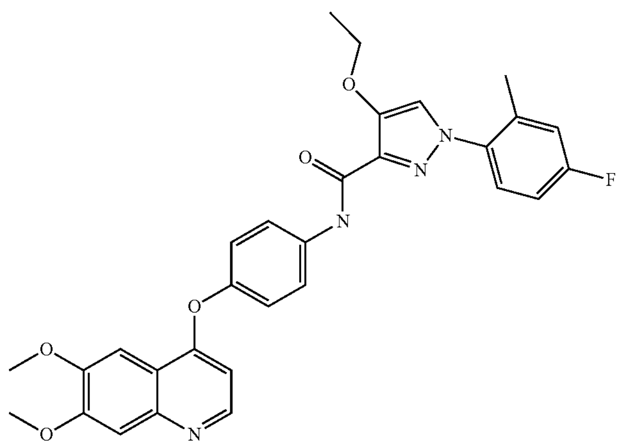 [SMILES: CCOc1cn(-c2ccc(F)cc2C)nc1C(=O)Nc1ccc(Oc2ccnc3cc(OC)c(OC)cc23)cc1] | N-[4-[(6,7-dimethoxy-4-quinolyl)oxy]phenyl]-4-ethoxy-1-(4-fluoro-2-methyl-phenyl)pyrazole-3-carboxamide |
| 28 | 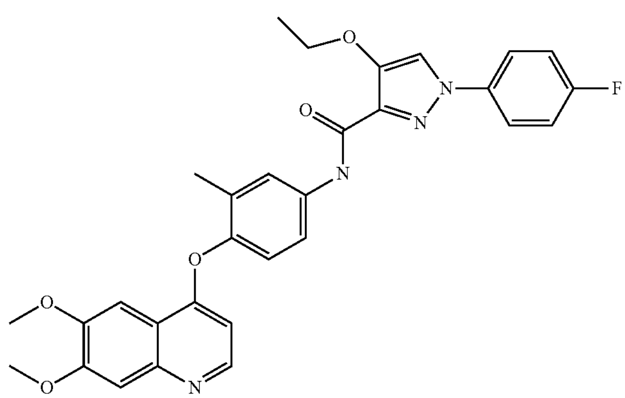 [SMILES: CCOc1cn(-c2ccc(F)cc2)nc1C(=O)Nc1ccc(Oc2ccnc3cc(OC)c(OC)cc23)c(C)c1] | N-[4-[(6,7-dimethoxy-4-quinolyl)oxy]-3-methyl-phenyl]-4-ethoxy-1-(4-fluorophenyl)pyrazole-3-carboxamide |
| 29 | 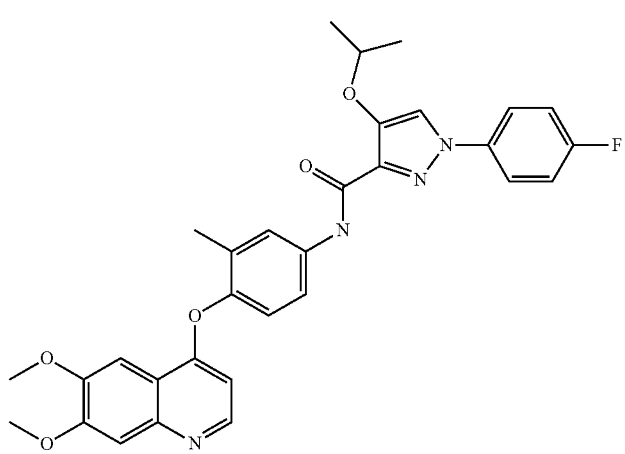 [SMILES: COc1cc2nccc(Oc3ccc(NC(=O)c4nn(-c5ccc(F)cc5)cc4OC(C)C)cc3C)c2cc1OC] | N-[4-[(6,7-dimethoxy-4-quinolyl)oxy]-3-methyl-phenyl]-1-(4-fluorophenyl)-4-isopropoxy-pyrazole-3-carboxamide |

TABLE 1-continued

| Example | Structure | Nomenclature |
|---|---|---|
| 30 | 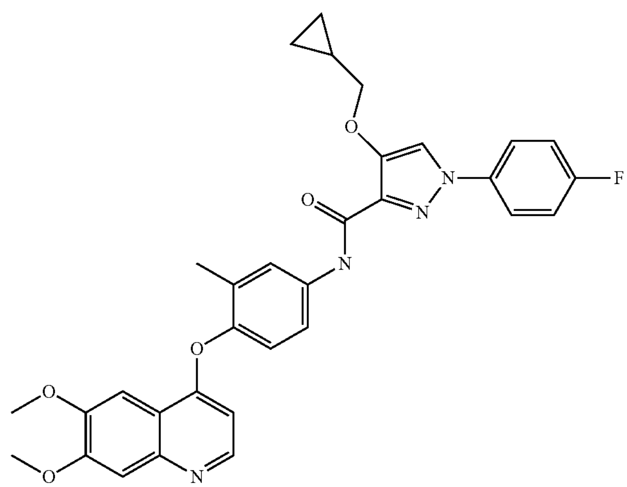 [SMILES: COc1cc2nccc(Oc3ccc(NC(=O)c4nn(-c5ccc(F)cc5)cc4OCC4CC4)cc3C)c2cc1OC] | 4-(cyclopropylmethoxy)-N-[4-[(6,7-dimethoxy-4-quinolyl)oxy]-3-methyl-phenyl]-1-(4-fluorophenyl)pyrazole-3-carboxamide |
| 31 | 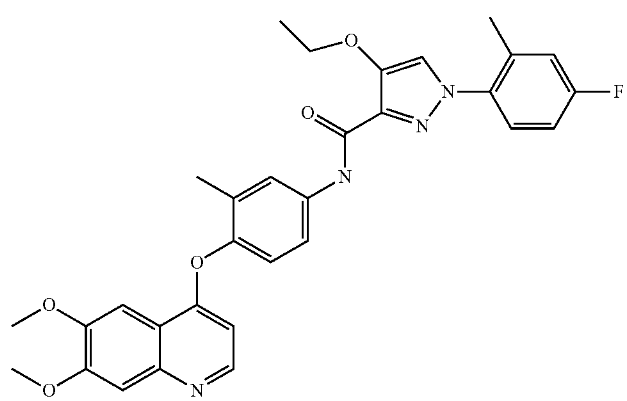 [SMILES: CCOc1cn(-c2ccc(F)cc2C)nc1C(=O)Nc1ccc(Oc2ccnc3cc(OC)c(OC)cc23)c(C)c1] | N-[4-[(6,7-dimethoxy-4-quinolyl)oxy]-3-methyl-phenyl]-4-ethoxy-1-(4-fluoro-2-methyl-phenyl)pyrazole-3-carboxamide |
| 32 | 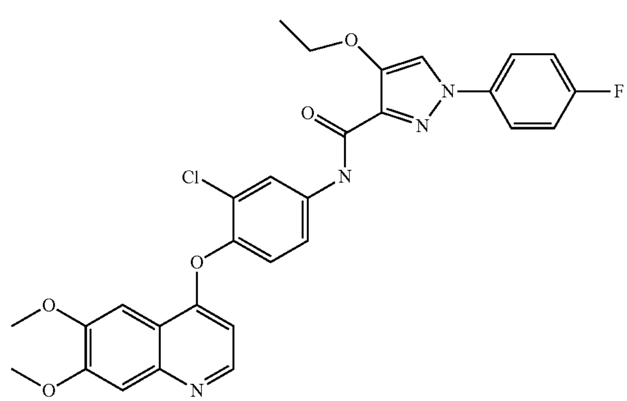 [SMILES: CCOc1cn(-c2ccc(F)cc2)nc1C(=O)Nc1ccc(Oc2ccnc3cc(OC)c(OC)cc23)c(Cl)c1] | N-[3-chloro-4-[(6,7-dimethoxy-4-quinolyl)oxy]phenyl]-4-ethoxy-1-(4-fluorophenyl)pyrazole-3-carboxamide |

TABLE 1-continued

| Example | Structure | Nomenclature |
|---|---|---|
| 33 | 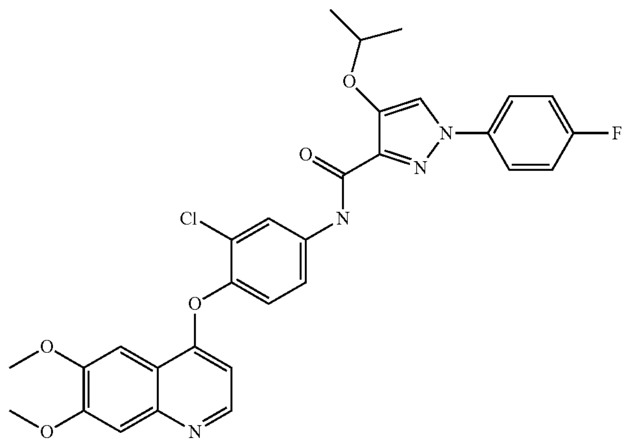 [SMILES: COc1cc2nccc(Oc3ccc(NC(=O)c4nn(-c5ccc(F)cc5)cc4OC(C)C)cc3Cl)c2cc1OC] | N-[3-chloro-4-[(6,7-dimethoxy-4-quinolyl)oxy]phenyl]-1-(4-fluorophenyl)-4-isopropoxy-pyrazole-3-carboxamide |
| 34 | 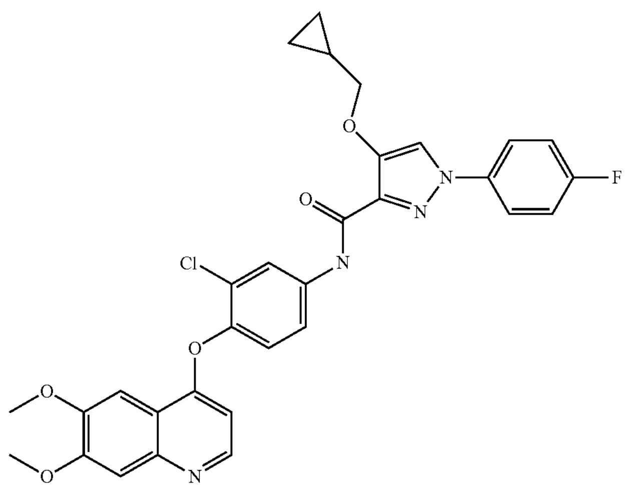 [SMILES: COc1cc2nccc(Oc3ccc(NC(=O)c4nn(-c5ccc(F)cc5)cc4OCC4CC4)cc3Cl)c2cc1OC] | N-[3-chloro-4-[(6,7-dimethoxy-4-quinolyl)oxy]phenyl]-4-(cyclopropylmethoxy)-1-(4-fluorophenyl)pyrazole-3-carboxamide |
| 35 | 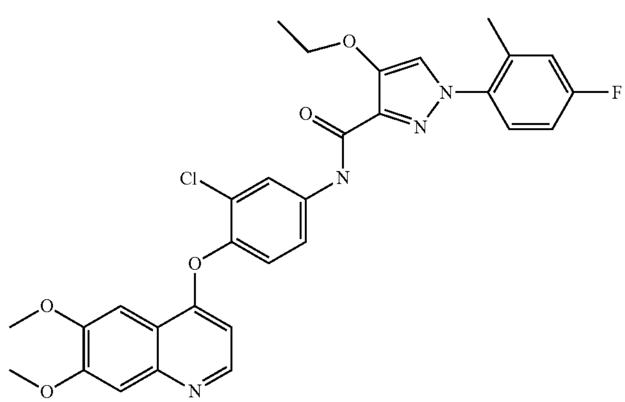 [SMILES: CCOc1cn(-c2ccc(F)cc2C)nc1C(=O)Nc1ccc(Oc2ccnc3cc(OC)c(OC)cc23)c(Cl)c1] | N-[3-chloro-4-[(6,7-dimethoxy-4-quinolyl)oxy]phenyl]-4-ethoxy-1-(4-fluoro-2-methyl-phenyl)pyrazole-3-carboxamide |

TABLE 1-continued

| Example | Structure | Nomenclature |
|---|---|---|
| 36 | 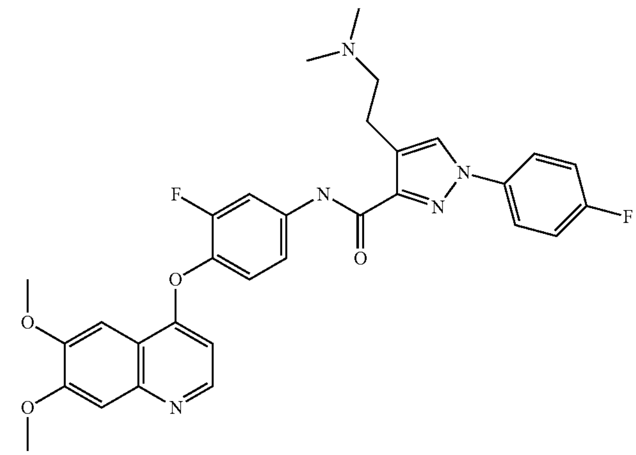 [SMILES: COc1cc2nccc(Oc3ccc(NC(=O)c4nn(-c5ccc(F)cc5)cc4CCN(C)C)cc3F)c2cc1OC] | N-(4-((6,7-dimethoxyquinolin-4-yl)oxy)-3-fluorophenyl)-4-(2-(dimethylamino)ethyl)-1-(4-fluorophenyl)-1H-pyrazole-3-carboxamide |
| 37 | 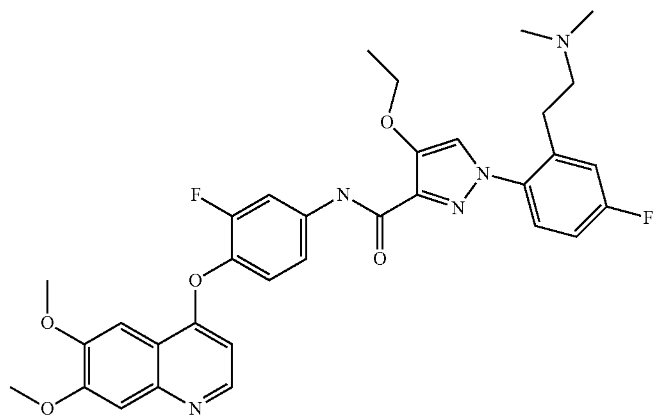 [SMILES: CCOc1cn(-c2ccc(F)cc2CCN(C)C)nc1C(=O)Nc1ccc(Oc2ccnc3cc(OC)c(OC)cc23)c(F)c1] | N-[4-[(6,7-dimethoxy-4-quinolyl)oxy]-3-fluoro-phenyl]-1-[2-(2-dimethylaminoethyl)-4-fluoro-phenyl]-4-ethoxy-pyrazole-3-carboxamide |
| 38 | 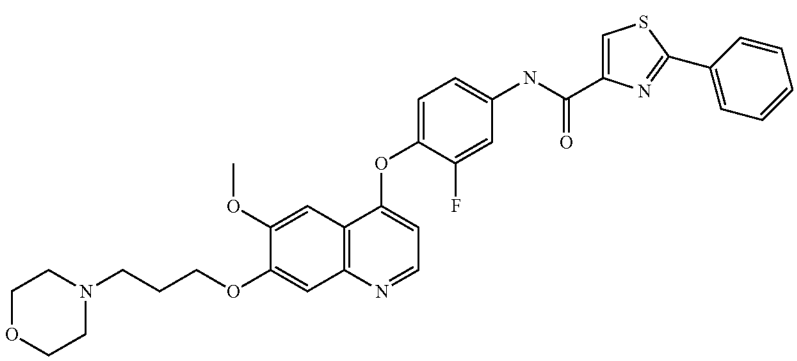 [SMILES: COc1cc2c(Oc3ccc(NC(=O)c4csc(-c5ccccc5)n4)cc3F)ccnc2cc1OCCCN1CCOCC1] | N-[3-fluoro-4-[[6-methoxy-7-(3-morpholinopropoxy)-4-quinolyl]oxy]phenyl]-2-phenyl-thiazole-4-carboxamide |
| 39 | 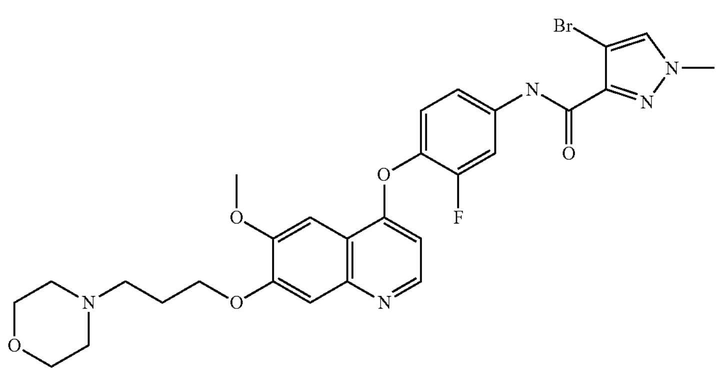 [SMILES: COc1cc2c(Oc3ccc(NC(=O)c4nn(C)cc4Br)cc3F)ccnc2cc1OCCCN1CCOCC1] | 4-bromo-N-[3-fluoro-4-[[6-methoxy-7-(3-morpholinopropoxy)-4-quinolyl]oxy]phenyl]-1-methyl-pyrazole-3-carboxamide |

TABLE 1-continued

| Example | Structure | Nomenclature |
|---|---|---|
| 40 | 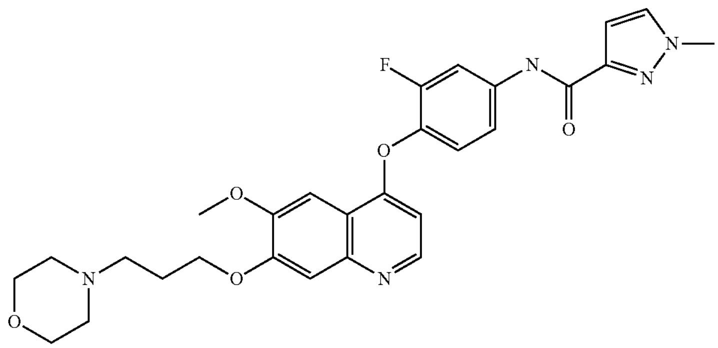 [SMILES: COc1cc2c(Oc3ccc(NC(=O)c4ccn(C)n4)cc3F)ccnc2cc1OCCCN1CCOCC1] | N-[3-fluoro-4-[[6-methoxy-7-(3-morpholinopropoxy)-4-quinolyl]oxy]phenyl]-1-methyl-pyrazole-3-carboxamide |
| 41 | 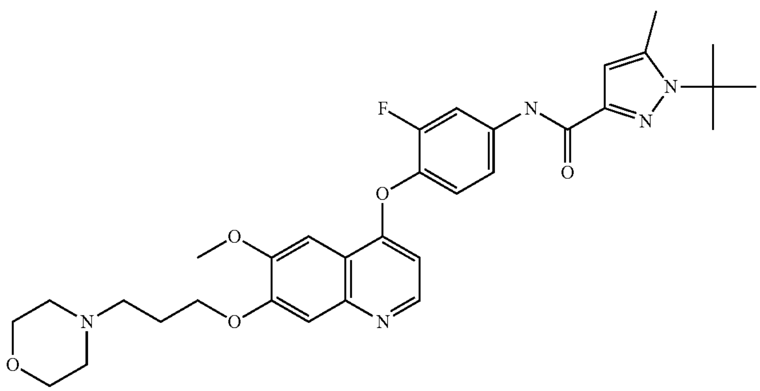 [SMILES: COc1cc2c(Oc3ccc(NC(=O)c4cc(C)n(C(C)(C)C)n4)cc3F)ccnc2cc1OCCCN1CCOCC1] | 1-tert-butyl-N-[3-fluoro-4-[[6-methoxy-7-(3-morpholinopropoxy)-4-quinolyl]oxy]phenyl]-5-methyl-pyrazole-3-carboxamide |
| 42 | 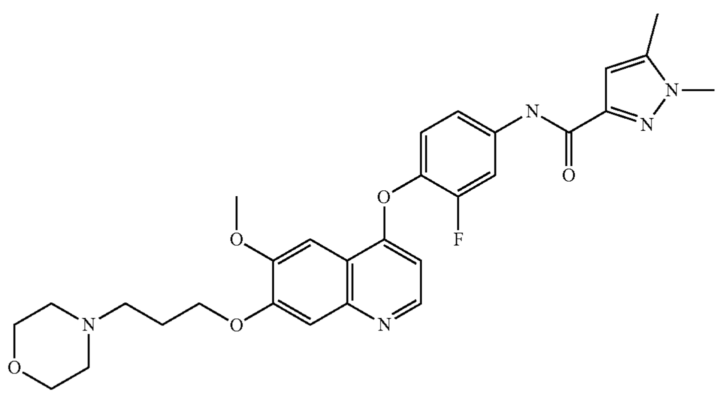 [SMILES: COc1cc2c(Oc3ccc(NC(=O)c4cc(C)n(C)n4)cc3F)ccnc2cc1OCCCN1CCOCC1] | N-[3-fluoro-4-[[6-methoxy-7-(3-morpholinopropoxy)-4-quinolyl]oxy]phenyl]-1,5-dimethyl-pyrazole-3-carboxamide |
| 43 | 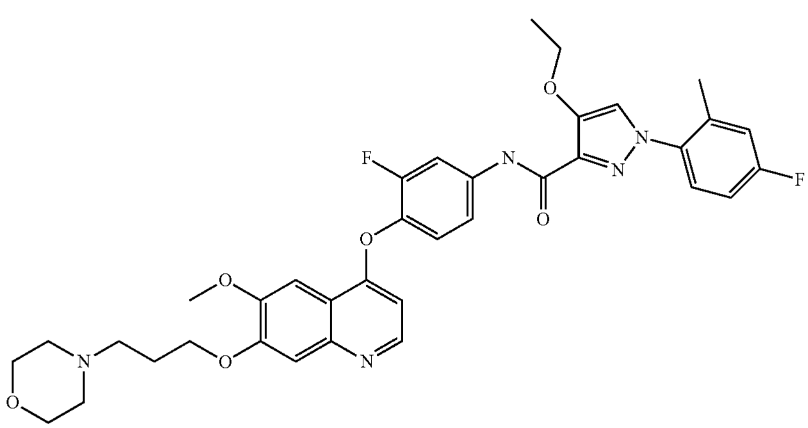 [SMILES: CCOc1cn(-c2ccc(F)cc2C)nc1C(=O)Nc1ccc(Oc2ccnc3cc(OCCCN4CCOCC4)c(OC)cc23)c(F)c1] | 4-ethoxy-N-[3-fluoro-4-[[6-methoxy-7-(3-morpholinopropoxy)-4-quinolyl]oxy]phenyl]-1-(4-fluoro-2-methyl-phenyl)pyrazole-3-carboxamide |

TABLE 1-continued

| Example | Structure | Nomenclature |
|---|---|---|
| 44 | 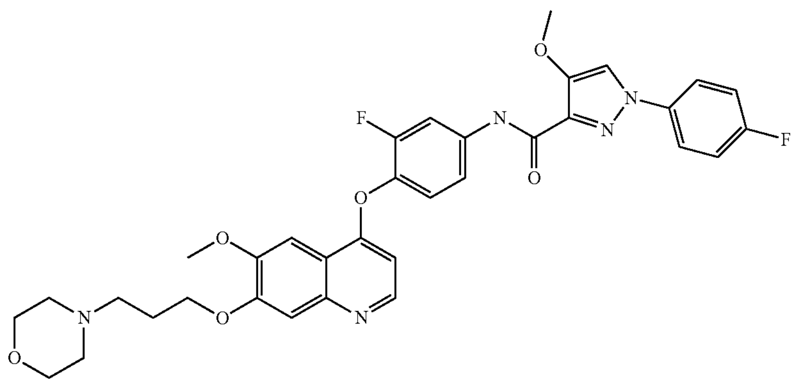 [SMILES: COc1cc2c(Oc3ccc(NC(=O)c4nn(-c5ccc(F)cc5)cc4OC)cc3F)ccnc2cc1OCCCN1CCOCC1] | N-[3-fluoro-4-[[6-methoxy-7-(3-morpholinopropoxy)-4-quinolyl]oxy]phenyl]-1-(4-fluorophenyl)-4-methoxy-pyrazole-3-carboxamide |
| 45 | 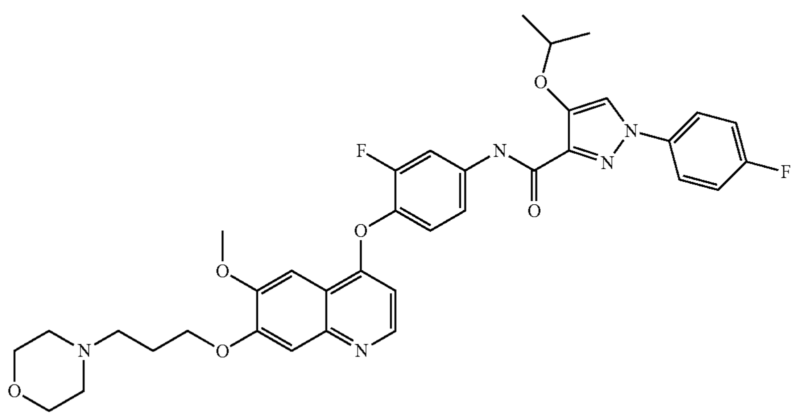 [SMILES: COc1cc2c(Oc3ccc(NC(=O)c4nn(-c5ccc(F)cc5)cc4OC(C)C)cc3F)ccnc2cc1OCCCN1CCOCC1] | N-[3-fluoro-4-[[6-methoxy-7-(3-morpholinopropoxy)-4-quinolyl]oxy]phenyl]-1-(4-fluorophenyl)-4-isopropoxy-pyrazole-3-carboxamide |
| 46 | 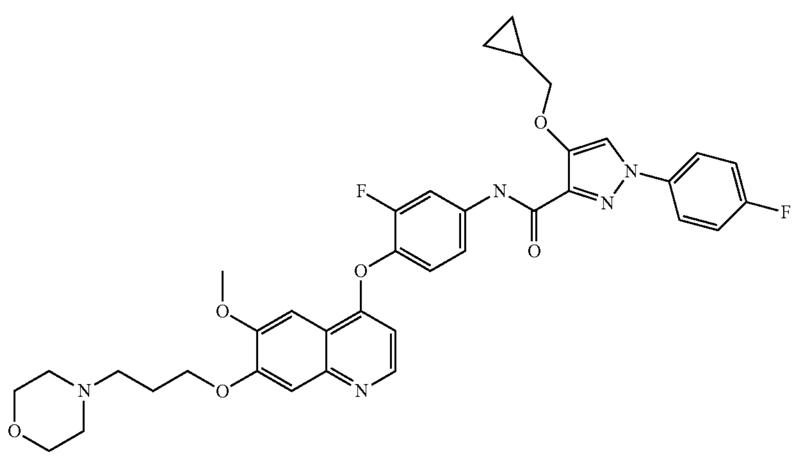 [SMILES: COc1cc2c(Oc3ccc(NC(=O)c4nn(-c5ccc(F)cc5)cc4OCC4CC4)cc3F)ccnc2cc1OCCCN1CCOCC1] | 4-(cyclopropylmethoxy)-N-[3-fluoro-4-[[6-methoxy-7-(3-morpholinopropoxy)-4-quinolyl]oxy]phenyl]-1-(4-fluorophenyl)pyrazole-3-carboxamide |

TABLE 1-continued

| Example | Structure | Nomenclature |
|---|---|---|
| 47 | 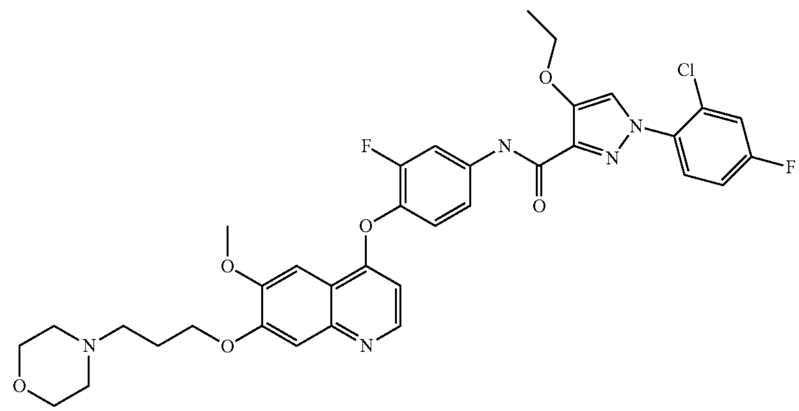 [SMILES: CCOc1cn(-c2ccc(F)cc2Cl)nc1C(=O)Nc1ccc(Oc2ccnc3cc(OCCCN4CCOCC4)c(OC)cc23)c(F)c1] | 1-(2-chloro-4-fluoro-phenyl)-4-ethoxy-N-[3-fluoro-4-[[6-methoxy-7-(3-morpholinopropoxy)-4-quinolyl]oxy]phenyl]pyrazole-3-carboxamide |
| 48 | 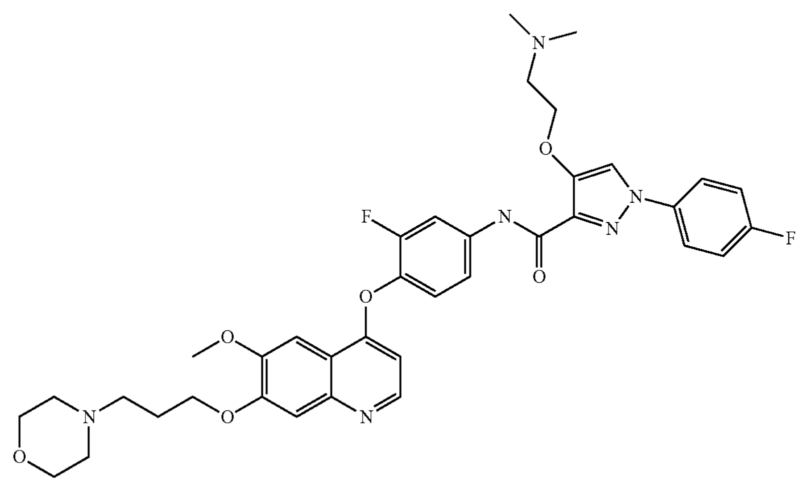 [SMILES: COc1cc2c(Oc3ccc(NC(=O)c4nn(-c5ccc(F)cc5)cc4OCCN(C)C)cc3F)ccnc2cc1OCCCN1CCOCC1] | 4-(2-dimethylaminoethoxy)-N-[3-fluoro-4-[[6-methoxy-7-(3-morpholinopropoxy)-4-quinolyl]oxy]phenyl]-1-(4-fluorophenyl)pyrazole-3-carboxamide |
| 49 | 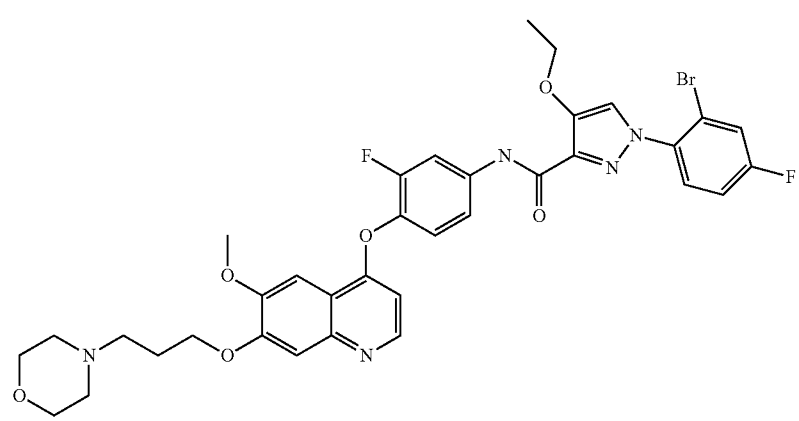 | 1-(2-bromo-4-fluoro-phenyl)-4-ethoxy-N-[3-fluoro-4-[[6-methoxy-7-(3-morpholinopropoxy)-4-quinolyl]oxy]phenyl]pyrazole-3-carboxamide |

TABLE 1-continued

| Example | Structure | Nomenclature |
|---|---|---|
| 50 | 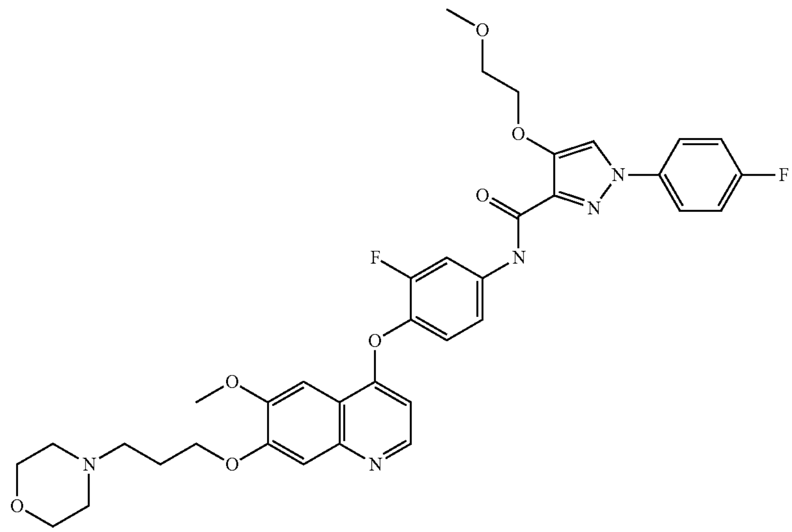 [SMILES: COCCOc1cn(-c2ccc(F)cc2)nc1C(=O)Nc1ccc(Oc2ccnc3cc(OCCCN4CCOCC4)c(OC)cc23)c(F)c1] | N-[3-fluoro-4-[[6-methoxy-7-(3-morpholinopropoxy)-4-quinolyl]oxy]phenyl]-1-(4-fluorophenyl)-4-(2-methoxyethoxy)pyrazole-3-carboxamide |
| 51 | 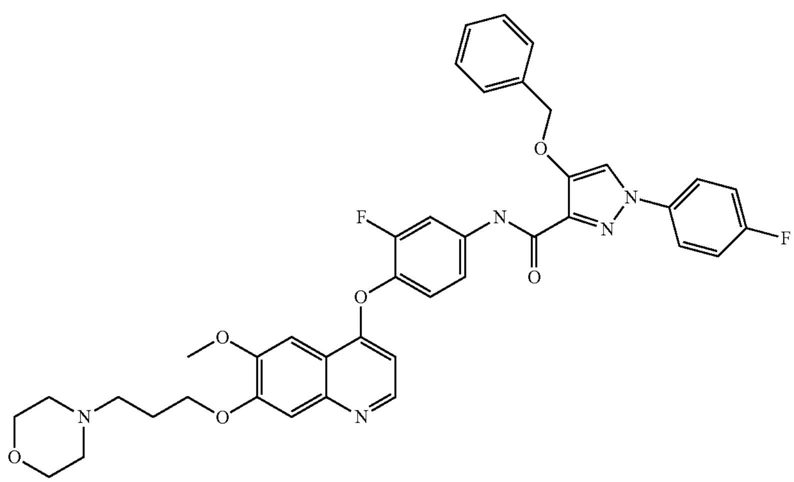 [SMILES: COc1cc2c(Oc3ccc(NC(=O)c4nn(-c5ccc(F)cc5)cc4OCc4ccccc4)cc3F)ccnc2cc1OCCCN1CCOCC1] | 4-benzyloxy-N-[3-fluoro-4-[[6-methoxy-7-(3-morpholinopropoxy)-4-quinolyl]oxy]phenyl]-1-(4-fluorophenyl)pyrazole-3-carboxamide |
| 52 | 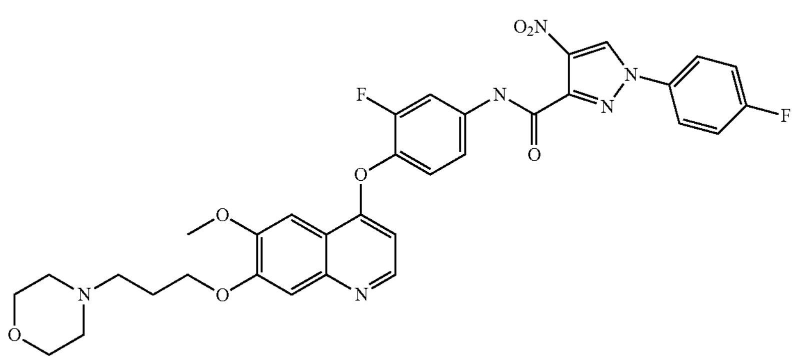 [SMILES: COc1cc2c(Oc3ccc(NC(=O)c4nn(-c5ccc(F)cc5)cc4[N+](=O)[O-])cc3F)ccnc2cc1OCCCN1CCOCC1] | N-[3-fluoro-4-[[6-methoxy-7-(3-morpholinopropoxy)-4-quinolyl]oxy]phenyl]-1-(4-fluorophenyl)-4-nitro-pyrazole-3-carboxamide |

TABLE 1-continued

| Example | Structure | Nomenclature |
|---|---|---|
| 53 | 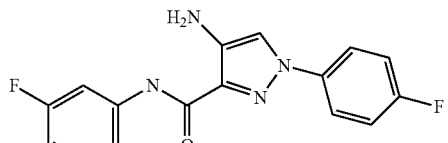 | 4-amino-N-[3-fluoro-4-[[6-methoxy-7-(3-morpholinopropoxy)-4-quinolyl]oxy]phenyl]-1-(4-fluorophenyl)pyrazole-3-carboxamide |
| 54 | 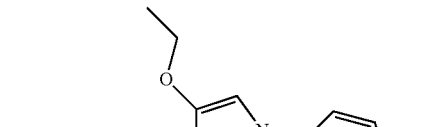 | N-[4-[[7-(3-aminopropoxy)-6-methoxy-4-quinolyl]oxy]-3-fluoro-phenyl]-4-ethoxy-1-(4-fluorophenyl)pyrazole-3-carboxamide |
| 55 | 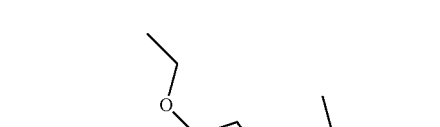 | N-[4-[[7-(3-aminopropoxy)-6-methoxy-4-quinolyl]oxy]-3-fluoro-phenyl]-4-ethoxy-1-(4-fluoro-2-methyl-phenyl)pyrazole-3-carboxamide |
| 56 | 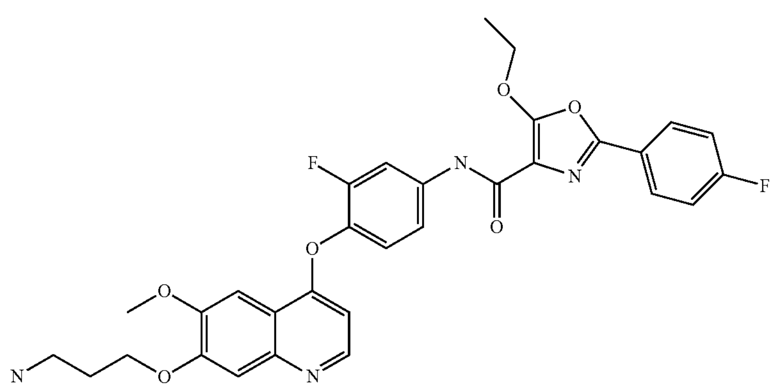 [SMILES: CCOc1oc(-c2ccc(F)cc2)nc1C(=O)Nc1ccc(Oc2ccnc3cc(OCCCN)c(OC)cc23)c(F)c1] | N-[4-[[7-(3-aminopropoxy)-6-methoxy-4-quinolyl]oxy]-3-fluoro-phenyl]-5-ethoxy-2-(4-fluorophenyl)oxazole-4-carboxamide |

TABLE 1-continued

| Example | Structure | Nomenclature |
|---|---|---|
| 57 | 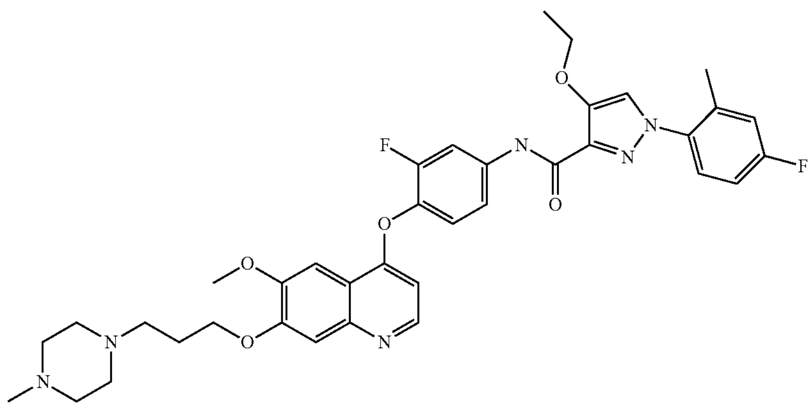 [SMILES: CCOc1cn(-c2ccc(F)cc2C)nc1C(=O)Nc1ccc(Oc2ccnc3cc(OCCCN4CCN(C)CC4)c(OC)cc23)c(F)c1] | 4-ethoxy-N-[3-fluoro-4-[[6-methoxy-7-[3-(4-methylpiperazin-1-yl)propoxy]-4-quinolyl]oxy]phenyl]-1-(4-fluoro-2-methyl-phenyl)pyrazole-3-carboxamide |
| 58 | 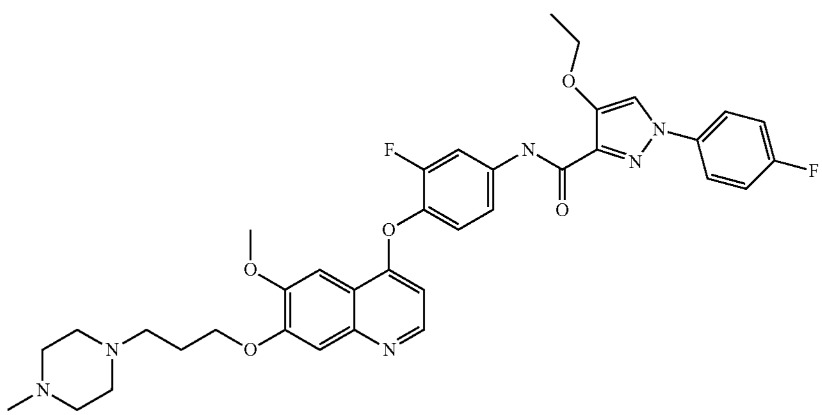 [SMILES: CCOc1cn(-c2ccc(F)cc2)nc1C(=O)Nc1ccc(Oc2ccnc3cc(OCCCN4CCN(C)CC4)c(OC)cc23)c(F)c1] | 4-ethoxy-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide |
| 59 | 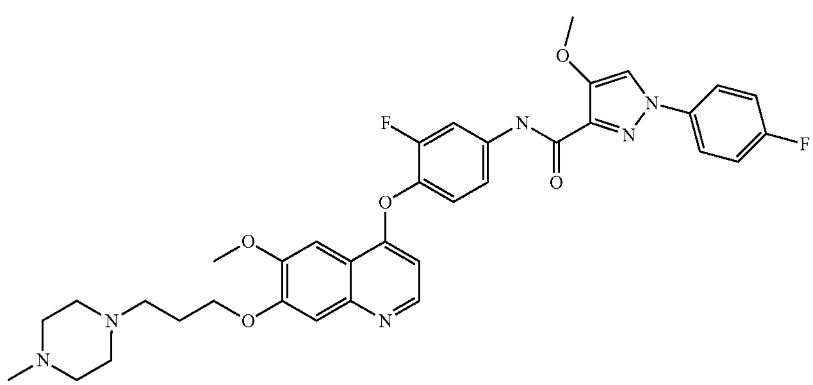 [SMILES: COc1cc2c(Oc3ccc(NC(=O)c4nn(-c5ccc(F)cc5)cc4OC)cc3F)ccnc2cc1OCCCN1CCN(C)CC1] | N-[3-fluoro-4-[[6-methoxy-7-[3-(4-methylpiperazin-1-yl)propoxy]-4-quinolyl]oxy]phenyl]-1-(4-fluorophenyl)-4-methoxy-pyrazole-3-carboxamide |

TABLE 1-continued

| Example | Structure | Nomenclature |
|---|---|---|
| 60 | 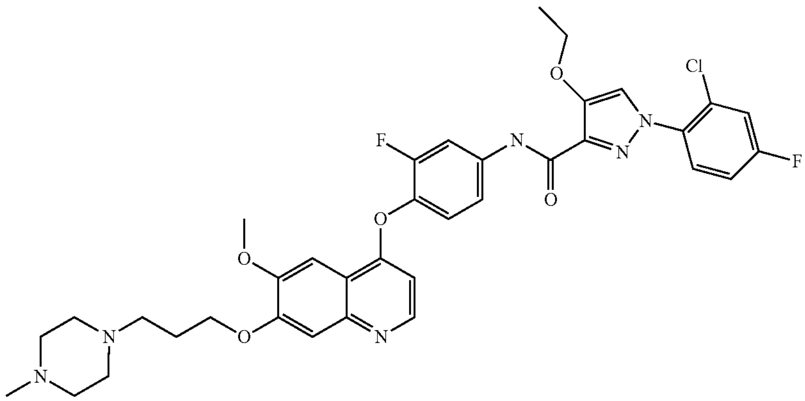 [SMILES: CCOc1cn(-c2ccc(F)cc2Cl)nc1C(=O)Nc1ccc(Oc2ccnc3cc(OCCCN4CCN(C)CC4)c(OC)cc23)c(F)c1] | 1-(2-chloro-4-fluoro-phenyl)-4-ethoxy-N-[3-fluoro-4-[[6-methoxy-7-[3-(4-methylpiperazin-1-yl)propoxy]-4-quinolyl]oxy]phenyl]pyrazole-3-carboxamide |
| 61 | 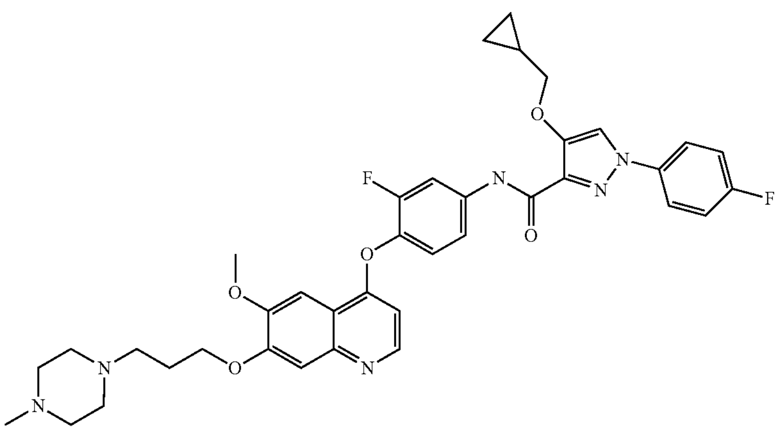 [SMILES: COc1cc2c(Oc3ccc(NC(=O)c4nn(-c5ccc(F)cc5)cc4OCC4CC4)cc3F)ccnc2cc1OCCCN1CCN(C)CC1] | 4-(cyclopropylmethoxy)-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide |
| 62 | 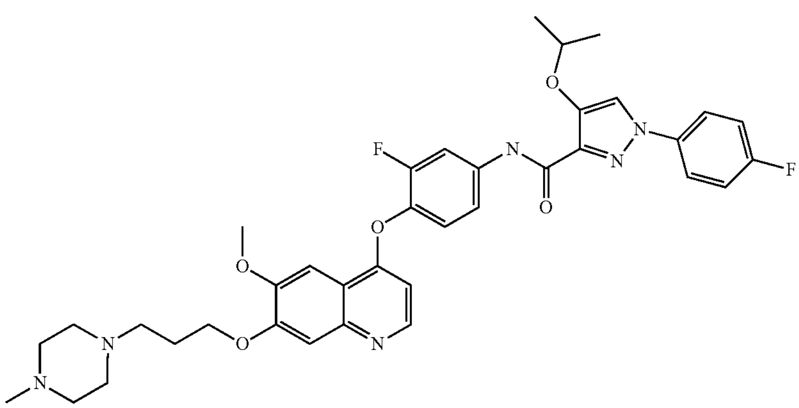 [SMILES: COc1cc2c(Oc3ccc(NC(=O)c4nn(-c5ccc(F)cc5)cc4OC(C)C)cc3F)ccnc2cc1OCCCN1CCN(C)CC1] | N-[3-fluoro-4-[[6-methoxy-7-[3-(4-methylpiperazin-1-yl)propoxy]-4-quinolyl]oxy]phenyl]-1-(4-fluorophenyl)-4-isopropoxy-pyrazole-3-carboxamide |

TABLE 1-continued

| Example | Structure | Nomenclature |
|---|---|---|
| 63 | 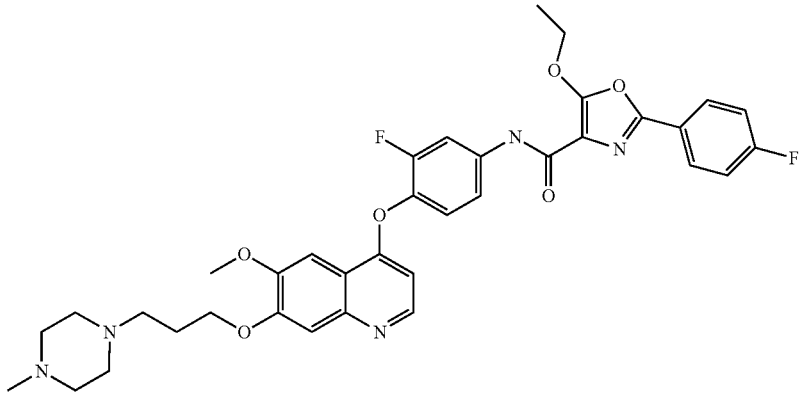 [SMILES: CCOc1oc(-c2ccc(F)cc2)nc1C(=O)Nc1ccc(Oc2ccnc3cc(OCCCN4CCN(C)CC4)c(OC)cc23)c(F)c1] | 5-ethoxy-N-[3-fluoro-4-[[6-methoxy-7-[3-(4-methylpiperazin-1-yl)propoxy]-4-quinolyl]oxy]phenyl]-2-(4-fluorophenyl)oxazole-4-carboxamide |
| 64 | 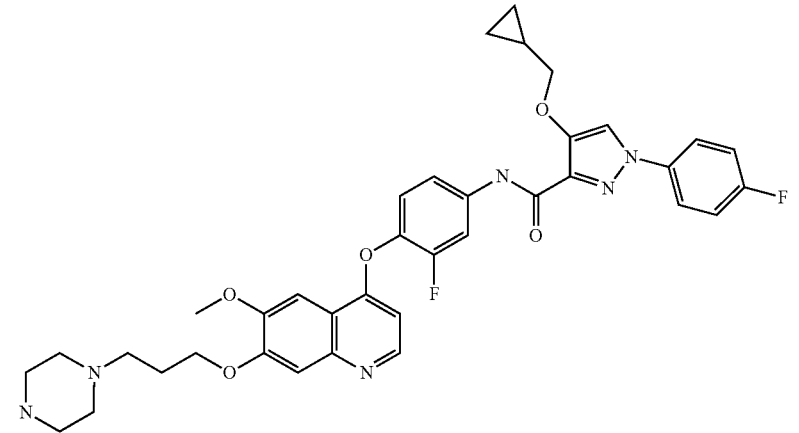 [SMILES: COc1cc2c(Oc3ccc(NC(=O)c4nn(-c5ccc(F)cc5)cc4OCC4CC4)cc3F)ccnc2cc1OCCCN1CCNCC1] | 4-(cyclopropylmethoxy)-N-[3-fluoro-4-[[6-methoxy-7-(3-piperazin-1-ylpropoxy)-4-quinolyl]oxy]phenyl]-1-(4-fluorophenyl)pyrazole-3-carboxamide trifluoroacetic acid salt |
| 65 | 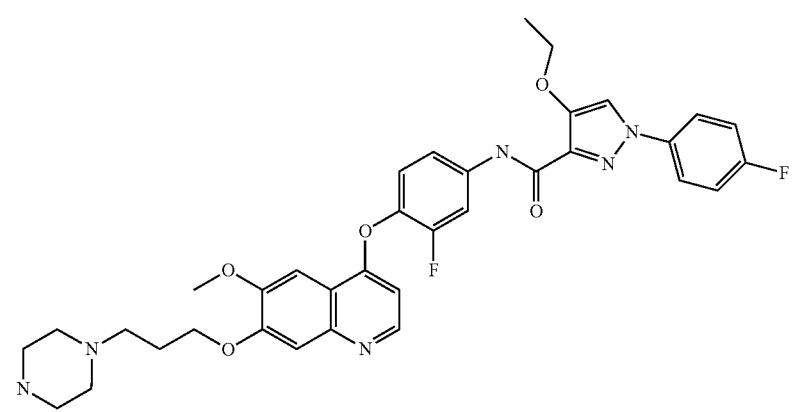 | 4-ethoxy-N-[3-fluoro-4-[[6-methoxy-7-(3-piperazin-1-ylpropoxy)-4-quinolyl]oxy]phenyl]-1-(4-fluorophenyl)pyrazole-3-carboxamide |

TABLE 1-continued

| Example | Structure | Nomenclature |
|---|---|---|
| 66 | 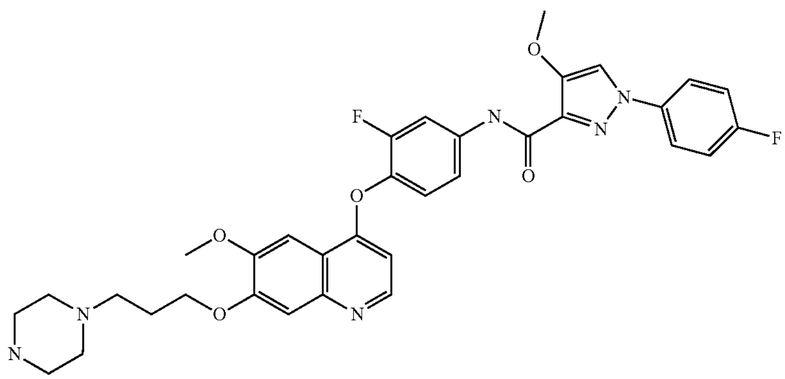 [SMILES: COc1cc2c(Oc3ccc(NC(=O)c4nn(-c5ccc(F)cc5)cc4OC)cc3F)ccnc2cc1OCCCN1CCNCC1] | N-[3-fluoro-4-[[6-methoxy-7-(3-piperazin-1-ylpropoxy)-4-quinolyl]oxy]phenyl]-1-(4-fluorophenyl)-4-methoxy-pyrazole-3-carboxamide |
| 67 | 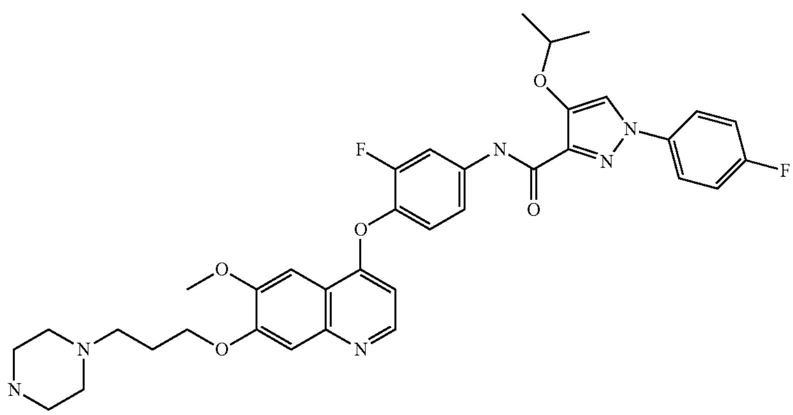 [SMILES: COc1cc2c(Oc3ccc(NC(=O)c4nn(-c5ccc(F)cc5)cc4OC(C)C)cc3F)ccnc2cc1OCCCN1CCNCC1] | N-[3-fluoro-4-[[6-methoxy-7-(3-piperazin-1-ylpropoxy)-4-quinolyl]oxy]phenyl]-1-(4-fluorophenyl)-4-isopropoxy-pyrazole-3-carboxamide |
| 68 | 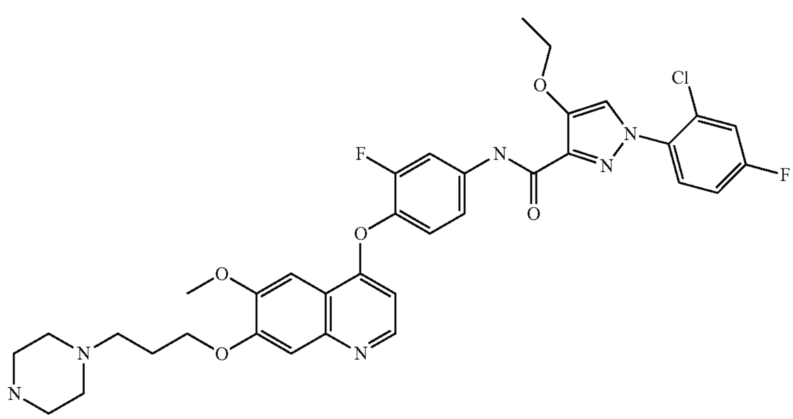 [SMILES: CCOc1cn(-c2ccc(F)cc2Cl)nc1C(=O)Nc1ccc(Oc2ccnc3cc(OCCCN4CCNCC4)c(OC)cc23)c(F)c1] | 1-(2-chloro-4-fluoro-phenyl)-4-ethoxy-N-[3-fluoro-4-[[6-methoxy-7-(3-piperazin-1-ylpropoxy)-4-quinolyl]oxy]phenyl]pyrazole-3-carboxamide |

TABLE 1-continued

| Example | Structure | Nomenclature |
|---|---|---|
| 69 | 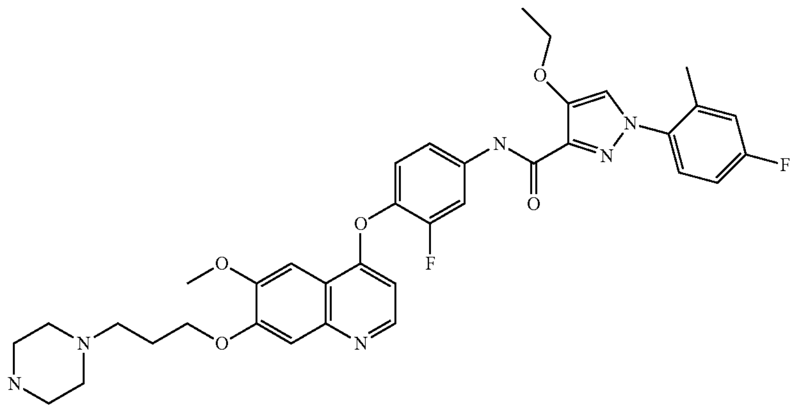 [SMILES: CCOc1cn(-c2ccc(F)cc2C)nc1C(=O)Nc1ccc(Oc2ccnc3cc(OCCCN4CCNCC4)c(OC)cc23)c(F)c1] | 4-ethoxy-N-[3-fluoro-4-[[6-methoxy-7-(3-piperazin-1-ylpropoxy)-4-quinolyl]oxy]phenyl]-1-(4-fluoro-2-methyl-phenyl)pyrazole-3-carboxamide |
| 70 | 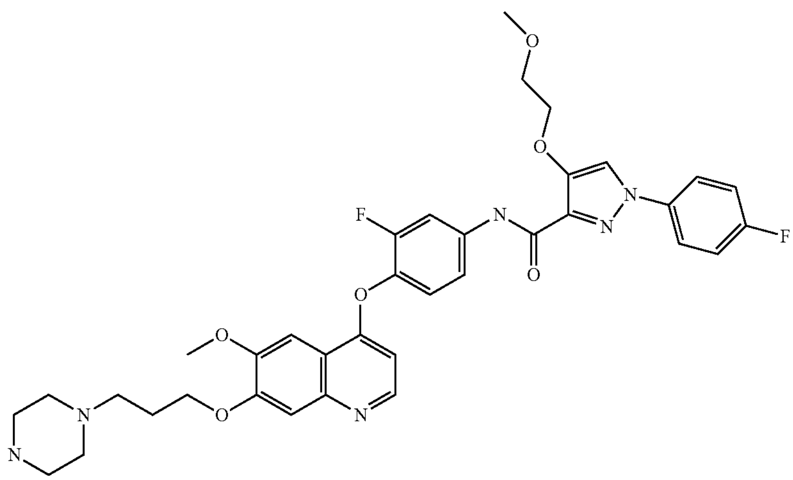 [SMILES: COCCOc1cn(-c2ccc(F)cc2)nc1C(=O)Nc1ccc(Oc2ccnc3cc(OCCCN4CCNCC4)c(OC)cc23)c(F)c1] | N-[3-fluoro-4-[[6-methoxy-7-(3-piperazin-1-ylpropoxy)-4-quinolyl]oxy]phenyl]-1-(4-fluorophenyl)-4-(2-methoxyethoxy)pyrazole-3-carboxamide |
| 71 | 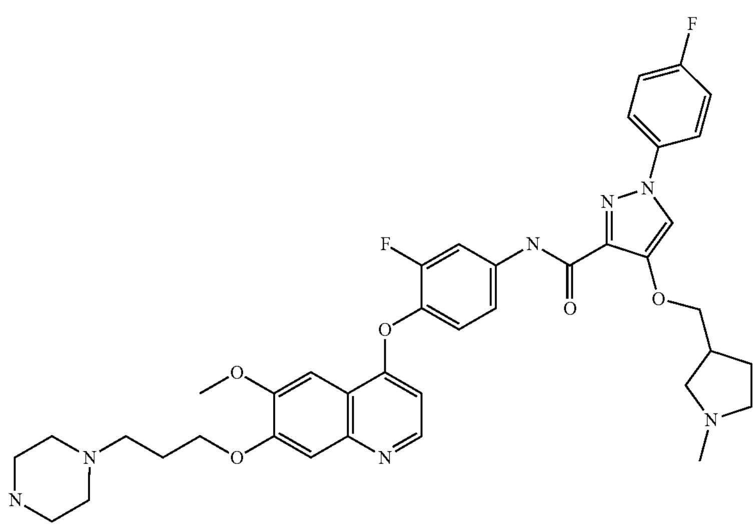 [SMILES: COc1cc2c(Oc3ccc(NC(=O)c4nn(-c5ccc(F)cc5)cc4OCC4CCN(C)C4)cc3F)ccnc2cc1OCCCN1CCNCC1] | N-[3-fluoro-4-[[6-methoxy-7-(3-piperazin-1-ylpropoxy)-4-quinolyl]oxy]phenyl]-1-(4-fluorophenyl)-4-[(1-methylpyrrolidin-3-yl)methoxy]pyrazole-3-carboxamide |

TABLE 1-continued

| Example | Structure | Nomenclature |
|---|---|---|
| 72 | 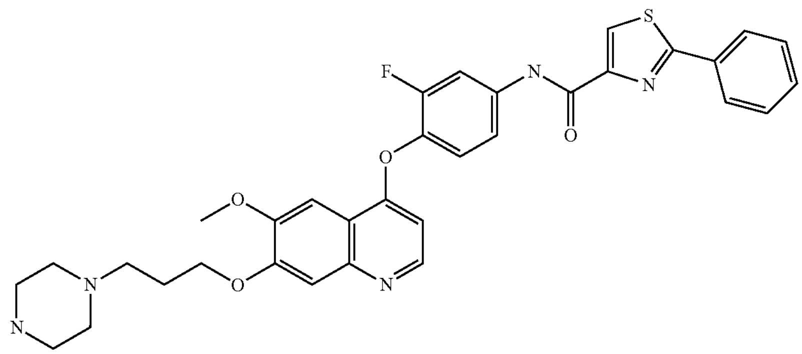 [SMILES: COc1cc2c(Oc3ccc(NC(=O)c4csc(-c5ccccc5)n4)cc3F)ccnc2cc1OCCCN1CCNCC1] | N-[3-fluoro-4-[[6-methoxy-7-(3-piperazin-1-ylpropoxy)-4-quinolyl]oxy]phenyl]-2-phenyl-thiazole-4-carboxamide |
| 73 | 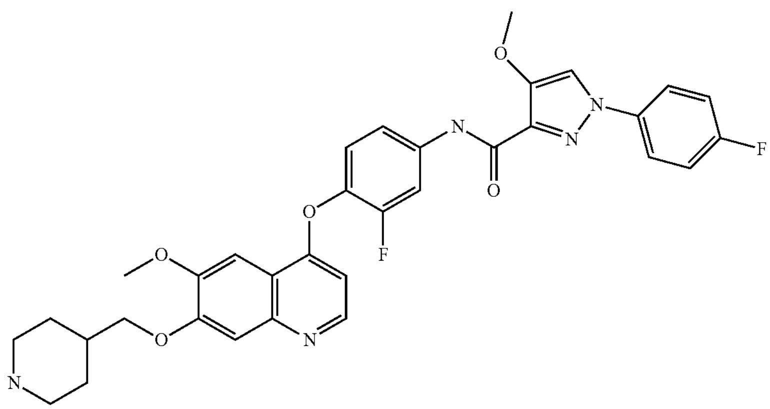 [SMILES: COc1cc2c(Oc3ccc(NC(=O)c4nn(-c5ccc(F)cc5)cc4OC)cc3F)ccnc2cc1OCC1CCNCC1] | N-[3-fluoro-4-[[6-methoxy-7-(4-piperidylmethoxy)-4-quinolyl]oxy]phenyl]-1-(4-fluorophenyl)-4-methoxy-pyrazole-3-carboxamide |
| 74 | 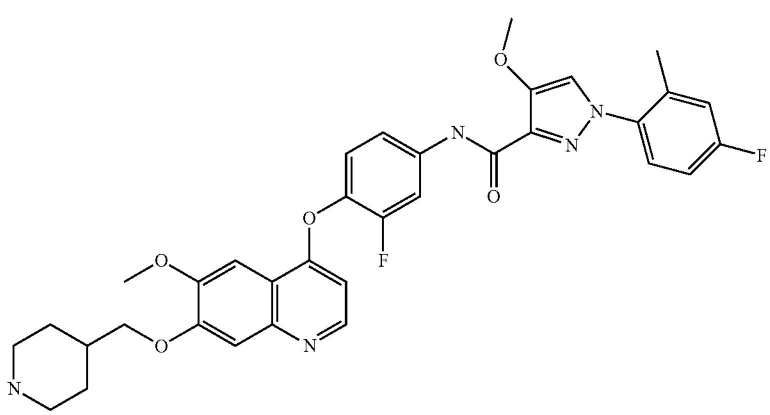 [SMILES: COc1cc2c(Oc3ccc(NC(=O)c4nn(-c5ccc(F)cc5C)cc4OC)cc3F)ccnc2cc1OCC1CCNCC1] | 4-ethoxy-N-[3-fluoro-4-[[6-methoxy-7-(4-piperidylmethoxy)-4-quinolyl]oxy]phenyl]-1-(4-fluoro-2-methyl-phenyl)pyrazole-3-carboxamide |

TABLE 1-continued

| Example | Structure | Nomenclature |
|---|---|---|
| 75 | 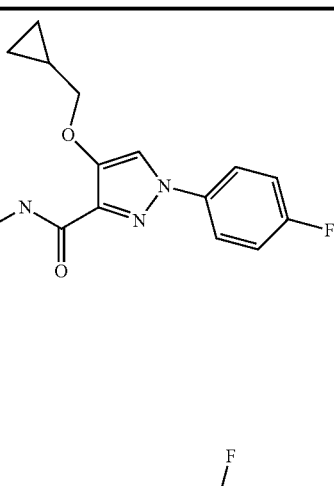 | 4-(cyclopropylmethoxy)-N-[3-fluoro-4-[[6-methoxy-7-(4-piperidylmethoxy)-4-quinolyl]oxy]phenyl]-1-(4-fluorophenyl)pyrazole-3-carboxamide |
| 76 | 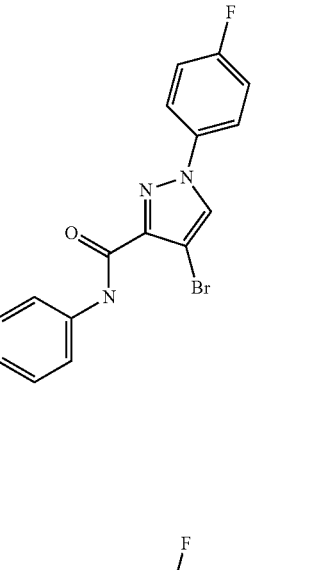 | 4-bromo-N-[3-fluoro-4-[[6-methoxy-7-(4-piperidylmethoxy)-4-quinolyl]oxy]phenyl]-1-(4-fluorophenyl)pyrazole-3-carboxamide |
| 77 | 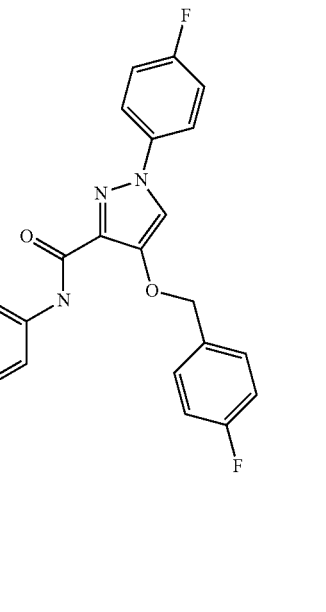 | N-[3-fluoro-4-[[6-methoxy-7-(4-piperidylmethoxy)-4-quinolyl]oxy]phenyl]-1-(4-fluorophenyl)-4-[(4-fluorophenyl)methoxy]pyrazole-3-carboxamide |

TABLE 1-continued

| Example | Structure | Nomenclature |
|---|---|---|
| 78 | 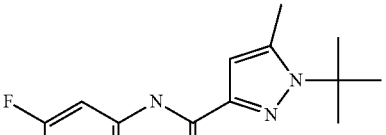 | 1-tert-butyl-N-[3-fluoro-4-[[6-methoxy-7-(4-piperidylmethoxy)-4-quinolyl]oxy]phenyl]-5-methyl-pyrazole-3-carboxamide |
| 79 | 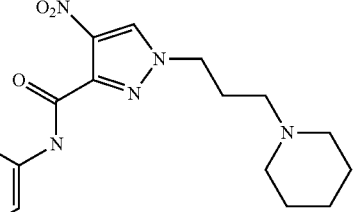 | N-[3-fluoro-4-[[6-methoxy-7-(4-piperidylmethoxy)-4-quinolyl]oxy]phenyl]-4-nitro-1-[3-(1-piperidyl)propyl]pyrazole-3-carboxamide |
| 80 | 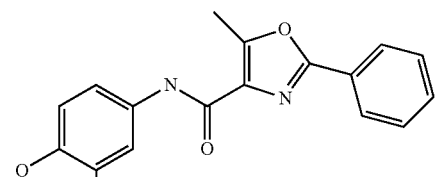 | N-[3-fluoro-4-[[6-methoxy-7-(4-piperidylmethoxy)-4-quinolyl]oxy]phenyl]-5-methyl-2-phenyl-oxazole-4-carboxamide |
| 81 | 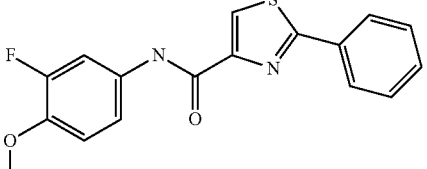 | N-[3-fluoro-4-[[6-methoxy-7-(4-piperidylmethoxy)-4-quinolyl]oxy]phenyl]-2-phenyl-thiazole-4-carboxamide |

TABLE 1-continued

| Example | Structure | Nomenclature |
|---|---|---|
| 82 | 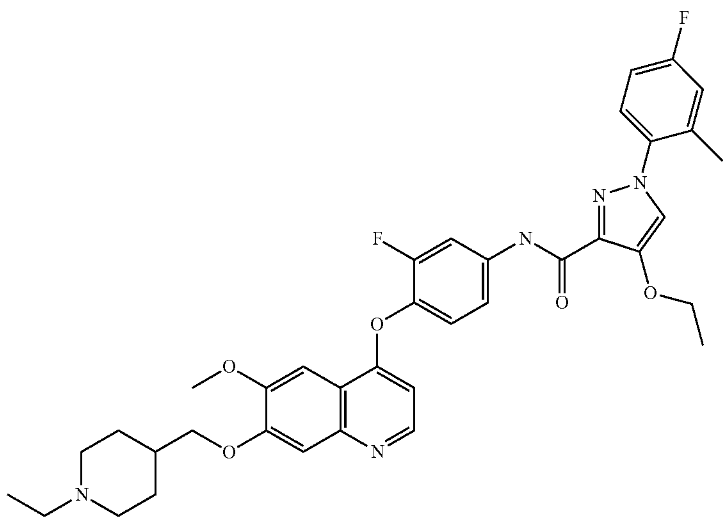 [SMILES: CCOc1cn(-c2ccc(F)cc2C)nc1C(=O)Nc1ccc(Oc2ccnc3cc(OCC4CCN(CC)CC4)c(OC)cc23)c(F)c1] | 4-ethoxy-N-[4-[[7-[(1-ethyl-4-piperidyl)methoxy]-6-methoxy-4-quinolyl]oxy]-3-fluoro-phenyl]-1-(4-fluoro-2-methyl-phenyl)pyrazole-3-carboxamide |
| 83 | 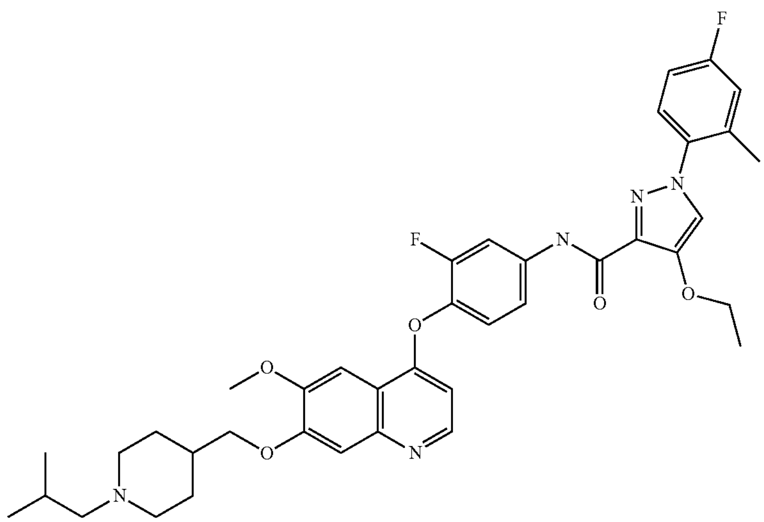 [SMILES: CCOc1cn(-c2ccc(F)cc2C)nc1C(=O)Nc1ccc(Oc2ccnc3cc(OCC4CCN(CC(C)C)CC4)c(OC)cc23)c(F)c1] | 4-ethoxy-N-[3-fluoro-4-[[7-[(1-isobutyl-4-piperidyl)methoxy]-6-methoxy-4-quinolyl]oxy]phenyl]-1-(4-fluoro-2-methyl-phenyl)pyrazole-3-carboxamide |
| 84 | 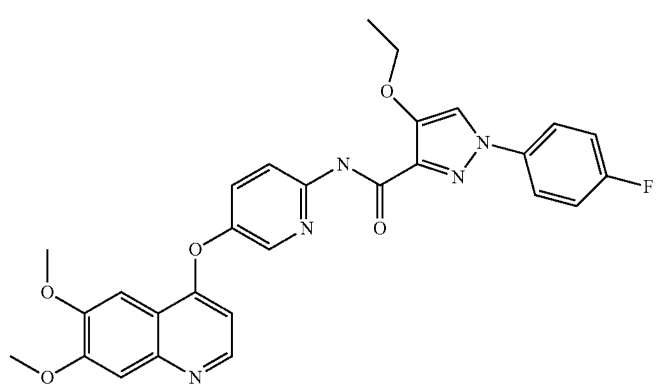 [SMILES: CCOc1cn(-c2ccc(F)cc2)nc1C(=O)Nc1ccc(Oc2ccnc3cc(OC)c(OC)cc23)cn1] | N-[5-[(6,7-dimethoxy-4-quinolyl)oxy]-2-pyridyl]-4-ethoxy-1-(4-fluorophenyl)pyrazole-3-carboxamide |

| Example | Structure | Nomenclature |
|---|---|---|
| 85 | 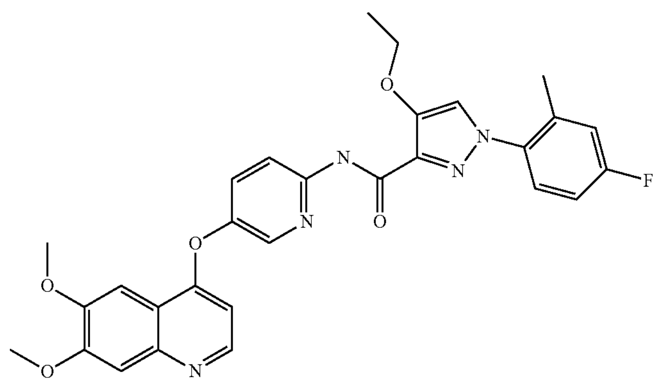 [SMILES: CCOc1cn(-c2ccc(F)cc2C)nc1C(=O)Nc1ccc(Oc2ccnc3cc(OC)c(OC)cc23)cn1] | N-[5-[(6,7-dimethoxy-4-quinolyl)oxy]-2-pyridyl]-4-ethoxy-1-(4-fluoro-2-methyl-phenyl)pyrazole-3-carboxamide |
| 86 | 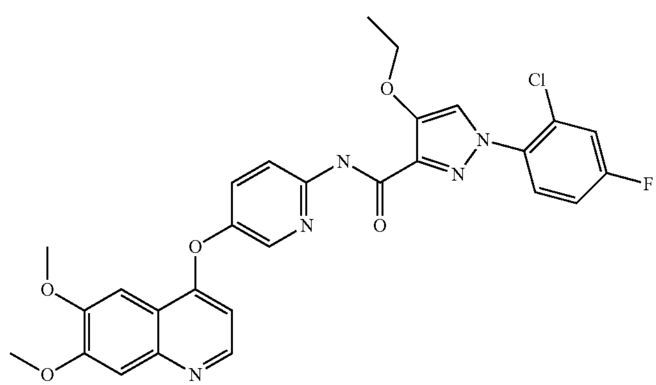 [SMILES: CCOc1cn(-c2ccc(F)cc2Cl)nc1C(=O)Nc1ccc(Oc2ccnc3cc(OC)c(OC)cc23)cn1] | 1-(2-chloro-4-fluoro-phenyl)-N-[5-[(6,7-dimethoxy-4-quinolyl)oxy]-2-pyridyl]-4-ethoxy-pyrazole-3-carboxamide |
| 87 | 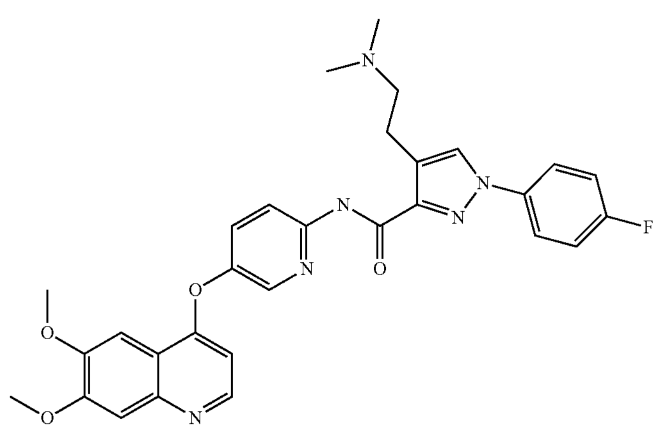 [SMILES: COc1cc2nccc(Oc3ccc(NC(=O)c4nn(-c5ccc(F)cc5)cc4CCN(C)C)nc3)c2cc1OC] | N-[5-[(6,7-dimethoxy-4-quinolyl)oxy]-2-pyridyl]-4-(2-dimethylaminoethyl)-1-(4-fluorophenyl)pyrazole-3-carboxamide |

TABLE 1-continued

| Example | Structure | Nomenclature |
|---|---|---|
| 88 | 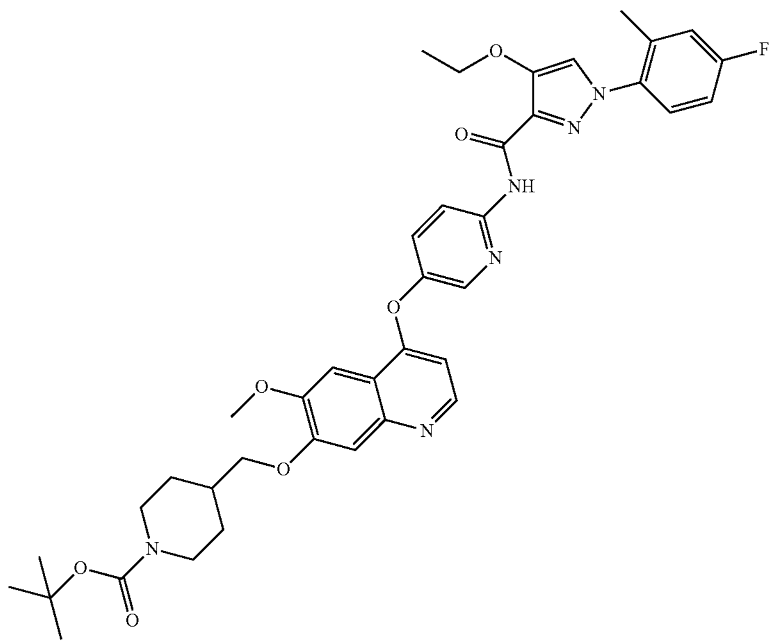 [SMILES: CCOc1cn(-c2ccc(F)cc2C)nc1C(=O)Nc1ccc(Oc2ccnc3cc(OCC4CCN(C(=O)OC(C)(C)C)CC4)c(OC)cc23)cn1] | tert-butyl 4-(((4-((6-(4-ethoxy-1-(4-fluoro-2-methylphenyl)-1H-pyrazole-3-carboxamido)pyridin-3-yl)oxy)-6-methoxyquinolin-7-yl)oxy)methyl)piperidine-1-carboxylate |
| 89 | 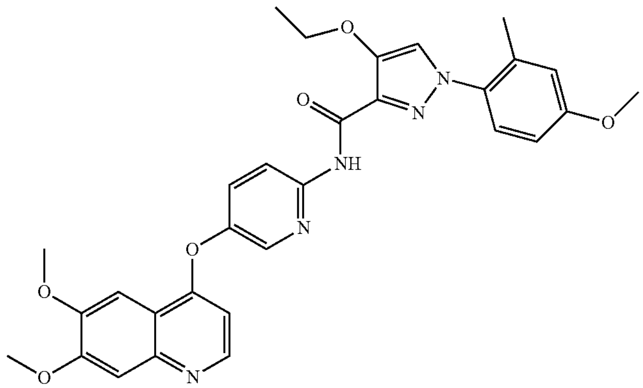 | N-(5-((6,7-dimethoxyquinolin-4-yl)oxy)pyridin-2-yl)-4-ethoxy-1-(4-methoxy-2-methylphenyl)-1H-pyrazole-3-carboxamide |
| 90 | 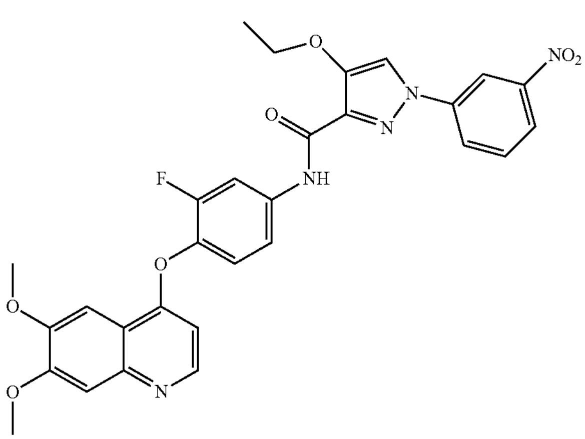 [SMILES: CCOc1cn(-c2cccc([N+](=O)[O-])c2)nc1C(=O)Nc1ccc(Oc2ccnc3cc(OC)c(OC)cc23)c(F)c1] | N-(4-((6,7-dimethoxyquinolin-4-yl)oxy)-3-fluorophenyl)-4-ethoxy-1-(3-nitrophenyl)-1H-pyrazole-3-carboxamide |

TABLE 1-continued

| Example | Structure | Nomenclature |
|---|---|---|
| 91 | 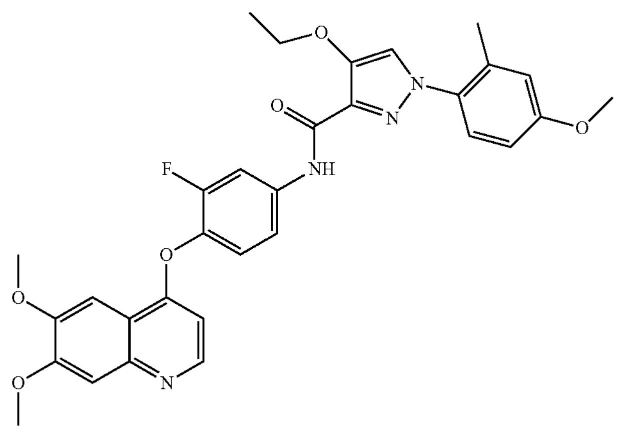 [SMILES: CCOc1cn(-c2ccc(OC)cc2C)nc1C(=O)Nc1ccc(Oc2ccnc3cc(OC)c(OC)cc23)c(F)c1] | N-(4-((6,7-dimethoxyquinolin-4-yl)oxy)-3-fluorophenyl)-4-ethoxy-1-(4-methoxy-2-methylphenyl)-1H-pyrazole-3-carboxamide |
| 92 | 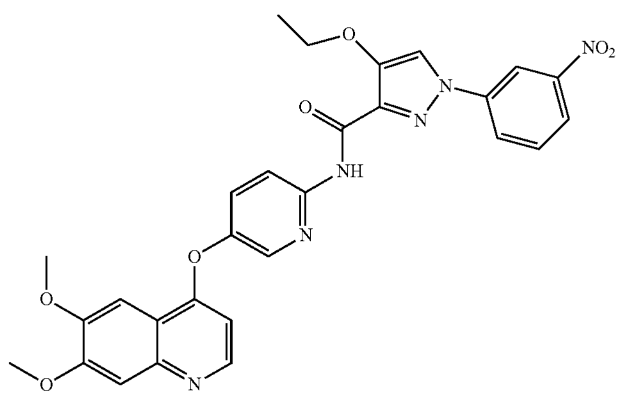 [SMILES: CCOc1cn(-c2cccc([N+](=O)[O-])c2)nc1C(=O)Nc1ccc(Oc2ccnc3cc(OC)c(OC)cc23)cn1] | N-(5-((6,7-dimethoxyquinolin-4-yl)oxy)pyridin-2-yl)-4-ethoxy-1-(3-nitrophenyl)-1H-pyrazole-3-carboxamide |
| 93 | 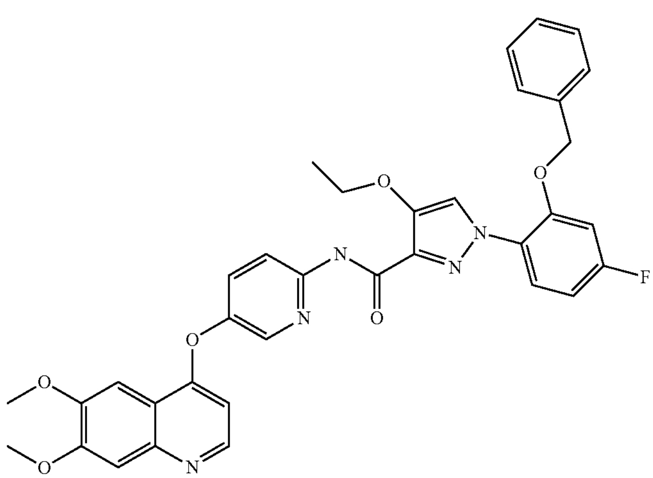 [SMILES: CCOc1cn(-c2ccc(F)cc2OCc2ccccc2)nc1C(=O)Nc1ccc(Oc2ccnc3cc(OC)c(OC)cc23)cn1] | 1-(2-(benzyloxy)-4-fluorophenyl)-N-(5-((6,7-dimethoxyquinolin-4-yl)oxy)pyridin-2-yl)-4-ethoxy-1H-pyrazole-3-carboxamide |

TABLE 1-continued

| Example | Structure | Nomenclature |
|---|---|---|
| 94 | 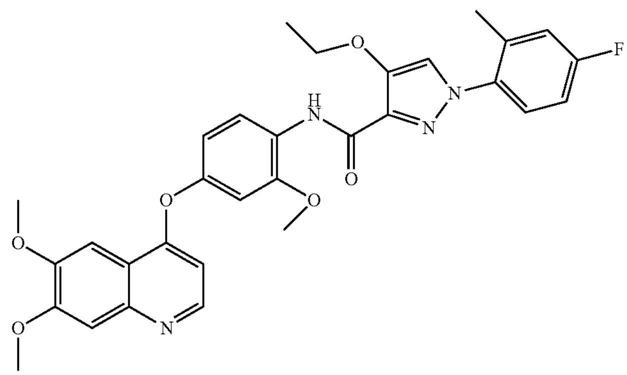 [SMILES: CCOc1cn(-c2ccc(F)cc2C)nc1C(=O)Nc1ccc(Oc2ccnc3cc(OC)c(OC)cc23)cc1OC] | N-(4-((6,7-dimethoxyquinolin-4-yl)oxy)-2-methoxyphenyl)-4-ethoxy-1-(4-fluoro-2-methylphenyl)-1H-pyrazole-3-carboxamide |
| 95 | 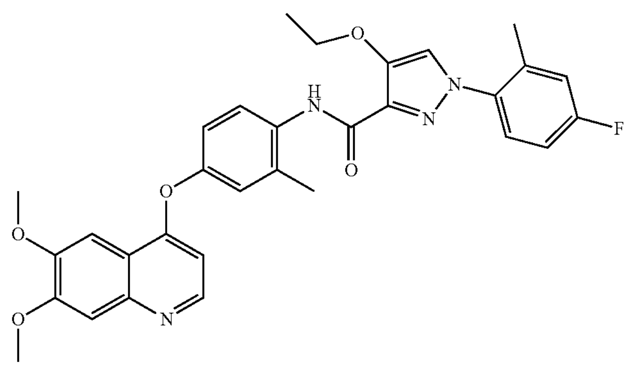 [SMILES: CCOc1cn(-c2ccc(F)cc2C)nc1C(=O)Nc1ccc(Oc2ccnc3cc(OC)c(OC)cc23)cc1C] | N-(4-((6,7-dimethoxyquinolin-4-yl)oxy)-2-methylphenyl)-4-ethoxy-1-(4-fluoro-2-methylphenyl)-1H-pyrazole-3-carboxamide |
| 96 | 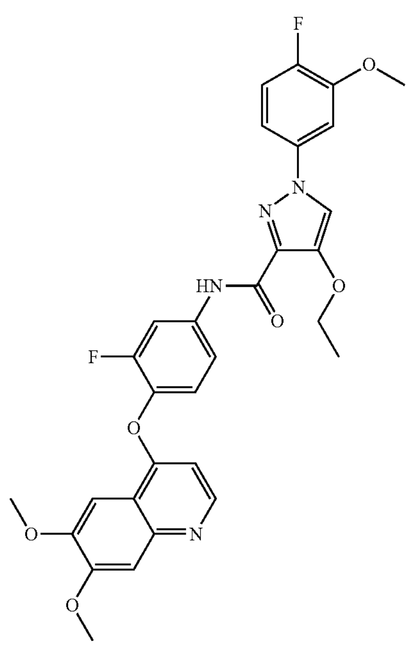 | N-(4-((6,7-dimethoxyquinolin-4-yl)oxy)-3-fluorophenyl)-4-ethoxy-1-(4-fluoro-3-methoxyphenyl)-1H-pyrazole-3-carboxamide |

TABLE 1-continued

| Example | Structure | Nomenclature |
|---|---|---|
| 97 | 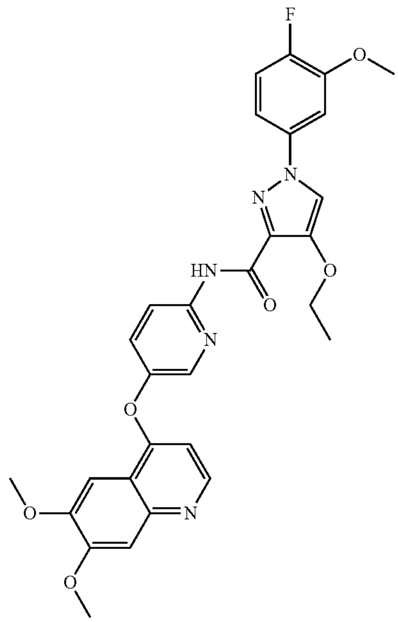 | N-(5-((6,7-dimethoxyquinolin-4-yl)oxy)pyridin-2-yl)-4-ethoxy-1-(4-fluoro-3-methoxyphenyl)-1H-pyrazole-3-carboxamide |
| 98 | 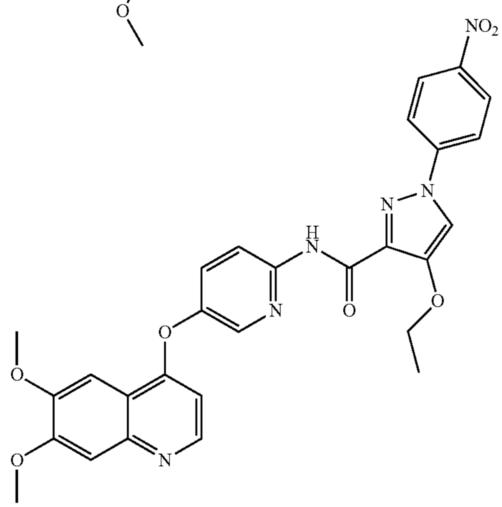 | N-(5-((6,7-dimethoxyquinolin-4-yl)oxy)pyridin-2-yl)-4-ethoxy-1-(4-nitrophenyl)-1H-pyrazole-3-carboxamide |
| 99 | 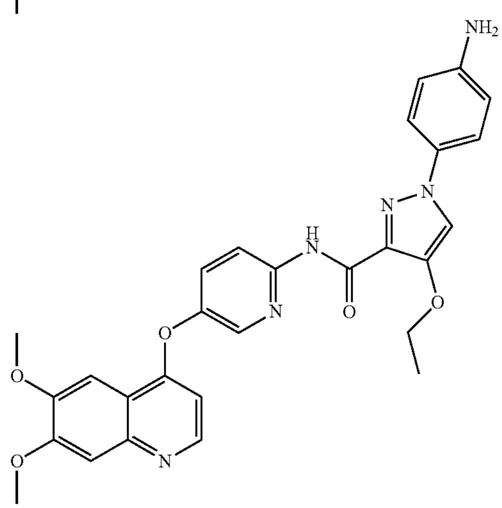 | 1-(4-aminophenyl)-N-(5-((6,7-dimethoxyquinolin-4-yl)oxy)pyridin-2-yl)-4-ethoxy-1H-pyrazole-3-carboxamide |

TABLE 1-continued
| Example | Structure | Nomenclature |
|---|---|---|
| 100 | 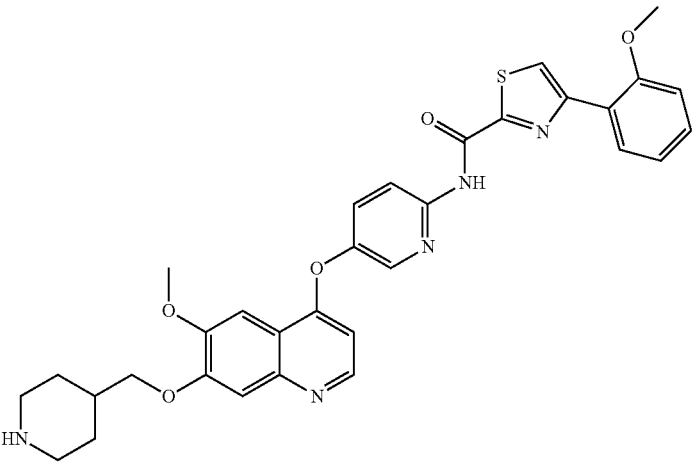 [SMILES: COc1cc2c(Oc3ccc(NC(=O)c4nc(-c5ccccc5OC)cs4)nc3)ccnc2cc1OCC1CCNCC1] | N-(5-((6-methoxy-7-(piperidin-4-ylmethoxy)quinolin-4-yl)oxy)pyridin-2-yl)-4-(2-methoxyphenyl)thiazole-2-carboxamide |
| 101 | 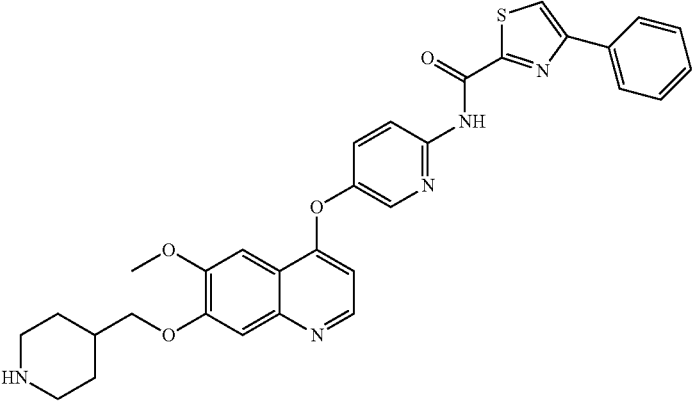 [SMILES: COc1cc2c(Oc3ccc(NC(=O)c4nc(-c5ccccc5)cs4)nc3)ccnc2cc1OCC1CCNCC1] | N-(5-((6-methoxy-7-(piperidin-4-ylmethoxy)quinolin-4-yl)oxy)pyridin-2-yl)-4-phenylthiazole-2-carboxamide |
| 102 | 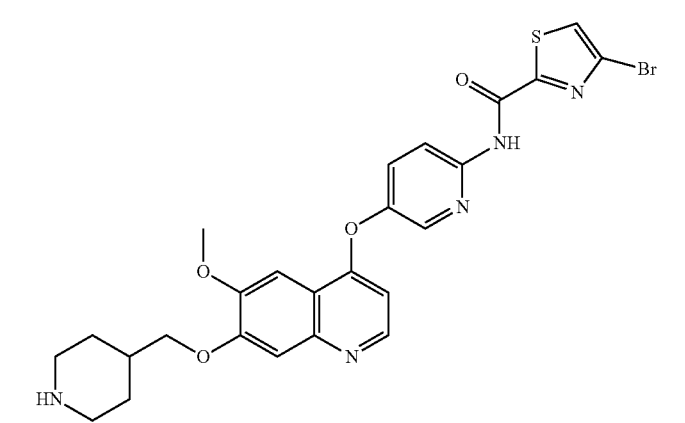 [SMILES: COc1cc2c(Oc3ccc(NC(=O)c4nc(Br)cs4)nc3)ccnc2cc1OCC1CCNCC1] | 4-bromo-N-(5-((6-methoxy-7-(piperidin-4-ylmethoxy)quinolin-4-yl)oxy)pyridin-2-yl)thiazole-2-carboxamide |

TABLE 1-continued

| Example | Structure | Nomenclature |
|---|---|---|
| 103 | 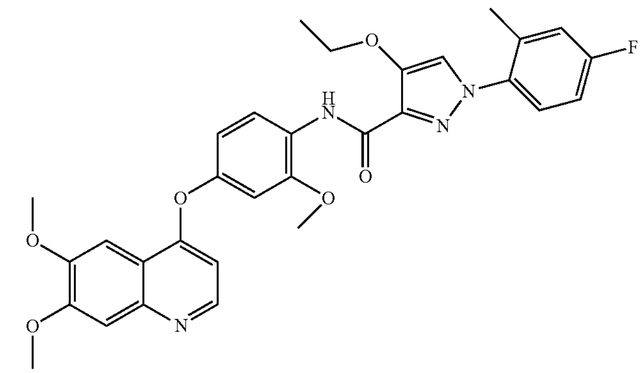 [SMILES: CCOc1cn(-c2ccc(F)cc2C)nc1C(=O)Nc1ccc(Oc2ccnc3cc(OC)c(OC)cc23)cc1OC] | N-(4-((6,7-dimethoxyquinolin-4-yl)oxy)-2-methoxyphenyl)-4-ethoxy-1-(4-fluoro-2-methylphenyl)-1H-pyrazole-3-carboxamide |
| 104 | 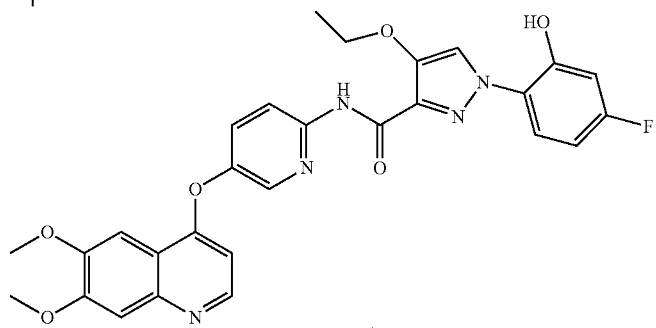 | N-(5-((6,7-dimethoxyquinolin-4-yl)oxy)pyridin-2-yl)-4-ethoxy-1-(4-fluoro-2-hydroxyphenyl)-1H-pyrazole-3-carboxamide |
| 105 | 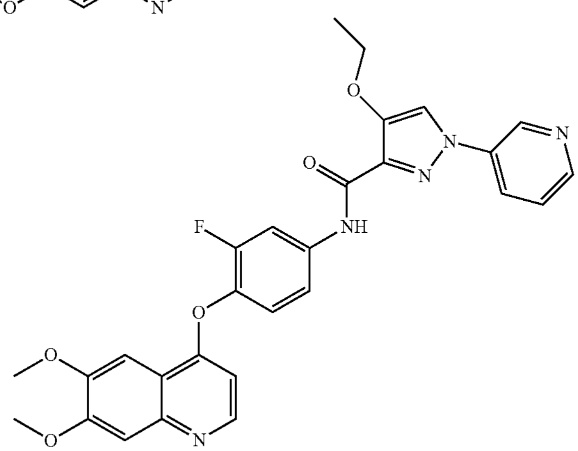 | N-(4-((6,7-dimethoxyquinolin-4-yl)oxy)-3-fluorophenyl)-4-ethoxy-1-(pyridin-3-yl)-1H-pyrazole-3-carboxamide |
| 106 | 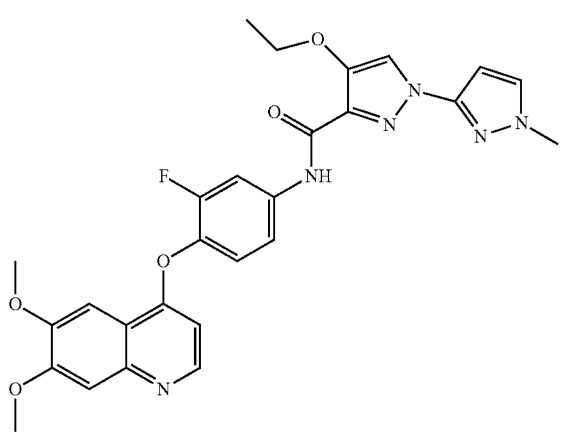 [SMILES: CCOc1cn(-c2ccn(C)n2)nc1C(=O)Nc1ccc(Oc2ccnc3cc(OC)c(OC)cc23)c(F)c1] | N-(4-((6,7-dimethoxyquinolin-4-yl)oxy)-3-fluorophenyl)-4-ethoxy-1'-methyl-1'H-[1,3'-bipyrazole]-3-carboxamide |

EXAMPLES

Preparation of Compounds

Abbreviations used in the description of the chemistry and in the Examples that follow are:

ACN (acetonitrile); br (broad); CDCl$_3$ (deuterated chloroform); cHex (cyclohexane); DCM (dichloromethane); DIPEA (di-iso-propylethylamine); DMF (dimethylformamide); DMSO (dimethyl sulfoxide); eq. (equivalent); ES (electrospray); EtOAc (ethyl acetate); EtOH (ethanol); HATU (O-(7-Azabenzotriazol-1-yl)-N,N,N',N'-tetramethyluronium hexafluorophosphate); HCl (hydrochloric acid); HOAc (acetic acid); H$_2$O (water); K$_2$CO$_3$ (potassium carbonate); KOH (potassium hydroxide); MeOH (methanol); MS (mass spectrometry); NaHCO$_3$ (sodium hydrogencarbonate); NH$_3$ (ammonia); NH$_4$Cl (ammonium chloride); NMR (nuclear magnetic resonance); Pd(dppf)Cl$_2$ ([1,1'-bis(diphenylphosphino)ferrocene]dichloro palladium(II) complex with dichloromethane); iPrOH (iso-propanol); RT (room temperature); sat. aq. (saturated aqueous); SiO$_2$ (silica gel); TEA (trifluoroacetic acid); THF (tetrahydrofurane).

Preparative Examples

Example 1

N-[4-[(6,7-dimethoxy-4-quinolyl)oxy]-3-fluoro-phenyl]-1,6-dimethyl-pyrazole-3-carboxamide trifluoroacetic acid salt (A3)

Step 1: 4-(2-fluoro-4-nitro-phenoxy)-6,7-dimethoxy-quinoline (A1)

A mixture of 6,7-dimethoxyquinolin-4-ol (1.4 g, 6.8 mmol, 1.0 eq.), 3,4-difluoro-nitrobenzene (1.44 g, 8.84 mmol, 1.3 eq.) and cesium carbonate (3.6 g, 10.9 mmol, 1.6 eq.) in dry DMF (10 mL) was heated for 1 h at 50° C. in a microwave oven. After cooling to RT the mixture was diluted with water and extracted with EtOAc. The combined organic phase was dried over Na$_2$SO$_4$ and evaporated in vacuo. The crude product was purified by flash chromatography on silica gel (DCM/MeOH=100:0 to 5:1) to yield the desired product A1 (909 mg, 2.64 mmol, 38.8%) as a yellow solid. $^1$H NMR (400 MHz, CDCl$_3$, 300K) δ 4.04 (s, 3H), 4.06 (s, 3H), 6.55 (d, J=5.2 Hz, 1H), 7.34 (dd, J=7.8 Hz, J=8.8 Hz, 1H), 7.44 (s, 1H), 7.46 (s, 1H), 8.13 (m, 1H), 8.19 (dd, J=9.8 Hz, J=2.5 Hz, 1H), 8.58 (d, J=5.2 Hz, 1H). MS (ES) C$_{17}$H$_{13}$FN$_2$O$_5$ requires: 344, found: 345 (M+H)$^+$. Furthermore an isomer (941 mg, 2.74 mmol, 40.2%) was isolated as a yellow solid. MS (ES) C$_{17}$H$_{13}$FN$_2$O$_6$ requires: 344. Found: 345 (M+H)$^+$.

Step 2: 4-[(6,7-dimethoxy-4-quinolyl)oxy]-3-fluoro-aniline (A2)

To a suspension of A1 (230 mg, 0.67 mmol, 1.0 eq.) in MeOH (50 mL) Pd/C (10% w/w, 23 mg) and aq. HCl-solution (1N, 1.34 mL, 2.0 eq.) were added. The reaction mixture was stirred under hydrogen atmosphere (1 atm) at RT for 48 h. The suspension was filtered through a pad of Celite®. The solvent was removed in vacuo and the crude product was purified using an Isolute® SPE column SCX, loading the reaction mixture as a MeOH solution and then eluting the desired compound with 2N NH$_3$ in MeOH. The title compound A2 was isolated after evaporation of the solvent under reduced pressure as a white solid (200 mg, 0.64 mmol, 95%). $^1$H NMR (400 MHz, d$_6$-DMSO, 300K) δ 3.92 (s, 6H), 4.97 (br s, 2H), 6.38 (d, J=5.3 Hz, 1H), 6.45 (dd, J=2.4 Hz, J=8.5 Hz, 1H), 6.53 (dd, J=2.4 Hz, J=13.2 Hz, 1H), 7.05 (t, J=9.0 Hz, 1H), 7.36 (s, 1H), 7.49 (s, 1H), 8.44 (d, J=5.3 Hz, 1H). MS (ES) C$_{17}$H$_{16}$FN$_2$O$_3$ requires: 314. Found: 315 (M+H)$^+$.

Step 3: N-[4-[(6,7-dimethoxy-4-quinolyl)oxy]-3-fluoro-phenyl]-1,5-dimethyl-pyrazole-3-carboxamide trifluoroacetate salt (A3)

To a solution of A2 (100 mg, 0.31 mmol, 1.0 eq.) in dry DCM (2.5 mL) and dry pyridine (2.5 mL) was added 1,5-dimethyl-1H-pyrazole-3-carbonyl chloride (56 mg, 0.38 mmol, 1.2 eq.) and the reaction mixture was stirred at RT overnight. The solvent was removed in vacuo. The residue was purified by reverse phase RP-HPLC (column: C18), using H$_2$O (0.1% TFA) and MeOH (0.1% TFA) as eluents. The desired fractions were lyophilized to yield the title compound A3 (61.8 mg, 36%) as a white powder. $^1$H NMR (400 MHz, d$_6$-DMSO, 300K) δ 2.30 (s, 3H), 3.83 (s, 3H), 4.00 (s, 6H), 6.57 (s, 1H), 6.87 (d, J=6.9 Hz, 1H), 7.51 (m, 2H), 7.69 (s, 1H), 7.84 (d, J=7.8 Hz, 1H), 8.11 (dd, J=2.3 Hz, J=13.5 Hz, 1H), 8.74 (d, J=6.3 Hz, 1H), 10.43 (s, 1H). MS (ES) C$_{23}$H$_{21}$FN$_4$O$_4$ requires: 436. Found: 437 (M+H)$^+$.

The Examples in the following table were prepared according to the procedure described in the previous Example 1.

| Example | Name | Mwt | [M + H]$^+$ |
|---|---|---|---|
| 2 | N-[4-[(6,7-dimethoxy-4-quinolyl)oxy]-3-fluoro-phenyl]-2-[4-(trifluoromethyl)phenyl]thiazole-4-carboxamide trifluoroacetic acid salt | 569 | 570 |
| 3 | 4-bromo-N-[4-[(6,7-dimethoxy-4-quinolyl)oxy]-3-fluoro-phenyl]-1-methyl-pyrazole-3-carboxamide trifluoroacetic acid salt | 501 | 501/503 |
| 4 | N-[4-[(6,7-dimethoxy-4-quinolyl)oxy]-3-fluoro-phenyl]-1-methyl-pyrazole-3-carboxamide trifluoroacetic acid salt | 422 | 423 |
| 5 | 1-tert-butyl-N-[4-[(6,7-dimethoxy-4-quinolyl)-oxy]-3-fluoro-phenyl]-5-methyl-pyrazole-3-carboxamide trifluoroacetic acid salt | 478 | 479 |
| 6 | N-[4-[(6,7-dimethoxy-4-quinolyl)oxy]-3-fluoro-phenyl]thiazole-2-carboxamide trifluoroacetic acid salt | 425 | 426 |
| 7 | N-[4-[(6,7-dimethoxy-4-quinolyl)oxy]-3-fluoro-phenyl]-2-methyl-thiazole-4-carboxamide trifluoroacetic acid salt | 439 | 440 |
| 8 | N-[4-[(6,7-dimethoxy-4-quinolyl)oxy]-3-fluoro-phenyl]-1-methyl-indazole-3-carboxamide trifluoroacetic acid salt | 472 | 473 |
| 9 | N-[4-[(6,7-dimethoxy-4-quinolyl)oxy]-3-fluoro-phenyl]-5-methyl-isoxazole-3-carboxamide trifluoroacetic acid salt | 423 | 424 |
| 10 | N-[4-[(6,7-dimethoxy-4-quinolyl)oxy]-3-fluoro-phenyl]-2-phenyl-thiazole-4-carboxamide trifluoroacetic acid salt | 501 | 502 |

Example 11

N-[4-[(6,7-dimethoxy-4-quinolyl)oxy]-3-fluoro-phenyl]-1-methyl-imidazole-2-carboxamide trifluoroacetic acid salt (B1)

1-Methyl-1H-imidazol-2-carboxylic acid (126 mg, 1 mmol, 1.0 eq.) in SOCl$_2$ (10 mL) was heated for 6 h under reflux. Solvent was removed in vacuo and the crude product was resolved in dry toluene and evaporated under reduced pressure again. The solid was solved in dry DCM (2 mL) and dry pyridine (2 mL) and 4-[(6,7-dimethoxy-4-quinolyl)oxy]-3-fluoro-aniline (A2) (376 mg, 1.2 mmol, 1.2 eq.) was added.

The reaction mixture was stirred at RT overnight. The solvent was removed in vacuo. The residue was purified by reverse phase RP-HPLC (column: C18), using H$_2$O (0.1% TFA) and MeOH (0.1% TFA) as eluents. The desired fractions were lyophilized to yield the title compound B1 (33 mg, 0.06 mmol, 6%) as a white powder. $^1$H NMR (400 MHz, d$_6$-DMSO, 300K) δ 3.99 (s, 3H), 4.02 (s, 3H), 4.03 (s, 3H), 6.94 (d, J=6.5 Hz, 1H), 7.12 (d, J=1.0 Hz, 1H), 7.48 (d, J=1.0 Hz, 1H), 7.55 (t, J=9.0 Hz, 1H), 7.56 (s, 1H), 7.73 (s, 1H), 7.87 (d, J=9.0 Hz, 1H), 8.13 (dd, J=2.4 Hz, J=13.3 Hz, 1H), 8.79 (d, J=6.5 Hz, 1H), 10.81 (s, 1H). MS (ES) C$_{22}$H$_{19}$FN$_4$O$_4$ requires: 422. Found: 423 (M+H)$^+$.

The Example in the following table was prepared according to the procedure described in the previous Example 11.

| Example | Name | Mwt | [M + H]$^+$ |
|---|---|---|---|
| 12 | N-[4-[(6,7-dimethoxy-4-quinolyl)oxy]-3-fluoro-phenyl]-1-methyl-imidazole-4-carboxamide | 422 | 423 |

Example 13

N-[4-[(6,7-dimethoxy-4-quinolyl)oxy]-3-fluoro-phenyl]-1-propyl-pyrazole-3-carboxamide (C1)

C1 was prepared from A2 and 1-propylpyrazole-3-carboxylic acid following the general procedure reported in Preparative Example 11. The residue was purified by reverse phase RP-HPLC (column: C18), using H$_2$O and ACN as eluents. The desired fractions were lyophilized to yield the title compound C1 (46 mg, 0.10 mmol, 17%) as a white powder. $^1$H NMR (400 MHz, d$_6$-DMSO, 300K) δ 0.85 (t, J=7.3 Hz, 3H), 1.86 (sext., J=7.3 Hz, 2H), 3.94 (s, 6H), 4.18 (t, J=7.3 Hz, 2H), 6.45 (d, J=5.1 Hz, 1H), 6.79 (d, J=2.3 Hz, 1H), 7.39 (s, 1H), 7.42 (t, J=9.0 Hz, 1H), 7.52 (s, 1H), 7.78 (d, J=9.0 Hz, 1H), 7.90 (d, J=2.3 Hz, 1H), 8.05 (dd, J=13.4 Hz, J=2.3 Hz, 1H), 8.46 (d, J=5.2 Hz, 1H), 10.34 (s, 1H). MS (ES) C$_{24}$H$_{23}$FN$_4$O$_4$ requires: 450. Found: 451 (M+H)$^+$.

The Examples in the following table were prepared according to the procedure described in the previous Example 13.

| Example | Name | Mwt | [M + H]$^+$ |
|---|---|---|---|
| 14 | N-[4-[(6,7-dimethoxy-4-quinolyl)oxy]-3-fluoro-phenyl]-1-[3-(1-piperidyl)propyl]pyrazole-3-carboxamide | 533 | 534 |
| 15 | N-[4-[(6,7-dimethoxy-4-quinolyl)oxy]-3-fluoro-phenyl]-1-(2,2,2-trifluoroethoxymethyl)pyrazole-3-carboxamide | 520 | 521 |

Example 16

N-[4-[(6,7-dimethoxy-4-quinolyl)oxy]-3-fluoro-phenyl]-4-ethoxy-1-(4-fluorophenyl)pyrazole-3-carboxamide (D5)

Step 1: Ethyl 1-(4-fluorophenyl)-4-hydroxy-pyrazole-3-carboxylate (D1)

To a solution of 4-fluoroaniline (10 g, 90.0 mmol, 1.0 eq.) in DCM/HOAc (1/1, 180 mL, 0.5M) at 0° C. was added dropwise a precooled solution of sodium nitrite (9.02 g, 108 mmol, 1.2 eq.) in conc. sulfuric acid (40 mL). After stirring for 30 min at 0° C. a mixture of ethyl 4-chloroacetoacetate (14.6 mL, 17.8 g, 108 mmol, 1.2 eq.) in HOAc (60 mL) and H$_2$O (120 mL) was added within 5 min. After further 15 min at 0° C. a solution of sodium acetate (100 g, 1.219 mol, 13.5 eq.) in H$_2$O (210 mL) was added slowly. The mixture was stirred for 30 min at 0° C. and 1 h at RT. DCM (200 mL) was added and the organic phase was separated. The aq. phase was extracted with DCM (3×100 mL). The combined organic phase was washed with water, phosphate buffer and subsequent with brine. The organic layer was dried over Na$_2$SO$_4$ and concentrated under reduced pressure to give the product ethyl 4-chloro-2-(4-fluorophenyl)azo-3-oxo-butanoate as a orange solid. MS (ES) C$_{12}$H$_{12}$ClFN$_2$O$_3$ requires: 286. Found: 287 (M+H)$^+$ and 309 (M+Na)$^+$.

Without further purification the crude material was dissolved in dry ethanol (180 mL) and after adding potassium acetate (12.4 g, 126 mmol, 1.4 eq.) the mixture was refluxed for 1 h. The reaction mixture was diluted with EtOAc and washed three times with water. The combined aq. phase was extracted with EtOAc. The combined organic phase was then washed with phosphate buffer and brine. The organic layer was dried over Na$_2$SO$_4$ and concentrated under reduced pressure. The crude product was crystallized from ethanol to give the desired product D1 as a brown solid (18.21 g, 81%). $^1$H NMR (400 MHz, d$_6$-DMSO, 300K) δ 1.29 (t, J=7.0 Hz, 3H), 4.28 (q, J=7.0 Hz, 2H), 7.33 (t, J=8.8 Hz, 2H), 7.83 (m, 2H), 8.03 (s, 1H), 9.15 (s, 1H). MS (ES) C$_{12}$H$_{11}$FN$_2$O$_3$ requires: 250. Found: 251 (M+H)$^+$ and 273 (M+Na)$^+$.

Step 2: ethyl 4-ethoxy-1-(4-fluorophenyl)pyrazole-3-carboxylate (D2)

To a mixture of D1 (9.6 g, 38 mmol, 1.0 eq.) and K$_2$CO$_3$ (6.8 g, 50 mmol, 1.3 eq.) in dry DMF (100 mL) was added at RT iodoethane (4.0 mL, 7.8 g, 50 mmol, 1.3 eq.). After stirring for 72 h at RT the mixture was cooled to 0° C. MeOH (5 mL) was added, the mixture was diluted with DCM (200 mL) and washed with water and phosphate buffer. The organic layer was dried over Na$_2$SO$_4$ and concentrated under reduced pressure to give the product D2 as a brown solid which was used without further purification in the subsequent step. MS (ES) C$_{14}$H$_{15}$FN$_2$O$_3$ requires: 278. Found: 279 (M+H)$^+$.

Step 3: 4-Ethoxy-1-(4-fluorophenyl)pyrazole-3-carboxylic acid (D3)

D2 (38 mmol, 1.0 eq.) and aq. KOH-solution (3M, 190 mmol, 5.0 eq.) in EtOH (152 mL) were heated for 45 min at 50° C. The mixture was cooled to RT and diluted with DCM and water. The aq. phase was washed a second time with DCM. The aq. phase was acidified with aq. HCl-solution (1N) to pH=1 and extracted with EtOAc. The combined organic phase was washed with brine and dried over Na$_2$SO$_4$. Removal of the solvent yielded the product D3 as a brown solid (8.88 g, 93% over 2 steps). $^1$H NMR (400 MHz, d$_6$-DMSO, 300K) δ 1.34 (t, J=7.0 Hz, 3H), 4.02 (q, J=7.0 Hz, 2H), 7.37 (dd, J=J=9.0 Hz, 2H), 7.87 (dd, J=9.0 Hz, J=4.6 Hz, 2H), 8.38 (s, 1H), 12.68 (br s, 1H). MS (ES) C$_{12}$H$_{11}$FN$_2$O$_3$ requires: 250. Found: 251 (M+H)$^+$ and 273 (M+Na)$^+$.

Step 4: 4-ethoxy-1-(4-fluorophenyl)pyrazole-3-carbonyl chloride (D4)

D3 (43 mg, 0.17 mmol, 1.0 eq.) was heated in thionyl chloride (1 mL) for 4 h at 67° C. Solvent was removed in vacuo and the crude material was resolved in dry toluene and evaporated under reduced pressure again to yield D4. The crude material was used in the next step without further purification.

Step 5: N-[4-[(6,7-dimethoxy-4-quinolyl)oxy]-3-fluoro-phenyl]-4-ethoxy-1-(4-fluorophenyl)pyrazole-3-carboxamide (D5)

Acid chloride D4 (0.17 mmol, 1.0 eq.) was dissolved in dry pyridine (1.5 mL) at 0° C. and A2 (34 mg, 0.11 mmol, 0.65 eq.) was added. The reaction was allowed to reach RT overnight. The mixture was diluted with EtOAc and washed twice with aq. KOH-solution (0.5N), twice with aq. sat. $NH_4Cl$-solution, and finally once with brine. The organic layer was dried over $Na_2SO_4$ and concentrated under reduced pressure. The crude product was purified by flash chromatography on silica gel (DCM/MeOH=100:0 to 10:1) to yield the desired product D5 (31 mg, 52% over 2 steps) as a white solid. $^1$H NMR (400 MHz, $d_6$-DMSO, 300K) δ 1.38 (t, J=7.0 Hz, 3H), 3.94 (s, 6H), 4.09 (q, J=7.0 Hz, 2H), 6.48 (d, J=5.3 Hz, 1H), 7.43 (m, 4H), 7.53 (s, 1H), 7.70 (d, J=9.4 Hz, 1H), 8.01 (m, 3H), 8.47 (m, 2H), 10.17 (s, 1H). MS (ES) $C_{29}H_{24}F_2N_4O_5$ requires: 546. Found: 547 $(M+H)^+$.

Example 17

N-[4-[(6,7-dimethoxy-4-quinolyl)oxy]-3-fluoro-phenyl]-1-(4-fluorophenyl)-4-methoxy-pyrazole-3-carboxamide trifluoroacetic acid salt (E4)

Step 1: ethyl 1-(4-fluorophenyl)-4-methoxy-pyrazole-3-carboxylate (E1)

E1 was prepared from D1 following the general procedure reported in Preparative Example 16 Step 2 using methyl iodide for the alkylation. MS (ES) $C_{13}H_{13}FN_2O_3$ requires: 264. Found: 265 $(M+H)^+$ and 287 $(M+Na)^+$.

Step 2: 1-(4-fluorophenyl)-4-methoxy-pyrazole-3-carboxylic acid (E2)

E1 (2 mmol, 1.0 eq.) and KOH (6 mmol, 3.0 eq.) in THF/$H_2O$ (1/1, 30 mL) were heated for 2 h at 60° C. The mixture was cooled to RT and then acidified with aq. HCl-solution (1N) to pH=1. The aq. phase was extracted with EtOAc. The combined organic phase was dried over $Na_2SO_4$. Removal of the solvent yielded the product E2 as a yellow solid (450 mg, 95%). $^1$H NMR (400 MHz, $d_6$-DMSO, 300K) δ 3.80 (s, 3H), 7.37 (dd, J=J=9.0 Hz, 2H), 7.87 (dd, J=9.0 Hz, J=4.7 Hz, 2H), 8.40 (s, 1H), 12.72 (br s, 1H). MS (ES) $C_{11}H_9FN_2O_3$ requires: 236. Found: 237 $(M+H)^+$.

Step 3: 1-(4-fluorophenyl)-4-methoxy-pyrazole-3-carbonyl chloride (E3)

E2 (100 mg, 0.42 mmol, 1.0 eq.) was heated in thionyl chloride (1 mL) for 4 h under reflux. Solvent was removed in vacuo and the crude material was resolved in dry toluene and evaporated under reduced pressure again to yield E3. The crude material was used in the next step without further purification.

Step 4: N-[4-[(6,7-dimethoxy-4-quinolyl)oxy]-3-fluoro-phenyl]-1-(4-fluorophenyl)-4-methoxy-pyrazole-3-carboxamide trifluoroacetic acid salt (E4)

Acid chloride E3 (0.42 mmol, 1.0 eq.) was dissolved in dry pyridine (2 mL) at RT and A2 (133 mg, 0.42 mmol, 1.0 eq.) was added. The reaction was stirred at RT overnight. After adding methanol (0.1 mL) the reaction mixture was concentrated under reduced pressure. The residue was purified by reverse phase RP-HPLC (column: C18), using $H_2O$ (0.1% TFA) and MeOH (0.1% TFA) as eluents. The desired fractions were lyophilized to yield the title compound E4 (36 mg, 0.13 mmol, 13%) as a white powder. $^1$H NMR (400 MHz, $d_6$-DMSO, 300K) δ 3.88 (s, 3H), 4.04 (s, 3H), 4.05 (s, 3H), 6.85 (s, 1H), 6.96 (d, J=6.4 Hz, 1H), 7.43 (dd, J=J=9.0 Hz, 2H), 7.57 (s, 1H), 7.59 (t, J=9.1 Hz, 1H), 7.75 (s, 1H), 7.81 (d, J=9.1 Hz, 1H), 8.02 (dd, J=9.0 Hz, J=4.8 Hz, 2H), 8.12 (dd, J=13.3 Hz, J=2.4 Hz, 1H), 8.52 (s, 1H), 8.81 (d, J=6.5 Hz, 1H), 10.30 (s, 1H). MS (ES) $C_{29}H_{22}F_2N_4O_5$ requires: 532. Found: 533 $(M+H)^+$.

Example 18

4-(cyclopropylmethoxy)-N-[4-[(6,7-dimethoxy-4-quinolyl)oxy]-3-fluoro-phenyl]-1-(4-fluorophenyl)pyrazole-3-carboxamide (F4)

Step 1: ethyl 4-(cyclopropylmethoxy)-1-(4-fluorophenyl)pyrazole-3-carboxylate (F1)

F1 was prepared from D1 following the general procedure reported in Preparative Example 16 Step 2 using (bromomethyl)cyclopropane for the alkylation. MS (ES) $C_{16}H_{17}FN_2O_3$ requires: 304. Found: 305 $(M+H)^+$ and 327 $(M+Na)$.

Step 2: 4-(cyclopropylmethoxy)-1-(4-fluorophenyl)pyrazole-3-carboxylic acid (F2)

F2 was prepared from F1 following the general procedure reported in Preparative Example 16 Step 3. $^1$H NMR (400 MHz, $d_6$-DMSO, 300K) δ 0.32 (dt, J=5.0 Hz, J=5.0 Hz, 2H), 0.57 (dt, J=8.0 Hz, J=5.0 Hz, 2H), 1.27 (m, 1H), 3.81 (d, J=7.0 Hz, 2H), 7.36 (t, J=8.9 Hz, 2H), 7.86 (dd, J=8.9 Hz, J=4.7 Hz, 2H), 8.37 (s, 1H), 12.69 (br s, 1H). MS (ES) $C_{14}H_{13}FN_2O_3$ requires: 276. Found: 277 $(M+H)^+$ and 299 $(M+Na)^+$.

Step 3: 4-(cyclopropylmethoxy)-1-(4-fluorophenyl)pyrazole-3-carbonyl chloride (F3)

F3 was prepared from F2 following the general procedure reported in Preparative Example 16 Step 4.

Step 4: 4-(cyclopropylmethoxy)-N-[4-[(6,7-dimethoxy-4-quinolyl)oxy]-3-fluoro-phenyl]-1-(4-fluorophenyl)pyrazole-3-carboxamide (F4)

F4 was prepared from F3 following the general procedure reported in Preparative Example 16 Step 5. $^1$H NMR (400 MHz, $CD_3OD$, 300K) δ 0.46 (m, 2H), 0.70 (m, 2H), 1.43 (m, 1H), 4.00 (d, J=7.2 Hz, 1H), 4.05 (s, 3H), 4.06 (s, 3H), 6.75 (d, J=5.5 Hz, 1H), 7.25 (t, J=8.8 Hz, 2H), 7.40 (s, 1H), 7.44 (t, J=8.8 Hz, 2H), 7.59 (m, 1H), 7.73 (s, 1H), 7.89 (m, 3H), 8.04 (dd, J=12.6 Hz, J=2.3 Hz, 1H), 8.18 (s, 1H), 8.55 (m, 1H). MS (ES) $C_{31}H_{26}F_2N_4O_5$ requires: 572. Found: 573 $(M+H)^+$.

Example 19

N-[4-[(6,7-dimethoxy-4-quinolyl)oxy]-3-fluoro-phenyl]-4-(2-dimethylaminoethoxy)-1-(4-fluorophenyl)pyrazole-3-carboxamide (G2)

Step 1: 4-(2-dimethylaminoethoxy)-1-(4-fluorophenyl)pyrazole-3-carbonyl chloride (G1)

G1 was prepared from D1 following the general procedure reported in Preparative Example 16 Step 2-4.

Step 2: N-[4-[(6,7-dimethoxy-4-quinolyl)oxy]-3-fluoro-phenyl]-4-(2-dimethylaminoethoxy)-1-(4-fluorophenyl)pyrazole-3-carboxamide (G2)

G2 was prepared from G1 following the general procedure reported in Preparative Example 16 Step 5. $^1$H NMR (400 MHz, d$_6$-DMSO, 300K) δ 2.45 (s, 6H), 2.95 (t, J=5.2 Hz, 2H), 3.96 (s, 6H), 4.25 (t, J=5.2 Hz, 2H), 6.49 (d, J=5.3 Hz, 1H), 7.43 (m, 3H), 7.48 (t, J=9.2 Hz, 1H), 7.54 (s, 1H), 7.71 (d, J=9.2 Hz, 1H), 8.00 (m, 3H), 8.49 (d, J=5.1 Hz, 1H), 8.59 (s, 1H), 10.27 (s, 1H). MS (ES) $C_{31}H_{29}F_2N_5O_5$ requires: 589. Found: 590 (M+H)$^+$.

Example 20

N-[4-[(6,7-dimethoxy-4-quinolyl)oxy]-3-fluoro-phenyl]-4-(3-dimethylaminopropoxy)-1-(4-fluorophenyl)pyrazole-3-carboxamide (H2)

Step 1: 4-(3-dimethylaminopropoxy)-1-(4-fluorophenyl)pyrazole-3-carbonyl chloride (H1)

H1 was prepared from D1 following the general procedure reported in Preparative Example 16 Step 2-4.

Step 2: N-[4-[(6,7-dimethoxy-4-quinolyl)oxy]-3-fluoro-phenyl]-4-(3-dimethylaminopropoxy)-1-(4-fluorophenyl)pyrazole-3-carboxamide (H2)

H2 was prepared from H1 following the general procedure reported in Preparative Example 16 Step 5. MS (ES) $C_{32}H_{31}F_2N_6O_6$ requires: 603. Found: 604 (M+H)$^+$.

Example 21

N-[4-[(6,7-dimethoxy-4-quinolyl)oxy]-3-fluoro-phenyl]-1-(4-fluorophenyl)-4-isopropoxy-pyrazole-3-carboxamide (I3)

Step 1: 1-(4-fluorophenyl)-4-isopropoxy-pyrazole-3-carboxylic acid (I1)

I1 was prepared from D1 following the general procedure reported in Preparative Example 16 Step 2 and 3. $^1$H NMR (400 MHz, d$_6$-DMSO, 300K) δ 1.29 (d, J=6.0 Hz, 6H), 4.34 (sept, J=6.0 Hz, 1H), 7.37 (t, J=8.8 Hz, 2H), 7.88 (dd, J=8.8 Hz, J=4.7 Hz, 2H), 8.39 (s, 1H), 12.63 (br s, 1H). MS (ES) $C_{13}H_{13}FN_2O_3$ requires: 264. Found: 265 (M+H)$^+$.

Step 2: 1-(4-fluorophenyl)-4-isopropoxy-pyrazole-3-carbonyl chloride (I2)

I2 was prepared from I1 following the general procedure reported in Preparative Example 16 Step 4.

Step 3: N-[4-[(6,7-dimethoxy-4-quinolyl)oxy]-3-fluoro-phenyl]-1-(4-fluorophenyl)-4-isopropoxy-pyrazole-3-carboxamide (I3)

I3 was prepared from I2 following the general procedure reported in Preparative Example 16 Step 5. $^1$H NMR (400 MHz, d$_6$-DMSO, 300K) δ 1.34 (d, J=6.1 Hz, 6H), 3.94 (s, 6H), 4.43 (sept., J=6.1 Hz, 1H), 6.47 (d, J=5.2 Hz, 1H), 7.42 (m, 4H), 7.53 (s, 1H), 7.68 (d, J=9.1 Hz, 1H), 8.02 (m, 3H), 8.48 (m, 2H), 10.15 (s, 1H). MS (ES) $C_{30}H_{26}F_2N_4O_6$ requires: 560. Found: 561 (M+H)$^+$.

Example 22

N-[4-[(6,7-dimethoxy-4-quinolyl)oxy]-3-fluoro-phenyl]-4-ethoxy-1-(4-fluoro-2-methyl-phenyl)pyrazole-3-carboxamide (J5)

Step 1: ethyl 1-(4-fluoro-2-methyl-phenyl)-4-hydroxy-pyrazole-3-carboxylate (J1)

J1 was prepared following the general procedure reported in Preparative Example 16 Step 1. $^1$H NMR (400 MHz, d$_6$-DMSO, 300K) δ 1.26 (t, J=7.1 Hz, 3H), 2.16 (s, 3H), 4.25 (q, J=7.1 Hz, 2H), 7.15 (ddd, J=8.5 Hz, J=J=3.0 Hz, 1H), 7.26 (dd, J=9.6 Hz, J=3.0 Hz, 1H), 7.39 (dd, J=8.5 Hz, J=5.5 Hz, 1H), 7.60 (s, 1H). MS (ES) $C_{13}H_{13}FN_2O_3$ requires: 264. Found: 265 (M+H)$^+$ and 287 (M+Na)$^+$.

Step 2: ethyl 4-ethoxy-1-(4-fluoro-2-methyl-phenyl)pyrazole-3-carboxylate (J2)

J2 was prepared from J1 following the general procedure reported in Preparative Example 16 Step 2 using iodoethane for the alkylation. MS (ES) $C_{16}H_{17}FN_2O_3$ requires: 292. Found: 293 (M+H)$^+$ and 315 (M+Na).

Step 3: 4-ethoxy-1-(4-fluoro-2-methyl-phenyl)pyrazole-3-carboxylic acid (J3)

J3 was prepared from J2 following the general procedure reported in Preparative Example 16 Step 3. MS (ES) $C_{13}H_{13}FN_2O_3$ requires: 264. Found: 265 (M+H)$^+$.

Step 4: 4-ethoxy-1-(4-fluoro-2-methyl-phenyl)pyrazole-3-carbonyl chloride (J4)

J4 was prepared from J3 following the general procedure reported in Preparative Example 16 Step 4.

Step 5: N-[4-[(6,7-dimethoxy-4-quinolyl)oxy]-3-fluoro-phenyl]-4-ethoxy-1-(4-fluoro-2-methyl-phenyl)pyrazole-3-carboxamide (J5)

J5 was prepared following the general procedure reported in Preparative Example 16 Step 5. $^1$H NMR (400 MHz, d$_6$-DMSO, 300K) δ 1.38 (t, J=7.0 Hz, 3H), 2.26 (s, 3H), 4.02 (s, 3H), 4.03 (s, 3H), 4.07 (q, J=7.0 Hz, 2H), 6.89 (d, J=6.4 Hz, 1H), 7.23 (dt, J=8.5 Hz, J=3.0 Hz, 1H), 7.33 (dd, J=9.9 Hz, J=3.0 Hz, 1H), 7.53 (m, 3H), 7.72 (s, 1H), 7.78 (d, J=9.2 Hz, 1H), 8.05 (s, 1H), 8.11 (dd, J=13.3 Hz, J=2.6 Hz, 1H), 8.77 (d, J=6.4 Hz, 1H), 10.24 (s, 1H). MS (ES) $C_{30}H_{26}F_2N_4O_5$ requires: 560. Found: 561 (M+H)$^+$.

Example 23

1-(2-chloro-4-fluoro-phenyl)-N-[4-[(6,7-dimethoxy-4-quinolyl)oxy]-3-fluoro-phenyl]-4-ethoxy-pyrazole-3-carboxamide (K3)

Step 1: 1-(2-chloro-4-fluoro-phenyl)-4-ethoxy-pyrazole-3-carboxylic acid (K1)

K1 was prepared following the general procedure reported in Preparative Example 16 Step 1-3. $^1$H NMR (400 MHz, $d_6$-DMSO, 300K) δ 1.31 (t, J=7.0 Hz, 3H), 3.96 (q, J=7.0 Hz, 2H), 7.40 (m, 1H), 7.66 (dd, J=8.9 Hz, J=5.6 Hz, 1H), 7.72 (dd, J=8.5 Hz, J=2.8 Hz, 1H), 7.98 (s, 1H), 12.64 (br s, 1H). MS (ES) $C_{12}H_{10}ClFN_2O_3$ requires: 284. Found: 285 (M+H)$^+$ and 307 (M+Na)$^+$.

Step 2: 1-(2-chloro-4-fluoro-phenyl)-4-ethoxy-pyrazole-3-carbonyl chloride (K2)

K2 was prepared from K1 following the general procedure reported in Preparative Example 16 Step 4.

Step 3: 1-(2-chloro-4-fluoro-phenyl)-N-[4-[(6,7-dimethoxy-4-quinolyl)oxy]-3-fluoro-phenyl]-4-ethoxy-pyrazole-3-carboxamide (K3)

K3 was prepared following the general procedure reported in Preparative Example 16 Step 5. $^1$H NMR (400 MHz, CDCl$_3$, 300K) δ 1.56 (t, J=6.9 Hz, 3H), 4.05 (s, 3H), 4.07 (s, 3H), 4.18 (q, J=6.9 Hz, 2H), 6.45 (d, J=5.3 Hz, 1H), 7.14 (ddd, J=10.0 Hz, J=7.4 Hz, J=2.7 Hz, 1H), 7.23 (t, J=8.8 Hz, 1H), 7.29 (dd, J=8.0 Hz, J=2.7 Hz, 1H), 7.38 (d, J=8.8 Hz, 1H), 7.45 (s, 1H), 7.55 (s, 1H), 7.59 (s, 1H), 7.62 (dd, J=8.8 Hz, J=5.3 Hz, 1H), 7.91 (dd, J=12.1 Hz, J=2.7 Hz, 1H), 8.50 (d, J=5.3 Hz, 1H), 8.90 (s, 1H). MS (ES) $C_{26}H_{23}ClF_2N_4O_6$ requires: 580. Found: 581 (M+H)$^+$.

Example 24

N-[4-[(6,7-dimethoxy-4-quinolyl)oxy]phenyl]-4-ethoxy-1-(4-fluorophenyl)pyrazole-3-carboxamide (L2)

Step 1: 4-((6,7-dimethoxyquinolin-4-yl)oxy)aniline (L1)

L1 was prepared from 6,7-dimethoxyquinolin-4-ol and 4-fluoro-nitrobenzene following the general procedure reported in Preparative Example 1 Step 1-2. $^1$H NMR (400 MHz, $d_6$-DMSO, 300K) δ 3.91 (s, 3H), 3.92 (s, 3H), 5.16 (br s, 2H), 6.36 (d, J=5.3 Hz, 1H), 6.65 (d, J=8.8 Hz, 2H), 6.91 (d, J=8.8 Hz, 2H), 7.34 (s, 1H), 7.49 (s, 1H), 8.41 (d, J=5.3 Hz, 1H). MS (ES) $C_{17}H_{16}N_2O_3$ requires: 296. Found: 297 (M+H)$^+$.

Step 2: N-[4-[(6,7-dimethoxy-4-quinolyl)oxy]phenyl]-4-ethoxy-1-(4-fluorophenyl)pyrazole-3-carboxamide (L2)

L2 was prepared from L1 and D4 following the general procedure reported in Preparative Example 16 Step 5. $^1$H NMR (400 MHz, $d_6$-DMSO, 300K) δ 1.38 (t, J=7.0 Hz, 3H), 3.93 (s, 3H), 3.94 (s, 3H), 4.10 (q, J=7.0 Hz, 2H), 6.51 (d, J=5.4 Hz, 1H), 7.28 (d, J=9.1 Hz, 2H), 7.39 (m, 3H), 7.53 (s, 1H), 7.91 (d, J=9.1 Hz, 2H), 7.98 (m, 2H), 8.47 (s, 1H), 8.49 (d, J=5.4 Hz, 1H), 9.98 (s, 1H). MS (ES) $C_{29}H_{25}FN_4O_5$ requires: 528. Found: 529 (M+H)$^+$.

The Examples in the following table were prepared according to the procedure described in the previous Example 24.

| Example | Name | Mwt | [M + H]$^+$ |
|---|---|---|---|
| 25 | N-[4-[(6,7-dimethoxy-4-quinolyl)oxy]phenyl]-1-(4-fluorophenyl)-4-isopropoxy-pyrazole-3-carboxamide | 542 | 543 |
| 26 | 4-(cyclopropylmethoxy)-N-[4-[(6,7-dimethoxy-4-quinolyl)oxy]phenyl]-1-(4-fluorophenyl)pyrazole-3-carboxamide | 554 | 555 |
| 27 | N-[4-[(6,7-dimethoxy-4-quinolyl)oxy]phenyl]-4-ethoxy-1-(4-fluoro-2-methyl-phenyl)pyrazole-3-carboxamide | 542 | 543 |

Example 28

N-[4-[(6,7-dimethoxy-4-quinolyl)oxy]-3-methyl-phenyl]-4-ethoxy-1-(4-fluorophenyl)pyrazole-3-carboxamide (M2)

Step 1: 4-[(6,7-dimethoxy-4-quinolyl)oxy]-3-methyl-aniline (M1)

M1 was prepared from 6,7-dimethoxyquinolin-4-ol and 1-fluoro-2-methyl-4-nitrobenzene following the general procedure reported in Preparative Example 1 Step 1-2. $^1$H NMR (400 MHz, $d_5$-DMSO, 300K) δ 1.93 (s, 3H), 3.92 (s, 6H), 5.06 (br s, 2H), 6.24 (d, J=5.2 Hz, 1H), 6.48 (dd, J=8.4 Hz, J=2.5 Hz, 1H), 6.53 (d, J=2.5 Hz, 1H), 6.83 (d, J=8.4 Hz, 1H), 7.35 (s, 1H), 7.53 (s, 1H), 8.40 (d, J=5.2 Hz, 1H). MS (ES) $C_{19}H_{19}N_2O_3$ requires: 310. Found: 311 (M+H)$^+$.

Step 2: N-[4-[(6,7-dimethoxy-4-quinolyl)oxy]-3-methyl-phenyl]-4-ethoxy-1-(4-fluorophenyl)pyrazole-3-carboxamide (M2)

M2 was prepared from M1 and D4 following the general procedure reported in Preparative Example 16 Step 5. $^1$H NMR (400 MHz, $d_5$-DMSO, 300K) δ 1.38 (t, J=7.0 Hz, 3H), 2.11 (s, 3H), 3.94 (s, 3H), 3.95 (s, 3H), 4.10 (q, J=7.0 Hz, 2H), 6.30 (d, J=5.2 Hz, 1H), 7.18 (d, J=8.7 Hz, 1H), 7.39 (m, 3H), 7.57 (s, 1H), 7.74 (dd, J=8.7 Hz, J 2.4 Hz, 1H), 7.83 (d, J=2.4 Hz, 1H), 7.99 (m, 2H), 8.44 (d, J=5.2 Hz, 1H), 8.47 (s, 1H), 9.90 (s, 1H). MS (ES) $C_{30}H_{27}FN_4O_5$ requires: 542. Found: 543 (M+H)$^+$.

The Examples in the following table were prepared according to the procedure described in the previous Example 28.

| Example | Name | Mwt | [M + H]$^+$ |
|---|---|---|---|
| 29 | N-[4-[(6,7-dimethoxy-4-quinolyl)oxy]-3-methyl-phenyl]-1-(4-fluorophenyl)-4-isopropoxy-pyrazole-3-carboxamide | 556 | 557 |
| 30 | 4-(cyclopropylmethoxy)-N-[4-[(6,7-dimethoxy-4-quinolyl)oxy]-3-methyl-phenyl]-1-(4-fluorophenyl)pyrazole-3-carboxamide | 568 | 569 |
| 31 | N-[4-[(6,7-dimethoxy-4-quinolyl)oxy]-3-methyl-phenyl]-4-ethoxy-1-(4-fluoro-2-methyl-phenyl)pyrazole-3-carboxamide | 556 | 557 |

Example 32

N-[3-chloro-4-[(6,7-dimethoxy-4-quinolyl)oxy]phenyl]-4-ethoxy-1-(4-fluorophenyl)pyrazole-3-carboxamide (N2)

Step 1:
3-chloro-4-[(6,7-dimethoxy-4-quinolyl)oxy]aniline (N1)

N1 was prepared from 6,7-dimethoxyquinolin-4-ol and 2-chloro-1-fluoro-4-nitrobenzene following the general procedure reported in Preparative Example 1 Step 1-2. $^1$H NMR (400 MHz, $d_6$-DMSO, 300K) δ 3.92 (s, 6H), 5.45 (br s, 2H), 6.28 (d, J=5.3 Hz, 1H), 6.61 (dd, J=8.7 Hz, J=2.6 Hz, 1H), 6.78 (d, J=2.6 Hz, 1H), 7.07 (d, J=8.7 Hz, 1H), 7.36 (s, 1H), 7.50 (s, 1H), 8.42 (d, J=5.3 Hz, 1H). MS (ES) $C_{17}H_{16}ClN_2O_3$ requires: 330. Found: 331 (M+H)$^+$.

Step 2: N-[3-chloro-4-[(6,7-dimethoxy-4-quinolyl)oxy]phenyl]-4-ethoxy-1-(4-fluorophenyl)pyrazole-3-carboxamide (N2)

N2 was prepared from N1 and D4 following the general procedure reported in Preparative Example 16 Step 5. $^1$H NMR (400 MHz, $d_6$-DMSO, 300K) δ 1.37 (t, J=7.0 Hz, 3H), 3.94 (s, 6H), 4.09 (q, J=7.0 Hz, 2H), 6.37 (d, J=5.2 Hz, 1H), 7.42 (m, 4H), 7.53 (s, 1H), 7.87 (dd, J=8.7 Hz, J=2.5 Hz, 1H), 8.00 (m, 2H), 8.21 (d, J=2.5 Hz, 1H), 8.46 (m, 2H), 10.16 (s, 1H). MS (ES) $C_{29}H_{24}ClFN_4O_6$ requires: 562. Found: 563 (M+H)$^+$.

The Examples in the following table were prepared according to the procedure described in the previous Example 32.

| Example | Name | Mwt | [M + H]$^+$ |
|---|---|---|---|
| 33 | N-[3-chloro-4-[(6,7-dimethoxy-4-quinolyl)oxy]phenyl]-1-(4-fluorophenyl)-4-isopropoxy-pyrazole-3-carboxamide | 576 | 577 |
| 34 | N-[3-chloro-4-[(6,7-dimethoxy-4-quinolyl)oxy]phenyl]-4-(cyclopropylmethoxy)-1-(4-fluorophenyl)pyrazole-3-carboxamide | 588 | 589 |
| 35 | N-[3-chloro-4-[(6,7-dimethoxy-4-quinolyl)oxy]phenyl]-4-ethoxy-1-(4-fluoro-2-methyl-phenyl)pyrazole-3-carboxamide | 576 | 577 |

Example 36

N-(4-((6,7-dimethoxyquinolin-4-yl)oxy)-3-fluorophenyl)-4-(2-(dimethylamino)ethyl)-1-(4-fluorophenyl)-1H-pyrazole-3-carboxamide (O3)

Step 1: Ethyl 4-[2-ethoxyvinyl]-1-(4-fluorophenyl)pyrazole-3-carboxylate (O1)

To a solution of D1 (500 mg, 2.0 mmol, 1.0 eq.) and 2,6-lutidine (0.3 mL, 2.8 mmol, 1.4 eq.) in dry DCM (10 mL) at 0° C. was added trifluoromethanesulfonic anhydride (1M in DCM, 2.4 mL, 2.4 mmol, 1.2 eq.). After 45 min the mixture was diluted with DCM and washed twice with aq. NaHCO$_3$-solution. After drying over MgSO$_4$ the solvent was removed in vacuo.

The crude material was resolved in dry DMF (15 mL) under N$_2$-atmosphere. Than cis-tributyl[2-ethoxyethenyl]stannane (1083 mg, 3 mmol, 1.5 eq.) and tetrakis(triphenylphosphine)-palladium (123 mg, 0.2 mmol, 0.1 eq.) were added and the mixture was heated for 5 h at 90° C. EtOAC was added and the organic phase was washed, three times with aq. NaHCO$_3$-solution. The organic phase was dried over MgSO$_4$ and solvents were removed in vacuo. The crude material was used without further purification. MS (ES) $C_{16}H_{17}FN_2O_3$ requires: 304. Found: 305 (M+H)$^+$ and 327 (M+Na)$^+$.

Step 2: 4-(2-dimethylaminoethyl)-1-(4-fluorophenyl)pyrazole-3-carboxylic acid (O2)

A solution of O1 (2 mmol) in TFA/DCM (1/1 mixture, 15 mL) was stirred for 2 h at RT. The solvents were removed in vacuo. The crude material was resolved in dry EtOH (5 mL) and dimethylamine in EtOH (5.6N, 1.07 mL, 6 mmol, 3.0 eq.) was added. After stirring for 2 h, sodium cyanoborohydride (376 mg, 6 mmol, 3.0 eq.) was added and the mixture was stirred further for 12 h. After adding water the solvents were removed in vacuo. The crude material was solved in EtOAc and washed twice with aq. NaHCO$_3$-solution, dried over MgSO$_4$ and evaporated in vacuo. The crude material was purified using an Isolute® SPE column SCX, loading the reaction mixture as a MeOH-solution and than eluting the desired compound with 2N NH$_3$ in MeOH yielding ethyl 4-(2-(dimethylamino)ethyl)-1-(4-fluorophenyl)-1H-pyrazole-3-carboxylate. MS (ES) $C_{16}H_{20}FN_3O_2$ requires: 305. Found: 306 (M+H)$^+$.

The crude material and sodium hydroxide (160 mg, 4.0 mmol, 2.0 eq.) was stirred in dioxane/water (1/1, 8 mL) for 12 h at RT. The solvents were removed in vacuo and the residue was purified by reverse phase RP-HPLC (column: C18), using H$_2$O and ACN as eluents. The desired fractions were lyophilized to yield the title compound O2 (198 mg, 0.71 mmol, 36%) as a white powder. MS (ES) $C_{14}H_{16}FN_3O_2$ requires: 277. Found: 278 (M+H)$^+$.

Step 3: N-(4-((6,7-dimethoxyquinolin-4-yl)oxy)-3-fluorophenyl)-4-(2-(dimethylamino)ethyl)-1-(4-fluorophenyl)-1H-pyrazole-3-carboxamide (O3)

To a solution of A2 (50 mg, 0.16 mmol, 1.0 eq), O2 (44 mg, 0.16 mmol, 1.0 eq.) and DIPEA (62 mg, 0.48 mmol, 3.0 eq.) in dry DMF (4 mL) was added HATU (121 mg, 0.32 mmol, 2.0 eq.). The mixture was stirred for 12 h at 60° C. Then the mixture was diluted with EtOAc and washed three times with aq. NaHCO$_3$-solution. The organic phase was dried over MgSO$_4$ and evaporated in vacuo. The residue was purified by reverse phase RP-HPLC (column: C18), using H$_2$O and ACN as eluents. The desired fractions were lyophilized to yield the desired compound O3 with impurities. A subsequent purification by chromatography on silica gel (DCM/MeOH=20:1) yielded the product O3 (15 mg, 0.026 mmol, 16%) as a white solid. $^1$H NMR (400 MHz, $d_6$-DMSO, 300K) δ 2.34 (s, 6H), 2.72 (m, 2H), 2.98 (t, J=7.4 Hz, 2H), 3.94 (s, 6H), 6.47 (d, J=5.3 Hz, 1H), 7.40 (s, 1H), 7.44 (m, 3H), 7.53 (s, 1H), 7.77 (d, J=8.8 Hz, 1H), 8.03 (m, 3H), 8.48 (d, J=5.3 Hz, 1H), 8.51 (s, 1H), 10.44 (s, 1H). MS (ES) $C_{31}H_{29}F_2N_5O_4$ requires: 573. Found: 574 (M+H)$^+$.

Example 37

N-[4-[(6,7-dimethoxy-4-quinolyl)oxy]-3-fluorophenyl]-1-[2-(2-dimethylaminoethyl)-4-fluoro-phenyl]-4-ethoxy-pyrazole-3-carboxamide (P7)

Step 1: ethyl 1-(2-bromo-4-fluoro-phenyl)-4-hydroxy-pyrazole-3-carboxylate (P1)

To a solution of 2-bromo-4-fluoroaniline (10 g, 52.6 mmol, 1.0 eq.) in DCM/HOAc (1/1, 160 mL, 0.3M) at 0° C. was added dropwise a precooled solution of sodium nitrite (4.1 g, 57.9 mmol, 1.1 eq.) in conc. sulfuric acid (20 mL). After stirring for 30 min at 0° C. a mixture of ethyl 4-chloroacetoacetate (14.6 mL, 17.8 g, 108 mmol, 1.2 eq.) in HOAc (40 mL) and $H_2O$ (80 mL) was added within 5 min. After further 15 min at 0° C. a solution of sodium acetate (72 g, 0.878 mol, 16.7 eq.) in $H_2O$ (140 mL) was added slowly. The mixture stirred for 30 min at 0° C. and than 12 h at RT. DCM (200 mL) was added and the organic phase was separated. The aq. phase was extracted with DCM (3×100 mL). The combined organic phase was washed with water, phosphate buffer and subsequent with brine. The organic layer was dried over $Na_2SO_4$ and concentrated under reduced pressure to give the product ethyl 2-(2-bromo-4-fluoro-phenyl)azo-4-chloro-3-oxo-butanoate as a red solid. MS (ES) $C_{12}H_{11}BrClFN_2O_3$ requires: 365. Found: 365/367 (M+H)$^+$.

Without further purification the crude material was dissolved in dry ethanol (130 mL) and after adding potassium acetate (7.1 g, 71 mmol, 1.4 eq.) the mixture was refluxed for 20 min. The reaction mixture was diluted with EtOAc and washed three times with water. The combined aq. phase was extracted with EtOAc. The combined organic phase was then washed with phosphate buffer and brine. The organic layer was dried over $Na_2SO_4$ and concentrated under reduced pressure. The desired product P1 was obtained as a yellow solid (18.19 g, 81%) and was used without further purification in the subsequent step. $^1$H NMR (400 MHz, CDCl$_3$, 300K) δ 1.44 (t, J=7.1 Hz, 3H), 4.47 (q, J=7.1 Hz, 2H), 7.13 (ddd, J=9.0 Hz, J=7.5 Hz, J=2.8 Hz, 1H), 7.41 (s, 1H), 7.42 (dd, J=7.5 Hz, J=2.8 Hz, 1H), 7.48 (dd, J=9.0 Hz, J=5.5 Hz, 1H). MS (ES) $C_{12}H_{10}BrFN_2O_3$ requires: 329. Found: 329/331 (M+H)$^+$ and 351/353 (M+Na)$^+$.

Step 2: ethyl 1-(2-bromo-4-fluoro-phenyl)-4-ethoxy-pyrazole-3-carboxylate (P2)

To a mixture of P1 (4.3 g, 13.1 mmol, 1.0 eq.) and $K_2CO_3$ (2.4 g, 17.3 mmol, 1.3 eq.) in dry DMF (55 mL) was added at RT iodoethane (1.38 mL, 2.7 g, 17.3 mmol, 1.3 eq.). After stirring for 12 h at RT the mixture was cooled to 0° C. MeOH (5 mL) was added, the mixture was diluted with DCM (200 mL) and washed with water and phosphate buffer.

The organic layer was dried over $Na_2SO_4$ and concentrated under reduced pressure. The crude product was purified by flash chromatography on silica gel (DCM/MeOH=100:0 to 5:1) to yield the desired product P2 (4.1 g, 86%) as a yellow solid. $^1$H NMR (400 MHz, CDCl$_3$, 300K) δ 1.40 (t, J=7.1 Hz, 3H), 1.47 (t, J=7.0 Hz, 3H), 4.06 (q, J=7.0 Hz, 2H), 4.43 (q, J=7.1 Hz, 2H), 7.13 (ddd, J=8.8 Hz, J=7.5 Hz, J=2.8 Hz, 1H), 7.41 (s, 1H), 7.42 (dd, J=8.8 Hz, J=2.8 Hz, 1H), 7.52 (dd, J=8.8 Hz, J=5.3 Hz, 1H). MS (ES) $C_{14}H_{14}BrFN_2O_3$ requires: 357. Found: 357/359 (M+H)$^+$.

Step 3: ethyl 4-ethoxy-1-[2-[(Z)-2-ethoxyvinyl]-4-fluoro-phenyl]pyrazole-3-carboxylate (P3)

A mixture of P2 (1 g, 2.8 mmol, 1.0 eq.), cis-tributyl[2-ethoxyethenyl]stannane (1.3 g, 3.1 mmol, 1.1 eq.) in DMF (9 mL) was degassed with a stream of $N_2$ for 15 min. Then Pd(PPh$_3$)$_4$ (170 mg, 0.15 mmol, 0.05 eq.) was added and the reaction mixture was heated to 100° C. for 45 min in the microwave oven. The mixture was concentrated under reduced pressure and the residue was purified by flash chromatography on silica gel (cHex/EtOAc=50:1 to 3:1) to yield the desired product P3 (820 mg, 84%) as a yellow oil. $^1$H NMR (400 MHz, CDCl$_3$, 300K) δ 1.35 (t, J=7.1 Hz, 3H), 1.38 (t, J=7.1 Hz, 3H), 1.44 (t, J=7.0 Hz, 3H), 4.00 (m, 4H), 4.40 (q, J=7.1 Hz, 2H), 4.81 (d, J=7.3 Hz, 1H), 6.23 (d, J=7.3 Hz, 1H), 6.88 (m, 1H), 7.26 (m, 2H), 7.88 (dd, J=10.6 Hz, J=2.8 Hz, 1H). MS (ES) $C_{19}H_{21}FN_2O_4$ requires: 348. Found: 349 (M+H)$^+$.

Step 4: ethyl 4-ethoxy-1-[4-fluoro-2-(2-oxoethyl) phenyl]pyrazole-3-carboxylate (P4)

P3 (820 mg, 2.3 mmol, 1.0 eq.) was stirred in TFA/DCM (1/2, 7.5 mL) at RT for 40 h. The mixture was concentrated under reduced pressure to yield the desired product P4 as an yellow oil. The crude material was used without further purification. MS (ES) $C_{16}H_{17}FN_2O_4$ requires: 320. Found: 321 (M+H)$^+$.

Step 5: ethyl 1-[2-(2-dimethylaminoethyl)-4-fluoro-phenyl]-4-ethoxy-pyrazole-3-carboxylate (P5)

A mixture of the crude product P4 (2.3 mmol, 1.0 eq.) and a solution of dimethylamine in MeOH (5.6M, 3 ml, 7 eq.) was stirred at RT for 2 h. After addition of sodium cyanoborohydride (215 mg, 3.4 mmol, 1.5 eq.) the mixture was stirred for 15 h at RT. Water was added and the aq. phase was extracted with EtOAc. The combined org. phase was washed with aq. sat. NaHCO$_3$-solution and dried over $Na_2SO_4$. The solvent was removed in vacuo and the crude was purified using an Isolute® SPE column SCX, loading the reaction mixture as a MeOH solution and than eluting the desired compound with 2N NH$_3$ in MeOH. The title compound P5 was isolated after evaporation of the solvent under reduced pressure as a yellow oil (138 mg, 0.4 mmol, 17%). MS (ES) $C_{19}H_{24}FN_3O_3$ requires: 349. Found: 350 (M+H)$^+$.

Step 6: 1-[2-(2-dimethylaminoethyl)-4-fluoro-phenyl]-4-ethoxy-pyrazole-3-carboxylic acid (P6)

P6 was prepared from P5 following the general procedure reported in Preparative Example 16 Step 3. The residue was purified by reversed-phase flash chromatography (H$_2$O/MeOH=100:0 to 1:10) to yield the desired product P6 (112 mg, 88%) as a white solid. MS (ES) $C_{16}H_{20}FN_3O_3$ requires: 321. Found: 322 (M+H)$^+$.

Step 7: N-(4-((6,7-dimethoxyquinolin-4-yl)oxy)-3-fluorophenyl)-1-(2-(2-(dimethylamino)ethyl)-4-fluorophenyl)-4-ethoxy-1H-pyrazole-3-carboxamide hydrochloride (P7)

Carboxylic acid P6 (117 mg, 0.36 mmol, 1.0 eq.) was heated in thionyl chloride (3 mL) for 4 h under reflux. Solvent was removed in vacuo and the crude material was resolved in dry toluene and evaporated under reduced pressure again.

The crude material was solved in dry pyridine (3 mL) and A2 (115 mg, 0.36 mmol, 1.0 eq.) was added. The mixture was stirred at RT for 12 h. Water was added and the mixture was evaporated in vacuo. The residue was purified by reverse phase RP-HPLC (column: C18), using H$_2$O and ACN as eluents. The desired fractions were lyophilized. The white solid (70 mg) was solved in water and ACN and than 1N HCl (0.13 mL) was added. The mixture was lyophilized to yield the title compound P7 (74 mg, 0.113 mmol, 32%) as a white powder. $^1$H NMR (400 MHz, MeOD, 300K) δ 1.57 (t, J=7.0 Hz, 3H), 2.97 (s, 6H), 3.08 (t, J=7.6 Hz, 2H), 3.55 (t, J=7.6 Hz, 2H), 4.04 (s, 3H), 4.05 (s, 3H), 4.28 (q, J=7.0 Hz, 2H), 6.66 (d, J=5.8 Hz, 1H), 7.25 (dt, J=8.6 Hz, J=2.8 Hz, 1H), 7.35 (dd, J=9.2 Hz, J=2.8 Hz, 1H), 7.41 (s, 1H), 7.45 (t, J=8.6 Hz, 1H), 7.53 (d, J=8.9 Hz, 1H), 7.60 (dd, J=8.9 Hz, J=5.0 Hz, 1H), 7.71 (s, 1H), 8.04 (m, 1H), 8.06 (s, 1H), 8.51 (d, J=5.8 Hz, 1H). MS (ES) $C_{33}H_{33}F_2N_5O_5$ requires: 617. Found: 618 $(M+H)^+$.

Example 38

N-[3-fluoro-4-[[6-methoxy-7-(3-morpholinopropoxy)-4-quinolyl]oxy]phenyl]-2-phenyl-thiazole-4-carboxamide (Q1)

Q1 was prepared from 3-fluoro-4-[[6-methoxy-7-(3-morpholinopropoxy)-4-quinolyl]oxy]aniline and 2-phenyl-1,3-thiazole-4-carbonyl chloride following the general procedure reported in Preparative Example 1 Step 3. $^1$H NMR (400 MHz, $d_4$-MeOD, 300K) δ 2.17 (m, 2H), 2.73 (m, 4H), 2.81 (t, J=7.4 Hz, 2H), 3.77 (t, J=4.7 Hz, 4H), 3.98 (s, 3H), 4.24 (t, J=6.0 Hz, 2H), 6.50 (d, J=5.4 Hz, 1H), 7.33 (s, 1H), 7.35 (t, J=8.8 Hz, 1H), 7.50 (m, 4H), 7.62 (s, 1H), 7.66 (d, J=8.8 Hz, 1H), 8.01 (dd, J=12.6 Hz, J=2.5 Hz, 1H), 8.07 (m, 2H), 8.32 (s, 1H), 8.39 (d, J=5.4 Hz, 1H). MS (ES) $C_{33}H_{31}FN_4O_5S$ requires: 614. Found: 615 $(M+H)^+$.

Example 39

4-bromo-N-[3-fluoro-4-[[6-methoxy-7-(3-morpholinopropoxy)-4-quinolyl]oxy]phenyl]-1-methyl-pyrazole-3-carboxamide (Q2)

Q2 was prepared from 3-fluoro-4-[[6-methoxy-7-(3-morpholinopropoxy)-4-quinolyl]oxy]aniline and 4-bromo-1-methyl-1H-pyrazole-3-carbonyl chloride following the general procedure reported in Preparative Example 1 Step 3. $^1$H NMR (400 MHz, $d_4$-MeOD, 300K) δ 2.20 (m, 2H), 2.73 (m, 4H), 2.81 (t, J=7.4 Hz, 2H), 3.80 (t, J=4.7 Hz, 4H), 4.02 (s, 3H), 4.05 (s, 3H), 4.29 (t, J=6.1 Hz, 2H), 6.54 (dd, J=5.4 Hz, J=1.0 Hz, 1H), 7.37 (t, J=9.0 Hz, 1H), 7.38 (s, 1H), 7.61 (d, J=8.8 Hz, 1H), 7.68 (s, 1H), 7.86 (s, 1H), 7.95 (dd, J=12.9 Hz, J=2.4 Hz, 1H), 8.45 (d, J=5.4 Hz, 1H). MS (ES) $C_{28}H_{29}BrFN_5O_5$ requires: 614. Found: 614/616 $(M+H)^+$.

Example 40

N-[3-fluoro-4-[[6-methoxy-7-(3-morpholinopropoxy)-4-quinolyl]oxy]phenyl]-1-methyl-pyrazole-3-carboxamide (Q3)

Q3 was prepared from 3-fluoro-4-[[6-methoxy-7-(3-morpholinopropoxy)-4-quinolyl]oxy]aniline and 1-methyl-1H-pyrazole-3-carbonyl chloride following the general procedure reported in Preparative Example 1 Step 3. $^1$H NMR (400 MHz, $d_4$-MeOD, 300K) δ 2.10 (m, 2H), 2.52 (m, 4H), 2.62 (t, J=7.5 Hz, 2H), 3.70 (t, J=4.7 Hz, 4H), 3.99 (s, 3H), 4.00 (s, 3H), 4.22 (t, J=6.2 Hz, 2H), 6.49 (d, J=5.4 Hz, 1H), 6.83 (d, J=2.3 Hz, 1H), 7.33 (m, 2H), 7.58 (d, J=8.8 Hz, 1H), 7.62 (s, 1H), 7.67 (d, J=2.4 Hz, 1H), 7.94 (dd, J=12.7 Hz, J=2.4 Hz, 1H), 8.40 (d, J=5.4 Hz, 1H). MS (ES) $C_{28}H_{30}FN_5O_5$ requires: 535. Found: 536 $(M+H)^+$.

Example 41

1-tert-butyl-N-[3-fluoro-4-[[6-methoxy-7-(3-morpholinopropoxy)-4-quinolyl]oxy]phenyl]-5-methyl-pyrazole-3-carboxamide (Q4)

Q4 was prepared from 3-fluoro-4-[[6-methoxy-7-(3-morpholinopropoxy)-4-quinolyl]oxy]aniline and 1-methyl-5-phenyl-1H-pyrazole-3-carbonyl chloride following the general procedure reported in Preparative Example 1 Step 3. MS (ES) $C_{32}H_{38}FN_5O_5$ requires: 591. Found: 592 $(M+H)^+$.

Example 42

N-[3-fluoro-4-[[6-methoxy-7-(3-morpholinopropoxy)-4-quinolyl]oxy]phenyl]-1,5-dimethyl-pyrazole-3-carboxamide (Q5)

Q5 was prepared from 3-fluoro-4-[[6-methoxy-7-(3-morpholinopropoxy)-4-quinolyl]oxy]aniline and 1,5-dimethyl-1H-pyrazole-3-carbonyl chloride following the general procedure reported in Preparative Example 1 Step 3. MS (ES) $C_{29}H_{32}FN_5O_5$ requires: 549. Found: 550 $(M+H)^+$.

Example 43

4-ethoxy-N-[3-fluoro-4-[[6-methoxy-7-(3-morpholinopropoxy)-4-quinolyl]oxy]phenyl]-1-(4-fluoro-2-methyl-phenyl)pyrazole-3-carboxamide (Q6)

Q6 was prepared from 3-fluoro-4-[[6-methoxy-7-(3-morpholinopropoxy)-4-quinolyl]oxy]aniline and J4 following the general procedure reported in Preparative Example 1 Step 3. $^1$H NMR (400 MHz, $d_6$-DMSO, 300K) δ 1.36 (t J=7.0 Hz, 3H), 1.96 (m, 2H), 2.25 (s, 3H), 2.38 (m, 4H), 2.46 (t, J=7.0 Hz, 2H), 3.57 (t, J=4.5 Hz, 4H), 3.94 (s, 3H), 4.04 (q, J=7.0 Hz, 2H), 4.19 (t, J=6.4 Hz, 2H), 6.44 (d, J=5.1 Hz, 1H), 7.21 (dt, J=8.6 Hz, J=2.9 Hz, 1H), 7.31 (dt, J=9.7 Hz, J=2.9 Hz, 1H), 7.39 (s, 1H), 7.41 (t, J=9.0 Hz, 1H), 7.51 (m, 2H), 7.69 (d, J=8.6 Hz, 1H), 8.02 (s, 1H), 8.02 (dd, J=13.3 Hz, J=2.3 Hz, 1H), 8.45 (d, J=5.2 Hz, 1H), 10.14 (s, 1H). MS (ES) $C_{36}H_{37}F_2N_5O_6$ requires: 673. Found: 674 $(M+H)^+$.

Example 44

N-[3-fluoro-4-[[6-methoxy-7-(3-morpholinopropoxy)-4-quinolyl]oxy]phenyl]-1-(4-fluorophenyl)-4-methoxy-pyrazole-3-carboxamide (Q7)

Q7 was prepared from 3-fluoro-4-[[6-methoxy-7-(3-morpholinopropoxy)-4-quinolyl]oxy]aniline and E3 following the general procedure reported in Preparative Example 1 Step 3. $^1$H NMR (400 MHz, $d_6$-DMSO, 300K) δ 2.01 (m, 2H), 2.51 (m, 6H), 3.61 (m, 4H), 3.86 (s, 3H), 3.94 (s, 3H), 4.20 (t, J=6.2 Hz, 2H), 6.46 (d, J=5.3 Hz, 1H), 7.43 (m, 4H), 7.53 (s, 1H), 7.72 (t, J=9.1 Hz, 1H), 8.01 (m, 3H), 8.47 (d, J=5.3 Hz, 1H), 8.49 (s, 1H), 10.19 (s, 1H). MS (ES) $C_{34}H_{33}F_2N_6O_6$ requires: 645. Found: 646 $(M+H)^+$.

Example 45

N-[3-fluoro-4-[[6-methoxy-7-(3-morpholinopropoxy)-4-quinolyl]oxy]phenyl]-1-(4-fluorophenyl)-4-isopropoxy-pyrazole-3-carboxamide (Q8)

Q8 was prepared from 3-fluoro-4-[[6-methoxy-7-(3-morpholinopropoxy)-4-quinolyl]oxy]aniline and 12 following the general procedure reported in Preparative Example 1 Step 3. $^1$H NMR (400 MHz, $d_6$-DMSO, 300K) δ 1.34 (d, J=6.0 Hz, 6H), 1.97 (m, 2H), 2.38 (m, 4H), 2.47 (m, 2H), 3.57 (t, J=4.6 Hz, 4H), 3.94 (s, 3H), 4.19 (t, J=6.3 Hz, 2H), 4.43 (sept, J=6.0 Hz, 1H), 6.46 (d, J=5.2 Hz, 1H), 7.42 (m, 4H), 7.59 (s, 1H), 7.68 (t, J=9.1 Hz, 1H), 8.01 (m, 3H), 8.46 (d, J=5.2 Hz, 1H), 8.49 (s, 1H), 10.15 (s, 1H). MS (ES) $C_{36}H_{37}F_2N_6O_6$ requires: 673. Found: 674 $(M+H)^+$.

The Examples in the following table were prepared according to the procedure described in the previous Example 45.

| Example | Name | Mwt | [M + H]+ |
|---|---|---|---|
| 46 | 4-(cyclopropylmethoxy)-N-[3-fluoro-4-[[6-methoxy-7-(3-morpholinopropoxy)-4-quinolyl]oxy]phenyl]-1-(4-fluorophenyl)pyrazole-3-carboxamide | 685 | 686 |
| 47 | 1-(2-chloro-4-fluoro-phenyl)-4-ethoxy-N-[3-fluoro-4-[[6-methoxy-7-(3-morpholinopropoxy)-4-quinolyl]oxy]phenyl]pyrazole-3-carboxamide | 694 | 695 |
| 48 | 4-(2-dimethylaminoethoxy)-N-[3-fluoro-4-[[6-methoxy-7-(3-morpholinopropoxy)-4-quinolyl]oxy]phenyl]-1-(4-fluorophenyl)pyrazole-3-carboxamide | 702 | 703 |
| 49 | 1-(2-bromo-4-fluoro-phenyl)-4-ethoxy-N-[3-fluoro-4-[[6-methoxy-7-(3-morpholinopropoxy)-4-quinolyl]oxy]phenyl]pyrazole-3-carboxamide | 738 | 738/740 |
| 50 | N-[3-fluoro-4-[[6-methoxy-7-(3-morpholinopropoxy)-4-quinolyl]oxy]phenyl]-1-(4-fluorophenyl)-4-(2-methoxyethoxy)pyrazole-3-carboxamide | 689 | 690 |
| 51 | 4-benzyloxy-N-[3-fluoro-4-[[6-methoxy-7-(3-morpholinopropoxy)-4-quinolyl]oxy]phenyl]-1-(4-fluorophenyl)pyrazole-3-carboxamide | 721 | 722 |
| 52 | N-[3-fluoro-4-[[6-methoxy-7-(3-morpholinopropoxy)-4-quinolyl]oxy]phenyl]-1-(4-fluorophenyl)-4-nitro-pyrazole-3-carboxamide | 660 | 661 |
| 53 | 4-amino-N-[3-fluoro-4-[[6-methoxy-7-(3-morpholinopropoxy)-4-quinolyl]oxy]phenyl]-1-(4-fluorophenyl)pyrazole-3-carboxamide | 630 | 631 |

Example 54

N-[4-[[7-(3-aminopropoxy)-6-methoxy-4-quinolyl]oxy]-3-fluoro-phenyl]-4-ethoxy-1-(4-fluorophenyl)pyrazole-3-carboxamide ($R^3$)

Step 1: tert-butyl N-[3-[[4-(2-fluoro-4-nitro-phenoxy)-6-methoxy-7-quinolyl]oxy]propyl]carbamate ($R^1$)

To a solution of 4-(2-fluoro-4-nitro-phenoxy)-6-methoxy-quinolin-7-ol (511 mg, 1.55 mmol, 1.0 eq.) and potassium carbonate (428 mg, 3.1 mmol, 2.0 eq.) in dry DMF (10 mL) was added tert-butyl(3-bromopropyl)carbamate (480 mg, 2.01 mmol, 1.3 eq.). The mixture was stirred for 3 h at 90° C. and then cooled to RT. EtOAc was added and the organic phase was washed three times with water. The organic phase was dried over MgSO$_4$ and solvents were removed in vacuo. The desired product R1 was obtained as brown oil and was used without further purification in the next step. MS (ES) $C_{24}H_{26}FN_3O_7$ requires: 487. Found: 488 (M+H)+.

Step 2: tert-butyl N-[3-[[4-(4-amino-2-fluoro-phenoxy)-6-methoxy-7-quinolyl]oxy]propyl]carbamate ($R^2$)

A suspension of R1 (1.55 mmol, 1.0 eq.) and Pd/C (10% w/w, 75 mg) in MeOH (30 mL) was stirred under hydrogen atmosphere (1 atm) at RT for 5 h. The suspension was filtered through a pad of Celite®. The solvent was removed in vacuo. The product $R^2$ was obtained as yellow solid (708 mg, 1.55 mmol, 100%). The crude material was used without further purification. $^1$H NMR (400 MHz, d$_6$-DMSO, 300K) δ 1.37 (s, 9H), 1.92 (quint., J=6.4 Hz, 2H), 3.13 (quart., J=6.4 Hz, 2H), 3.93 (s, 3H), 4.14 (t, J=6.4 Hz, 2H), 5.46 (br s, 2H), 6.36 (d, J=5.3 Hz, 1H), 6.45 (dd, J=8.7 Hz, J=2.4 Hz, 1H), 6.53 (dd, J=13.1 Hz, J=2.4 Hz, 1H), 6.88 (m, 1H), 7.05 (t, J=8.9 Hz, 1H), 7.34 (s, 1H), 7.49 (s, 1H), 8.43 (d, J=5.3 Hz, 1H). MS (ES) $C_{24}H_{28}FN_3O_5$ requires: 457. Found: 458 (M+H)+.

Step 3: N-[4-[[7-(3-aminopropoxy)-6-methoxy-4-quinolyl]oxy]-3-fluoro-phenyl]-4-ethoxy-1-(4-fluorophenyl)pyrazole-3-carboxamide (R3)

Tert-butyl N-[3-[[4-[[4-ethoxy-1-(4-fluorophenyl)pyrazole-3-carbonyl]amino]-2-fluoro-phenoxy]-6-methoxy-7-quinolyl]oxy]propyl]carbamate was prepared from R2 and D4 following the general procedure reported in Preparative Example 1 Step 3.

Then the crude material was stirred in TFA/DCM (1/1) for 3 h at RT. The reaction mixture was concentrated under reduced pressure and the residue was purified by reverse phase RP-HPLC (column: C18), using H$_2$O and MeOH as eluents. The desired fractions were lyophilized to yield the title compound $R^3$ as a white powder. $^1$H NMR (400 MHz, d$_4$-MeOD, 300K) δ 1.59 (t, J=7.0 Hz, 3H), 2.29 (m, 2H), 3.27 (t, J=6.8 Hz, 2H), 4.03 (s, 3H), 4.19 (q, J=7.0 Hz, 2H), 4.35 (t, J=5.6 Hz, 2H), 6.55 (d, J=5.3 Hz, 1H), 7.24 (t, J=8.7 Hz, 2H), 7.36 (t, J=9.0 Hz, 1H), 7.38 (s, 1H), 7.55 (d, J=9.0 Hz, 1H), 7.68 (s, 1H), 7.88 (m, 2H), 7.99 (dd, J=12.6 Hz, J=2.4 Hz, 1H), 8.16 (s, 1H), 8.44 (d, J=5.3 Hz, 1H). MS (ES) $C_{31}H_{29}F_2N_5O_5$ requires: 589. Found: 590 (M+H)+.

The Examples in the following table were prepared according to the procedure described in the previous Example 54.

| Example | Name | Mwt | [M + H]+ |
|---|---|---|---|
| 55 | N-[4-[[7-(3-aminopropoxy)-6-methoxy-4-quinolyl]oxy]-3-fluoro-phenyl]-4-ethoxy-1-(4-fluoro-2-methyl-phenyl)pyrazole-3-carboxamide | 603 | 604 |
| 56 | N-[4-[[7-(3-aminopropoxy)-6-methoxy-4-quinolyl]oxy]-3-fluoro-phenyl]-5-ethoxy-2-(4-fluorophenyl)oxazole-4-carboxamide | 590 | 591 |

Example 57

4-ethoxy-N-[3-fluoro-4-[[6-methoxy-7-[3-(4-methylpiperazin-1-yl)propoxy]-4-quinolyl]oxy]phenyl]-1-(4-fluoro-2-methyl-phenyl)pyrazole-3-carboxamide (S2)

Step 1: 3-fluoro-4-[[6-methoxy-7-[3-(4-methylpiperazin-1-yl)propoxy]-4-quinolyl]oxy]aniline (S1)

S1 was prepared from 4-(2-fluoro-4-nitro-phenoxy)-6-methoxy-quinolin-7-ol and 1-(3-chloropropyl)-4-methylpiperazine following the general procedure reported in Preparative Example 54 Step 1-2. $^1$H NMR (400 MHz, d$_6$-DMSO, 300K) δ 1.95 (quint., J=6.8 Hz, 2H), 2.14 (s, 3H), 2.22-2.47 (m, 10H), 3.94 (s, 3H), 4.17 (t, J=6.5 Hz, 2H), 5.48 (br.s, 2H), 6.38 (d, J=5.2 Hz, 1H), 6.46 (dd, J=8.7 Hz, J=2.4 Hz, 1H), 6.55 (dd, J=13.2 Hz, J=2.4 Hz, 1H), 7.07 (t, J=9.0 Hz, 1H), 7.36 (s, 1H), 7.50 (s, 1H), 8.44 (d, J=5.2 Hz, 1H). MS (ES) $C_{24}H_{29}FN_4O_3$ requires: 440. Found: 441 (M+H)+.

Step 2: 4-ethoxy-N-[3-fluoro-4-[[6-methoxy-7-[3-(4-methylpiperazin-1-yl)propoxy]-4-quinolyl]oxy]phenyl]-1-(4-fluoro-2-methyl-phenyl)pyrazole-3-carboxamide (S2)

S2 was prepared from S1 and J4 following the general procedure reported in Preparative Example 1 Step 3. The crude product was purified by flash chromatography on silica gel (DCM/MeOH=100:0 to 5:1) to yield the desired product S2 (60 mg, 0.087 mmol, 77%) as a white solid. $^1$H NMR (400 MHz, d$_6$-DMSO, 300K) δ 1.36 (t, J=7.0 Hz, 3H), 1.95 (t, J=7.3 Hz, 2H), 2.17 (m, 4H), 2.25 (m, 4H), 2.30-2.50 (m, 8H), 3.94 (s, 3H), 4.05 (q, J=7.0 Hz, 2H), 4.17 (t, J=6.4 Hz, 2H), 6.44 (d, J=5.2 Hz, 1H), 7.21 (dt, J=8.6 Hz, J=2.5 Hz, 1H), 7.31 (dd, J=9.8 Hz, J=2.5 Hz, 1H), 7.37 (s, 1H), 7.41 (t, J=9.0 Hz, 1H), 7.50 (m, 2H), 7.69 (d, J=9.0 Hz, 1H), 8.01 (dd, J=13.1 Hz, J=2.5 Hz, 1H), 8.02 (s, 1H), 8.46 (d, J=5.2 Hz, 1H), 10.14 (s, 1H). MS (ES) $C_{37}H_{40}F_2N_6O_6$ requires: 686. Found: 687 (M+H)$^+$.

The Examples in the following table were prepared according to the procedure described in the previous Example 57.

| Example | Name | Mwt | [M + H]$^+$ |
|---|---|---|---|
| 58 | 4-ethoxy-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide | 672 | 673 |
| 59 | N-[3-fluoro-4-[[6-methoxy-7-[3-(4-methylpiperazin-1-yl)propoxy]-4-quinolyl]oxy]phenyl]-1-(4-fluorophenyl)-4-methoxy-pyrazole-3-carboxamide | 658 | 659 |
| 60 | 1-(2-chloro-4-fluoro-phenyl)-4-ethoxy-N-[3-fluoro-4-[[6-methoxy-7-[3-(4-methylpiperazin-1-yl)propoxy]-4-quinolyl]oxy]phenyl]pyrazole-3-carboxamide | 706 | 707 |
| 61 | 4-(cyclopropylmethoxy)-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide | 698 | 699 |
| 62 | N-[3-fluoro-4-[[6-methoxy-7-[3-(4-methylpiperazin-1-yl)propoxy]-4-quinolyl]oxy]phenyl]-1-(4-fluorophenyl)-4-isopropoxy-pyrazole-3-carboxamide | 686 | 687 |
| 63 | 5-ethoxy-N-[3-fluoro-4-[[6-methoxy-7-[3-(4-methylpiperazin-1-yl)propoxy]-4-quinolyl]oxy]phenyl]-2-(4-fluorophenyl)oxazole-4-carboxamide | 673 | 674 |

Example 64

4-(cyclopropylmethoxy)-N-[3-fluoro-4-[[6-methoxy-7-(3-piperazin-1-ylpropoxy)-4-quinolyl]oxy]phenyl]-1-(4-fluorophenyl)pyrazole-3-carboxamide trifluoroacetic acid salt (T2)

Step 1: tert-butyl 4-[3-[[4-(4-amino-2-fluoro-phenoxy)-6-methoxy-7-quinolyl]oxy]propyl]piperazine-1-carboxylate (T1)

T1 was prepared from 4-(2-fluoro-4-nitro-phenoxy)-6-methoxy-quinolin-7-ol and tert-butyl 4-(3-chloropropyl)piperazine-1-carboxylate following the general procedure reported in Preparative Example 54 Step 1-2. $^1$H NMR (400 MHz, d$_6$-DMSO, 300K) δ 1.38 (s, 9H), 1.96 (m, 2H), 2.23 (m, 4H), 2.47 (m, 2H), 3.30 (m, 4H), 3.92 (s, 3H), 4.17 (t, J=6.3 Hz, 2H), 5.46 (br s, 2H), 6.37 (d, J=5.2 Hz, 1H), 6.45 (dd, J=8.9 Hz, J=1.8 Hz, 1H), 6.54 (dd, J=13.1 Hz, J=2.4 Hz, 1H), 7.05 (t, J=8.9 Hz, 1H), 7.35 (s, 1H), 7.49 (s, 1H), 8.42 (d, J=5.2 Hz, 1H). MS (ES) $C_{29}H_{35}FN_4O_5$ requires: 526. Found: 527 (M+H)$^+$.

Step 2: 4-(cyclopropylmethoxy)-N-[3-fluoro-4-[[6-methoxy-7-(3-piperazin-1-ylpropoxy)-4-quinolyl]oxy]phenyl]-1-(4-fluorophenyl)pyrazole-3-carboxamide trifluoroacetic acid salt (T2)

Tert-butyl 4-[3-[[4-[[4-[[4-(cyclopropylmethoxy)-1-(4-fluorophenyl)pyrazole-3-carbonyl]-amino]-2-fluoro-phenoxy]-6-methoxy-7-quinolyl]oxy]propyl]piperazine-1-carboxylate was prepared from T1 and F3 following the general procedure reported in Preparative Example 1 Step 3. The crude material was stirred in TFA/DCM (1/1) for 3 h at RT. The reaction mixture was concentrated under reduced pressure and the residue was purified by reverse phase RP-HPLC (column: C18, using H$_2$O (0.1% TFA) and MeOH (0.1% TFA) as eluents. The desired fractions were lyophilized to yield the title compound T2 as a white powder. $^1$H NMR (400 MHz, d$_6$-DMSO, 300K) δ 0.35 (m, 2H), 0.58 (m, 2H), 1.30 (m, 1H), 1.94 (m, 2H), 2.32 (m, 2H), 2.41 (t, J=7.2 Hz, 2H), 2.71 (m, 4H), 3.87 (d, J=7.1 Hz, 2H), 3.93 (s, 3H), 4.17 (t, J=6.4 Hz, 2H), 6.45 (d, J=5.3 Hz, 1H), 7.39 (m, 4H), 7.45 (t, J=9.1 Hz, 1H), 7.52 (s, 1H), 7.68 (d, J=8.8 Hz, 1H), 8.00 (m, 4H), 8.45 (d, J=5.3 Hz, 1H), 8.46 (s, 1H), 10.18 (s, 1H). MS (ES) $C_{37}H_{38}F_2N_6O_6$ requires: 684. Found: 685 (M+H)$^+$.

The Examples in the following table were prepared according to the procedure described in the previous Example 64.

| Example | Name | Mwt | [M + H]$^+$ |
|---|---|---|---|
| 65 | 4-ethoxy-N-[3-fluoro-4-[[6-methoxy-7-(3-piperazin-1-ylpropoxy)-4-quinolyl]oxy]phenyl]-1-(4-fluorophenyl)pyrazole-3-carboxamide | 658 | 659 |
| 66 | N-[3-fluoro-4-[[6-methoxy-7-(3-piperazin-1-ylpropoxy)-4-quinolyl]oxy]phenyl]-1-(4-fluorophenyl)-4-methoxy-pyrazole-3-carboxamide | 644 | 645 |
| 67 | N-[3-fluoro-4-[[6-methoxy-7-(3-piperazin-1-ylpropoxy)-4-quinolyl]oxy]phenyl]-1-(4-fluorophenyl)-4-isopropoxy-pyrazole-3-carboxamide | 672 | 673 |
| 68 | 1-(2-chloro-4-fluoro-phenyl)-4-ethoxy-N-[3-fluoro-4-[[6-methoxy-7-(3-piperazin-1-ylpropoxy)-4-quinolyl]oxy]phenyl]pyrazole-3-carboxamide | 692 | 693 |
| 69 | 4-ethoxy-N-[3-fluoro-4-[[6-methoxy-7-(3-piperazin-1-ylpropoxy)-4-quinolyl]oxy]phenyl]-1-(4-fluoro-2-methyl-phenyl)pyrazole-3-carboxamide | 672 | 673 |
| 70 | N-[3-fluoro-4-[[6-methoxy-7-(3-piperazin-1-ylpropoxy)-4-quinolyl]oxy]phenyl]-1-(4-fluorophenyl)-4-(2-methoxyethoxy)pyrazole-3-carboxamide | 688 | 689 |
| 71 | N-[3-fluoro-4-[[6-methoxy-7-(3-piperazin-1-ylpropoxy)-4-quinolyl]oxy]phenyl]-1-(4-fluorophenyl)-4-[(1-methylpyrrolidin-3-yl)methoxy]pyrazole-3-carboxamide | 727 | 728 |
| 72 | N-[3-fluoro-4-[[6-methoxy-7-(3-piperazin-1-ylpropoxy)-4-quinolyl]oxy]phenyl]-2-phenyl-thiazole-4-carboxamide trifluoroacetic acid salt | 613 | 614 |

Example 73

N-[3-fluoro-4-[[6-methoxy-7-(4-piperidylmethoxy)-4-quinolyl]oxy]phenyl]-1-(4-fluorophenyl)-4-methoxy-pyrazole-3-carboxamide (U2)

Step 1: tert-butyl 4-[[4-(4-amino-2-fluoro-phenoxy)-6-methoxy-7-quinolyl]oxymethyl]piperidine-1-carboxylate (U1)

U1 was prepared from 4-(2-fluoro-4-nitro-phenoxy)-6-methoxy-quinolin-7-ol and tert-butyl 4-(bromomethyl)piperidine-1-carboxylate following the general procedure reported in Preparative Example 54 Step 1-2. $^1$H NMR (400 MHz, CDCl$_3$, 300K) δ 1.22 (m, 2H), 1.40 (s, 9H), 1.82 (d, J=12.7 Hz, 2H), 2.10 (m, 1H), 2.69 (t, J=12.3 Hz, 2H), 3.77

(m, 2H), 3.96 (s, 3H), 3.97 (m, 2H), 4.10 (m, 2H), 6.31 (d, J=5.2 Hz, 1H), 6.46 (m, 2H), 6.96 (t, J=8.7 Hz, 1H), 7.31 (s, 1H), 7.51 (s, 1H), 8.40 (d, J=5.2 Hz, 1H). MS (ES) $C_{27}H_{32}FN_3O_5$ requires: 497. Found: 498 (M+H)$^+$.

Step 2: N-[3-fluoro-4-[[6-methoxy-7-(4-piperidyl-methoxy)-4-quinolyl]oxy]phenyl]-1-(4-fluorophenyl)-4-methoxy-pyrazole-3-carboxamide (U2)

Tert-butyl 4-[[4-[2-fluoro-4-[[1-(4-fluorophenyl)-4-methoxy-pyrazole-3-carbonyl]amino]-phenoxy]-6-methoxy-7-quinolyl]oxymethyl]piperidine-1-carboxylate was prepared from U1 and E3 following the general procedure reported in Preparative Example 1 Step 3. The crude material was stirred in TFA/DCM (1/1) for 3 h at RT. The reaction mixture was concentrated under reduced pressure and the residue was purified by reverse phase RP-HPLC (column: C18), using H$_2$O and MeOH as eluents. The desired fractions were lyophilized to yield the title compound U2 as a white powder. $^1$H NMR (400 MHz, d$_6$-DMSO, 300K) δ 1.50 (q, J=12.3 Hz, 2H), 1.97 (d, J=13.0 Hz, 2H), 2.18 (m, 1H), 2.95 (m, 2H), 3.33 (m, 2H), 3.85 (s, 3H), 3.95 (s, 3H), 4.07 (d, J=6.2 Hz, 2H), 6.48 (d, J=5.2 Hz, 1H), 7.41 (m, 4H), 7.54 (s, 1H), 7.72 (d, J=8.7 Hz, 1H), 8.00 (m, 3H), 8.47 (d, J=5.2 Hz, 1H), 8.50 (s, 1H), 10.26 (s, 1H). MS (ES) $C_{33}H_{31}F_2N_5O_5$ requires: 615. Found: 616 (M+H)$^+$.

The Examples in the following table were prepared according to the procedure described in the previous Example 73.

| Example | Name | Mwt | [M + H]$^+$ |
|---|---|---|---|
| 74 | 4-ethoxy-N-[3-fluoro-4-[[6-methoxy-7-(4-piperidylmethoxy)-4-quinolyl]oxy]phenyl]-1-(4-fluoro-2-methyl-phenyl)pyrazole-3-carboxamide | 643 | 644 |
| 75 | 4-(cyclopropylmethoxy)-N-[3-fluoro-4-[[6-methoxy-7-(4-piperidylmethoxy)-4-quinolyl]oxy]phenyl]-1-(4-fluorophenyl)pyrazole-3-carboxamide | 655 | 656 |
| 76 | 4-bromo-N-[3-fluoro-4-[[6-methoxy-7-(4-piperidylmethoxy)-4-quinolyl]oxy]phenyl]-1-(4-fluorophenyl)pyrazole-3-carboxamide | 664 | 664/666 |
| 77 | N-[3-fluoro-4-[[6-methoxy-7-(4-piperidylmethoxy)-4-quinolyl]oxy]phenyl]-1-(4-fluorophenyl)-4-[(4-fluorophenyl)methoxy]pyrazole-3-carboxamide | 709 | 710 |
| 78 | 1-tert-butyl-N-[3-fluoro-4-[[6-methoxy-7-(4-piperidylmethoxy)-4-quinolyl]oxy]phenyl]-5-methyl-pyrazole-3-carboxamide | 561 | 562 |
| 79 | N-[3-fluoro-4-[[6-methoxy-7-(4-piperidylmethoxy)-4-quinolyl]oxy]phenyl]-4-nitro-1-[3-(1-piperidyl)propyl]pyrazole-3-carboxamide | 661 | 662 |
| 80 | N-[3-fluoro-4-[[6-methoxy-7-(4-piperidylmethoxy)-4-quinolyl]oxy]phenyl]-5-methyl-2-phenyl-oxazole-4-carboxamide | 582 | 583 |
| 81 | N-[3-fluoro-4-[[6-methoxy-7-(4-piperidylmethoxy)-4-quinolyl]oxy]phenyl]-2-phenyl-thiazole-4-carboxamide trifluoroacetic acid salt | 584 | 585 |

Example 82

4-ethoxy-N-[4-[[7-[(1-ethyl-4-piperidyl)methoxy]-6-methoxy-4-quinolyl]oxy]-3-fluoro-phenyl]-1-(4-fluoro-2-methyl-phenyl)pyrazole-3-carboxamide (V1)

Example 74 (39 mg, 0.06 mmol, 1.0 eq.) and acetaldehyde (5 mg, 0.12 mmol, 2.0 eq.) in dry MeOH (5 mL) was stirred for 2 h at RT. After adding sodium cyanoborohydride (6 mg, 0.09 mmol, 1.5 eq.) the mixture was stirred for 12 h. The mixture was diluted with EtOAc and the organic phase was washed twice with aq.NaHO$_3$-solution. The organic phase was dried and solvents were removed in vacuo. The residue was purified by reverse phase RP-HPLC (column: C18), using H$_2$O and MeOH as eluents. The desired fractions were lyophilized to yield the title compound V01 as a white powder. MS (ES) $C_{37}H_{39}F_2N_5O_5$ requires: 671. Found: 672 (M+H)$^+$.

The Example in the following table was prepared according to the procedure described in the previous Example 82.

| Example | Name | Mwt | [M + H]$^+$ |
|---|---|---|---|
| 83 | 4-ethoxy-N-[3-fluoro-4-[[7-[(1-isobutyl-4-piperidyl)methoxy]-6-methoxy-4-quinolyl]oxy]phenyl]-1-(4-fluoro-2-methyl-phenyl)pyrazole-3-carboxamide | 699 | 700 |

Example 84

N-[5-[(6,7-dimethoxy-4-quinolyl)oxy]-2-pyridyl]-4-ethoxy-1-(4-fluorophenyl)pyrazole-3-carboxamide trifluoroacetic acid salt (W3)

Step 1:
6,7-dimethoxy-4-[(6-nitro-3-pyridyl)oxy]quinoline (W1)

A mixture of 6,7-dimethoxyquinolin-4-ol (2.02 g, 9.8 mmol, 1.0 eq.), 5-fluoro-2-nitro-pyridine (1.96 g, 13.78 mmol, 1.4 eq.) and cesium carbonate (4.8 g, 14.7 mmol, 1.5 eq.) in dry DMF (10 mL) was heated for 1 h at 80° C. in a microwave oven. After cooling to RT the mixture was diluted with water and extracted with DCM. The combined organic phase was dried over Na$_2$SO$_4$ and evaporated in vacuo. The crude product was purified by flash chromatography on silica gel (DCM/MeOH=100:0 to 10:1) to yield the desired product W1 (1.28 g, 40%) as a yellow solid. $^1$H NMR (400 MHz, d$_6$-DMSO, 300K) δ 3.88 (s, 3H), 3.94 (s, 3H), 6.92 (d, J=5.2 Hz, 1H), 7.41 (s, 1H), 7.45 (s, 1H), 7.98 (dd, J=2.7 Hz, J=9.0 Hz, 1H), 8.40 (d, J=9.0 Hz, 1H), 8.60 (d, J=5.2 Hz, 1H), 8.66 (d, J=2.7 Hz, 1H). MS (ES) $C_{16}H_{13}N_3O_5$ requires: 327. Found: 328 (M+H)$^+$.

Step 2:
5-[(6,7-dimethoxy-4-quinolyl)oxy]pyridin-2-amine (W2)

W1 (1.28 g, 3.91 mmol) in EtOH (40 mL) was reduced in an H-Cube® hydrogenation reactor (Pd/C cartridge, H$_2$=100 bar, T=60° C., flow=0.7 mL/min). After evaporation of the solvent the crude material was purified by flash chromatography on silica gel (DCM/MeOH=100:0 to 5:1) to yield the desired product W2 (0.48 g, 41%) as a white solid. $^1$H NMR (400 MHz, d$_6$-DMSO, 300K) δ 3.92 (s, 6H), 6.03 (br s, 2H), 6.40 (d, J=5.2 Hz, 1H), 6.55 (d, J=8.9 Hz, 1H), 7.35 (m, 2H), 7.49 (s, 1H), 7.88 (d, J=2.9 Hz, 1H), 8.43 (d, J=5.2 Hz, 1H). MS (ES) $C_{16}H_{15}N_3O_3$ requires: 297. Found: 298 (M+H)$^+$.

Step 3: N-[5-[(6,7-dimethoxy-4-quinolyl)oxy]-2-pyridyl]-4-ethoxy-1-(4-fluorophenyl)pyrazole-3-carboxamide trifluoroacetic acid salt (W3)

W3 was prepared from W2 and D4 following the general procedure reported in Preparative Example 1 Step 3. $^1$H NMR (400 MHz, d$_6$-DMSO, 300K) δ 1.42 (t, J=7.0 Hz, 3H), 4.02 (s, 3H), 4.03 (s, 3H), 4.18 (q, J=7.0 Hz, 2H), 7.03 (d, J=6.5 Hz, 1H), 7.40 (t, J=8.9 Hz, 1H), 7.58 (s, 1H), 7.76 (s, 1H), 7.98 (m, 3H), 8.43 (d, J=8.9 Hz, 1H), 8.52 (d, J=3.0 Hz, 1H), 8.56 (s, 1H), 8.82 (d, J=6.6 Hz, 1H), 9.97 (s, 1H). MS (ES) C$_{28}$H$_{24}$FN$_5$O$_5$ requires: 529. Found: 530 (M+H)$^+$.

The Examples in the following table were prepared according to the procedure described in the previous Example 84.

| Example | Name | Mwt | [M + H]$^+$ |
|---|---|---|---|
| 85 | N-[5-[(6,7-dimethoxy-4-quinolyl)oxy]-2-pyridyl]-4-ethoxy-1-(4-fluoro-2-methyl-phenyl)pyrazole-3-carboxamide | 543 | 544 |
| 86 | 1-(2-chloro-4-fluoro-phenyl)-N-[5-[(6,7-dimethoxy-4-quinolyl)oxy]-2-pyridyl]-4-ethoxy-pyrazole-3-carboxamide | 563 | 564 |
| 87 | N-[5-[(6,7-dimethoxy-4-quinolyl)oxy]-2-pyridyl]-4-(2-dimethylaminoethyl)-1-(4-fluorophenyl)pyrazole-3-carboxamide | 556 | 557 |

Example 88

Tert-butyl 4-(((4-((6-(4-ethoxy-1-(4-fluoro-2-methylphenyl)-1H-pyrazole-3-carboxamido)pyridin-3-yl)oxy)-6-methoxyquinolin-7-yl)oxy)methyl)piperidine-1-carboxylate (X1)

X1 was prepared from tert-butyl 4-(((4-((6-aminopyridin-3-yl)oxy)-6-methoxyquinolin-7-yl)oxy)methyl)piperidine-1-carboxylate and J4 following the general procedure reported in Preparative Example 16 Step 5. $^1$H NMR (400 MHz, d$_4$-MeOH, 300K) δ 1.32 (m, 2H), 1.46 (s, 9H), 1.53 (t, J=7.0 Hz, 3H), 1.90 (m, 2H), 2.12 (m, 1H), 2.27 (s, 3H), 2.84 (m, 2H), 4.00 (s, 3H), 4.03 (m, 2H), 4.14 (m, 2H), 4.22 (q, J=7.00 Hz, 3H), 6.59 (d, J=5.4 Hz, 1H), 7.08 (dt, J=2.5 Hz, J=8.2 Hz, 1H), 7.15 (dd, J=2.5 Hz, J=9.3 Hz, 1H), 7.32 (s, 1H), 7.42 (m, 1H), 7.63 (s, 1H), 7.76 (m, 1H), 7.84 (s, 1H), 8.31 (m, 1H), 8.45 (m, 2H). MS (ES) C$_{36}$H$_{43}$FN$_6$O$_7$ requires: 726. Found: 727 (M+H)$^+$.

Example 89

N-(5-((6,7-dimethoxyquinolin-4-yl)oxy)pyridin-2-yl)-4-ethoxy-1-(4-methoxy-2-methylphenyl)-1H-pyrazole-3-carboxamide (X2)

Following the general procedure reported in Preparative Example 16 Step 5 X2 was prepared from W2 and 4-ethoxy-1-(4-methoxy-2-methylphenyl)-1H-pyrazole-3-carbonyl chloride, which was prepared similar to Preparative Example 16 step 1-4. $^1$H NMR (400 MHz, d$_6$-DMSO, 300K) δ 1.41 (t, J=7.0 Hz, 3H), 2.21 (s, 3H), 3.81 (s, 3H), 3.93 (s, 3H), 3.94 (s, 3H), 4.15 (q, J=7.0 Hz, 2H), 6.54 (d, J=5.2 Hz, 1H), 6.91 (dd, J=8.7 Hz, J=2.8 Hz, 1H), 6.98 (d, J=2.8 Hz, 1H), 7.36 (d, J=8.7 Hz, 1H), 7.41 (s, 1H), 7.53 (s, 1H), 7.85 (dd, J=2.9 Hz, J=9.0 Hz, 1H), 8.04 (s, 1H), 8.35 (d, J=9.0 Hz, 1H), 8.39 (d, J=2.9 Hz, 1H), 8.49 (d, J=5.2 Hz, 1H), 9.68 (s, 1H). MS (ES) C$_{30}$H$_{28}$N$_6$O$_6$ requires: 555. Found: 556 (M+H)$^+$.

Example 90

N-(4-((6,7-dimethoxyquinolin-4-yl)oxy)-3-fluorophenyl)-4-ethoxy-1-(3-nitrophenyl)-1H-pyrazole-3-carboxamide (X3)

Following the general procedure reported in Preparative Example 16 Step 5 X3 was prepared from A2 and 4-ethoxy-1-(3-nitrophenyl)-1H-pyrazole-3-carbonyl chloride, which was prepared similar to Preparative Example 16 step 1-4. MS (ES) C$_{29}$H$_{24}$N$_5$O$_7$ requires: 573. Found: 574 (M+H)$^+$.

Example 91

N-(4-((6,7-dimethoxyquinolin-4-yl)oxy)-3-fluorophenyl)-4-ethoxy-1-(4-methoxy-2-methylphenyl)-1H-pyrazole-3-carboxamid (X4)

Following the general procedure reported in Preparative Example 16 Step 5×4 was prepared from A2 and 4-ethoxy-1-(4-methoxy-2-methylphenyl)-1H-pyrazole-3-carbonyl chloride, which was prepared similar to Preparative Example 16 step 1-4. $^1$H NMR (400 MHz, d$_6$-DMSO, 300K) δ 1.36 (t, J=7.0 Hz, 3H), 2.20 (s, 3H), 3.80 (s, 3H), 3.94 (s, 6H), 4.05 (q, J=7.0 Hz, 2H), 6.46 (d, J=5.2 Hz, 1H), 6.90 (dd, J=2.9 Hz, J=8.8 Hz, 1H), 6.98 (d, J=2.7 Hz, 1H), 7.36 (d, J=8.8 Hz, 1H), 7.40 (s, 1H), 7.43 (d, J=9.0 Hz, 1H), 7.53 (s, 1H), 7.71 (d, J=9.0 Hz, 1H), 7.95 (s, 1H), 8.03 (dd, J=2.4 Hz, J=13.3 Hz, 1H), 8.47 (d, J=5.2 Hz, 1H), 10.10 (s, 1H). MS (ES) C$_{31}$H$_{29}$FN$_4$O$_6$ requires: 572. Found: 573 (M+H)$^+$.

Example 92

N-(5-((6,7-dimethoxyquinolin-4-yl)oxy)pyridin-2-yl)-4-ethoxy-1-(3-nitrophenyl)-1H-pyrazole-3-carboxamide (X5)

Following the general procedure reported in Preparative Example 16 Step 5×5 was prepared from W2 and 4-ethoxy-1-(3-nitrophenyl)-1H-pyrazole-3-carbonyl chloride, which was prepared similar to Preparative Example 16 step 1-4. MS (ES) C$_{28}$H$_{24}$N$_6$O$_7$ requires: 556. Found: 557 (M+H)$^+$.

Example 93

1-(2-(benzyloxy)-4-fluorophenyl)-N-(5-((6,7-dimethoxyquinolin-4-yl)oxy)pyridin-2-yl)-4-ethoxy-1H-pyrazole-3-carboxamide (X6)

Following the general procedure reported in Preparative Example 16 Step 5 X6 was prepared from W2 and 1-(2-(benzyloxy)-4-fluorophenyl)-4-ethoxy-1H-pyrazole-3-carbonyl chloride, which was prepared similar to Preparative Example 16 step 1-4. $^1$H NMR (400 MHz, CDCl$_3$, 300K) δ 1.45 (t, J=7.0 Hz, 3H), 4.01 (s, 3H), 4.07 (s, 3H), 5.14 (s, 2H), 6.48 (d, J=5.3 Hz, 1H), 6.83 (m, 1H), 7.26 (m, 1H), 7.40 (m, 5H), 7.46 (s, 1H), 7.56 (s, 1H), 7.60 (dd, J=2.9 Hz, J=9.0 Hz, 1H), 7.76 (s, 1H), 7.85 (m, 1H), 8.26 (d, J=2.9 Hz, 1H), 8.52 (d, J=5.3 Hz, 1H), 8.59 (d, J=9.0 Hz, 1H), 9.53 (s, 1H). MS (ES) C$_{35}$H$_{30}$FN$_5$O$_6$ requires: 635. Found: 636 (M+H)$^+$.

Example 94

N-(4-((6,7-dimethoxyquinolin-4-yl)oxy)-2-methoxyphenyl)-4-ethoxy-1-(4-fluoro-2-methylphenyl)-1H-pyrazole-3-carboxamide (X7)

Following the general procedure reported in Preparative Example 16 Step 5 X7 was prepared from J4 and 4-((6,7-dimethoxyquinolin-4-yl)oxy)-2-methoxyaniline, which was prepared similar to Preparative Example 1 step 1-2. $^1$H NMR (400 MHz, CDCl$_3$, 300K) δ 1.58 (t, J=7.0 Hz, 3H), 2.27 (s, 3H), 3.91 (s, 3H), 4.05 (s, 3H), 4.06 (s, 3H), 4.15 (q, J=7.0 Hz, 2H), 6.52 (d, J=5.3 Hz, 1H), 6.77 (d, J=2.5 Hz, 1H), 6.85 (dd, J=2.5 Hz, J=8.8 Hz, 1H), 7.00 (m, 2H), 7.32 (s, 1H), 7.34 (dd, J=5.3 Hz, J=8.8 Hz, 1H), 7.44 (s, 1H), 7.58 (s, 1H), 8.50 (d, J=5.3 Hz, 1H), 8.76 (d, J=8.8 Hz, 1H), 9.50 (s, 1H). MS (ES) $C_{31}H_{29}FN_4O_6$ requires: 572. Found: 573 $(M+H)^+$.

Example 95

N-(4-((6,7-dimethoxyquinolin-4-yl)oxy)-2-methylphenyl)-4-ethoxy-1-(4-fluoro-2-methylphenyl)-1H-pyrazole-3-carboxamide (X8)

Following the general procedure reported in Preparative Example 16 Step 5×8 was prepared from J4 and 4-((6,7-dimethoxyquinolin-4-yl)oxy)-2-methylaniline, which was prepared similar to Preparative Example 1 step 1-2. $^1$H NMR (400 MHz, CDCl$_3$, 300K) δ 1.56 (t, J=7.0 Hz, 3H), 2.28 (s, 3H), 2.39 (s, 3H), 4.05 (s, 6H), 4.18 (q, J=7.0 Hz, 2H), 6.51 (d, J=5.3 Hz, 1H), 7.02 (m, 3H), 7.09 (dd, J=2.7 Hz, J=8.8 Hz, 1H), 7.35 (m, 2H), 7.44 (s, 1H), 7.57 (s, 1H), 8.41 (d, J=8.8 Hz, 1H), 8.49 (d, J=5.3 Hz, 1H), 8.78 (s, 1H). MS (ES) $C_{31}H_{29}FN_4O_5$ requires: 556. Found: 557 $(M+H)^+$.

Example 96

N-(4-((6,7-dimethoxyquinolin-4-yl)oxy)-3-fluorophenyl)-4-ethoxy-1-(4-fluoro-3-methoxyphenyl)-1H-pyrazole-3-carboxamide (X9)

Following the general procedure reported in Preparative Example 16 Step 5 X9 was prepared from A2 and 4-ethoxy-1-(4-fluoro-3-methoxyphenyl)-1H-pyrazole-3-carbonyl chloride, which was prepared similar to Preparative Example 16 step 1-4. $^1$H NMR (400 MHz, d$_6$-DMSO, 300K) δ 1.39 (t, J=7.0 Hz, 3H), 3.94 (s, 6H), 3.96 (s, 3H), 4.10 (q, J=7.0 Hz, 2H), 6.48 (d, J=5.2 Hz, 1H), 7.40 (m, 2H), 7.46 (t, J=9.0 Hz, 1H), 7.52 (m, 2H), 7.70 (m, 2H), 8.03 (dd, J=2.4 Hz, J=13.2 Hz, 1H), 8.48 (d, J=5.2 Hz, 1H), 8.52 (s, 1H), 10.19 (s, 1H). MS (ES) $C_{30}H_{26}F_2N_4O_6$ requires: 576. Found: 577 $(M+H)^+$.

Example 97

N-(5-((6,7-dimethoxyquinolin-4-yl)oxy)pyridin-2-yl)-4-ethoxy-1-(4-fluoro-3-methoxyphenyl)-1H-pyrazole-3-carboxamide (X10)

Following the general procedure reported in Preparative Example 16 Step 5 X10 was prepared from W2 and 4-ethoxy-1-(4-fluoro-3-methoxyphenyl)-1H-pyrazole-3-carbonyl chloride, which was prepared similar to Preparative Example 16 step 1-4. $^1$H NMR (400 MHz, d$_6$-DMSO, 300K) δ 1.43 (t, J=7.0 Hz, 3H), 3.97 (s, 3H), 4.02 (s, 6H), 4.19 (q, J=7.0 Hz, 2H), 6.99 (d, J=6.5 Hz, 1H), 7.39 (dd, J=8.9 Hz, J=10.9 Hz, 1H), 7.49 (m, 1H), 7.68 (dd, J=2.5 Hz, J=7.5 Hz, 1H), 7.72 (s, 1H), 7.75 (s, 1H), 8.01 (dd, J=2.9 Hz, J=9.0 Hz, 1H), 8.42 (d, J=9.0 Hz, 1H), 8.52 (d, J=2.9 Hz, 1H), 8.60 (s, 1H), 8.80 (d, J=6.5 Hz, 1H), 9.97 (s, 1H). MS (ES) $C_{29}H_{26}FN_5O_6$ requires: 559. Found: 560 $(M+H)^+$.

Example 98

N-(5-((6,7-dimethoxyquinolin-4-yl)oxy)pyridin-2-yl)-4-ethoxy-1-(4-nitrophenyl)-1H-pyrazole-3-carboxamide (X11)

Following the general procedure reported in Preparative Example 16 Step 5 X11 was prepared from W2 and 4-ethoxy-1-(4-nitrophenyl)-1H-pyrazole-3-carbonyl chloride, which was prepared similar to Preparative Example 16 step 1-4. $^1$H NMR (400 MHz, d$_6$-DMSO, 300K) δ 1.43 (t, J=7.0 Hz, 3H), 3.93 (s, 3H), 3.94 (s, 3H), 4.20 (q, J=7.0 Hz, 2H), 6.56 (d, J=5.2 Hz, 1H), 7.40 (s, 1H), 7.53 (s, 1H), 7.87 (dd, J=2.9 Hz, J=9.1 Hz, 1H), 8.22 (d, J=9.1 Hz, 2H), 8.34 (d, J=9.1 Hz, 1H), 8.41 (m, 3H), 8.48 (d, J=5.3 Hz, 1H), 8.75 (s, 1H), 10.04 (s, 1H). MS (ES) $C_{28}H_{24}N_6O_7$ requires: 556. Found: 557 $(M+H)^+$.

Example 99

1-(4-aminophenyl)-N-(5-((6,7-dimethoxyquinolin-4-yl)oxy)pyridin-2-yl)-4-ethoxy-1H-pyrazole-3-carboxamide (X12)

A suspension of X11 (357 mg, 0.64 mmol), and Pd/C (10% w/w, 35 mg) in a mixture of aq. HCl-solution (6N, 1.5 mL). DCM (20 mL) and MeOH (40 mL) was stirred under hydrogen atmosphere (1 atm) at RT for 2 h. The mixture was diluted with DCM (100 mL) and aq. NaHCO$_3$-solution (50 mL). The org. phase was separated and the aq. phase was extracted twice with DCM (50 mL). The combined org. phase was dried over Na$_2$SO$_4$ and concentrated under reduced pressure. The residue was solved in MeCN (20 mL) and H$_2$O (5 mL) and lyophilized yielding X12 (322 mg, 95%) as a beige solid. $^1$H NMR (400 MHz, d$_6$-DMSO, 300K) δ 1.42 (t, J=7.0 Hz, 3H), 3.94 (s, 3H), 3.95 (s, 3H), 4.17 (q, J=7.0 Hz, 2H), 5.35 (s, 2H), 6.55 (d, J=5.2 Hz, 1H), 6.66 (d, J=8.8 Hz; 2H), 7.41 (s, 1H), 7.54 (m, 3H), 7.86 (dd, J=2.9 Hz, J=8.9 Hz, 1H), 8.30 (s, 1H), 8.37 (m, 2H), 8.49 (d, J=5.3 Hz, 1H), 9.71 (s, 1H). MS (ES) $C_{28}H_{26}N_6O_6$ requires: 526. Found: 527 $(M+H)^+$.

Example 100

N-(5-((6-methoxy-7-(piperidin-4-ylmethoxy)quinolin-4-yl)oxy)pyridin-2-yl)-4-(2-methoxyphenyl)thiazole-2-carboxamide (X13)

Following the general procedure reported in Preparative Example 16 Step 5 X13 was prepared from tert-butyl 4-(((4-((6-aminopyridin-3-yl)oxy)-6-methoxyquinolin-7-yl)oxy)methyl)piperidine-1-carboxylate and 4-(2-methoxyphenyl)thiazole-2-carbonyl chloride, which was prepared similar to Preparative Example 16 step 4 from commercially available 4-(2-methoxyphenyl)thiazole-2-carboxylic acid. $^1$H NMR (400 MHz, d$_6$-DMSO, 300K) δ 1.40 (m, 2H), 1.87 (d, J=12.6 Hz, 2H), 2.07 (m, 1H), 2.76 (t, J=11.8 Hz, 2H), 3.18 (d, J=12.6 Hz, 2H), 3.93 (s, 3H), 3.95 (s, 3H), 4.02 (d, J=6.4 Hz, 2H), 6.57 (d, J=5.2 Hz, 1H), 7.09 (t, J=7.6 Hz, 1H), 7.18 (d, J=8.4 Hz, 1H), 7.39 (m, 2H), 7.53 (s, 1H), 7.90 (dd, J=2.8 Hz, J=9.0 Hz, 1H), 8.29 (d, J=9.0 Hz, 1H), 8.49 (m, 4H). MS (ES) $C_{32}H_{31}N_6O_6S$ requires: 597. Found: 598 $(M+H)^+$.

Example 101

N-(5-((6-methoxy-7-(piperidin-4-ylmethoxy)quinolin-4-yl)oxy)pyridin-2-yl)-4-phenylthiazole-2-carboxamide (X14)

A mixture of tert-butyl 4-(((4-((6-aminopyridin-3-yl)oxy)-6-methoxyquinolin-7-yl)oxy)methyl)piperidine-1-carboxylate (70 mg, 0.14 mmol), 4-phenylthiazole-2-carboxylic acid (46 mg, 0.21 mmol), DIPEA (56 mg, 0.43 mmol) and HATU (110 mg, 0.29 mmol) in dry DMF (5 mL) was stirred for 72 h at 55° C. The solution was diluted with EtOAc (150 mL) and washed twice with aq.NaHCO$_3$-solution and once with brine. The residue was dissolved in 50% TFA in DCM (5 mL) and stirred for 2 h at RT. The mixture was concentrated under reduced pressure. The residue was purified by reverse phase RP-HPLC (column: C18), using H$_2$O and ACN as eluents. The desired fractions were lyophilized to yield the title compound X14 (25 mg, 30%) as a white powder. $^1$H NMR (400 MHz, d$_6$-DMSO, 300K) δ 1.25 (m, 2H), 1.76 (d, J=12.0 Hz, 2H), 1.95 (m, 1H), 2.55 (t, J=11.0 Hz, 2H), 3.00 (d, J=12.0 Hz, 2H), 3.94 (s, 3H), 3.99 (d, J=6.3 Hz, 2H), 6.58 (d, J=5.2 Hz, 1H), 7.41 (m, 2H), 7.51 (m, 3H), 7.90 (dd, J=2.9 Hz, J=9.0 Hz, 1H), 8.17 (d, J=7.4 Hz, 2H), 8.29 (d, J=9.0 Hz, 1H), 8.48 (d, J=2.9 Hz, 1H), 8.50 (d, J=5.2 Hz, 1H), 8.55 (s, 1H). MS (ES) C$_3$H$_{29}$N$_5$O$_4$S requires: 567. Found: 568 (M+H)$^+$.

Example 102

4-bromo-N-(5-((6-methoxy-7-(piperidin-4-ylmethoxy)quinolin-4-yl)oxy)pyridin-2-yl)thiazole-2-carboxamide (X15)

Following the general procedure reported in Preparative Example 16 Step 5 X15 was prepared from tert-butyl 4-(((4-((6-aminopyridin-3-yl)oxy)-6-methoxyquinolin-7-yl)oxy)methyl)piperidine-1-carboxylate and 4-bromothiazole-2-carbonyl chloride, which was prepared similar to Preparative Example 16 step 4 from commercially available 4-bromothiazole-2-carboxylic acid. $^1$H NMR (400 MHz, d$_6$-DMSO, 300K) δ 1.53 (m, 2H), 1.98 (d, J=12.5 Hz, 2H), 2.18 (m, 1H), 2.95 (m, 2H), 3.33 (m, 2H), 3.94 (s, 3H), 4.08 (d, J=6.3 Hz, 2H), 6.58 (d, J=5.2 Hz, 1H), 7.45 (s, 1H), 7.54 (m, 1H), 7.87 (dd, J=2.9 Hz, J=9.0 Hz, 1H), 8.19 (d, J=9.0 Hz, 1H), 8.31 (s, 1H), 8.45 (d, J=2.9 Hz, 1H), 8.50 (d, J=5.2 Hz, 1H), 10.61 (br s, 1H). MS (ES) C$_{25}$H$_{24}$BrN$_5$O$_4$S requires: 570. Found: 570/572 (M−1-H)$^+$.

Example 103

N-(4-((6,7-dimethoxyquinolin-4-yl)oxy)-2-methoxyphenyl)-4-ethoxy-1-(4-fluoro-2-methylphenyl)-1H-pyrazole-3-carboxamide (X16)

Following the general procedure reported in Preparative Example 16 Step 5 X16 was prepared from J4 and 4-((6,7-dimethoxyquinolin-4-yl)oxy)-2-methoxyaniline, which was prepared similar to Preparative Example 1 step 1-2. $^1$H NMR (400 MHz, d$_6$-DMSO, 300K) δ 1.58 (t, J=7.0 Hz, 3H), 2.27 (s, 3H), 3.91 (s, 3H), 4.05 (s, 3H), 4.06 (s, 3H), 4.15 (q, J=7.0 Hz, 2H), 6.53 (d, J=5.3 Hz, 1H), 6.77 (d, J=2.5 Hz, 1H), 6.85 (dd, J=2.5 Hz, J=8.8 Hz, 1H), 7.00 (m, 2H), 7.32 (s, 1H), 7.35 (dd, J=8.6 Hz, J=5.3 Hz, 1H), 7.44 (s, 1H), 7.58 (s, 1H), 8.50 (d, J=5.3 Hz, 1H), 8.76 (d, J=8.8 Hz, 1H), 9.50 (s, 1H). MS (ES) C$_{31}$H$_{29}$FN$_4$O$_6$ requires: 572. Found: 573 (M+H)$^+$.

Example 104

N-(5-((6,7-dimethoxyquinolin-4-yl)oxy)pyridin-2-yl)-4-ethoxy-1-(4-fluoro-2-hydroxyphenyl)-1H-pyrazole-3-carboxamide (X18)

A suspension of X6 (60 mg, 0.09 mmol) and Pd/C (10% w/w, 6 mg) in EtOH (50 mL) was stirred under hydrogen atmosphere (1 atm) at RT for 15 h. The suspension was filtered through a pad of Celite®. The solvent was removed in vacuo. The residue was purified by reverse phase RP-HPLC (column: C18), using H$_2$O and ACN as eluents. The desired fractions were lyophilized to yield the title compound X18 (1.2 mg, 2%) as a white solid. $^1$H NMR (400 MHz, CDCl$_3$, 300K) δ 1.61 (t, J=7.0 Hz, 3H), 4.06 (s, 3H), 4.07 (s, 3H), 4.26 (q, J=7.0 Hz, 2H), 6.48 (d, J=5.2 Hz, 1H), 6.68 (dt, J=2.6 Hz, J=8.4 Hz, 1H), 6.87 (dd, J=2.3 Hz, J=9.8 Hz, 1H), 7.31 (dd, J=5.7 Hz, J=9.0 Hz, 1H), 7.44 (s, 1H), 7.56 (s, 1H), 7.61 (dd, J=2.8 Hz, J=9.0 Hz, 1H), 7.68 (s, 1H), 8.28 (d, J=2.8 Hz, 1H), 8.53 (m, 2H), 9.49 (s, 1H). MS (ES) C$_{28}$H$_{24}$FN$_6$O$_6$ requires: 545. Found: 546 (M+H)$^+$.

Example 105

N-(4-((6,7-dimethoxyquinolin-4-yl)oxy)-3-fluorophenyl)-4-ethoxy-1-(pyridin-3-yl)-1H-pyrazole-3-carboxamide (X19)

Following the general procedure reported in Preparative Example 16 Step 5 X19 was prepared from A2 and 4-ethoxy-1-(pyridin-3-yl)-1H-pyrazole-3-carbonyl chloride, which was prepared similar to Preparative Example 16 step 1-4. $^1$H NMR (400 MHz, d$_6$-DMSO, 300K) δ 1.39 (t, J=7.0 Hz, 3H), 3.96 (s, 6H), 4.10 (q, J=7.0 Hz, 2H), 6.56 (d, J=5.5 Hz, 1H), 7.43 (s, 1H), 7.49 (t, J=9.0 Hz, 1H), 7.57 (s, 1H), 7.60 (dd, J=4.7 Hz, J=8.4 Hz, 1H), 7.73 (d, J=9.0 Hz, 1H), 8.04 (dd, J=2.4 Hz, J=13.2 Hz, 1H), 8.35 (d, J=8.4 Hz, 1H), 8.54 (d, J=5.5 Hz, 1H), 8.57 (dd, J=1.4 Hz, J=4.7 Hz, 1H), 8.59 (s, 1H), 9.24 (s, 1H), 10.25 (s, 1H). MS (ES) C$_{28}$H$_{24}$FN$_6$O$_6$ requires: 529. Found: 530 (M+H)$^+$.

Example 106

N-(4-((6,7-dimethoxyquinolin-4-yl)oxy)-3-fluorophenyl)-4-ethoxy-1'-methyl-1'H-[1,3'-bipyrazole]-3-carboxamide (X20)

Following the general procedure reported in Preparative Example 16 Step 5 X20 was prepared from A2 and 4-ethoxy-1'-methyl-1'H-[1,3'-bipyrazole]-3-carbonyl chloride, which was prepared similar to Preparative Example 16 step 1-4. $^1$H NMR (400 MHz, d$_6$-DMSO, 300K) δ 1.36 (t, J=7.0 Hz, 3H), 3.85 (s, 3H), 4.01 (s, 3H), 4.02 (s, 3H), 4.06 (q, J=7.0 Hz, 2H), 6.57 (d, J=2.1 Hz, 1H), 6.88 (d, J=6.2 Hz, 1H), 7.52 (s, 1H), 7.56 (m, 2H), 7.71 (s, 1H), 7.76 (d, J=8.9 Hz, 1H), 8.08 (dd, J=2.1 Hz, J=13.1 Hz, 1H), 8.17 (s, 1H), 8.75 (d, J=6.2 Hz, 1H), 10.34 (s, 1H). MS (ES) C$_{27}$H$_{25}$FN$_6$O$_5$ requires: 532. Found: 533 (M+H)$^+$.

Biological Assays

The exemplified compounds described herein were tested for activity and were found to have an IC$_{50}$ value less than 10 uM, particularly less than 500 nM, in one of the following assays:

1. Enzymatic Axl Assay:

The IMAP FP Sreening Express Kit (Molecular Devices) was employed for the detection of Axl activity in vitro. In brief, a mix of FITC-labeled substrate peptide (400 nM final concentration; 5FITC-KKKKEEIYFFFG-NH$_2$, Seq ID No. 01) and recombinant Axl kinase (30 nM final concentration; Proqinase) was preincubated with a compound according to formula (I) at the suitable concentrations. Reaction was started by addition of ATP (Adenosine-5'-triphosphate, Sigma Aldrich) to a final concentration of 22 μM. Except proteins and substrates the reaction buffer conditions were 20 mM HEPES (2-(4-(2-Hydroxyethyl)-1-piperazine)-ethanesulfonic acid) pH 8.0, 1 mM DTT (Dithiothreitol), 10 mM MgCl$_2$ and 0.01% Brij35 (all Sigma Aldrich). After incubation of 1 hour the reaction was stopped by addition of IMAP binding buffer, containing the large M(III)-based nanoparticles, who bind to the phosphorylated fluorescent substrate. This reduces the rotational speed of the bound substrate increasing its polarization signal. Finally, the fluorescence polarization was determined using an EnVision Multilabel-reader 2104 (Perkin Elmer).

2. Axl Binding Assay:

The principle behind this assay is based upon the binding and displacement of an Alexa Fluor 647-labeled tracer to the kinase of interest. Binding of the tracer to the kinase is detected using an EU-labeled anti-tag antibody. Simultaneous binding of both the tracer and antibody to the kinase gives rise to a FRET-signal. Binding of an inhibitor to the kinase competes for binding with the tracer, resulting in a loss of FRET-signal. At first a compound according to formula (I) was diluted in 20 mM Hepes pH 8.0, 1 mM DTT, 10 mM $MgCl_2$ and 0.01% Brij35. Next Axl kinase (5 nM final concentration; Proqinase), kinase tracer (15 nM final concentration; Invitrogen) and LanthaScreen Eu-Anti-GST antibody (2 nM final concentration; Invitrogen) was mixed with suitable compound dilutions and incubated for 1 hour. FRET-signal was quantified employing an EnVision Multilabelreader 2104 (Perkin Elmer).

3. Cellular Axl Phosphorylation Assay:

HEK293 embryonal kidney fibroblasts were transfected in 96 wells with a plasmid containing Axl cDNA. As transfection reagent Superfect (Qiagen) was used. Transfection of the sole vector backbone served as negative control of Axl expression. After overnight incubation the cellular supernatant was replaced with fresh medium. On the following day the Axl-expressing cells were incubated for 1 hour with a compound according to formula (I) at the suitable concentrations. Cells were lysed with buffer and lysates were investigated for Axl expression and phosphorylation employing antibodies H-124 (Santa Cruz) and AF2228 (R&D), respectively. The mesoscale technology was used for quantification.

Table 2 shows activity data in the Axl binding assay and cellular Axl phosphorylation assay for selected compounds of the invention. Inhibition is indicated as $IC_{50}$ with the following key: A=$IC_{50}$ less than 0.5 uM; B=$IC_{50}$ greater than 0.5 uM, but less than 5.0 uM; C=$IC_{50}$ greater than 5.0 uM; -=not measured

TABLE 2

| Example | Nomenclature | Axl binding assay | Cellular Axl phosphorylation assay |
|---|---|---|---|
| 1 | N-[4-[(6,7-dimethoxy-4-quinolyl)oxy]-3-fluoro-phenyl]-1,5-dimethyl-pyrazole-3-carboxamide | B | B |
| 2 | N-[4-[(6,7-dimethoxy-4-quinolyl)oxy]-3-fluoro-phenyl]-2-[4-(trifluoromethyl)phenyl]thiazole-4-carboxamide | B | — |
| 3 | 4-bromo-N-[4-[(6,7-dimethoxy-4-quinolyl)oxy]-3-fluoro-phenyl]-1-methyl-pyrazole-3-carboxamide | B | B |
| 4 | N-[4-[(6,7-dimethoxy-4-quinolyl)oxy]-3-fluoro-phenyl]-1-methyl-pyrazole-3-carboxamide | B | B |
| 5 | 1-tert-butyl-N-[4-[(6,7-dimethoxy-4-quinolyl)oxy]-3-fluoro-phenyl]-5-methyl-pyrazole-3-carboxamide | A | A |
| 6 | N-[4-[(6,7-dimethoxy-4-quinolyl)oxy]-3-fluoro-phenyl]thiazole-2-carboxamide | B | — |
| 8 | N-[4-[(6,7-dimethoxy-4-quinolyl)oxy]-3-fluoro-phenyl]-1-methyl-indazole-3-carboxamide | B | — |
| 9 | N-[4-[(6,7-dimethoxy-4-quinolyl)oxy]-3-fluoro-phenyl]-5-methyl-isoxazole-3-carboxamide | B | — |
| 10 | N-[4-[(6,7-dimethoxy-4-quinolyl)oxy]-3-fluoro-phenyl]-2-phenyl-thiazole-4-carboxamide | B | B |
| 13 | N-[4-[(6,7-dimethoxy-4-quinolyl)oxy]-3-fluoro-phenyl]-1-propyl-pyrazole-3-carboxamide | B | A |
| 15 | N-[4-[(6,7-dimethoxy-4-quinolyl)oxy]-3-fluoro-phenyl]-1-(2,2,2-trifluoroethoxymethyl)pyrazole-3-carboxamide | B | A |
| 16 | N-[4-[(6,7-dimethoxy-4-quinolyl)oxy]-3-fluoro-phenyl]-4-ethoxy-1-(4-fluorophenyl)pyrazole-3-carboxamide | A | A |
| 17 | N-[4-[(6,7-dimethoxy-4-quinolyl)oxy]-3-fluoro-phenyl]-1-(4-fluorophenyl)-4-methoxy-pyrazole-3-carboxamide | A | A |
| 18 | 4-(cyclopropylmethoxy)-N-[4-[(6,7-dimethoxy-4-quinolyl)oxy]-3-fluoro-phenyl]-1-(4-fluorophenyl)pyrazole-3-carboxamide | A | A |
| 19 | N-[4-[(6,7-dimethoxy-4-quinolyl)oxy]-3-fluoro-phenyl]-4-(2-dimethylaminoethoxy)-1-(4-fluorophenyl)pyrazole-3-carboxamide | A | A |
| 20 | N-[4-[(6,7-dimethoxy-4-quinolyl)oxy]-3-fluoro-phenyl]-4-(2-dimethylaminoethoxy)-1-(4-fluorophenyl)pyrazole-3-carboxamide | B | B |
| 21 | N-[4-[(6,7-dimethoxy-4-quinolyl)oxy]-3-fluoro-phenyl]-1-(4-fluorophenyl)-4-isopropoxy-pyrazole-3-carboxamide | A | A |
| 22 | N-[4-[(6,7-dimethoxy-4-quinolyl)oxy]-3-fluoro-phenyl]-4-ethoxy-1-(4-fluoro-2-methyl-phenyl)pyrazole-3-carboxamide | A | A |
| 23 | 1-(2-chloro-4-fluoro-phenyl)-N-[4-[(6,7-dimethoxy-4-quinolyl)oxy]-3-fluoro-phenyl]-4-ethoxy-pyrazole-3-carboxamide | A | A |

TABLE 2-continued

| Example | Nomenclature | Axl binding assay | Cellular Axl phosphorylation assay |
|---|---|---|---|
| 24 | N-[4-[(6,7-dimethoxy-4-quinolyl)oxy]phenyl]-4-ethoxy-1-(4-fluorophenyl)pyrazole-3-carboxamide | A | A |
| 25 | N-[4-[(6,7-dimethoxy-4-quinolyl)oxy]phenyl]-1-(4-fluorophenyl)-4-isopropoxy-pyrazole-3-carboxamide | A | A |
| 26 | 4-(cyclopropylmethoxy)-N-[4-[(6,7-dimethoxy-4-quinolyl)oxy]phenyl]-1-(4-fluorophenyl)pyrazole-3-carboxamide | A | A |
| 27 | N-[4-[(6,7-dimethoxy-4-quinolyl)oxy]phenyl]-4-ethoxy-1-(4-fluoro-2-methyl-phenyl)pyrazole-3-carboxamide | A | A |
| 28 | N-[4-[(6,7-dimethoxy-4-quinolyl)oxy]-3-methyl-phenyl]-4-ethoxy-1-(4-fluorophenyl)pyrazole-3-carboxamide | A | A |
| 29 | N-[4-[(6,7-dimethoxy-4-quinolyl)oxy]-3-methyl-phenyl]-1-(4-fluorophenyl)-4-isopropoxy-pyrazole-3-carboxamide | A | A |
| 30 | 4-(cyclopropylmethoxy)-N-[4-[(6,7-dimethoxy-4-quinolyl)oxy]-3-methyl-phenyl]-1-(4-fluorophenyl)pyrazole-3-carboxamide | A | A |
| 31 | N-[4-[(6,7-dimethoxy-4-quinolyl)oxy]-3-methyl-phenyl]-4-ethoxy-1-(4-fluoro-2-methyl-phenyl)pyrazole-3-carboxamide | A | A |
| 32 | N-[3-chloro-4-[(6,7-dimethoxy-4-quinolyl)oxy]phenyl]-4-ethoxy-1-(4-fluorophenyl)pyrazole-3-carboxamide | A | A |
| 33 | N-[3-chloro-4-[(6,7-dimethoxy-4-quinolyl)oxy]phenyl]-1-(4-fluorophenyl)-4-isopropoxy-pyrazole-3-carboxamide | A | A |
| 34 | N-[3-chloro-4-[(6,7-dimethoxy-4-quinolyl)oxy]phenyl]-4-(cyclopropylmethoxy)-1-(4-fluorophenyl)pyrazole-3-carboxamide | A | A |
| 35 | N-[3-chloro-4-[(6,7-dimethoxy-4-quinolyl)oxy]phenyl]-4-ethoxy-1-(4-fluoro-2-methyl-phenyl)pyrazole-3-carboxamide | A | A |
| 36 | N-(4-((6,7-dimethoxyquinolin-4-yl)oxy)-3-fluorophenyl)-4-(2-(dimethylamino)ethyl)-1-(4-fluorophenyl)-1H-pyrazole-3-carboxamide | A | A |
| 37 | N-[4-[(6,7-dimethoxy-4-quinolyl)oxy]-3-fluoro-phenyl]-1-[2-(2-dimethylaminoethyl)-4-fluoro-phenyl]-4-ethoxy-pyrazole-3-carboxamide | A | A |
| 38 | N-[3-fluoro-4-[[6-methoxy-7-(3-morpholinopropoxy)-4-quinolyl]oxy]phenyl]-2-phenyl-thiazole-4-carboxamide | A | A |
| 39 | 4-bromo-N-[3-fluoro-4-[[6-methoxy-7-(3-morpholinopropoxy)-4-quinolyl]oxy]phenyl]-1-methyl-pyrazole-3-carboxamide | B | A |
| 40 | N-[3-fluoro-4-[[6-methoxy-7-(3-morpholinopropoxy)-4-quinolyl]oxy]phenyl]-1-methyl-pyrazole-3-carboxamide | B | A |
| 41 | 1-tert-butyl-N-[3-fluoro-4-[[6-methoxy-7-(3-morpholinopropoxy)-4-quinolyl]oxy]phenyl]-5-methyl-pyrazole-3-carboxamide | A | A |
| 42 | N-[3-fluoro-4-[[6-methoxy-7-(3-morpholinopropoxy)-4-quinolyl]oxy]phenyl]-1,5-dimethyl-pyrazole-3-carboxamide | A | A |
| 43 | 4-ethoxy-N-[3-fluoro-4-[[6-methoxy-7-(3-morpholinopropoxy)-4-quinolyl]oxy]phenyl]-1-(4-fluoro-2-methyl-phenyl)pyrazole-3-carboxamide | A | A |
| 44 | N-[3-fluoro-4-[[6-methoxy-7-(3-morpholinopropoxy)-4-quinolyl]oxy]phenyl]-1-(4-fluorophenyl)-4-methoxy-pyrazole-3-carboxamide | A | A |
| 45 | N-[3-fluoro-4-[[6-methoxy-7-(3-morpholinopropoxy)-4-quinolyl]oxy]phenyl]-1-(4-fluorophenyl)-4-isopropoxy-pyrazole-3-carboxamide | A | A |
| 46 | 4-(cyclopropylmethoxy)-N-[3-fluoro-4-[[6-methoxy-7-(3-morpholinopropoxy)-4-quinolyl]oxy]phenyl]-1-(4-fluorophenyl)pyrazole-3-carboxamide | A | A |
| 47 | 1-(2-chloro-4-fluoro-phenyl)-4-ethoxy-N-[3-fluoro-4-[[6-methoxy-7-(3-morpholinopropoxy)-4-quinolyl]oxy]phenyl]pyrazole-3-carboxamide | A | A |

TABLE 2-continued

| Example | Nomenclature | Axl binding assay | Cellular Axl phosphorylation assay |
|---|---|---|---|
| 48 | 4-(2-dimethylaminoethoxy)-N-[3-fluoro-4-[[6-methoxy-7-(3-morpholinopropoxy)-4-quinolyl]oxy]phenyl]-1-(4-fluorophenyl)pyrazole-3-carboxamide | A | A |
| 49 | 1-(2-bromo-4-fluoro-phenyl)-4-ethoxy-N-[3-fluoro-4-[[6-methoxy-7-(3-morpholinopropoxy)-4-quinolyl]oxy]phenyl]pyrazole-3-carboxamide | A | A |
| 50 | N-[3-fluoro-4-[[6-methoxy-7-(3-morpholinopropoxy)-4-quinolyl]oxy]phenyl]-1-(4-fluorophenyl)-4-(2-methoxyethoxy)pyrazole-3-carboxamide | A | A |
| 51 | 4-benzyloxy-N-[3-fluoro-4-[[6-methoxy-7-(3-morpholinopropoxy)-4-quinolyl]oxy]phenyl]-1-(4-fluorophenyl)pyrazole-3-carboxamide | A | A |
| 52 | N-[3-fluoro-4-[[6-methoxy-7-(3-morpholinopropoxy)-4-quinolyl]oxy]phenyl]-1-(4-fluorophenyl)-4-nitro-pyrazole-3-carboxamide | A | A |
| 53 | 4-amino-N-[3-fluoro-4-[[6-methoxy-7-(3-morpholinopropoxy)-4-quinolyl]oxy]phenyl]-1-(4-fluorophenyl)pyrazole-3-carboxamide | A | A |
| 54 | N-[4-[[7-(3-aminopropoxy)-6-methoxy-4-quinolyl]oxy]-3-fluoro-phenyl]-4-ethoxy-1-(4-fluorophenyl)pyrazole-3-carboxamide | A | A |
| 55 | N-[4-[[7-(3-aminopropoxy)-6-methoxy-4-quinolyl]oxy]-3-fluoro-phenyl]-4-ethoxy-1-(4-fluoro-2-methyl-phenyl)pyrazole-3-carboxamide | A | A |
| 56 | N-[4-[[7-(3-aminopropoxy)-6-methoxy-4-quinolyl]oxy]-3-fluoro-phenyl]-5-ethoxy-2-(4-fluorophenyl)oxazole-4-carboxamide | A | A |
| 57 | 4-ethoxy-N-[3-fluoro-4-[[6-methoxy-7-[3-(4-methylpiperazin-1-yl)propoxy]-4-quinolyl]oxy]phenyl]-1-(4-fluoro-2-methyl-phenyl)pyrazole-3-carboxamide | A | A |
| 58 | 4-ethoxy-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide | A | A |
| 59 | N-[3-fluoro-4-[[6-methoxy-7-[3-(4-methylpiperazin-1-yl)propoxy]-4-quinolyl]oxy]phenyl]-1-(4-fluorophenyl)-4-methoxy-pyrazole-3-carboxamide | A | A |
| 60 | 1-(2-chloro-4-fluoro-phenyl)-4-ethoxy-N-[3-fluoro-4-[[6-methoxy-7-[3-(4-methylpiperazin-1-yl)propoxy]-4-quinolyl]oxy]phenyl]pyrazole-3-carboxamide | A | A |
| 61 | 4-(cyclopropylmethoxy)-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide | A | A |
| 62 | N-[3-fluoro-4-[[6-methoxy-7-[3-(4-methylpiperazin-1-yl)propoxy]-4-quinolyl]oxy]phenyl]-1-(4-fluorophenyl)-4-isopropoxy-pyrazole-3-carboxamide | A | A |
| 63 | 5-ethoxy-N-[3-fluoro-4-[[6-methoxy-7-[3-(4-methylpiperazin-1-yl)propoxy]-4-quinolyl]oxy]phenyl]-2-(4-fluorophenyl)oxazole-4-carboxamide | A | A |
| 64 | 4-(cyclopropylmethoxy)-N-[3-fluoro-4-[[6-methoxy-7-(3-piperazin-1-yl propoxy)-4-quinolyl]oxy]phenyl]-1-(4-fluorophenyl)pyrazole-3-carboxamide trifluoroacetic acid salt | A | A |
| 65 | 4-ethoxy-N-[3-fluoro-4-[[6-methoxy-7-(3-piperazin-1-ylpropoxy)-4-quinolyl]oxy]phenyl]-1-(4-fluorophenyl)pyrazole-3-carboxamide | A | A |
| 66 | N-[3-fluoro-4-[[6-methoxy-7-(3-piperazin-1-ylpropoxy)-4-quinolyl]oxy]phenyl]-1-(4-fluorophenyl)-4-methoxy-pyrazole-3-carboxamide | A | A |
| 67 | N-[3-fluoro-4-[[6-methoxy-7-(3-piperazin-1-ylpropoxy)-4-quinolyl]oxy]phenyl]-1-(4-fluorophenyl)-4-isopropoxy-pyrazole-3-carboxamide | A | A |

TABLE 2-continued

| Example | Nomenclature | Axl binding assay | Cellular Axl phosphorylation assay |
|---|---|---|---|
| 68 | 1-(2-chloro-4-fluoro-phenyl)-4-ethoxy-N-[3-fluoro-4-[[6-methoxy-7-(3-piperazin-1-ylpropoxy)-4-quinolyl]oxy]phenyl]pyrazole-3-carboxamide | A | A |
| 69 | 4-ethoxy-N-[3-fluoro-4-[[6-methoxy-7-(3-piperazin-1-ylpropoxy)-4-quinolyl]oxy]phenyl]-1-(4-fluoro-2-methyl-phenyl)pyrazole-3-carboxamide | A | A |
| 70 | N-[3-fluoro-4-[[6-methoxy-7-(3-piperazin-1-ylpropoxy)-4-quinolyl]oxy]phenyl]-1-(4-fluorophenyl)-4-(2-methoxyethoxy)pyrazole-3-carboxamide | A | A |
| 71 | N-[3-fluoro-4-[[6-methoxy-7-(3-piperazin-1-ylpropoxy)-4-quinolyl]oxy]phenyl]-1-(4-fluorophenyl)-4-[(1-methylpyrrolidin-3-yl)methoxy]pyrazole-3-carboxamide | A | B |
| 72 | N-[3-fluoro-4-[[6-methoxy-7-(3-piperazin-1-ylpropoxy)-4-quinolyl]oxy]phenyl]-2-phenyl-thiazole-4-carboxamide | A | A |
| 73 | N-[3-fluoro-4-[[6-methoxy-7-(4-piperidylmethoxy)-4-quinolyl]oxy]phenyl]-1-(4-fluorophenyl)-4-methoxy-pyrazole-3-carboxamide | A | A |
| 74 | 4-ethoxy-N-[3-fluoro-4-[[6-methoxy-7-(4-piperidylmethoxy)-4-quinolyl]oxy]phenyl]-1-(4-fluoro-2-methyl-phenyl)pyrazole-3-carboxamide | A | A |
| 75 | 4-(cyclopropylmethoxy)-N-[3-fluoro-4-[[6-methoxy-7-(4-piperidylmethoxy)-4-quinolyl]oxy]phenyl]-1-(4-fluorophenyl)pyrazole-3-carboxamide | A | A |
| 76 | 4-bromo-N-[3-fluoro-4-[[6-methoxy-7-(4-piperidylmethoxy)-4-quinolyl]oxy]phenyl]-1-(4-fluorophenyl)pyrazole-3-carboxamide | A | A |
| 77 | N-[3-fluoro-4-[[6-methoxy-7-(4-piperidylmethoxy)-4-quinolyl]oxy]phenyl]-1-(4-fluorophenyl)-4-[(4-fluorophenyl)methoxy]pyrazole-3-carboxamide | A | A |
| 78 | 1-tert-butyl-N-[3-fluoro-4-[[6-methoxy-7-(4-piperidylmethoxy)-4-quinolyl]oxy]phenyl]-5-methyl-pyrazole-3-carboxamide | A | A |
| 80 | N-[3-fluoro-4-[[6-methoxy-7-(4-piperidylmethoxy)-4-quinolyl]oxy]phenyl]-5-methyl-2-phenyl-oxazole-4-carboxamide | A | A |
| 81 | N-[3-fluoro-4-[[6-methoxy-7-(4-piperidylmethoxy)-4-quinolyl]oxy]phenyl]-2-phenyl-thiazole-4-carboxamide | A | B |
| 82 | 4-ethoxy-N-[4-[[7-[(1-ethyl-4-piperidyl)methoxy]-6-methoxy-4-quinolyl]oxy]-3-fluoro-phenyl]-1-(4-fluoro-2-methyl-phenyl)pyrazole-3-carboxamide | A | A |
| 83 | 4-ethoxy-N-[3-fluoro-4-[[7-[(1-isobutyl-4-piperidyl)methoxy]-6-methoxy-4-quinolyl]oxy]phenyl]-1-(4-fluoro-2-methyl-phenyl)pyrazole-3-carboxamide | A | A |
| 84 | N-[5-[(6,7-dimethoxy-4-quinolyl)oxy]-2-pyridyl]-4-ethoxy-1-(4-fluorophenyl)pyrazole-3-carboxamide | A | A |
| 85 | N-[5-[(6,7-dimethoxy-4-quinolyl)oxy]-2-pyridyl]-4-ethoxy-1-(4-fluoro-2-methyl-phenyl)pyrazole-3-carboxamide | A | A |
| 86 | 1-(2-chloro-4-fluoro-phenyl)-N-[5-[(6,7-dimethoxy-4-quinolyl)oxy]-2-pyridyl]-4-ethoxy-pyrazole-3-carboxamide | A | A |
| 87 | N-[5-[(6,7-dimethoxy-4-quinolyl)oxy]-2-pyridyl]-4-(2-dimethylaminoethyl)-1-(4-fluorophenyl)pyrazole-3-carboxamide | B | A |
| 89 | N-(5-((6,7-dimethoxyquinolin-4-yl)oxy)pyridin-2-yl)-4-ethoxy-1-(4-methoxy-2-methylphenyl)-1H-pyrazole-3-carboxamide | A | A |
| 90 | N-(4-((6,7-dimethoxyquinolin-4-yl)oxy)-3-fluorophenyl)-4-ethoxy-1-(3-nitrophenyl)-1H-pyrazole-3-carboxamide | A | A |
| 91 | N-(4-((6,7-dimethoxyquinolin-4-yl)oxy)-3-fluorophenyl)-4-ethoxy-1-(4-methoxy-2-methylphenyl)-1H-pyrazole-3-carboxamide | A | A |

TABLE 2-continued

| Example | Nomenclature | Axl binding assay | Cellular Axl phosphorylation assay |
|---|---|---|---|
| 92 | N-(5-((6,7-dimethoxyquinolin-4-yl)oxy)pyridin-2-yl)-4-ethoxy-1-(3-nitrophenyl)-1H-pyrazole-3-carboxamide | A | A |
| 94 | N-(4-((6,7-dimethoxyquinolin-4-yl)oxy)-2-methoxyphenyl)-4-ethoxy-1-(4-fluoro-2-methylphenyl)-1H-pyrazole-3-carboxamide | A | A |
| 95 | N-(4-((6,7-dimethoxyquinolin-4-yl)oxy)-2-methylphenyl)-4-ethoxy-1-(4-fluoro-2-methylphenyl)-1H-pyrazole-3-carboxamide | A | B |
| 96 | N-(4-((6,7-dimethoxyquinolin-4-yl)oxy)-3-fluorophenyl)-4-ethoxy-1-(4-fluoro-3-methoxyphenyl)-1H-pyrazole-3-carboxamide | A | A |
| 97 | N-(5-((6,7-dimethoxyquinolin-4-yl)oxy)pyridin-2-yl)-4-ethoxy-1-(4-fluoro-3-methoxyphenyl)-1H-pyrazole-3-carboxamide | A | A |
| 98 | N-(5-((6,7-dimethoxyquinolin-4-yl)oxy)pyridin-2-yl)-4-ethoxy-1-(4-nitrophenyl)-1H-pyrazole-3-carboxamide | B | A |
| 99 | 1-(4-aminophenyl)-N-(5-((6,7-dimethoxyquinolin-4-yl)oxy)pyridin-2-yl)-4-ethoxy-1H-pyrazole-3-carboxamide | A | A |
| 100 | N-(5-((6-methoxy-7-(piperidin-4-ylmethoxy)quinolin-4-yl)oxy)pyridin-2-yl)-4-(2-methoxyphenyl)thiazole-2-carboxamide | B | — |
| 101 | N-(5-((6-methoxy-7-(piperidin-4-ylmethoxy)quinolin-4-yl)oxy)pyridin-2-yl)-4-phenylthiazole-2-carboxamide | A | A |
| 102 | 4-bromo-N-(5-((6-methoxy-7-(piperidin-4-ylmethoxy)quinolin-4-yl)oxy)pyridin-2-yl)thiazole-2-carboxamide | A | A |
| 103 | N-(4-((6,7-dimethoxyquinolin-4-yl)oxy)-2-methoxyphenyl)-4-ethoxy-1-(4-fluoro-2-methylphenyl)-1H-pyrazole-3-carboxamide | A | A |
| 104 | N-(5-((6,7-dimethoxyquinolin-4-yl)oxy)pyridin-2-yl)-4-ethoxy-1-(4-fluoro-2-hydroxyphenyl)-1H-pyrazole-3-carboxamide | A | A |
| 105 | N-(4-((6,7-dimethoxyquinolin-4-yl)oxy)-3-fluorophenyl)-4-ethoxy-1-(pyridin-3-yl)-1H-pyrazole-3-carboxamide | A | A |
| 106 | N-(4-((6,7-dimethoxyquinolin-4-yl)oxy)-3-fluorophenyl)-4-ethoxy-1'-methyl-1'H-[1,3'-bipyrazole]-3-carboxamide | A | — |
| Ref1 | N-(4-((6,7-dimethoxyquinolin-4-yl)oxy)-3-fluorophenyl)-1-phenyl-5-(trifluoromethyl)-1H-pyrazole-4-carboxamide | >10 μM | — |
| Ref2 | N-(4-((6,7-dimethoxyquinolin-4-yl)oxy)-3-fluorophenyl)-5-phenylisoxazole-3-carboxamide | >10 μM | — |
| Ref3 | N-(4-((6,7-dimethoxyquinolin-4-yl)oxy)phenyl)furan-2-carboxamide | >10 μM | — |
| Ref4 | N-(4-((6,7-dimethoxyquinolin-4-yl)oxy)phenyl)thiophene-3-carboxamide | 7042 nM | — |
| Ref5 | N-(4-((6,7-dimethoxyquinolin-4-yl)oxy)phenyl)isonicotinamide | >10 μM | — |
| Ref6 | N-(4-((6,7-dimethoxyquinolin-4-yl)oxy)phenyl)thiophene-2-carboxamide | 8293 nM | — |
| Ref7 | N-(4-((6,7-dimethoxyquinolin-4-yl)oxy)phenyl)picolinamide | 9302 nM | — |

SOURCE FOR REFERENCE EXAMPLES REF1 TO REF7

Ref1: Example 20 on page 106/107 of WO2008035209A2 (D01 in the ESR)
Ref2: Example 21 on page 106/107 of WO2008035209A2
Ref3: Compound 64, Example 53 on page 47 of EP0860433A1 (D02 in the ESR)
Ref4: Compound 65, Example 54 on page 47 of EP0860433A1
Ref5: Compound 71, Example 60 on page 49 of EP0860433A1
Ref6: Compound 72, Example 61 on page 49 of EP0860433A1
Ref7: Compound 77, Example 61 on page 50 of EP0860433A1

It is obvious from Table 2 that all Reference Examples (Ref1-Ref7) exhibit worse Axl binding assay data which are in the range of 10 μM and higher. In contrast to the seven Reference Examples the compounds of the present invention are in average ten to hundred times more effective in the Axl binding assay.

It seems that the substitution pattern and the position of the hetero atoms and especially the position of the nitrogen atom in the substituent D is important for the better activity of the inventive compounds. Comparing compound 21 of WO2008035209A2 with example 9 of the present invention, both compounds are markedly similar. However compound 21 of WO2008035209A2 shows in the Axl binding assay a worse value of larger than 10 μM while example 9 shows 3.389 μM.

It can be concluded that the position of the heteroatoms and the phenyl substitution in the isoxazole ring (ring D) is not suitable in comparison to example 9 of the present invention. Thus it seems to be important that a nitrogen atom is present in substituent D in direct vicinity to the carbon atom which is attached to the amide group. Thus the isoxazole residue as substituent D should be linked through the 3-yl-carbon atom to the amide group and not through the 4-yl-carbon atom or the 5-yl-carbon atom as done in compound 21 of WO2008035209A2. From Example 80 (Axl binding assay 0.184 uM) of the present invention it can be followed that the oxazole group as substituent D should be linked to the amide group through 2-yl-carbon atom or the 4-yl-carbon atom but not through the 5-yl-carbon atom.

The same conclusion can be drawn from the comparison of compound 20 of WO2008035209A2 with example 17 of the present invention which are again very similar and differ only in the substitution pattern of substituent D. Example 17 wherein the pyrazole residue is linked to the amide group through the 3-yl-carbon atom shows in the Axl binding assay a value of 0.172 μM, while compound 20 of WO2008035209A2, wherein the pyrazole residue is linked to the amide group through the 4-yl-carbon atom shows with >10 μM a much more worse binding/inhibition in the Axl binding assay.

Thus it can be concluded that the compounds disclosed in WO2008035209A2 which are very similar to the compounds of the present invention exhibit the wrong substitution pattern especially in regard to substituent D and thus have lower activity and potency as anti-cancer drug for Axl receptor tyrosine kinase induced disorders as proved by the Axl binding assay.

In regard to the compounds 64, 65, 71, 72 and 77 as disclosed in EP0860433A1 which was cited as D02 in the European Search Report it can be stated that all these compounds are not potent in the Axl binding assay, since they exhibit values of about 10 μM and higher which is in average 10 to 100 times less potent than the compounds of the present invention. Since these compounds 64, 65, 71, 72 and 77 as disclosed in EP0860433A1 differ in comparision to the inventive compounds mainly in the substituent D it can be concluded that furane, thiophene and pyridine substituents as ring D are not suitable substituents in order to obtain highly potent inhibitors of the Axl receptor tyrosine kinase. Thus it seems important that substituent D is a five-membered heterocyclic ring and not a six-membered heterocyclic ring and that it is moreover important that the substituent D contains at least one nitrogen and still more preferably two nitrogen atoms.

However, in regard to the most similar compounds 64, 65, 71, 72 and 77 disclosed in EP0860433A1 it can be stated that they do not have the right substitution pattern especially at substituent D and that the compounds of the present invention are much more potent as demonstrated by the data of the Axl binding assay.

Thus the compounds of the present invention are superior in regard to the compounds of EP0860433A1 as well as of WO2008035209A2.

WO2007146824A2 was cited as D03 in the European Search Report (ESR). D03 does not cite any novelty destroying compounds for the present invention and does even not cite any similar compound. In WO2007146824A2 not a single compound is disclosed which has a 5-membered nitrogen heterocycle as substituent D so that the compounds of WO2007146824A2 are regarded as less relevant. Even compounds such as compounds 134, 172, 175, 176, 177, 178, 195 or 196 are only insignificantly similar to the compounds of the present invention.

Furthermore we have observed that the quinolines without such carboxy-substituted residue D of the present invention shows very weak to no activity in the Axl binding assay (Table 3). Through the introduction of a carboxy-substituted residue D described in this invention very potent inhibitors of the Axl kinase were invented. This further stresses the importance of the carboxy-substituted residue D of the present invention for obtaining potent inhibitors of the Axl kinase.

TABLE 3

| Nomenclature | Structure | Axl binding assay |
|---|---|---|
| 4-((6,7-dimethoxyquinolin-4-yl)oxy)-3-fluoroaniline | 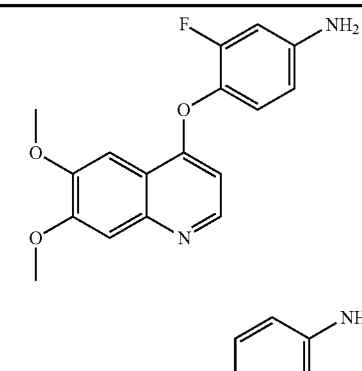 | >10000 nM |
| 4-((6,7-dimethoxyquinolin-4-yl)oxy)aniline | 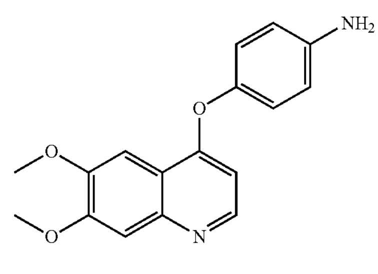 [SMILES: COc1cc2nccc(Oc3ccc(N)cc3)c2cc1OC] | >10000 nM |

TABLE 3-continued

| Nomenclature | Structure | Axl binding assay |
|---|---|---|
| 4-((6,7-dimethoxyquinolin-4-yl)oxy)-3-methylaniline | 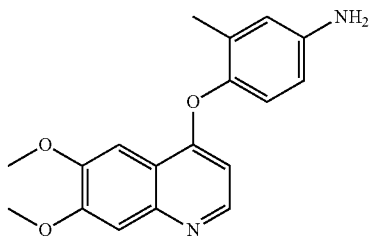 [SMILES: COc1cc2nccc(Oc3ccc(N)cc3C)c2cc1OC] | >10000 nM |
| 3-chloro-4-((6,7-dimethoxyquinolin-4-yl)oxy)aniline | 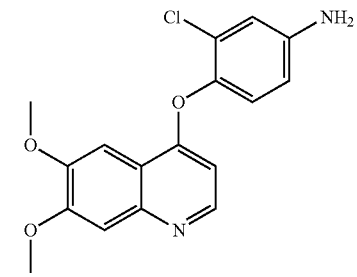 | >10000 nM |
| 5-((6,7-dimethoxyquinolin-4-yl)oxy)pyridin-2-amine | 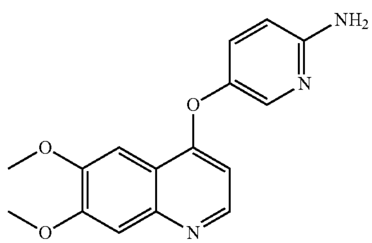 [SMILES: COc1cc2nccc(Oc3ccc(N)nc3)c2cc1OC] | >10000 nM |
| 4-((6,7-dimethoxyquinolin-4-yl)oxy)-2-methoxyaniline | 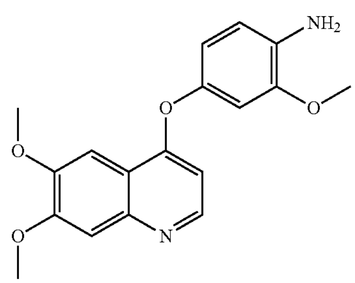 [SMILES: COc1cc(Oc2ccnc3cc(OC)c(OC)cc23)ccc1N] | >10000 nM |
| 4-((6,7-dimethoxyquinolin-4-yl)oxy)-2-methylaniline | 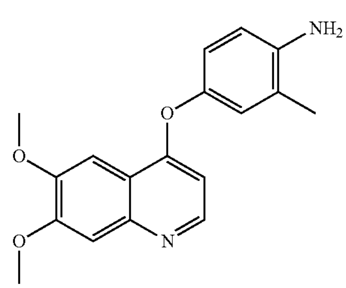 [SMILES: COc1cc2nccc(Oc3ccc(N)c(C)c3)c2cc1OC] | >10000 nM |

TABLE 3-continued

| Nomenclature | Structure | Axl binding assay |
|---|---|---|
| 3-fluoro-4-((6-methoxy-7-(3-morpholinopropoxy)quinolin-4-yl)oxy)aniline | 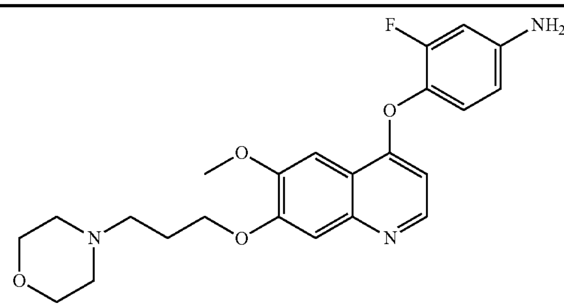 | 8503 nM |
| tert-butyl 4-(((4-(4-amino-2-fluorophenoxy)-6-methoxyquinolin-7-yl)oxy)methyl)piperidine-1-carboxylate | 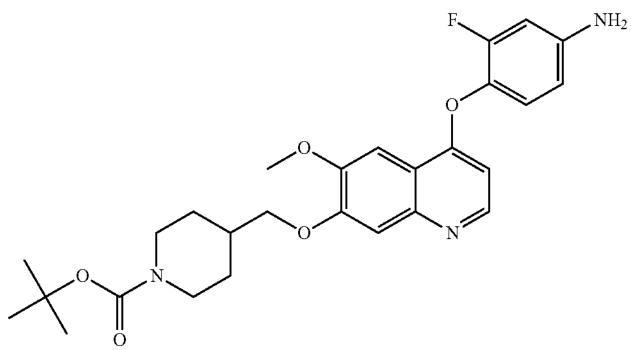 [SMILES: COc1cc2c(Oc3ccc(N)cc3F)ccnc2cc1OCC1CCN(C(=O)OC(C)(C)C)CC1] | >10000 nM |

Example 22 of the present invention was tested in an oncology in vivo model (orthotopic breast cancer model for metastasis):

Female BALB/c mice which developed tumours from 4T1 mouse breast tumour cells, (orthotopically inoculated into the third mammary fat pad) were selected for the study. The mice were randomised, based on tumour volume into four groups on Day 0 of the study. The mice in each group received treatment with either Vehicle Control (PEG400:H$_2$O (70:30, v/v)), Example 22 (32 or 106.5 mg/kg) or Cisplatin (4 mg/kg). The Vehicle Control and Example 22 were administered orally, twice daily (12 hours apart) for 15 days (Day 0-14) in a dosing volume of 5 mL/kg. Cisplatin was administered intravenously on Day 0, 7 and 14 in a dosing volume of 10 mL/kg. Remaining liver tissue from untreated and treated mice, and the liver from mice treated with Cisplatin was preserved in 10% neutral buffered formalin and embedded in paraffin. Liver sections were stained with haematoxylin and eosin, and micro-metastases were quantified. The number of liver metastasis was reduced significantly to roughly 50% by Example 22 (dosing 106.5 mg/kg) without any side effects.

The invention claimed is:
1. Compounds having the general formula (I)

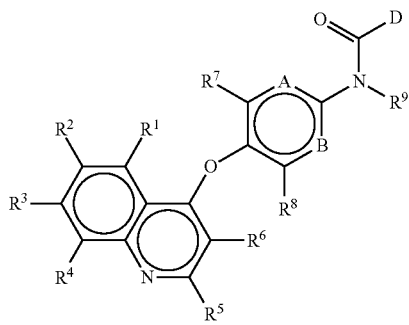

formula (I)

wherein
A represents C—$R^{10}$, N;
B represents C—$R^{11}$, N;
D represents one of the following heterocycles

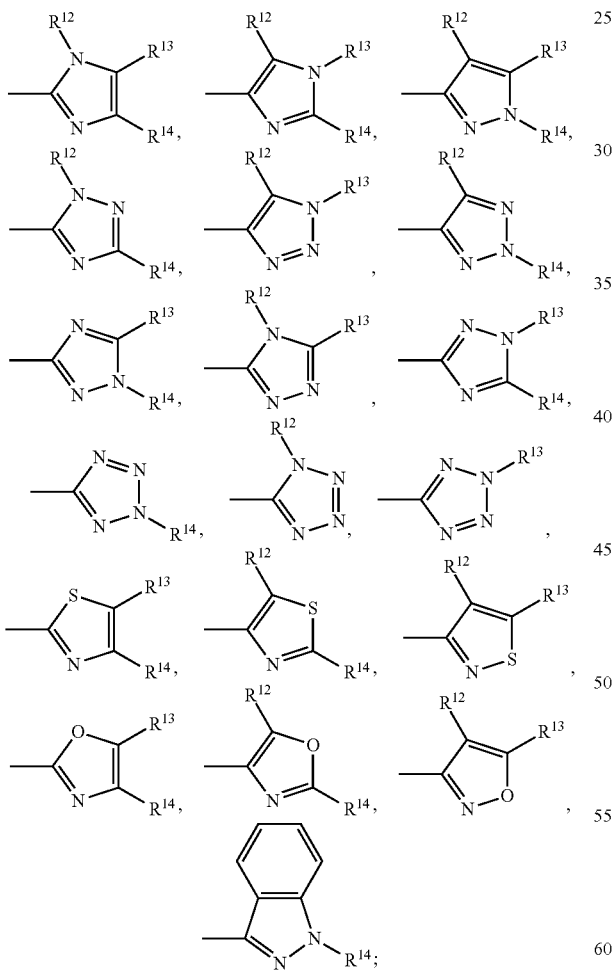

$R^1$, $R^4$, $R^{88}$, $R^{92}$, $R^{100}$ are selected independently of each other from —H, —F, —Cl, —Br, —I, —OH, —$NH_2$, —$NHR^{19}$, —$NR^{19}R^{20}$, —$OCH_3$, —$OC_2H_5$, —$OC_3H_7$, —$OCH(CH_3)_2$, —$OC(CH_3)_3$, —$OC_4H_9$, —$NO_2$, —CHO, —$COCH_3$, —$COC_2H_5$, —O-cyclo-$C_3H_5$, —$OCH_2$-cyclo-$C_3H_5$, —O—$C_2H_4$-cyclo-$C_3H_5$, —OPh, —$COC_3H_7$, —COCH($CH_3$)$_2$, —COC($CH_3$)$_3$, —COOH, —$COOCH_3$, —$COOC_2H_5$, —$COOC_3H_7$, —COOCH($CH_3$)$_2$, —COOC($CH_3$)$_3$, —OOC—$CH_3$, —OOC—$C_2H_5$, —OOC—$C_3H_7$, —OOC—CH($CH_3$)$_2$, —OOC—C($CH_3$)$_3$, —$NHCH_3$, —$NHC_2H_5$, —$NHC_3H_7$, —NHCH($CH_3$)$_2$, —NHC($CH_3$)$_3$, —N($CH_3$)$_2$, —N($C_2H_5$)$_2$, —N($C_3H_7$)$_2$, —N[CH($CH_3$)$_2$]$_2$, —N[C($CH_3$)$_3$]$_2$, —$OCF_3$, —$OC_2F_5$, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, cyclo-$C_3H_5$, —$CH_2$-cyclo-$C_3H_5$, —$CH_3$, —$C_2H_5$, —$C_3H_7$, —CH($CH_3$)$_2$, —$C_4H_9$, —$CH_2$—CH($CH_3$)$_2$, —CH($CH_3$)—$C_2H_5$, —C($CH_3$)$_3$, —$C_5H_{11}$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —CH($C_2H_5$)$_2$, —$C_2H_4$—CH($CH_3$)$_2$, —$C_6H_{13}$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —CH=$CH_2$, —$CH_2$—CH=$CH_2$, —C($CH_3$)=$CH_2$, —CH=CH—$CH_3$, —$C_2H_4$—CH=$CH_2$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$C_2H_4$—C($CH_3$)=$CH_2$, —$CH_2$—CH($CH_3$)—CH=$CH_2$, —CH($CH_3$)—$CH_2$—CH=$CH_2$, —$CH_2$—CH=C($CH_3$)$_2$, —$CH_2$—C($CH_3$)=CH—$CH_3$, —CH($CH_3$)—CH=CH—$CH_3$, —CH=CH—CH($CH_3$)$_2$, —CH=C($CH_3$)—$C_2H_5$, —C($CH_3$)=CH—$C_2H_5$, —C($CH_3$)=C($CH_3$)$_2$, —C($CH_3$)$_2$—CH=$CH_2$, —CH($CH_3$)—C($CH_3$)=$CH_2$, —C($CH_3$)=$CH_2$, —C($CH_3$)=CH—CH=$CH_2$, —CH=C($CH_3$)—CH=$CH_2$, —CH=CH—C($CH_3$)=$CH_2$, —$C_4H_5$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—C($CH_3$)=$CH_2$, —$C_2H_4$—CH($CH_3$)—CH=$CH_2$, —$CH_2$—CH($CH_3$)—$CH_2$—CH=$CH_2$, —CH($CH_3$)—$C_2H_4$—CH=$CH_2$, —$C_2H_4$—CH=C($CH_3$)$_2$, —$C_2H_4$—C($CH_3$)=CH—$CH_3$, —$CH_2$—CH($CH_3$)—CH=CH—$CH_3$, —CH($CH_3$)—$CH_2$—CH=CH—$CH_3$, —$CH_2$—CH=CH—CH($CH_3$)$_2$, —$CH_2$—CH=C($CH_3$)—$C_2H_5$, —$CH_2$—C($CH_3$)=CH—$C_2H_5$, —CH($CH_3$)—CH=CH—$C_2H_5$, —CH=CH—$CH_2$—CH($CH_3$)$_2$, —CH=CH—CH($CH_3$)—$C_2H_5$, —CH=C($CH_3$)—$C_3H_7$, —C($CH_3$)=CH—$C_3H_7$, —$CH_2$—CH($CH_3$)—C($CH_3$)=$CH_2$, —CH($CH_3$)—$CH_2$—C($CH_3$)=$CH_2$, —CH($CH_3$)—CH($CH_3$)—CH=$CH_2$, —$CH_2$—C($CH_3$)$_2$—CH=$CH_2$, —C($CH_3$)$_2$—$CH_2$—CH=$CH_2$, —$CH_2$—C($CH_3$)=C($CH_3$)$_2$, —CH($CH_3$)—CH=C($CH_3$)$_2$, —C($CH_3$)$_2$—CH=CH—$CH_3$, —CH($CH_3$)—C($CH_3$)=CH—$CH_3$, —CH=C($CH_3$)—CH($CH_3$)$_2$, —C($CH_3$)=CH—CH($CH_3$)$_2$, —C($CH_3$)=C($CH_3$)—$C_2H_5$, —CH=CH—C($CH_3$)$_3$, —C($CH_3$)$_2$—C($CH_3$)=$CH_2$, —CH($C_2H_5$)—C($CH_3$)=$CH_2$, —C($C_2H_5$)=$CH_2$, —$CH_2$—C($C_3H_7$)=$CH_2$, —$CH_2$—C $(C_2H_5)=CH-CH_3$, $-CH(C_2H_5)-CH=CH-CH_3$, $-C(C_4H_9)=CH_2$, $-C(C_3H_7)=CH-CH_3$, $-C(C_2H_5)=CH-C_2H_5$, $-C(C_2H_5)=C(CH_3)_2$, $-C[C(CH_3)_3]=CH_2$, $-C[CH(CH_3)(C_2H_5)]=CH_2$, $-C[CH_2-CH(CH_3)_2]=CH_2$, $-C_2H_4-CH=CH-CH=CH_2$, $-CH_2-CH=CH-CH_2-CH=CH_2$, $-CH=CH-C_2H_4-CH=CH_2$, $-CH_2-CH=CH-CH=CH-CH_3$, $-CH=CH-CH_2-CH=CH-CH_3$, $-CH=CH-CH=CH-C_2H_5$, $-CH_2-CH=CH-C(CH_3)=CH_2$, $-CH_2-CH=C(CH_3)-CH=CH_2$, $-CH_2-C(CH_3)=CH-CH=CH_2$, $-CH(CH_3)-CH=CH-CH=CH_2$, $-CH=CH-CH_2-C(CH_3)=CH_2$, $-CH=CH-CH(CH_3)-CH=CH_2$, $-CH=C(CH_3)-CH_2-CH=CH_2$, $-C(CH_3)=CH-CH_2-CH=CH_2$, $-CH=CH-CH=C(CH_3)_2$, $-CH=CH-C(CH_3)=CH-CH_3$, $-CH=C(CH_3)-CH=CH-CH_3$, $-C(CH_3)=CH-CH=CH-CH_3$, $-CH=C(CH_3)-C(CH_3)=CH_2$, $-C(CH_3)=CH-C(CH_3)=CH_2$, $-C(CH_3)=C(CH_3)-CH=CH_2$, $CH-CH=CH-CH=CH-CH_2$, $-C\equiv CH$, $-C\equiv C-CH_3$, $-CH_2-C\equiv CH$, $-C_2H_4-C\equiv CH$, $-CH_2-C\equiv C-CH_3$, $-C\equiv C-C_2H_5$, $-C_3H_6-C\equiv CH$, $-C_2H_4-C\equiv C-CH_3$, $-CH_2-C\equiv C-C_2H_5$, $-C\equiv C-C_3H_7$, $-CH(CH_3)-C\equiv CH$, $-CH_2-CH(CH_3)-C\equiv CH$, $-CH(CH_3)-CH_2-C\equiv CH$, $-CH(CH_3)-C\equiv C-CH_3$, $-C_4H_8-C\equiv CH$, $-C_3H_6-C\equiv C-CH_3$, $-C_2H_4-C\equiv C-C_2H_5$, $-CH_2-C\equiv C-C_3H_7$, $-C\equiv C-C_4H_9$, $-C_2H_4-CH(CH_3)-C\equiv CH$, $-CH_2-CH(CH_3)-CH_2-C\equiv CH$, $-CH(CH_3)-C_2H_4-C\equiv CH$, $-CH_2-CH(CH_3)-C\equiv C-CH_3$, $-CH(CH_3)-CH_2-C\equiv C-CH_3$, $-CH(CH_3)-C\equiv C-C_2H_5$, $-CH_2-C\equiv C-CH(CH_3)_2$, $-C\equiv C-CH(CH_3)-C_2H_5$, $-C\equiv C-CH_2-CH(CH_3)_2$, $-C\equiv C-C(CH_3)_3$, $-CH(C_2H_5)-C\equiv C-CH_3$, $-C(CH_3)_2-C\equiv C-CH_3$, $-CH(C_2H_5)-CH_2-C\equiv CH$, $-CH_2-CH(C_2H_5)-C\equiv CH$, $-C(CH_3)_2-CH_2-C\equiv CH$, $-CH_2-C(CH_3)_2-C\equiv CH$, $-CH(CH_3)-CH(CH_3)-C\equiv CH$, $-CH(C_3H_7)-C\equiv CH$, $-C(CH_3)(C_2H_5)-C\equiv CH$, $-C\equiv C-C\equiv CH$, $-CH_2-C\equiv C-C\equiv CH$, $-C\equiv C-C\equiv C-CH_3$, $-CH(C\equiv CH)_2$, $-C_2H_4-C\equiv C-C\equiv CH$, $-CH_2-C\equiv C-CH_2-C\equiv CH$, $-C\equiv C-C_2H_4-C\equiv CH$, $-C\equiv C-C\equiv C-C_2H_5$, $-C\equiv C-CH_2-C\equiv C-CH_3$, $-C\equiv C-C\equiv C-C_2H_5$, $-C\equiv C-CH(CH_3)-C\equiv CH$, $-CH(CH_3)-C\equiv C-C\equiv CH$, $-CH(C\equiv CH)-CH_2-C\equiv CH$, $-C(C\equiv CH)_2-CH_3$, $-CH_2-CH(C\equiv CH)_2$, $-CH(C\equiv CH)-C\equiv C-CH_3$; $R^{21}$, $R^{35}$, $R^{36}$;

$R^2$ and $R^3$ are selected independently of each other from $-R^{88}$, $-R^{37}$, $-R^{38}$, $-R^{54}$, $-O-R^{54}$, $-R^{55}$, $-O-R^{55}$, $-R^{56}$, $-O-R^{56}$, $-R^{57}$, $-O-R^{57}$, wherein the $C_{1-6}$alkyl, $C_{2-6}$alkenyl, $C_{2-6}$alkynyl or $C_{1-6}$alkoxy groups represented by $R^{88}$ are optionally mono- or polysubstituted by $-OH$, $-F$, $-Cl$, $-Br$, $-I$, $-O-R^{71}$, $R^{72}$, $-R^{138}$, $-COOH$, $-COOCH_3$, $-COOC_2H_5$, $-COOC_3H_7$, $-COOCH(CH_3)_2$, $-COOC(CH_3)_3$, $-(C=O)-NR^{16}R^{17}$, $-SO_2-NR^{16}R^{17}$, $-SO_m-R^{16}R^{17}$, $-CR^{16}R^{17}H$, $-NR^{16}R^{17}$;

or $R^2$ and/or $R^3$ are selected independently of each other from $-O-R^{18}$, $-O-CR^{73}R^{74}-R^{18}$, $-O-CR^{73}R^{74}-CR^{75}R^{76}-R^{18}$, $-O-CR^{73}R^{74}-CR^{75}R^{76}-CR^{77}R^{78}-R^{18}$, $-O-CR^{73}R^{74}-CR^{75}R^{76}-CR^{77}R^{78}-CR^{79}R^{80}-R^{18}$, $-O-CR^{73}R^{74}-CR^{75}R^{76}-CR^{77}R^{78}-CR^{79}R^{80}-CR^{81}R^{82}-R^{18}$, $-O-CR^{73}R^{74}-CR^{75}R^{76}-CR^{77}R^{78}-CR^{79}R^{80}-CR^{81}R^{82}-CR^{83}R^{84}-R^{18}$, $R^{73}$-$R^{84}$ independently of each other represent $-H$, $-OH$, $-F$, $-Cl$, $-Br$, $-I$, $-R^{85}$;

$R^{18}$ represents $-H$, $-OH$, $-F$, $-Cl$, $-Br$, $-I$, $-O-R^{86}$, $-R^{87}$, $-COOH$, $-COOCH_3$, $-COOC_2H_5$, $-COOC_3H_7$, $-COOCH(CH_3)_2$, $-COOC(CH_3)_3$, $-(C=O)-NR^{16}R^{17}$, $-SO_2-NR^{16}R^{17}$, $-SO_m-R^{16}R^{17}$, $-CR^{16}R^{17}H$, $-NR^{16}R^{17}$; m=0, 1, 2;

$R^5$ and $R^6$, which may be the same or different, represent $-H$, $-OH$, $-F$, $-Cl$, $-Br$, $-I$, $-CN$, $-NO_2$, $-CH_3$, $-C_2H_5$, $-C_3H_7$, $-CH(CH_3)_2$, $-C_4H_9$, $-CH_2-CH(CH_3)_2$, cyclo-$C_3H_5$, $-CH_2$-cyclo-$C_3H_5$, $-CH(CH_3)-C_2H_5$, $-C(CH_3)_3$, $-C_5H_{11}$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-CH(C_2H_5)_2$, $-C_2H_4-CH(CH_3)_2$, $-C_6H_{13}$, $-C_3H_6-CH(CH_3)_2$, $-C_2H_4-CH(CH_3)-C_2H_5$, $-CH(CH_3)-C_4H_9$, $-CH_2-CH(CH_3)-C_3H_7$, $-CH(CH_3)-CH_2-CH(CH_3)_2$, $-CH(CH_3)-CH(CH_3)-C_2H_5$, $-CH_2-CH(CH_3)-CH(CH_3)_2$, $-CH_2-C(CH_3)_2-C_2H_5$, $-C(CH_3)_2-C_3H_7$, $-C(CH_3)_2-CH(CH_3)_2$, $-C_2H_4-C(CH_3)_3$, $-CH(CH_3)-C(CH_3)_3$, $-CH=CH_2$, $-CH_2-CH=CH_2$, $-C(CH_3)=CH_2$, $-CH=CH-CH_3$, $-C_2H_4-CH=CH_2$, $-CH_2-CH=CH-CH_3$, $-CH=CH-C_2H_5$, $-CH_2-C(CH_3)=CH_2$, $-CH(CH_3)-CH=CH$, $-CH=C(CH_3)_2$, $-C(CH_3)=CH-CH_3$, $-CH=CH-CH=CH_2$, $-C_3H_6-CH=CH_2$, $-C_2H_4-CH=CH-CH_3$, $-CH_2-CH=CH-C_2H_5$, $-CH=CH-C_3H_7$, $-CH_2-CH=CH-CH=CH_2$, $-CH=CH-CH-CH_3$, $-CH=CH-CH_2-CH=CH_2$, $-C(CH_3)=CH-CH=CH_2$, $-CH=C(CH_3)-CH=CH_2$, $-CH=CH-C(CH_3)=CH_2$, $-C_2H_4-C(CH_3)=CH_2$, $-CH_2-CH(CH_3)-CH=CH_2$, $-CH(CH_3)-CH_2-CH=CH_2$, $-CH_2-CH=C(CH_3)_2$, $-CH_2-C(CH_3)=CH-CH_3$, $-CH(CH_3)-CH=CH-CH_3$, $-CH=CH-CH(CH_3)_2$, $-CH=C(CH_3)-C_2H_5$, $-C(CH_3)=CH-C_2H_5$, $-C(CH_3)=C(CH_3)_2$, $-C(CH_3)_2-CH=CH_2$, $-CH(CH_3)-C(CH_3)=CH_2$, $-C(CH_3)=CH-CH_3$, $-CH=CH-CH_2$, $-CH=C(CH_3)-CH=CH_2$, $-C_3H_6-CH=CH-CH_3$, $-C_2H_4-CH=CH-C_2H_5$, $-CH_2-CH=CH-C_3H_7$, $-CH=CH-C_4H_9$, $-C_3H_6-C(CH_3)=CH_2$, $-C_2H_4-CH(CH_3)-CH=CH_2$, $-CH(CH_3)-CH=CH_2$, $-CH_2-CH(CH_3)-CH_2-CH=CH_2$, $-CH(CH_3)-C_2H_4-CH=CH_2$, $-C_2H_4-CH=C(CH_3)_2$, $-C_2H_4-C(CH_3)=CH-CH_3$, $-CH_2-CH(CH_3)-CH=CH-CH_3$, $-CH(CH_3)-CH_2-CH=CH-CH_3$, $-CH_2-CH=C(CH_3)-C_2H_5$, $-CH_2-C(CH_3)=CH-C_2H_5$, $-CH(CH_3)-CH=CH-C_2H_5$, $-CH=CH-CH_2-CH(CH_3)_2$, $-CH=CH-CH(CH_3)-C_2H_5$, $-CH=C(CH_3)-C_3H_7$, $-C(CH_3)=CH-C_3H_7$, $-CH_2-CH(CH_3)-C(CH_3)=CH_2$, $-CH(CH_3)-CH_2-C(CH_3)=CH_2$, $-CH(CH_3)-CH(CH_3)-CH=CH_2$, $-CH_2-C(CH_3)_2-CH=CH_2$, $-C(CH_3)_2-CH_2-CH=CH_2$, $-CH(CH_3)-CH=C(CH_3)_2$, $-C(CH_3)_2-CH=CH-CH_3$, $-CH=CH-C(CH_3)-CH(CH_3)_2$, $-CH=C(CH_3)-CH(CH_3)_2$, $-C(CH_3)=C(CH_3)-C_2H_5$, $-CH=C(CH_3)-C_2H_5$, $-CH=CH_2$, $-CH(C_2H_5)-C(CH_3)=CH_2$, $-C(CH_3)$ —(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[C(CH₃)₃]═CH₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH═CH₂, —CH═CH—C₂H₄—CH═CH₂, —CH₂—CH═CH—CH═CH—CH₃, —CH═CH—CH₂—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH═CH—CH═CH₂, —CH═CH—CH₂—C(CH₃)═CH₂, —CH═CH—CH(CH₃)—CH═CH₂, —CH═C(CH₃)—CH₂—CH═CH₂, —C(CH₃)═CH—CH₂—CH═CH₂, —CH═CH—CH═C(CH₃)₂, —CH═CH—C(CH₃)═CH—CH₃, —CH═C(CH₃)—CH═CH—CH₃, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₅—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡C—CH₃, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —O—R⁸⁹;

R⁷, R⁸, R¹⁰ and R¹¹, which may be the same or different, represent —H, —F, —Cl, —Br, —I, —CN, —NO₂, —CH₃, —C₂H₅, —C₃H₇, —CH(CH₃)₂, cyclo-C₃H₅, —CH₂-cyclo-C₃H₅, —C₄H₉, —CH₂—CH(CH₃)₂, —CH(CH₃)—C₂H₅, —C(CH₃)₃, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—CH(CH₃)₂, —CH(C₂H₅)—CH(CH₃)₂, —C(CH₃)₂—C₃H₇, —C₂H₄—C(CH₃)₃, —CH(CH₃)—C(CH₃)₃, —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C(CH₃)═CH₂, —CH(CH₃)—CH═CH, —CH═CH(CH₃)₂, —C(CH₃)═CH—CH₃, —CH═CH—CH═CH₂, —C₃H₆—CH═CH₂, —C₂H₄—CH═CH—CH₃, —CH₂—CH═CH—C₂H₅, —CH═CH—C₃H₇, —CH₂—CH═CH—CH═CH₂, —CH═CH—CH═CH—CH₃, —CH═CH—CH₂—CH═CH₂, —CH═CH₂, —C(CH₃)═CH—CH═CH₂, —CH═C(CH₃)—CH═CH₂, —CH═CH—C(CH₃)═CH₂, —C₂H₄—C(CH₃)═CH₂, —CH₂—CH(CH₃)—CH═CH₂, —CH(CH₃)—CH₂—CH═CH₂, —CH₂—CH═C(CH₃)₂, —CH₂—C(CH₃)═CH—CH₃, —CH(CH₃)—CH═CH—CH₃, —CH═CH—CH(CH₃)₂, —CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —C(CH₃)₂—CH═CH₂, —CH═C(CH₃)—CH═CH₂, —C₄H₈—CH═CH₂, —C₃H₆—CH═CH—CH₃, —C₂H₄—CH═CH—C₂H₅, —CH₂—CH═CH—C₃H₇, —CH═CH—C₄H₉, —C₃H₆—C(CH₃)═CH₂, —C₂H₄—CH(CH₃)—CH═CH₂, —CH₂—CH(CH₃)—CH₂—CH═CH₂, —CH(CH₃)—C₂H₄—CH═CH₂, —C₂H₄—CH═C(CH₃)₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH₂—CH(CH₃)—C(CH₃)═CH₂, —CH(CH₃)—CH(CH₃)—CH═CH₂, —CH(CH₃)—CH₂—C(CH₃)═CH₂, —CH(CH₃)—CH(CH₃)—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH(CH₃)—C(CH₃)═CH—CH₃, —CH═C(CH₃)—CH(CH₃)₂, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[C(CH₃)₃]═CH₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH═CH₂, —CH═CH—C₂H₄—CH═CH₂, —CH₂—CH═CH—CH═CH—CH₃, —CH═CH—CH₂—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH═CH—CH═CH₂, —CH═CH—CH₂—C(CH₃)═CH₂, —CH═CH—CH(CH₃)—CH═CH₂, —CH═C(CH₃)—CH₂—CH═CH₂, —C(CH₃)═CH—CH₂—CH═CH₂, —CH═CH—CH═C(CH₃)₂, —CH═CH—C(CH₃)═CH—CH₃, —CH═C(CH₃)—CH═CH—CH₃, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—

C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃, —O—R⁹⁰, —O—R¹¹¹, wherein the C₁₋₆alkyl, C₂₋₆alkenyl, C₂₋₆alkynyl and C₁₋₆alkoxy groups are optionally mono- or polysubstituted by —OH, —F, —Cl, —Br, —I;

R⁹ represents —H, —R⁹¹;

R¹² represent —R⁹², —CN, —R⁹³, —R⁹⁴, —OR⁹⁴, phenyl, naphtalinyl, wherein the C₁₋₆alkyl, C₂₋₆alkenyl, C₂₋₆alkynyl or C₁₋₆alkoxy groups represented by R⁹² are optionally mono- or polysubstituted by —OH, —F, —Cl, —Br, —I, —O—R⁹⁵, R⁹⁶, —COOH, —COOCH₃, —COOC₂H₅, —COOC₃H₇, —COOCH(CH₃)₂, —COOC(CH₃)₃, —(C=O)—NR¹⁶R¹⁷, —SO₂—NR¹⁶R¹⁷, —SO_m—R¹⁶R¹⁷, —CR¹⁶R¹⁷H, —NR¹⁶R¹⁷; and wherein the saturated or unsaturated three- to twelve-membered carbocyclic or heterocyclic ring systems represented by R¹³⁷ are optionally mono- or polysubstituted by —OH, —F, —Cl, —Br, —I, —R⁹⁶;

R¹³ is selected from —H, —OH, —F, —Cl, —Br, —I, —NO₂, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH₃, —CH=CH—CH₂—CH₃, —CH=CH—CH₂—CH=CH—CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —C(CH₃)=C(CH₃)₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —CH(CH₃)—C₂H₄—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —CH(CH₃)—CH₂—C(CH₃)=CH₂, —CH(CH₃)—CH(CH₃)—CH=CH₂, —CH₂—C(CH₃)₂—CH=CH₂, —C(CH₃)₂—CH₂—CH=CH₂, —CH(CH₃)—CH=C(CH₃)₂, —C(CH₃)₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH=CH—CH=CH₂, —CH=CH—CH(CH₃)—CH=CH₂, —CH=C(CH₃)—CH₂—CH=CH₂, —C(CH₃)=CH—CH₂—CH=CH₂, —CH=CH—CH₂—C(CH₃)=CH₂, —CH=CH—CH=CH—CH=CH₂, —CH=CH—CH=C(CH₃)₂, —CH=CH—C(CH₃)=CH—CH₃, —CH=C(CH₃)—CH=CH—CH₃, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_6$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —CH$_2$—CH(C≡CH)$_2$, —CH(C≡CH)—C≡C—CH$_3$, cyclo-C$_3$H$_5$, —O—R$^{97}$, —R$^{98}$, —R$^{99}$;

when R$^{12}$ and R$^{13}$ represent alkenylene groups, R$^{12}$ and R$^{13}$ may combine to form a condensed aromatic ring together with the atoms of residue D to which R$^{12}$ and R$^{13}$ are attached in order to form a bicyclic group with residue D;

R$^{14}$ represents
(i) —H, —OH, —F, —Cl, —Br, —I, —NO$_2$, —CN, —NH$_2$;
(ii) —R$^{100}$, —R$^{101}$, —R$^{102}$, —O—R$^{102}$, —R$^{103}$, —O—R$^{103}$, —R$^{136}$, wherein the C$_{1-6}$alkyl, C$_{2-6}$alkenyl, C$_{2-6}$alkynyl and C$_{1-6}$alkoxy groups represented by R$^{100}$ and the ether groups represented by —R$^{136}$ are optionally mono- or polysubstituted by —OH, —F, —Cl, —Br, —I, —O—R$^{104}$, —R$^{105}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$;
(iii) —R$^{113}$, wherein the saturated or unsaturated three- to twelve-membered carbocyclic or heterocyclic ring system represented by —R$^{113}$ is optionally mono- or polysubstituted by —F, —Cl, —Br, —I, —OH, —NO$_2$, —NH$_2$, —C$_2$H$_4$—N(CH$_3$)$_2$, —CN, —CF$_3$, =O, —R$^{16}$, —R$^{17}$, —R$^{106}$, —O—R$^{107}$, —R$^{108}$, —R$^{109}$, a saturated or unsaturated three- to eight-membered carbocyclic or heterocyclic group, wherein the C$_{1-6}$alkyl groups represented by R$^{106}$, the C$_{1-6}$alkenyl groups represented by R$^{108}$, the C$_{2-6}$alkynyl groups represented by R$^{109}$, the C$_{1-6}$alkoxy groups represented by —O—R$^{107}$ are optionally mono- or polysubstituted by —OH, —F, —Cl, —Br, —I, —O—R$^{104}$, —R$^{105}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$;

R$^{16}$ and R$^{17}$, which may be the same or different, represent —H, —R$^{112}$, optionally substituted by —OH, —F, —Cl, —Br, —I, —NH$_2$, —CN;

or alternatively R$^{16}$ and R$^{17}$ may combine with the nitrogen atom attached thereto to form a saturated or unsaturated five to eight-membered heterocyclic group selected from —R$^{114}$; which is optionally mono- or polysubstituted by —OH, =O, —R$^{116}$, —R$^{117}$, —R$^{118}$, —O—R$^{119}$, —R$^{120}$, or a saturated or unsaturated three- to twelve-membered carbocyclic or heterocyclic ring system selected from —R$^{115}$; wherein the C$_{1-6}$alkyl group represented by R$^{116}$, C$_m$alkenyl group represented by R$^{117}$, C$_m$alkynyl group represented by R$^{118}$ are optionally substituted by —OH, —R$^{122}$, or a saturated or unsaturated three- to twelve-membered carbocyclic or heterocyclic ring system selected from —R$^{121}$;

amino group in which one or two hydrogen atoms on the amino group are optionally substituted by —R$^{123}$, or a saturated or unsaturated three- to twelve-membered carbocyclic or heterocyclic ring system selected from —R$^{124}$, and the C$_{1-6}$alkyl group represented by R$^{123}$ is optionally substituted by —OH, —R$^{125}$, or a saturated or unsaturated three- to twelve-membered carbocyclic or heterocyclic ring system selected from —R$^{126}$;

or a saturated or unsaturated three- to twelve-membered carbocyclic ring system selected from —R$^{127}$; optionally substituted by —OH, =O, —R$^{128}$, —R$^{129}$, —R$^{130}$, —O—R$^{131}$, —R$^{132}$, or a saturated or unsaturated three- to twelve-membered carbocyclic or heterocyclic ring system selected from —R$^{133}$, wherein the C$_{1-6}$alkyl group represented by R$^{128}$, C$_{2-6}$alkenyl group represented by R$^{129}$ and C$_{2-6}$alkynyl group represented by R$^{135}$ are optionally substituted by —OH, —R$^{134}$, or a saturated or unsaturated three- to twelve-membered carbocyclic or heterocyclic ring system selected from —R$^{135}$;

when the carbocyclic or heterocyclic group is substituted by C$_{1-6}$alkyl groups, two alkyl groups may combine together to form an alkylene chain; and the carbocyclic or heterocyclic group may be condensed with another saturated or unsaturated five to seven-membered carbocyclic or heterocyclic group to form a bicyclic group;

R$^{19}$, R$^{20}$, R$^{71}$, R$^{85}$, R$^{86}$, R$^{89}$, R$^{90}$, R$^{91}$, R$^{95}$, R$^{97}$, R$^{104}$, R$^{106}$, R$^{107}$, R$^{110}$, R$^{111}$, R$^{112}$, R$^{116}$, R$^{119}$, R$^{122}$, R$^{123}$, R$^{125}$, R$^{128}$, R$^{131}$ and R$^{134}$ independently of each other represent —CH$_3$, —H, —CF$_3$, -Ph, —CH$_2$-Ph, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —O$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—C(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$;

R$^{21}$ and R$^{98}$ represent independently of each other —CR$^{22}$R$^{23}$R$^{24}$, —CR$^{23}$R$^{24}$—CR$^{25}$R$^{26}$R$^{22}$—, CR$^{23}$R$^{24}$—CR$^{25}$R$^{26}$—CR$^{27}$R$^{28}$R$^{22}$, —CR$^{23}$R$^{24}$—CR$^{25}$R$^{26}$—CR$^{27}$R$^{28}$—CR$^{29}$R$^{30}$R$^{22}$, —CR$^{23}$R$^{24}$—CR$^{25}$R$^{26}$—CR$^{27}$R$^{28}$—CR$^{29}$R$^{30}$—CR$^{31}$R$^{32}$R$^{22}$, —CR$^{23}$R$^{24}$—CR$^{25}$R$^{26}$—CR$^{27}$R$^{28}$—CR$^{29}$R$^{30}$—CR$^{31}$R$^{32}$—CR$^{33}$R$^{34}$R$^{22}$;

R$^{22}$-R$^{34}$ independently of each other represent —H, —F, —Cl, —Br, —I, —CH$_3$, —CF$_3$, —OCH$_3$, —OCF$_3$, —C$_2$H$_5$, —C$_3$H$_7$;

R$^{35}$ and R$^{99}$ represent independently of each other —O—CR$^{22}$R$^{23}$R$^{24}$, —O—CR$^{23}$R$^{24}$—CR$^{25}$R$^{26}$R$^{22}$, —O—CR$^{23}$R$^{24}$—CR$^{25}$R$^{26}$—CR$^{27}$R$^{28}$R$^{22}$, O—CR$^{23}$R$^{24}$—CR$^{25}$R$^{26}$—CR$^{27}$R$^{28}$—CR$^{29}$R$^{30}$R$^{22}$, —O—CR$^{23}$R$^{24}$—CR$^{25}$R$^{26}$—CR$^{27}$R$^{28}$—CR$^{29}$R$^{30}$—CR$^{31}$R$^{32}$R$^{22}$, —O—CR$^{23}$R$^{24}$—CR$^{25}$R$^{26}$—CR$^{27}$R$^{28}$—CR$^{29}$R$^{30}$—CR$^{31}$R$^{32}$—CR$^{33}$R$^{34}$R$^{22}$;

R$^{36}$, R$^{72}$, R$^{87}$, R$^{96}$, R$^{105}$, R$^{120}$, R$^{132}$ and R$^{136}$ represent independently of each other —CR$^{23}$R$^{24}$—XH, —X—CR$^{22}$R$^{23}$R$^{24}$, —X—CR$^{23}$R$^{24}$—CR$^{25}$R$^{26}$R$^{22}$, —CR$^{23}$R$^{24}$—X—CR$^{25}$R$^{26}$R$^{22}$, —CR$^{23}$R$^{24}$—CR$^{25}$R$^{26}$—XH, —X—CR$^{23}$R$^{24}$—CR$^{25}$R$^{26}$—CR$^{27}$R$^{28}$R$^{22}$, —CR$^{23}$R$^{24}$—X—CR$^{25}$R$^{26}$—CR$^{27}$R$^{28}$R$^{22}$, —CR$^{23}$R$^{24}$—CR$^{25}$R$^{26}$—X—CR$^{27}$R$^{28}$R$^{22}$, —CR$^{23}$R$^{24}$—CR$^{25}$R$^{26}$—CR$^{27}$R$^{28}$—XH, —X—CR$^{23}$R$^{24}$—CR$^{25}$R$^{26}$—CR$^{27}$R$^{28}$—CR$^{29}$R$^{30}$R$^{22}$, —CR$^{23}$R$^{24}$—X—CR$^{28}$R$^{28}$—CR$^{27}$R$^{28}$—CR$^{29}$R$^{30}$R$^{22}$, —CR$^{23}$R$^{24}$—CR$^{28}$R$^{28}$—X—CR$^{27}$R$^{28}$—CR$^{29}$R$^{30}$R$^{22}$, —CR$^{23}$R$^{24}$—CR$^{25}$R$^{26}$—CR$^{27}$R$^{28}$—X—CR$^{29}$R$^{30}$R$^{22}$, —CR²³R²⁴—CR²⁵R²⁶—CR²⁷R²⁸—CR²⁹R³⁰—XH,
—X—CR²³R²⁴—CR²⁵R²⁶—CR²⁷R²⁸—CR²⁹R³⁰—CR³¹R³²R²², —CR²³R²⁴—X—CR²⁵R²⁶—CR²⁷R²⁸—CR²⁹R³⁰—CR³¹R³²R²², —CR²³R²⁴—CR²⁵R²⁶—X—CR²⁷R²⁸—CR²⁹R³⁰—CR³¹R³²R²², —CR²³R²⁴—CR²⁵R²⁶—CR²⁷R²⁸—X—CR²⁹R³⁰—CR³¹R³²R²², —CR²³R²⁴—CR²⁵R²⁶—CR²⁷R²⁸—CR²⁹R³⁰—X—CR³¹R³²R²², —CR²³R²⁴—CR²⁵R²⁶—CR²⁷R²⁸—CR²⁹R³⁰—CR³¹R³²—XH, —X—CR²³R²⁴—CR²⁵R²⁶—CR²⁷R²⁸—CR²⁹R³⁰—CR³¹R³²—CR³³R³⁴R²², —CR²³R²⁴—X—CR²⁵R²⁶—CR²⁷R²⁸—CR²⁹R³⁰—CR³¹R³²—CR³³R³⁴R²², —CR²³R²⁴—CR²⁵R²⁵—X—CR²⁷R²⁸—CR²⁹R³⁰—CR³¹R³²—CR³³R³⁴R²², —CR²³R²⁴—CR²⁵R²⁶—CR²⁷R²⁸—X—CR²⁹R³⁰—CR³¹R³²—CR³³R³⁴R²², —CR²³R²⁴—CR²⁵R²⁶—CR²⁷R²⁸—CR²⁹R³⁰—X—CR³¹R³²—CR³³R³⁴R²², —CR²³R²⁴—CR²⁵R²⁶—CR²⁷R²⁸—CR²⁹R³⁰—CR³¹R³²—X—CR³³R³⁴R²², —CR²³R²⁴—CR²⁵R²⁶—CR²⁷R²⁸—CR²⁹R³⁹—CR³¹R³²—CR³³R³⁴—XH;

X represents —O—, —CO—, —O—CO—

$R^{37}$, $R^{38}$, $R^{93}$ and $R^{101}$ represent independently of each other —CR⁴⁰R⁴¹—YH, —Y—CR³⁹R⁴⁰—R⁴¹, —Y—CR⁴⁰—R⁴¹—CR⁴²R⁴³R³⁹, —CR⁴⁰R⁴¹—Y—CR⁴²R⁴³R³⁹, —CR⁴⁰R⁴¹—CR⁴²R⁴³—YH, —Y—CR⁴⁰R⁴¹—CR⁴²R⁴³—CR⁴⁴R⁴⁵R³⁹, —CR⁴⁰R⁴¹—Y—CR⁴²R⁴³—CR⁴⁴R⁴⁵R³⁹, —CR⁴⁰R⁴¹—CR⁴²R⁴³—Y—CR⁴⁴R⁴⁵R³⁹, —CR⁴⁰R⁴¹—CR⁴²R⁴³—CR⁴⁴R⁴⁵—YH, —Y—CR⁴⁰R⁴¹—CR⁴²R⁴³—CR⁴⁴R⁴⁵—CR⁴⁶R⁴⁷R³⁹, —CR⁴⁰R⁴¹—Y—CR⁴²R⁴³—CR⁴⁴R⁴⁵—CR⁴⁶R⁴⁷R³⁹, —CR⁴⁰R⁴¹—CR⁴²R⁴³—Y—CR⁴⁴R⁴⁵—CR⁴⁶R⁴⁷R³⁹, —CR⁴⁰R⁴¹—CR⁴²R⁴³—CR⁴⁴R⁴⁵—Y—CR⁴⁶R⁴⁶R³⁹, —CR⁴⁰R⁴²—CR⁴²R⁴³—CR⁴⁴R⁴⁵—CR⁴⁶R⁴⁷—YH, —Y—CR⁴⁰R⁴¹—CR⁴²R⁴³—CR⁴⁴R⁴⁵—CR⁴⁶R⁴⁷—CR⁴⁸R⁴⁹R³⁹, —CR⁴⁰R⁴¹—Y—CR⁴²R⁴³—CR⁴⁴R⁴⁵—CR⁴⁶R⁴⁷—CR⁴⁸R⁴⁹R³⁹, —CR⁴⁰R⁴¹—CR⁴²R⁴³—Y—CR⁴⁴R⁴⁵—CR⁴⁶R⁴⁷—CR⁴⁸R⁴⁹R³⁹, —CR⁴⁰R⁴¹—CR⁴²R⁴³—CR⁴⁴R⁴⁵—Y—CR⁴⁶R⁴⁷—CR⁴⁸R⁴⁹R³⁹, —CR⁴⁰R⁴¹—CR⁴²R⁴³—CR⁴⁴R⁴⁵—CR⁴⁶R⁴⁷—Y—CR⁴⁸R⁴⁹R³⁹, —CR⁴⁰R⁴¹—CR⁴²R⁴³—CR⁴⁴R⁴⁵—CR⁴⁶R⁴⁷—CR⁴⁸R⁴⁹—YH, —Y—CR⁴⁰R⁴¹—CR⁴²R⁴³—CR⁴⁴R⁴⁵—CR⁴⁶R⁴⁷—CR⁴⁶R⁴⁹—CR⁵⁰R⁵¹R³⁹, —CR⁴⁰R⁴¹—Y—CR⁴²R⁴³—CR⁴⁴R⁴⁵—CR⁴⁶R⁴⁷—CR⁴⁸R⁴⁹—CR⁵⁰R⁵¹R³⁹, —CR⁴⁰R⁴¹—CR⁴²R⁴³—Y—CR⁴⁴R⁴⁵—CR⁴⁶R⁴⁷—CR⁴⁸R⁴⁹—CR⁵⁰R⁵¹R³⁹, —CR⁴⁰R⁴¹—CR⁴²R⁴³—CR⁴⁴R⁴⁵—Y—CR⁴⁶R⁴⁷—CR⁴⁸R⁴⁹—CR⁵⁰R⁵¹R³⁹, —CR⁴⁰R⁴¹—CR⁴²R⁴³—CR⁴⁴R⁴⁵—CR⁴⁶R⁴⁷—Y—CR⁴⁸R⁴⁹—CR⁵⁰R⁵¹R³⁹, CR⁴⁰R⁴¹—CR⁴²R⁴³—CR⁴⁴R⁴⁵—CR⁴⁶R⁴⁷—CR⁴⁸R⁴⁹—Y—CR⁵⁰R⁵¹R³⁹—CR⁴⁰R⁴¹—CR⁴²R⁴³—CR⁴⁴R⁴⁵—CR⁴⁶R⁴⁷—CR⁴⁸R⁴⁹—CR⁵⁰R⁵¹—YH;

$R^{39}$-$R^{53}$ represent independently of each other —H, —CH₃, —C₂H₅, —C₃H₇;

Y represents —NR⁵²—CO—, —CO—NR⁵³—;

$R^{54}$, $R^{55}$ and $R^{102}$ represent independently of each other

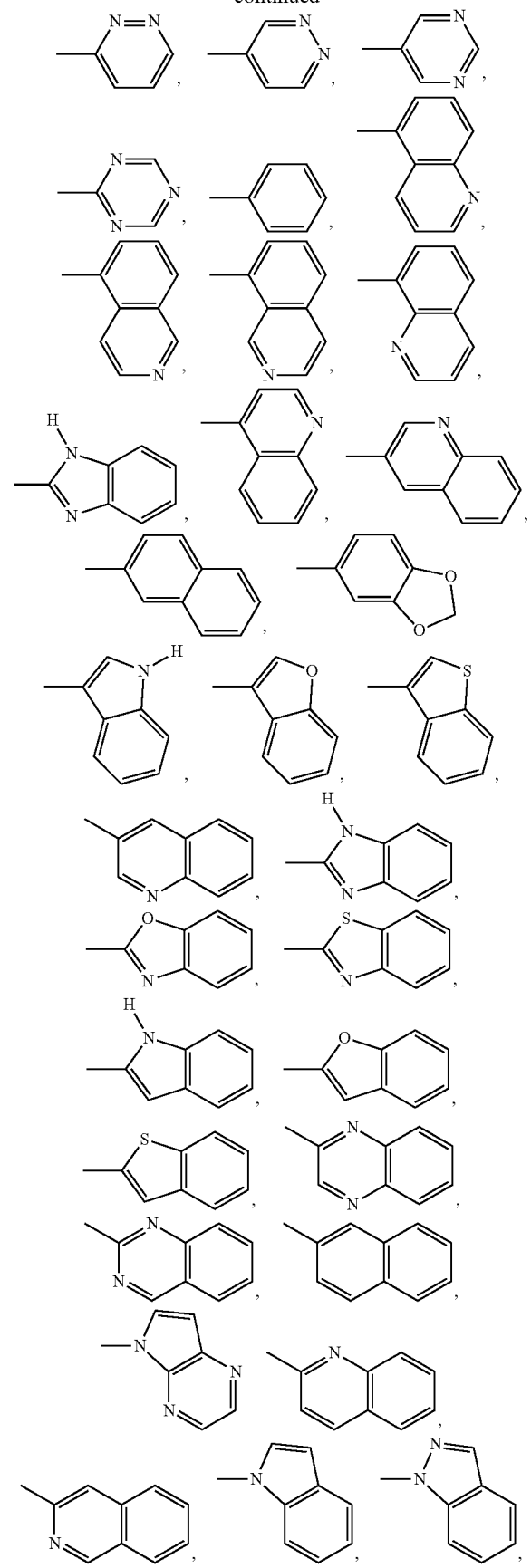

-continued

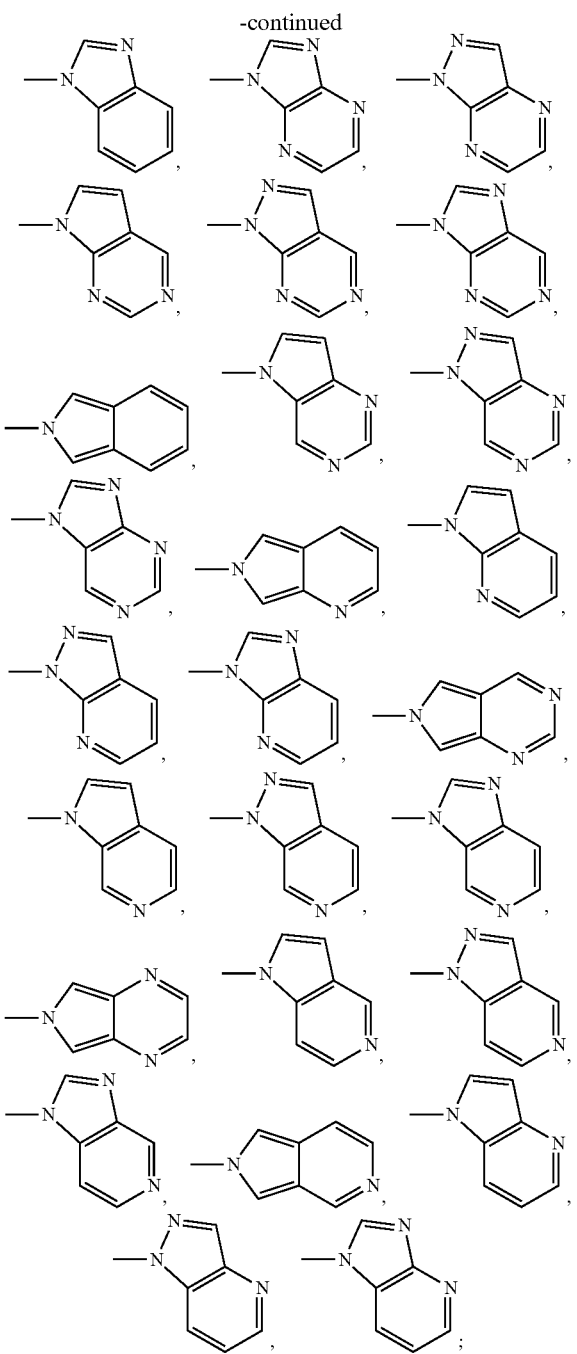

R$^{56}$, R$^{57}$, R$^{94}$ and R$^{103}$ represent independently of each other —CR$^{58}$R$^{16}$R$^{17}$, —CR$^{69}$R$^{60}$, —CR$^{16}$R$^{17}$CR$^{61}$R$^{62}$R$^{58}$, —CR$^{59}$R$^{60}$—CR$^{61}$R$^{62}$R$^{58}$, —R$^{60}$R$^{16}$R$^{17}$R$^{58}$, —CR$^{16}$R$^{17}$—CR$^{61}$R$^{62}$ CR$^{63}$R$^{64}$R$^{58}$, —R$^{59}$R$^{60}$—CR$^{61}$R$^{62}$—CR$^{63}$R$^{64}$R$^{58}$, —CR$^{59}$R$^{60}$—CR$^{16}$R$^{17}$—CR$^{63}$R$^{64}$R$^{58}$, —CR$^{59}$R$^{60}$— CR$^{61}$R$^{62}$—CR$^{16}$R$^{17}$R$^{58}$, R$^{16}$R$^{17}$—CR$^{61}$R$^{62}$— CR$^{63}$R$^{64}$—CR$^{65}$R$^{66}$R$^{58}$, —CR$^{59}$R$^{60}$—CR$^{61}$R$^{62}$— CR$^{63}$R$^{64}$—CR$^{65}$R$^{66}$R$^{58}$, —CR$^{59}$R$^{60}$—CR$^{16}$R$^{17}$— CR$^{63}$R$^{64}$—CR$^{66}$R$^{67}$R$^{58}$, —CR$^{59}$R$^{60}$—CR$^{61}$R$^{62}$— CR$^{16}$R$^{17}$—CR$^{65}$R$^{66}$R$^{58}$, —CR$^{59}$R$^{60}$—CR$^{61}$R$^{62}$— CR$^{63}$R$^{64}$—CR$^{16}$R$^{17}$R$^{58}$, —R$^{17}$—CR$^{61}$R$^{62}$— CR$^{63}$R$^{64}$—CR$^{65}$R$^{66}$—CR$^{67}$R$^{68}$R$^{58}$, —CR$^{69}$R$^{60}$— CR$^{61}$R$^{62}$—CR$^{63}$R$^{64}$—CR$^{65}$R$^{66}$—CR$^{67}$R$^{68}$R$^{58}$, —CR$^{59}$R$^{60}$—CR$^{16}$R$^{17}$—CR$^{63}$R$^{64}$—CR$^{65}$R$^{66}$— CR$^{67}$R$^{68}$R$^{58}$, —CR$^{59}$R$^{60}$—CR$^{61}$R$^{62}$—CR$^{16}$R$^{17}$— CR$^{65}$R$^{66}$—CR$^{67}$R$^{68}$R$^{69}$, —CR$^{59}$R$^{60}$—CR$^{61}$R$^{62}$— CR$^{63}$R$^{64}$—CR$^{16}$R$^{17}$—CR$^{67}$R$^{68}$R$^{58}$, —CR$^{59}$R$^{60}$— CR$^{61}$R$^{62}$—CR$^{63}$R$^{64}$—CR$^{65}$R$^{66}$—CR$^{16}$R$^{17}$R$^{58}$, —CR$^{16}$R$^{17}$—CR$^{61}$R$^{62}$—CR$^{63}$R$^{64}$—CR$^{65}$R$^{66}$— CR$^{67}$R$^{68}$—CR$^{69}$R$^{70}$R$^{58}$, —CR$^{59}$R$^{60}$—CR$^{16}$R$^{17}$— CR$^{63}$R$^{64}$—CR$^{65}$R$^{66}$—CR$^{67}$R$^{68}$—CR$^{69}$R$^{76}$R$^{58}$, —CR$^{59}$R$^{66}$—CR$^{61}$R$^{62}$—CR$^{16}$R$^{17}$—CR$^{65}$R$^{66}$— CR$^{67}$R$^{65}$—CR$^{69}$R$^{70}$R$^{55}$, —CR$^{59}$R$^{60}$—CR$^{61}$R$^{62}$— CR$^{63}$R$^{64}$—CR$^{16}$R$^{17}$—CR$^{67}$R$^{68}$—CR$^{69}$R$^{70}$R$^{55}$, —CR$^{59}$R$^{60}$—CR$^{61}$R$^{62}$—CR$^{63}$R$^{64}$—CR$^{66}$R$^{66}$— CR$^{16}$R$^{17}$—CR$^{69}$R$^{76}$R$^{68}$, —CR$^{59}$R$^{66}$—CR$^{61}$R$^{62}$— CR$^{63}$R$^{64}$—CR$^{65}$R$^{66}$—CR$^{67}$R$^{68}$—CR$^{16}$R$^{17}$R$^{58}$, R$^{58}$-R$^{70}$ represent independently of each other —H, —NH$_2$, —OH, —F, —Cl, —Br, —I, —R$^{71}$, —O—R$^{71}$, —R$^{72}$, —O—R$^{95}$, —R$^{96}$, —O—R$^{104}$, —R$^{105}$, —COOH, —COOCH$_3$, —COOC$_2$H$_5$, —COOC$_3$H$_7$, —COOCH(CH$_3$)$_2$, —COOC(CH$_3$)$_3$, —(C=O)—NR$^{16}$R$^{17}$, —SO$_2$—NR$^{16}$R$^{17}$, —SO$_m$—R$^{16}$R$^{17}$, —CR$^{16}$R$^{17}$H, —NR$^{16}$R$^{17}$;

R$^{107}$, R$^{117}$ and R$^{129}$ represent independently of each other —CH=CH$_2$, —CH$_2$—CH=CH$_2$, —H, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH$_2$, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —C(C$_2$H$_5$)=C(CH$_3$)—CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)

=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —CH=CH—C₂H₄—CH=CH₂, —CH₂—CH=CH—CH=CH—CH₃, —CH=CH—CH₂—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH=CH—C(CH₃)=CH—CH₃, —CH=C(CH₃)—CH=CH—CH₃, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂;

R¹⁰⁹, R¹¹⁸ and R¹³⁰ represent independently of each other —H, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—CH₃, —CH₂—C≡C—C₃H₇, —C≡C—C₄H₉, —C₂H₄—CH(CH₃)—C≡CH, —CH₂—CH(CH₃)—CH₂—C≡CH, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —C≡C—C(CH₃)₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃;

R¹¹³, R¹¹⁵, R¹²¹, R¹²⁴, R¹²⁶, R¹²⁷, R¹³³, R¹³⁵, R¹³⁷ and R¹³⁸ independently of each other represent

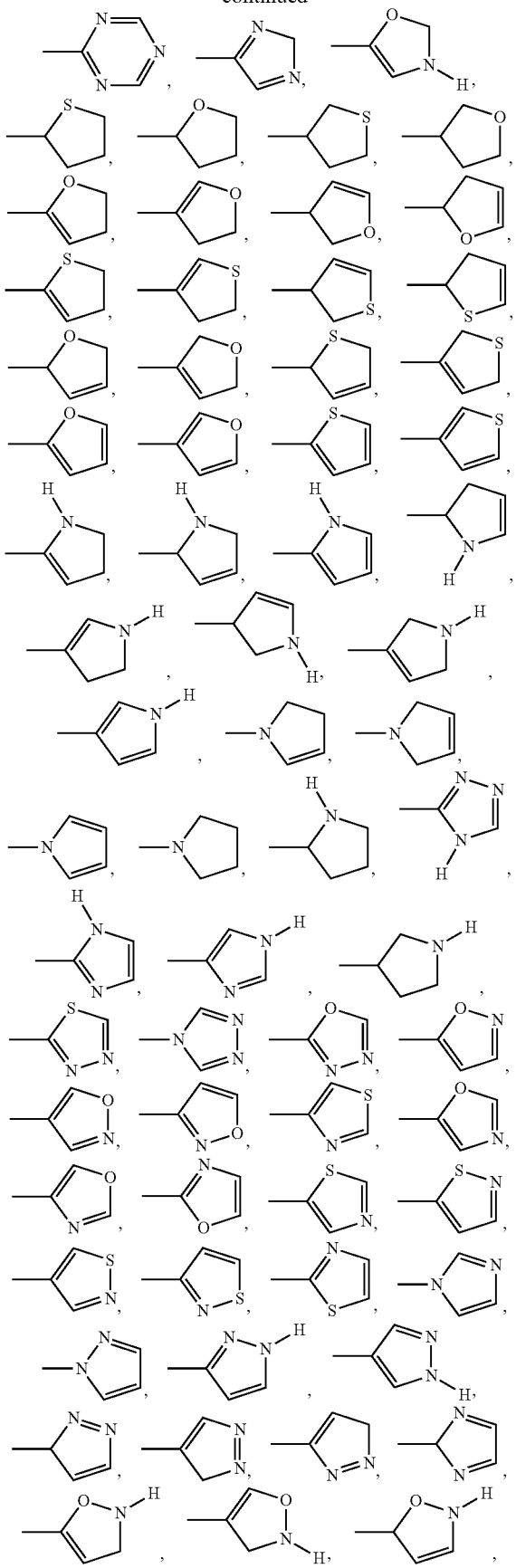

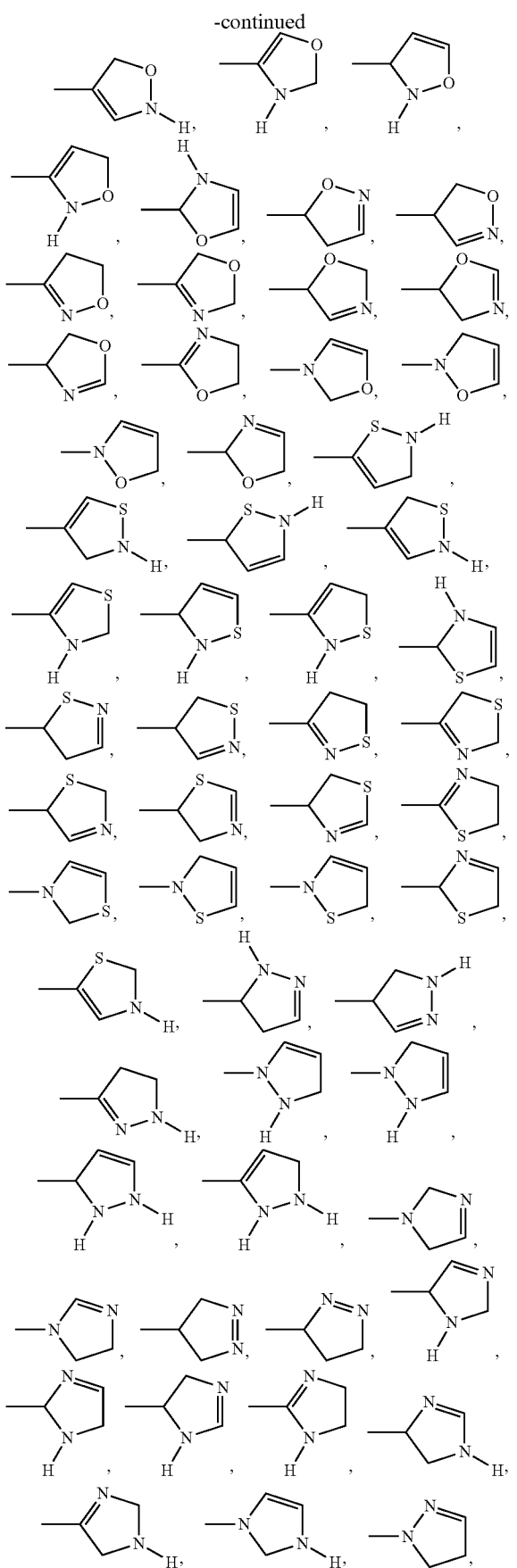
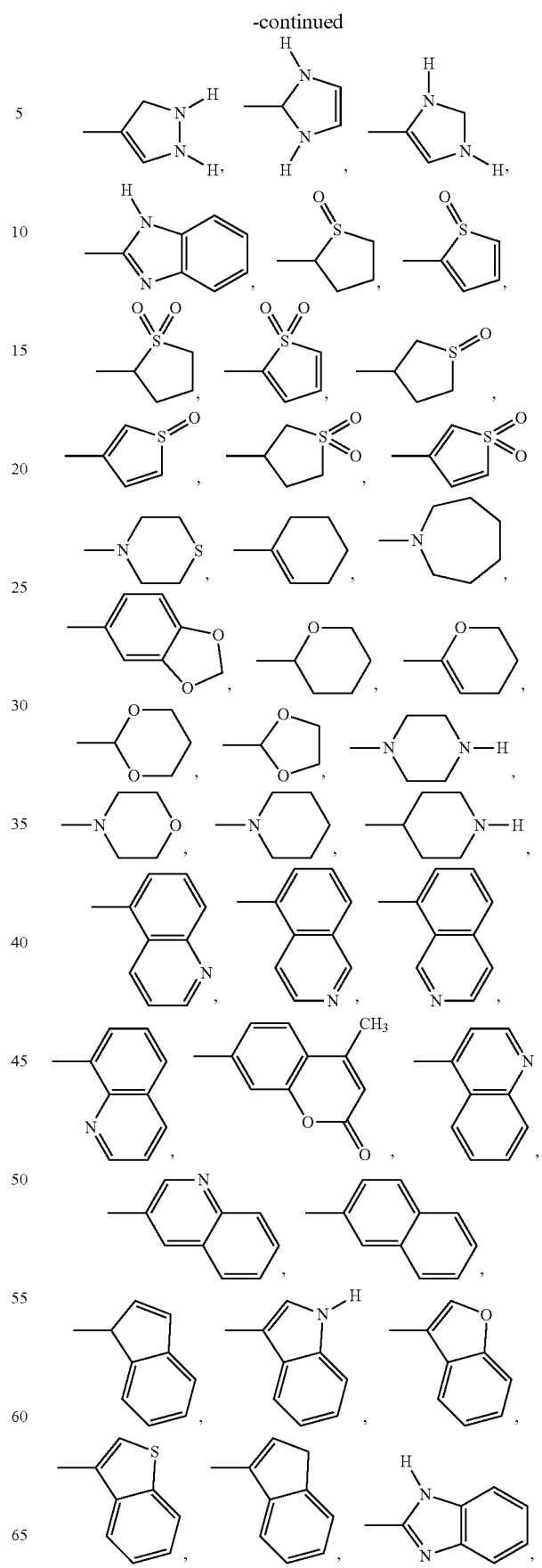

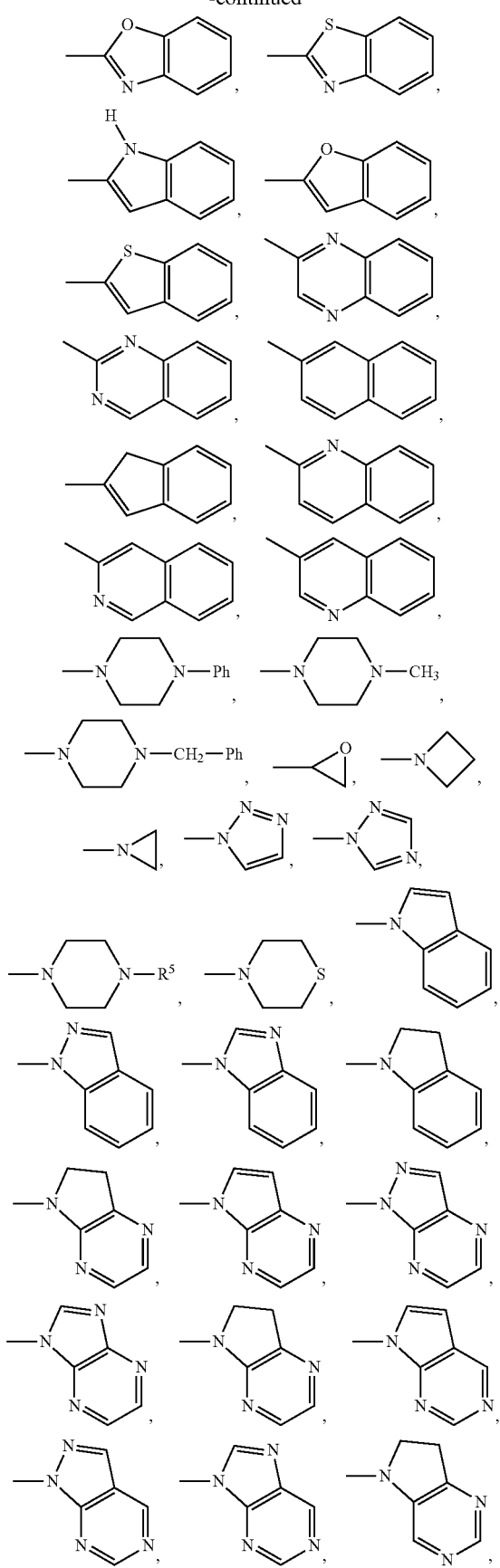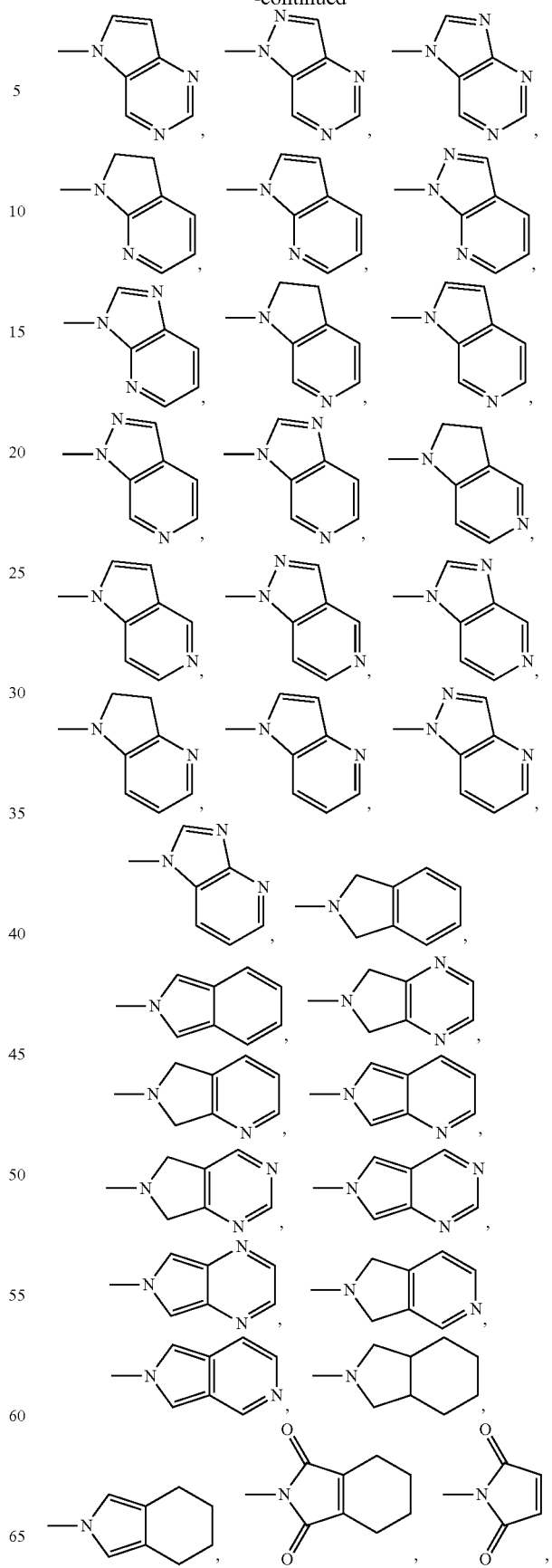

183
-continued

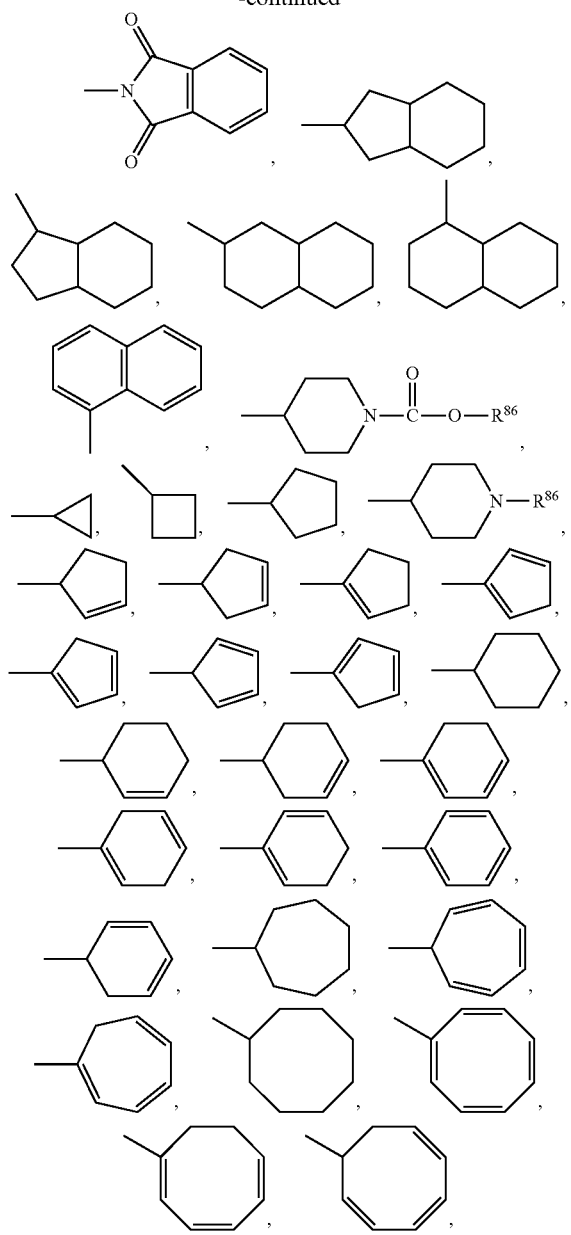

$R^{114}$ represents

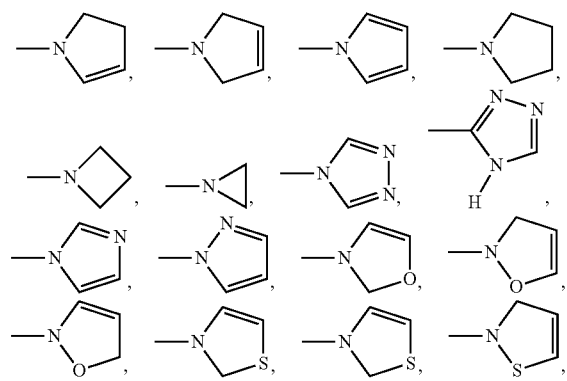

184
-continued

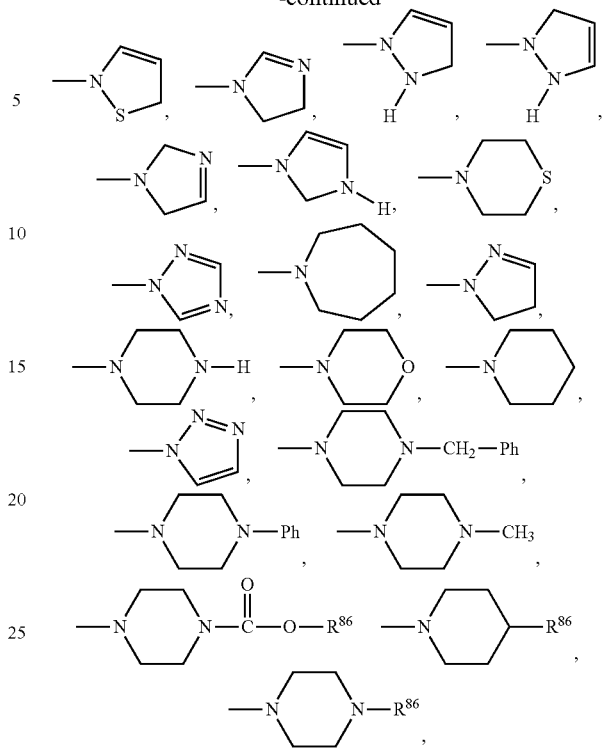

and enantiomers, stereoisomeric forms, mixtures of enantiomers, diastereomers, mixtures of diastereomers, prodrugs, hydrates, solvates, acid salt forms, tautomers, and racemates of the above mentioned compounds and pharmaceutically acceptable salts thereof.

2. The compounds according to claim 1, wherein the residue D represents one of the following heterocycles,

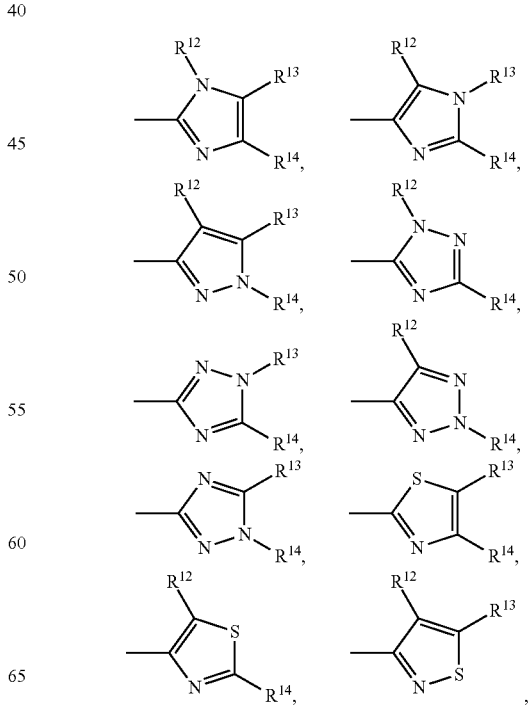

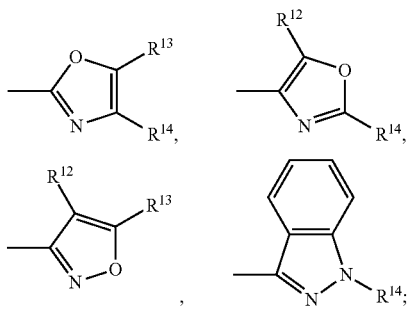

and the substituents $R^{12}$-$R^{14}$ have the meanings as defined in formula (I).

3. The compounds according to claim 1, wherein $R^1$, $R^4$, $R^5$ and $R^6$ are selected from hydrogen or $C_{1-6}$alkyl, particularly from hydrogen.

4. The compounds according to any of claims 1 to 3, having the general formula (Ia)

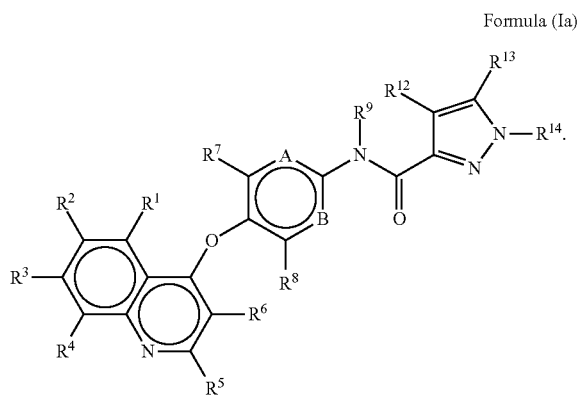

Formula (Ia)

5. The compounds according to any of claims 1 to 3, having the general formula (Ib) or the general formula (Ic)

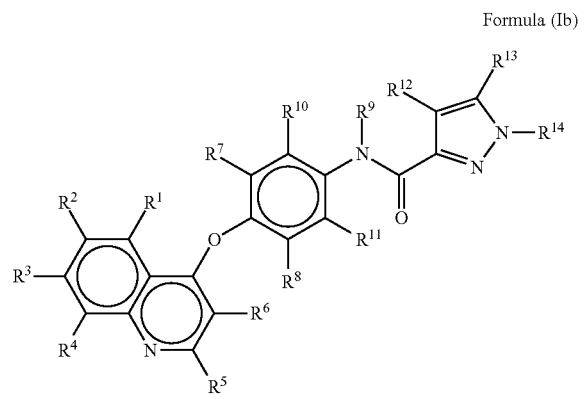

Formula (Ib)

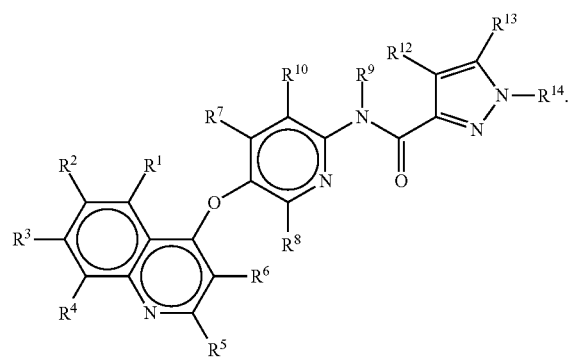

Formula (Ic)

6. The compounds according to any of claims 1 to 3, wherein $R^9$ is a hydrogen atom.

7. The compound according to claim 1, wherein the compound is selected from the group of compounds comprising N-[4-[(6,7-dimethoxy-4-quinolyl)oxy]-3-fluoro-phenyl]-1,5-dimethyl-pyrazole-3-carboxamide N-[4-[(6,7-dimethoxy-4-quinolyl)oxy]-3-fluoro-phenyl]-2-[4-(trifluoromethyl)phenyl]thiazole-4-carboxamide 4-bromo-N-[4-[(6,7-dimethoxy-4-quinolyl)oxy]-3-fluoro-phenyl]-1-methyl-pyrazole-3-carboxamide N-[4-[(6,7-dimethoxy-4-quinolyl)oxy]-3-fluoro-phenyl]-1-methyl-pyrazole-3-carboxamide 1-tert-butyl-N-[4-[(6,7-dimethoxy-4-quinolyl)oxy]-3-fluoro-phenyl]-5-methyl-pyrazole-3-carboxamide N-[4-[(6,7-dimethoxy-4-quinolyl)oxy]-3-fluoro-phenyl]thiazole-2-carboxamide N-[4-[(6,7-dimethoxy-4-quinolyl)oxy]-3-fluoro-phenyl]-2-methyl-thiazole-4-carboxamide N-[4-[(6,7-dimethoxy-4-quinolyl)oxy]-3-fluoro-phenyl]-1-methyl-indazole-3-carboxamide N-[4-[(6,7-dimethoxy-4-quinolyl)oxy]-3-fluoro-phenyl]-5-methyl-isoxazole-3-carboxamide N-[4-[(6,7-dimethoxy-4-quinolyl)oxy]-3-fluoro-phenyl]-2-phenyl-thiazole-4-carboxamide N-[4-[(6,7-dimethoxy-4-quinolyl)oxy]-3-fluoro-phenyl]-1-methyl-imidazole-2-carboxamide N-[4-[(6,7-dimethoxy-4-quinolyl)oxy]-3-fluoro-phenyl]-1-methyl-imidazole-4-carboxamide N-[4-[(6,7-dimethoxy-4-quinolyl)oxy]-3-fluoro-phenyl]-1-propyl-pyrazole-3-carboxamide N-[4-[(6,7-dimethoxy-4-quinolyl)oxy]-3-fluoro-phenyl]-1-[3-(1-piperidyl)propyl]pyrazole-3-carboxamide N-[4-[(6,7-dimethoxy-4-quinolyl)oxy]-3-fluoro-phenyl]-1-(2,2,2-trifluoroethoxymethyl)pyrazole-3-carboxamide N-[4-[(6,7-dimethoxy-4-quinolyl)oxy]-3-fluoro-phenyl]-4-ethoxy-1-(4-fluorophenyl)pyrazole-3-carboxamide N-[4-[(6,7-dimethoxy-4-quinolyl)oxy]-3-fluoro-phenyl]-1-(4-fluorophenyl)-4-methoxy-pyrazole-3-carboxamide 4-(cyclopropylmethoxy)-N-[4-[(6,7-dimethoxy-4-quinolyl)oxy]-3-fluoro-phenyl]-1-(4-fluorophenyl)pyrazole-3-carboxamide N-[4-[(6,7-dimethoxy-4-quinolyl)oxy]-3-fluoro-phenyl]-4-(2-dimethylaminoethoxy)-1-(4-fluorophenyl)pyrazole-3-carboxamide N-[4-[(6,7-dimethoxy-4-quinolyl)oxy]-3-fluoro-phenyl]-4-(2-dimethylaminoethoxy)-1-(4-fluorophenyl)pyrazole-3-carboxamide N-[4-[(6,7-dimethoxy-4-quinolyl)oxy]-3-fluoro-phenyl]-1-(4-fluorophenyl)-4-isopropoxy-pyrazole-3-carboxamide N-[4-[(6,7-dimethoxy-4-quinolyl)oxy]-3-fluoro-phenyl]-4-ethoxy-1-(4-fluoro-2-methyl-phenyl)pyrazole-3-carboxamide 1-(2-chloro-4-fluoro-phenyl)-N-[4-[(6,7-dimethoxy-4-quinolyl)oxy]-3-fluoro-phenyl]-4-ethoxy-pyrazole-3-carboxamide N-[4-[(6,7-dimethoxy-4-quinolyl)oxy]phenyl]-4-ethoxy-1-(4-fluorophenyl)pyrazole-3-carboxamide N-[4-[(6,7-dimethoxy-4-quinolyl)oxy]phenyl]-1-(4-fluorophenyl)-4-isopropoxy-pyrazole-3-carboxamide 4-(cyclopropylmethoxy)-N-[4-[(6,7-dimethoxy-4-quinolyl)oxy]phenyl]-1-(4-fluorophenyl)pyrazole-3-carboxamide N-[4-[(6,7-dimethoxy-4-quinolyl)oxy]phenyl]-4-ethoxy-1-(4-fluoro-2-methyl-phenyl)pyrazole-3-carboxamide N-[4-[(6,7-dimethoxy-4-quinolyl)oxy]-3-methyl-phenyl]-4-ethoxy-1-(4-fluorophenyl)pyrazole-3-carboxamide N-[4-[(6,7-dimethoxy-4-quinolyl)oxy]-3-methyl-phenyl]-1-(4-fluorophenyl)-4-isopropoxy-pyrazole-3-carboxamide 4-(cyclopropylmethoxy)-N-[4-[(6,7-dimethoxy-4-quinolyl)oxy]-3-methyl-phenyl]-1-(4-fluorophenyl)pyrazole-3-carboxamide N-[4-[(6,7-dimethoxy-4-quinolyl)oxy]-3-methyl-phenyl]-4-ethoxy-1-(4-fluoro-2-methyl-phenyl)pyrazole-3-carboxamide N-[3-chloro-4-[(6,7-dimethoxy-4-quinolyl)oxy]phenyl]-4-ethoxy-1-(4-fluorophenyl)pyrazole-3-carboxamide N-[3-chloro-4-[(6,7-dimethoxy-4-quinolyl)oxy]phenyl]-1-(4-fluorophenyl)-4-isopropoxy-pyrazole-3-carboxamide N-[3-chloro-4-[(6,7-dimethoxy-4-quinolyl)oxy]phenyl]-4-(cyclopropylmethoxy)-1-(4-fluorophenyl)pyrazole-3-carboxamide N-[3-chloro-4-[(6,7-dimethoxy-4-quinolyl)oxy]phenyl]-4-ethoxy-1-(4-fluoro-2-methyl-phenyl)pyrazole-3-carboxamide N-(4-((6,7-dimethoxyquinolin-4-yl)oxy)-3-fluorophenyl)-4-(2-(dimethylamino)ethyl)-1-(4-fluorophenyl)-1H-pyrazole-3-carboxamide N-[4-[(6,7-dimethoxy-4-quinolyl)oxy]-3-fluoro-phenyl]-1-[2-(2-dimethylaminoethyl)-4-fluoro-phenyl]-4-ethoxy-pyrazole-3-carboxamide N-[3-fluoro-4-[[6-methoxy-7-(3-morpholinopropoxy)-4-quinolyl]oxy]phenyl]-2-phenyl-thiazole-4-carboxamide 4-bromo-N-[3-fluoro-4-[[6-methoxy-7-(3-morpholinopropoxy)-4-quinolyl]oxy]phenyl]-1-methyl-pyrazole-3-carboxamide N-[3-fluoro-4-[[6-methoxy-7-(3-morpholinopropoxy)-4-quinolyl]oxy]phenyl]-1-methyl-pyrazole-3-carboxamide 1-tert-butyl-N-[3-fluoro-4-[[6-methoxy-7-(3-morpholinopropoxy)-4-quinolyl]oxy]phenyl]-5-methyl-pyrazole-3-carboxamide N-[3-fluoro-4-[[6-methoxy-7-(3-morpholinopropoxy)-4-quinolyl]oxy]phenyl]-1,5-dimethyl-pyrazole-3-carboxamide 4-ethoxy-N-[3-fluoro-4-[[6-methoxy-7-(3-morpholinopropoxy)-4-quinolyl]oxy]phenyl]-1-(4-fluoro-2-methyl-phenyl)pyrazole-3-carboxamide N-[3-fluoro-4-[[6-methoxy-7-(3-morpholinopropoxy)-4-quinolyl]oxy]phenyl]-1-(4-fluorophenyl)-4-methoxy-pyrazole-3-carboxamide N-[3-fluoro-4-[[6-methoxy-7-(3-morpholinopropoxy)-4-quinolyl]oxy]phenyl]-1-(4-fluorophenyl)-4-isopropoxy-pyrazole-3-carboxamide 4-(cyclopropylmethoxy)-N-[3-fluoro-4-[[6-methoxy-7-(3-morpholinopropoxy)-4-quinolyl]oxy]phenyl]-1-(4-fluorophenyl)pyrazole-3-carboxamide 1-(2-chloro-4-fluoro-phenyl)-4-ethoxy-N-[3-fluoro-4-[[6-methoxy-7-(3-morpholinopropoxy)-4-quinolyl]oxy]phenyl]pyrazole-3-carboxamide 4-(2-dimethylaminoethoxy)-N-[3-fluoro-4-[[6-methoxy-7-(3-morpholinopropoxy)-4-quinolyl]oxy]phenyl]-1-(4-fluorophenyl)pyrazole-3-carboxamide 1-(2-bromo-4-fluoro-phenyl)-4-ethoxy-N-[3-fluoro-4-[[6-methoxy-7-(3-morpholinopropoxy)-4-quinolyl]oxy]phenyl]pyrazole-3-carboxamide N-[3-fluoro-4-[[6-methoxy-7-(3-morpholinopropoxy)-4-quinolyl]oxy]phenyl]-1-(4-fluorophenyl)-4-(2-methoxyethoxy)pyrazole-3-carboxamide 4-benzyloxy-N-[3-fluoro-4-[[6-methoxy-7-(3-morpholinopropoxy)-4-quinolyl]oxy]phenyl]-1-(4-fluorophenyl)pyrazole-3-carboxamide N-[3-fluoro-4-[[6-methoxy-7-(3-morpholinopropoxy)-4-quinolyl]oxy]phenyl]-1-(4-fluorophenyl)-4-nitro-pyrazole-3-carboxamide 4-amino-N-[3-fluoro-4-[[6-methoxy-7-(3-morpholinopropoxy)-4-quinolyl]oxy]phenyl]-1-(4-fluorophenyl)pyrazole-3-carboxamide N-[4-[[7-(3-aminopropoxy)-6-methoxy-4-quinolyl]oxy]-3-fluoro-phenyl]-4-ethoxy-1-(4-fluorophenyl)pyrazole-3-carboxamide N-[4-[[7-(3-aminopropoxy)-6-methoxy-4-quinolyl]oxy]-3-fluoro-phenyl]-4-ethoxy-1-(4-fluoro-2-methyl-phenyl)pyrazole-3-carboxamide N-[4-[[7-(3-aminopropoxy)-6-methoxy-4-quinolyl]oxy]-3-fluoro-phenyl]-5-ethoxy-2-(4-fluorophenyl)oxazole-4-carboxamide 4-ethoxy-N-[3-fluoro-4-[[6-methoxy-7-[3-(4-methylpiperazin-1-yl)propoxy]-4-quinolyl]oxy]phenyl]-1-(4-fluoro-2-methyl-phenyl)pyrazole-3-carboxamide 4-ethoxy-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide N-[3-fluoro-4-[[6-methoxy-7-[3-(4-methylpiperazin-1-yl)propoxy]-4-quinolyl]oxy]phenyl]-1-(4-fluorophenyl)-4-methoxy-pyrazole-3-carboxamide 1-(2-chloro-4-fluoro-phenyl)-4-ethoxy-N-[3-fluoro-4-[[6-methoxy-7-[3-(4-methylpiperazin-1-yl)propoxy]-4-quinolyl]oxy]phenyl]pyrazole-3-carboxamide 4-(cyclopropylmethoxy)-N-[3-fluoro-4-[[6-methoxy-7-[3-(4-methylpiperazin-1-yl)propoxy]-4-quinolyl]oxy]phenyl]-1-(4-fluorophenyl)pyrazole-3-carboxamide N-[3-fluoro-4-[[6-methoxy-7-[3-(4-methylpiperazin-1-yl)propoxy]-4-quinolyl]oxy]phenyl]-1-(4-fluorophenyl)-4-isopropoxy-pyrazole-3-carboxamide 5-ethoxy-N-[3-fluoro-4-[[6-methoxy-7-[3-(4-methylpiperazin-1-yl)propoxy]-4-quinolyl]oxy]phenyl]-2-(4-fluorophenyl)oxazole-4-carboxamide 4-(cyclopropylmethoxy)-N-[3-fluoro-4-[[6-methoxy-7-(3-piperazin-1-ylpropoxy)-4-quinolyl]oxy]phenyl]-1-(4-fluorophenyl)pyrazole-3-carboxamide trifluoroacetic acid salt 4-ethoxy-N-[3-fluoro-4-[[6-methoxy-7-(3-piperazin-1-ylpropoxy)-4-quinolyl]oxy]phenyl]-1-(4-fluorophenyl)pyrazole-3-carboxamide N-[3-fluoro-4-[[6-methoxy-7-(3-piperazin-1-ylpropoxy)-4-quinolyl]oxy]phenyl]-1-(4-fluorophenyl)-4-methoxy-pyrazole-3-carboxamide N-[3-fluoro-4-[[6-methoxy-7-(3-piperazin-1-ylpropoxy)-4-quinolyl]oxy]phenyl]-1-(4-fluorophenyl)-4-isopropoxy-pyrazole-3-carboxamide
1-(2-chloro-4-fluoro-phenyl)-4-ethoxy-N-[3-fluoro-4-[[6-methoxy-7-(3-piperazin-1-ylpropoxy)-4-quinolyl]oxy]phenyl]pyrazole-3-carboxamide
4-ethoxy-N-[3-fluoro-4-[[6-methoxy-7-(3-piperazin-1-ylpropoxy)-4-quinolyl]oxy]phenyl]-1-(4-fluoro-2-methyl-phenyl)pyrazole-3-carboxamide
N-[3-fluoro-4-[[6-methoxy-7-(3-piperazin-1-ylpropoxy)-4-quinolyl]oxy]phenyl]-1-(4-fluorophenyl)-4-(2-methoxyethoxyl)pyrazole-3-carboxamide
N-[3-fluoro-4-[[6-methoxy-7-(3-piperazin-1-ylpropoxy)-4-quinolyl]oxy]phenyl]-1-(4-fluorophenyl)-4-[(1-methylpyrrolidin-3-yl)methoxy]pyrazole-3-carboxamide
N-[3-fluoro-4-[[6-methoxy-7-(3-piperazin-1-ylpropoxy)-4-quinolyl]oxy]phenyl]-2-phenyl-thiazole-4-carboxamide
N-[3-fluoro-4-[[6-methoxy-7-(4-piperidylmethoxy)-4-quinolyl]oxy]phenyl]-1-(4-fluorophenyl)-4-methoxy-pyrazole-3-carboxamide
4-ethoxy-N-[3-fluoro-4-[[6-methoxy-7-(4-piperidylmethoxy)-4-quinolyl]oxy]phenyl]-1-(4-fluoro-2-methyl-phenyl)pyrazole-3-carboxamide
4-(cyclopropylmethoxy)-N-[3-fluoro-4-[[6-methoxy-7-(4-piperidylmethoxy)-4-quinolyl]oxy]phenyl]-1-(4-fluorophenyl)pyrazole-3-carboxamide
4-bromo-N-[3-fluoro-4-[[6-methoxy-7-(4-piperidylmethoxy)-4-quinolyl]oxy]phenyl]-1-(4-fluorophenyl)pyrazole-3-carboxamide
N-[3-fluoro-4-[[6-methoxy-7-(4-piperidylmethoxy)-4-quinolyl]oxy]phenyl]-1-(4-fluorophenyl)-4-[(4-fluorophenyl)methoxy]pyrazole-3-carboxamide
1-tert-butyl-N-[3-fluoro-4-[[6-methoxy-7-(4-piperidylmethoxy)-4-quinolyl]oxy]phenyl]-5-methyl-pyrazole-3-carboxamide
N-[3-fluoro-4-[[6-methoxy-7-(4-piperidylmethoxy)-4-quinolyl]oxy]phenyl]-4-nitro-1-[3-(1-piperidyl)propyl]pyrazole-3-carboxamide
N-[3-fluoro-4-[[6-methoxy-7-(4-piperidylmethoxy)-4-quinolyl]oxy]phenyl]-5-methyl-2-phenyl-oxazole-4-carboxamide
N-[3-fluoro-4-[[6-methoxy-7-(4-piperidylmethoxy)-4-quinolyl]oxy]phenyl]-2-phenyl-thiazole-4-carboxamide
4-ethoxy-N-[4-[[7-[(1-ethyl-4-piperidyl)methoxy]-6-methoxy-4-quinolyl]oxy]-3-fluoro-phenyl]-1-(4-fluoro-2-methyl-phenyl)pyrazole-3-carboxamide
4-ethoxy-N-[3-fluoro-4-[[7-((1-isobutyl-4-piperidyl)methoxy]-6-methoxy-4-quinolyl]oxy]phenyl]-1-(4-fluoro-2-methyl-phenyl)pyrazole-3-carboxamide
N-[5-[(6,7-dimethoxy-4-quinolyl)oxy]-2-pyridyl]-4-ethoxy-1-(4-fluorophenyl)pyrazole-3-carboxamide
N-[5-[(6,7-dimethoxy-4-quinolyl)oxy]-2-pyridyl]-4-ethoxy-1-(4-fluoro-2-methyl-phenyl)pyrazole-3-carboxamide
1-(2-chloro-4-fluoro-phenyl)-N-[5-[(6,7-dimethoxy-4-quinolyl)oxy]-2-pyridyl]-4-ethoxy-pyrazole-3-carboxamide
N-[5-[(6,7-dimethoxy-4-quinolyl)oxy]-2-pyridyl]-4-(2-dimethylaminoethyl)-1-(4-fluorophenyl)pyrazole-3-carboxamide
tert-butyl 4-(((4-((6-(4-ethoxy-1-(4-fluoro-2-methylphenyl)-1H-pyrazole-3-carboxamido)pyridin-3-yl)oxy)-6-methoxyquinolin-7-yl)oxy)methyl)piperidine-1-carboxylate
N-(5-((6,7-dimethoxyquinolin-4-yl)oxy)pyridin-2-yl)-4-ethoxy-1-(4-methoxy-2-methylphenyl)-1H-pyrazole-3-carboxamide
N-(4-((6,7-dimethoxyquinolin-4-yl)oxy)-3-fluorophenyl)-4-ethoxy-1-(3-nitrophenyl)-1H-pyrazole-3-carboxamide
N-(4-((6,7-dimethoxyquinolin-4-yl)oxy)-3-fluorophenyl)-4-ethoxy-1-(4-methoxy-2-methylphenyl)-1H-pyrazole-3-carboxamide
N-(5-((6,7-dimethoxyquinolin-4-yl)oxy)pyridin-2-yl)-4-ethoxy-1-(3-nitrophenyl)-1H-pyrazole-3-carboxamide
1-(2-(benzyloxy)-4-fluorophenyl)-N-(5-((6,7-dimethoxyquinolin-4-yl)oxy)pyridin-2-yl)-4-ethoxy-1H-pyrazole-3-carboxamide
N-(4-((6,7-dimethoxyquinolin-4-yl)oxy)-2-methoxyphenyl)-4-ethoxy-1-(4-fluoro-2-methylphenyl)-1H-pyrazole-3-carboxamide
N-(4-((6,7-dimethoxyquinolin-4-yl)oxy)-2-methylphenyl)-4-ethoxy-1-(4-fluoro-2-methylphenyl)-1H-pyrazole-3-carboxamide
N-(4-((6,7-dimethoxyquinolin-4-yl)oxy)-3-fluorophenyl)-4-ethoxy-1-(4-fluoro-3-methoxyphenyl)-1H-pyrazole-3-carboxamide
N-(5-((6,7-dimethoxyquinolin-4-yl)oxy)pyridin-2-yl)-4-ethoxy-1-(4-fluoro-3-methoxyphenyl)-1H-pyrazole-3-carboxamide
N-(5-((6,7-dimethoxyquinolin-4-yl)oxy)pyridin-2-yl)-4-ethoxy-1-(4-nitrophenyl)-1H-pyrazole-3-carboxamide
1-(4-aminophenyl)-N-(5-((6,7-dimethoxyquinolin-4-yl)oxy)pyridin-2-yl)-4-ethoxy-1H-pyrazole-3-carboxamide
N-(5-((6-methoxy-7-(piperidin-4-ylmethoxy)quinolin-4-yl)oxy)pyridin-2-yl)-4-(2-methoxyphenyl)thiazole-2-carboxamide
N-(5-((6-methoxy-7-(piperidin-4-ylmethoxy)quinolin-4-yl)oxy)pyridin-2-yl)-4-phenylthiazole-2-carboxamide
4-bromo-N-(5-((6-methoxy-7-(piperidin-4-ylmethoxy)quinolin-4-yl)oxy)pyridin-2-yl)thiazole-2-carboxamide
N-(4-((6,7-dimethoxyquinolin-4-yl)oxy)-2-methoxyphenyl)-4-ethoxy-1-(4-fluoro-2-methylphenyl)-1H-pyrazole-3-carboxamide
N-(5-((6,7-dimethoxyquinolin-4-yl)oxy)pyridin-2-yl)-4-ethoxy-1-(4-fluoro-2-hydroxyphenyl)-1H-pyrazole-3-carboxamide
N-(4-((6,7-dimethoxyquinolin-4-yl)oxy)-3-fluorophenyl)-4-ethoxy-1-(pyridin-3-yl)-1H-pyrazole-3-carboxamide
N-(4-((6,7-dimethoxyquinolin-4-yl)oxy)-3-fluorophenyl)-4-ethoxy-1'-methyl-1'H-[1,3'-bipyrazole]-3-carboxamide.

8. A compound according to claim 1 for use as pharmaceutically active agent.

9. The compound of claim 8 as efficient inhibitors of TAM family RTKs.

10. The compound of claim 8 as suitable pharmaceutically active agents for the treatment of disorders associated with, accompanied by and/or caused by TAM family RTKs hyperfunction.

11. The compound of claim 9 for the treatment of Axl receptor tyrosine induced disorders.

12. The compound of claim 11, wherein the Axl receptor tyrosine kinase induced disorders are selected from a group comprising hyperproliferative disorders.

13. The compound of claim 12, wherein the Axl receptor tyrosine kinase induced disorders are selected from the group comprising cancer and primary tumor metastases.

14. The compound of claim 13, wherein the Axl receptor tyrosine kinase induced disorders are selected from adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome, colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear tumors, nose tumors and throat tumors, hematologic neoplasias, hairy cell leukemia, urethral cancer, skin cancer, skin testis cancer, brain tumors, brain metastases, testicle cancer, hypophysis tumor, carcinoids, Kaposi's sarcoma, laryngeal cancer, germ cell tumor, bone cancer, colorectal carcinoma, head and neck tumors, colon carcinoma, craniopharyngiomas, oral cancer, cancer of the central nervous system, liver cancer, liver metastases, leukemia, eyelid tumor, lung cancer, lymph node cancer, lymphomas, stomach cancer, malignant melanoma, malignant neoplasia, malignant tumors of the gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma, thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

15. Pharmaceutical composition comprising at least one compound according to claim 1 as an active ingredient, together with at least one pharmaceutically acceptable carrier, excipient and/or diluent.

* * * * *